US010106556B2

(12) United States Patent
Ikeda et al.

(10) Patent No.: US 10,106,556 B2
(45) Date of Patent: Oct. 23, 2018

(54) HETEROCYCLIC COMPOUND

(71) Applicant: TAKEDA PHARMACEUTICAL COMPANY LIMITED, Osaka-shi, Osaka (JP)

(72) Inventors: Shuhei Ikeda, Fujisawa (JP); Tatsuki Koike, Fujisawa (JP); Jumpei Aida, Fujisawa (JP); Makoto Fushimi, New York, NY (US); Tomokazu Kusumoto, Fujisawa (JP); Hideyuki Sugiyama, Fujisawa (JP); Masako Miyazaki, Fujisawa (JP); Hidekazu Tokuhara, Fujisawa (JP); Yasushi Hattori, Fujisawa (JP); Makoto Kamata, Fujisawa (JP)

(73) Assignee: TAKEDA PHARMACEUTICAL COMPANY LIMITED, Osaka-shi, Osaka (JP)

( * ) Notice: Subject to any disclaimer, the term of this patent is extended or adjusted under 35 U.S.C. 154(b) by 0 days.

(21) Appl. No.: 15/563,161

(22) PCT Filed: Mar. 29, 2016

(86) PCT No.: PCT/JP2016/060134

§ 371 (c)(1),
(2) Date: Sep. 29, 2017

(87) PCT Pub. No.: WO2016/158956

PCT Pub. Date: Oct. 6, 2016

(65) Prior Publication Data

US 2018/0079756 A1 Mar. 22, 2018

(30) Foreign Application Priority Data

Aug. 28, 2015 (JP) ................................ 2015-169733

(51) Int. Cl.

| | |
|---|---|
| ***C07D 498/04*** | (2006.01) |
| ***C07D 413/14*** | (2006.01) |
| ***C07D 401/06*** | (2006.01) |
| ***C07D 413/06*** | (2006.01) |
| ***C07D 417/14*** | (2006.01) |
| ***C07D 471/04*** | (2006.01) |
| ***C07D 401/10*** | (2006.01) |
| ***C07D 413/10*** | (2006.01) |
| ***C12N 9/99*** | (2006.01) |
| ***A61K 31/454*** | (2006.01) |
| ***A61K 31/4709*** | (2006.01) |
| ***A61K 31/538*** | (2006.01) |
| ***A61K 31/5383*** | (2006.01) |

(52) U.S. Cl.

CPC .......... *C07D 498/04* (2013.01); *A61K 31/454* (2013.01); *A61K 31/4709* (2013.01); *A61K 31/538* (2013.01); *A61K 31/5383* (2013.01); *C07D 401/06* (2013.01); *C07D 401/10* (2013.01); *C07D 413/06* (2013.01); *C07D 413/10* (2013.01); *C07D 413/14* (2013.01); *C07D 417/14* (2013.01); *C07D 471/04* (2013.01); *C12N 9/99* (2013.01)

(58) Field of Classification Search

CPC .. C07D 401/10; C07D 413/10; C07D 413/14; C07D 417/14; C07D 498/04

See application file for complete search history.

(56) References Cited

FOREIGN PATENT DOCUMENTS

| | | | |
|---|---|---|---|
| JP | 2012-524800 | A | 10/2012 |
| JP | 2012-524810 | A | 10/2012 |
| JP | 2013-536852 | A | 9/2013 |
| WO | 01/64676 | A2 | 9/2001 |
| WO | 2004/054974 | A2 | 1/2004 |
| WO | 2010/124082 | A1 | 10/2010 |
| WO | 2010/124086 | A1 | 10/2010 |
| WO | 2010/124121 | A1 | 10/2010 |
| WO | 2010/124122 | A1 | 10/2010 |
| WO | 2011/058766 | A1 | 5/2011 |

(Continued)

OTHER PUBLICATIONS

International Search Report dated Jul. 5, 2016 issued in corresponding International Application No. PCT/JP2016/060134.

(Continued)

*Primary Examiner* — Erich A Leeser

(74) *Attorney, Agent, or Firm* — Nath, Goldberg & Meyer; Joshua B. Goldberg; Scott H. Blackman

(57) ABSTRACT

The present invention provides a compound having an MAGL inhibitory action, which is expected to be useful as an agent for the prophylaxis or treatment of neurodegenerative diseases (e.g., Alzheimer's disease, Parkinson's disease, Huntington's disease, amyotrophic lateral sclerosis, traumatic brain injury, glaucoma, multiple sclerosis etc.), anxiety disorder, pains (e.g., inflammatory pain, cancerous pain, neurogenic pain etc.), epilepsy, depression and the like.

The present invention relates a compound represented by the formula (I):

(I)

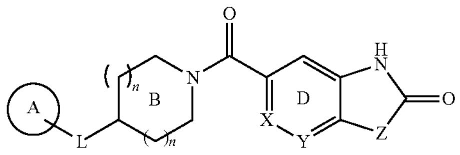

wherein each symbol is as described in the specification, or a salt thereof.

20 Claims, 2 Drawing Sheets

Specification includes a Sequence Listing.

(56) References Cited

FOREIGN PATENT DOCUMENTS

| | | | | |
|---|---|---|---|---|
| WO | WO 2011/058766 | * | 5/2011 | ........... A61K 31/445 |
| WO | 2012/030907 A1 | | 3/2012 | |
| WO | 2012/044613 A1 | | 4/2012 | |
| WO | 2012/054716 A1 | | 4/2012 | |
| WO | 2013/049289 A1 | | 4/2013 | |
| WO | 2013/049293 A1 | | 4/2013 | |
| WO | 2015/099196 A1 | | 7/2015 | |

OTHER PUBLICATIONS

Funk, "Prostaglandins and Leukotrienes: Advances in Eicosanoid Biology", Science, vol. 294, pp. 1871-1875, Nov. 2001.
Lue, et al., "Microglia Activation and Anti-inflammatory Regulation in Alzheimer's Disease", Mol. Neurobiol, vol. 41, pp. 115-128, 2010.
Yoshiyama, et al. "Synapse Loss and Microglial Activation Precede Tangles in a P301S Tauopathy Mouse Model", Neuron, vol. 53, pp. 337-351, Feb. 2007.
Perry, et al., "Microglia in neurodegenerative disease", Nature Reviews Neurology, vol. 6, pp. 193-201, Apr. 2010.
Dinh, et al., "A role for monoglyceride lipase in 2-arachidonoylglycerol inactivation", Chemistry and Physics of Lipids, vol. 121, pp. 149-158, 2002.
Piro, et al., "A Dysregulated Endocannabinoid-Eicosanoid Network Supports Pathogenesis in a Mouse Model of Alzheimer's Disease", Cell Reports, vol. 1, pp. 617-623, Jun. 2012.
Mechoulam, et al., "Identification of an Endogenous 2-Monoglyceride, Present in Canine Gut, that Binds to Cannabinoid Receptors", Biochemical Pharmacology, vol. 50, No. 1, pp. 83-90, 1995.
Devane, et al., "Determination and Characterization of a Cannabinoid Receptor in Rat Brain", Molecular Pharmacology, vol. 34, pp. 605-613, 1988.
Ashton, et al., "Expression of the cannabinoid CB2 receptor in the rat cerebellum: An immunohistochemical study", Neuroscience Letters, vol. 396, pp. 113-116, 2006.
Aso, et al., "CB1 Agonist ACEA Protects Neurons and Reduces the Cognitive Impairment of ABPP/PS1 Mice", Journal of Alzheimer's Disease, vol. 30, pp. 439-459, 2012.
Chen, et al., "Endocannabinoid 2-Arachidonoylglycerol Protects Neurons Against B-Amyloid Insults", Neuroscience, vol. 178, pp. 159-168, 2011.
Ouchi, et al., "Microglial Activation and Dopamine Terminal Loss in Early Parkinson's Disease", Annals of Neurology, vol. 57, pp. 168-175, 2005.
Nomura, et al., "Endocannabinoid Hydrolysis Generates Brain Prostaglandins That Promote Neuroinflammation", Science, vol. 334, pp. 809-813, Nov. 2011.
Turner, et al., "Evidence of widespread cerebral microglial activation in amyotrophic lateral sclerosis: an [11C](R)-PK11195 positron emission tomography study", Neurobiology Disease, vol. 15, pp. 601-609, 2004.
Kim, et al., "AM1241, a cannabinoid CB2 receptor selective compound, delays disease progression in a mouse model of amyotrophic lateral sclerosis", European Journal of Pharmacology, vol. 542, pp. 100-105, 2006.
Palazuelos, et al., "Microglial CB2 cannaboid receptors are neuroprotective in Huntington's disease excitotoxicity", Brain, vol. 132, pp. 3152-3164, 2009.
Lourbopoulos, et al., "Administration of 2-arachidonoylglycerol ameliorates both acute and chronic experimental autoimmune encephalomyelitis", Brain Research, vol. 1390, pp. 126-141, 2011.
Panikashvili, et al., "An endogenous cannabinoid (20AG) is neuroprotective after brain injury", Letters to Nature, vol. 413, pp. 527-531, Oct. 2001.
Njie, et al., "Aqueous humor outflow effects of 2-arachidonylglycerol", Experimental Eye Research, vol. 87, pp. 106-114, 2008.
Almeida-Santos, et al., "Modulation of anxiety-like behavior by the endocanabinoid 2-arachidonoylglycerol (2-AG) in the dorsolateral periaqueductal gray", Behavioral Brain Research, vol. 252, pp. 10-17, 2013.
Guindon, et al., "The antinociceptive effects of intraplantar injections of 2-arachidonoyl glycerol are mediated by cannabinoid CB2 receptors", British Journal of Pharmacology, vol. 150, pp. 693-701, 2007.
Khasabova, et al., "Increasing 2-arachidonoyl glycerol signaling in the periphery attenuates mechanical hyperalgesia in a model of bone cancer pain", Pharmacological Research, vol. 64, pp. 60-67, 2011.
Maroso, et al., "Toll-like receptor 4 and high-mobility group box-1 are involved in ictogenesis and can be targeted to reduce seizures", Nature Medicine, vol. 16, No. 4, pp. 413-419, Apr. 2010.
Naderi, et al., "Modulation of Anticonvulsant Effects of Cannabinoid Compounds by GABA—A Receptor Agonist in Acute Pentylenetetrazole Model of Seizure in Rat", Neurochem Res, vol. 36, pp. 1520-1525, 2011.
Zhong, et al., "Monoacylglycerol Lipase Inhibition Blocks Chronic Stress-Induced Depressive-Like Behaviors via Activation of mTOR Signaling", Neuropsychopharmacology, vol. 39, pp. 1763-1776, 2014.
Greco, et al., "Activation of CB2 receptors as a potential therapeutic target for migraine: evaluation in an animal model", The Journal of Headache and Pain, vol. 15, No. 14, pp. 1-8, 2014.
Joice, et al., "Modulation of blood-brain barrier permeability by neutrophils: in vitro and in vivo studies", Brain Research, vol. 1298, pp. 13-23, 2009.
Lara-Celador, et al., "Endocannabinoids reduce cerebral damage after hypoxic-ischemic injury in perinatal rats", Brain Research, vol. 1474, pp. 91-99, 2012.
SciFinder, CAS Registry No. 1625094-31-6.

* cited by examiner

HETEROCYCLIC COMPOUND

This is a National Phase Application filed under 35 U.S.C. 371 as a national stage of PCT/JP2016/060134, filed Mar. 29, 2016, an application claiming the benefit of Japanese Application No. 2015-067930, filed Mar. 30, 2015 and Japanese Application No. 2015-169733, filed Aug. 28, 2015, the content of each of which is hereby incorporated by reference in its entirety.

TECHNICAL FIELD

The present invention relates to a heterocyclic compound having a monoacylglycerol lipase (sometimes to be abbreviated as "MAGL" in the present specification) inhibitory action, a pharmaceutical composition containing same, and the like.

"The Sequence Listing submitted in text format (.txt) filed on Sep. 29, 2017, named "sequencelisting.txt", (created on Sep. 28, 2017, 6.43 MB), is incorporated herein by reference."

BACKGROUND OF THE INVENTION

Arachidonic acid (sometimes to be abbreviated as "AA" in the present specification), and eicosanoids, which are products in vivo, have been reported to cause inflammation in the central nervous system and peripheral [non-patent document 1: Science, vol. 294, pages 1871-1875, 2001]. An inhibitor that suppresses arachidonic acid production pathway, and eicosanoid production pathway is promising as a therapeutic drug for inflammatory diseases, and non-steroidal anti-inflammatory drugs such as cyclooxygenase inhibitor and the like have been used as therapeutic drugs for inflammatory pain. However, when a cyclooxygenase inhibitor is used for a long time, digestive tract disorders are sometimes developed as side effects, thus posing a problem. In addition, cardiovascular side effects such as myocardial infarction, cerebral infarction and the like also pose problems in recent years.

Neuroinflammation accompanied by activation of glial cells has been suggested to be a pathological change characteristic of neurodegenerative diseases (e.g., Alzheimer's disease etc.) [non-patent document 2: Molecular Neurobiology (Mol. Neurobiol), vol. 41, pages 115-128, 2010]. It has been reported that anti-inflammatory drugs suppress activation of glial cells and suppress neurodegenerative progression in an animal model of tau overexpression (human variant tau transgenic mouse etc.) which is a pathological characteristic of Alzheimer's disease [non-patent document 3: Neuron, vol. 53, pages 337-351, 2007]. In addition, the effectiveness of suppression of neuroinflammation for the treatment of neurodegenerative diseases such as Alzheimer's disease and the like has been suggested [non-patent document 4: Nature Reviews Neurology (Nat. Rev. Neurol.), vol. 6, pages 193-201, 2010], and a therapeutic drug that suppresses neuroinflammation is promising as a therapeutic or prophylactic drug for neurodegenerative diseases.

Monoacylglycerol lipase (MAGL) is an enzyme that hydrolyzes monoacylglycerol into fatty acid and glycerol. In the central nervous system, the substrate of MAGL is 2-arachidonoylglycerol (also referred to as 2-AG in the present specification) which is degraded to arachidonic acid and glycerol [non-patent document 5: Chemistry and Physics of Lipids (Chem phys Lipids) vol. 121, pages 149-158, 2002]. In recent years, suppression of production of arachidonic acid and eicosanoids, suppression of activation of glial cell, suppression of production of inflammatory cytokine, and a decreasing action on the accumulation of Aβ plaque which is a pathological finding of Alzheimer's disease have been reported in a crossbred animal of MAGL deficient mouse and amyloid R (to be also referred to as Aβ in the present specification) overexpressing animal model (APP/PS1 double transgenic mouse etc.) [non-patent document 6: Cell Report (Cell Rep.), vol. 1, pages 617-623, 2012], and inhibitors etc. that suppress the action of MAGL are promising as a therapeutic or prophylactic drug for Alzheimer's disease.

In addition, as receptors of 2-AG, which is a substrate of MAGL, cannabinoid receptor 1 (to be referred to as CB1 in the present specification), and cannabinoid receptor 2 (to be referred to as CB2 in the present specification) have been identified [non-patent document 7: Biochemical Pharmacology (Biochem. Pharmcol.) vol. 50, 83-90, 1995]. CB1 is mainly expressed in the brain region [non-patent document 8: Molecular Pharmacology (Mol. Pharmacol.), vol. 34, pages 605-613, 1988], and CB2 is expressed in immune cells, and microglial cell in the brain region [non-patent document 9: Neuroscience Letters (Neurosci. Lett.), vol. 396, pages 113-116, 2006]. In recent years, it has been reported that CB1 receptor agonist improves cognitive function [non-patent document 10: Journal of Alzheimer's Disease (J. Alzheimers. Dis.), vol. 30, pages 439-459, 2012], and 2-AG, which is the substrate of MAGL, shows a protective action against neuronal cell death due to Aβ [non-patent document 11: Neuroscience, vol. 178, pages 159-168, 2011]. Therefore, MAGL inhibitor that suppresses degradation of 2-AG is promising as a therapeutic or prophylactic drug that suppresses neuroinflammation, neuronal cell death, Aβ accumulation and the like observed in Alzheimer's disease and having effects on not only symptomatic relief but also disease-modification.

Parkinson's disease, which is one of the neurodegenerative diseases, is a disease associated with movement disorders caused by the degeneration of midbrain substantia nigra dopaminergic neurons, in which activation of glial cell has been reported [non-patent document 12: Annals of Neurology (Ann. Neurol.) vol. 57, pages 168-175, 2005]. While 1-methyl-4-phenyl-1,2,3,6-tetrahydropyridine(1-methyl-4-phenyl-1,2,3,6-tetrahydropyridine) is known to induce midbrain dopaminergic neuronal cell death in substantia nigra, it has been reported to show a protective action against neuronal cell death in MAGL deficient mice [non-patent document 13: Science, vol. 334, pages 809-813, 2011]. Therefore, inhibitors etc. that suppress the action of MAGL are promising as new therapeutic drugs for Parkinson's disease.

Amyotrophic lateral sclerosis (to be referred to as ALS in the present specification) is a disease associated with degeneration of motor neuron, and an effective treatment method does not exist at present. Activation of glial cell in ALS has been reported [non-patent document 14: Neurobiology of Disease (Neurobiol. Dis.) vol. 15, pages 601-609, 2004]. It has also been reported that activation of CB2 suppresses progression of the disease in mutant superoxide dismutase overexpressing mice as an animal model of ALS [non-patent document 15: European Journal of Pharmacology (Eur. J. Pharmacol.), vol. 542, pages 100-105, 2006]. In addition, it has been reported that MAGL deficient mice are less susceptible to neuoroinflammation due to decreased arachidonic acids, which is an in vivo product of MAGL [non-patent document 13: Science, vol. 334, pages 809-813, 2011]. Therefore, an MAGL inhibitor is promising as a new therapeutic drug for ALS.

Huntington's disease which is one of the neurodegenerative diseases is a disease wherein a neurological function is lost by neuronal cell death and neuroinflammation due to polyglutamine aggregation. It has been reported that activation of CB2 suppresses neuroinflammation and shows a neuroprotective action in R6/2 mice as an animal model of Huntington's disease [non-patent document 16: Brain, vol. 132, pages 3152-3164, 2009]. In addition, it has been reported that MAGL deficient mice are less susceptible to neuoroinflammation due to decreased arachidonic acids, which is a product of MAGL [non-patent document 13: Science, vol. 334, pages 809-813, 2011]. Therefore, an MAGL inhibitor is promising as a new therapeutic drug for Huntington's disease.

2-AG, which is a substrate of MAGL, has been reported to suppress progression of the disease state in an autoimmune encephalomyelitis model, i.e., an animal model of multiple sclerosis which is one of the central demyelination diseases [non-patent document 17: Brain Research (Brain Res.), vol. 1390, pages 126-141, 2011]. In addition, it has been reported that MAGL deficient mice are less susceptible to neuoroinflammation due to decreased arachidonic acids, which is a product of MAGL [non-patent document 13: Science, vol. 334, pages 809-813, 2011]. Therefore, an MAGL inhibitor is promising as a new therapeutic drug for multiple sclerosis.

Traumatic brain injury (TBI) is a condition exerting an extremely harmful influence on the health of individuals, and an effective treatment method does not exist at present. 2-AG, which is a substrate of MAGL, has been reported to have a protective action against neuronal cell death in a closed head injury animal model [non-patent document 18: Nature, vol. 413, pages 527-531, 2001]. Therefore, an MAGL inhibitor is promising as a new therapeutic or prophylactic drug for traumatic brain injury.

Glaucoma most often causes loss of eyesight, and is considered a serious social problem. 2-AG, which is a substrate of MAGL, has been reported to activate aqueous outflow in an intraocular perfusion model [non-patent document 19: Experimental Eye Research (Exp. Eye Res.), vol. 87, pages 106-114, 2008]. Therefore, an MAGL inhibitor is promising as a new therapeutic or prophylactic drug for glaucoma.

Anxiety disorder is a mental disease that occurs highly frequently, and greatly influences the quality of life. 2-AG, which is a substrate of MAGL, has been reported to show an anti-anxiety action in an elevated plus maze test, which is an effective test system of anxiety disorder [non-patent document 20: Behavioural Brain Research (Behav. Brain Res.), vol. 252, pages 10-17, 2013]. Therefore, an MAGL inhibitor is promising as a new therapeutic drug for anxiety disorders.

2-AG, which is a substrate of MAGL, has been reported to show an antinociceptive effect in a formalin test [non-patent document 21: British Journal of Pharmacology, vol. 150, pages 693-701, 2007]. In addition, 2-AG has been reported to show effects in a mechanical hyperalgesia test which is a carcinomatous pain model [non-patent document 22: Pharmacological Research (Pharmacol. Res.), vol. 64, pages 60-67, 2011]. Therefore, an MAGL inhibitor is promising as a new therapeutic drug for inflammatory pain and neuropathic pain.

Epilepsy greatly influences daily life. It is known that neuroinflammation has been induced in the hippocampus of temporal lobe epilepsy patients, and neuroinflammation accompanied by activation of glial cells is involved in convulsive seizure [non-patent document 23: Nature Medicine (Nature Med.), vol. 16, pages 413-419, 2010]. 2-AG, which is a substrate of MAGL, has a suppressive action on pentylenetetrazole-induced convulsive attack, which is an acute convulsion model [non-patent document 24: Neurochemical Research (Neurochem. Res.), vol. 36, pages 1520-1525, 2011]. Therefore, an MAGL inhibitor is promising as a new therapeutic drug for epilepsy.

Depression is a disease that occurs highly frequently in the modern society, and greatly influences the quality of life. 2-AG, which is a substrate of MAGL, has been reported to show an anti-depression action on chronical stress model which is an effective test system of depression [non-patent document 25: Neuropsychopharmacology, vol. 39, pages 1763-1776, 2014]. Therefore, an MAGL inhibitor is promising as a new therapeutic drug for depression.

Migraine is a disease that occurs highly frequently in the modern society, and greatly influences the quality of life. One of the factors that develop migraine is neuroinflammation. Activation of CB2 has been reported to have an analgesic action in nitroglycerin-administered rat, which is an effective test system of migraine [non-patent document 26: Journal of Headache and Pain, vol. 15, No. 14, 2014]. Therefore, an MAGL inhibitor is promising as a new therapeutic drug for migraine.

Cerebral edema is a disease developed in association with various encephalopathies. One of the causes of cerebral edema is collapse of blood-brain barrier. Arachidonic acid and eicosanoids are known to collapse blood-brain barrier [non-patent document 27: Brain Research, vol. 1298, pages 13-23, 2009]. An inhibitor that suppresses the action of MAGL decreases production of arachidonic acid by MAGL. Therefore, an MAGL inhibitor is promising as a new therapeutic drug for cerebral edema.

Cerebral ischemia is one factor causing the onset of cerebral infarction. 2-AG, which is a substrate of MAGL, has been reported to have a brain protective action in a test system for cerebral ischemia [non-patent document 28: Brain Research, vol. 1474, pages 91-99, 2012]. Therefore, an MAGL inhibitor is promising as a new therapeutic drug for cerebral ischemia.

As the heterocyclic compound, the following compounds are known. Patent Document 1 describes that a compound represented by the following formula (I):

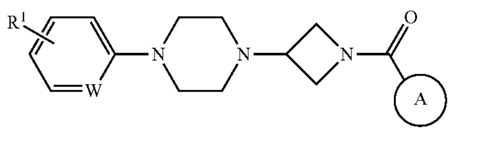

(I)

wherein each symbol is as defined in patent document 1, is an MAGL inhibitor and useful for the treatment of pain and the like.

Patent Document 2 describes that a compound represented by the following formula (I):

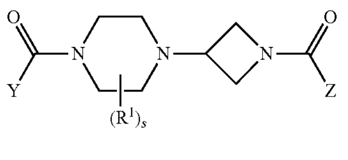

(I)

wherein each symbol is as defined in patent document 2, is an MAGL inhibitor and useful for the treatment of pain and the like.

Patent Document 3 describes that a compound represented by the following formula (I):

(I)

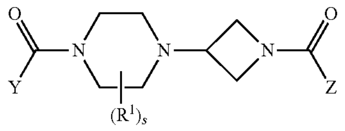

wherein each symbol is as defined in patent document 3, is an MAGL inhibitor and useful for the treatment of pain and the like.

Patent Document 4 describes that a compound represented by the following formula (I):

(I)

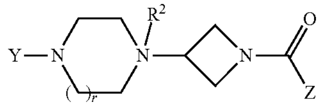

wherein each symbol is as defined in patent document 4, is an MAGL inhibitor and useful for the treatment of pain and the like.

Patent Document 5 describes that a compound represented by the following formula:

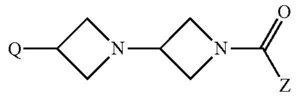

wherein each symbol is as defined in patent document 5, is useful as an MAGL inhibitor.

Patent Document 6 describes that compounds represented by the following formula:

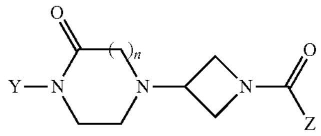

wherein each symbol is as defined in patent document 6, and the following formula:

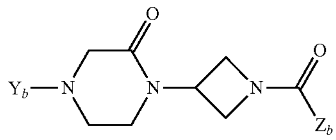

wherein each symbol is as defined in patent document 6, are useful as an MAGL inhibitor.

Patent Document 7 describes that a compound represented by the following formula:

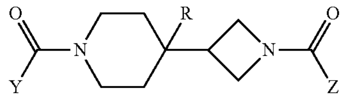

wherein each symbol is as defined in patent document 7, is useful as an MAGL inhibitor.

Patent Document 8 describes that a compound represented by the following formula (I):

(I)

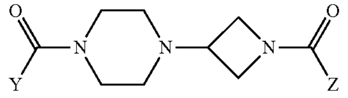

wherein each symbol is as defined in patent document 8, is an MAGL inhibitor and useful for the treatment, improvement or prophylaxis of metabolic disease (obesity, diabetes).

Patent Document 9 describes that a compound represented by the following formula (I):

(I)

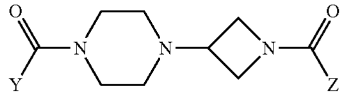

wherein each symbol is as defined in patent document 9, is an MAGL inhibitor and useful for the treatment, improvement or prophylaxis of metabolic disease (obesity, diabetes).

Patent Document 10 describes that a compound represented by the following formula (1):

(1)

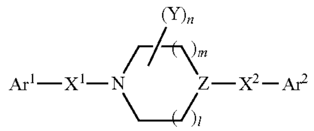

wherein each symbol is as defined in patent document 10, is a p-38α kinase inhibitor and useful for the treatment of inflammation or heart disease.

Patent Document 11 describes that a compound represented by the following formula:

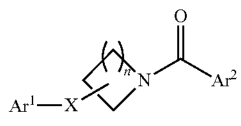

wherein each symbol is as defined in patent document 11, is a TTX-S channel blocker.

Patent Document 12 describes that a compound represented by the following formula:

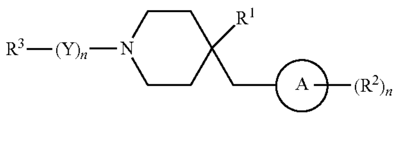

wherein each symbol is as defined in patent document 12, is an CCR5 antagonist and useful for the treatment of HIV infection.

Patent Document 13 describes that a compound represented by the following formula:

(I)

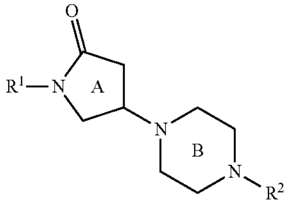

wherein each symbol is as defined in patent document 13, is an MAGL inhibitor and useful for the treatment, improvement or prophylaxis of neurodegenerative disease, anxiety disorder, pain or epilepsy.

In addition, a compound represented by the following formula:

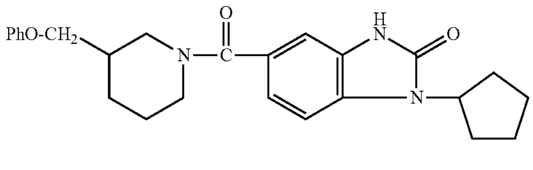

(CAS registry number: 1625094-31-6) is known.

DOCUMENT LIST

Patent Document

Patent Document 1: WO 2010/124122
Patent Document 2: WO 2010/124082
Patent Document 3: WO 2010/124086
Patent Document 4: WO 2010/124121
Patent Document 5: WO 2012/030907
Patent Document 6: WO 2012/044613
Patent Document 7: WO 2012/054716
Patent Document 8: WO 2013/049289
Patent Document 9: WO 2013/049293
Patent Document 10: WO 01/64676
Patent Document 11: WO 2011/058766
Patent Document 12: WO 2004/054974
Patent Document 13: WO 2015/099196

Non-Patent Document

Non-Patent document 1: Science, vol. 294, pages 1871-1875, 2001
Non-Patent document 2: Molecular Neurobiology (Mol. Neurobiol), vol. 41, pages 115-128, 2010
Non-Patent document 3: Neuron, vol. 53, pages 337-351, 2007
Non-Patent document 4: Nature Reviews Neurology (Nat. Rev. Neurol.), vol. 6, pages 193-201, 2010
Non-Patent document 5: Chemistry and Physics of Lipids (Chem phys Lipids) vol. 121, pages 149-158, 2002
Non-Patent document 6: Cell Report (Cell Rep.), vol. 1, page 617-623, 2012
Non-Patent document 7: Biochemical Pharmacology (Biochem. Pharmcol.) vol. 50, 83-90, 1995
Non-Patent document 8: Molecular Pharmacology (Mol. Pharmacol.), vol. 34, pages 605-613, 1988
Non-Patent document 9: Neuroscience Letters (Neurosci. Lett.), vol. 396, pages 113-116, 2006
Non-Patent document 10: Journal of Alzheimer's Disease (J. Alzheimers. Dis.), vol. 30, pages 439-459, 2012
Non-Patent document 11: Neuroscience, vol. 178, pages 159-168, 2011
Non-Patent document 12: Annals of Neurology (Ann. Neurol.) vol. 57, pages 168-175, 2005
Non-Patent document 13: Science, vol. 334, pages 809-813, 2011
Non-Patent document 14: Neurobiology of Disease (Neurobiol. Dis.) vol. 15, pages 601-609, 2004
Non-Patent document 15: European Journal of Pharmacology (Eur. J. Pharmacol.), vol. 542, pages 100-105, 2006
Non-Patent document 16: Brain, vol. 132, pages 3152-3164, 2009
Non-Patent document 17: Brain Research (Brain Res.), vol. 1390, pages 126-141, 2011
Non-Patent document 18: Nature, vol. 413, pages 527-531, 2001
Non-Patent document 19: Experimental Eye Research (Exp. Eye Res.), vol. 87, pages 106-114, 2008
Non-Patent document 20: Behavioural Brain Research (Behay. Brain Res.), vol. 252, pages 10-17, 2013
Non-Patent document 21: British Journal of Pharmacology, vol. 150, pages 693-701, 2007
Non-Patent document 22: Pharmacological Research (Pharmacol. Res.), vol. 64, pages 60-67, 2011
Non-Patent document 23: Nature Medicine (Nature Med.), vol. 16, pages 413-419, 2010
Non-Patent document 24: Neurochemical Research (Neurochem. Res.), vol. 36, pages 1520-1525, 2011
Non-Patent document 25: Neuropsychopharmacology, vol. 39, pages 1763-1776, 2014
Non-Patent document 26: Journal of Headache and Pain, vol. 15, No. 14, 2014
Non-Patent document 27: Brain Research, vol. 1298, pages 13-23, 2009
Non-Patent document 28: Brain Research, vol. 1474, pages 91-99, 2012

SUMMARY OF THE INVENTION

Problems to be Solved by the Invention

An object of the present invention is to provide a compound having an MAGL inhibitory action, which is expected to be useful as an agent for the prophylaxis or treatment of neurodegenerative diseases (e.g., Alzheimer's disease, Parkinson's disease, Huntington's disease, amyotrophic lateral sclerosis, traumatic brain injury, glaucoma, multiple sclerosis etc.), anxiety disorder, pains (e.g., inflammatory pain, cancerous pain, neurogenic pain etc.), epilepsy, depression and the like.

Means of Solving the Problems

The present inventors have conducted intensive studies in an attempt to solve the above-mentioned problems and found that a compound represented by the following formula (I) has an MAGL inhibitory action, and therefore, is expected to be useful as an agent for the prophylaxis or treatment of neurodegenerative diseases (e.g., Alzheimer's disease, Parkinson's disease, Huntington's disease, amyotrophic lateral sclerosis, traumatic brain injury, glaucoma, multiple sclerosis etc.), anxiety disorder, pains (e.g., inflammatory pain, cancerous pain, neurogenic pain etc.), epilepsy, depression and the like, which resulted in the completion of the present invention.

Accordingly, the present invention provides the following.

[1] A compound represented by the formula (I):

(I)

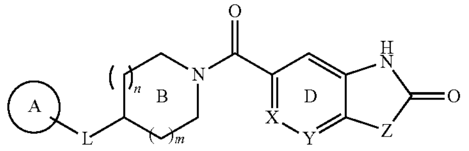

wherein m and n are each independently 0 or 1,

Ring A is an optionally further substituted cyclic group,

Ring B is an azetidine ring, a pyrrolidine ring or a piperidine ring, each of which is an optionally further substituted, Ring D is an optionally further substituted 6-membered aromatic ring, L is —$CH_2$—O—$CH_2$—, —O—$CR^1R^2$—, —CH($R^1$)—O—, —$CF_2$—$CH_2$—, —$CH_2$—$CF_2$— or —$CF_2$—, $R^1$ and $R^2$ is each independently a hydrogen atom, or an optionally substituted $C_{1-6}$ alkyl group, X and Y are each independently a carbon atom or a nitrogen atom, Z is —O—$CH_2$—, —NR—$CH_2$—, —$CH_2$—$CH_2$—, —CH═CH—, —$CH_2$—, —O—, —S— or —NR—, and R is a substituent, provided that 7-((4-(phenoxymethyl)piperidin-1-yl)carbonyl)-1H-pyrido[2,3-b][1,4]oxazin-2(3H)-one, 7-((4-((3-methoxyphenoxy)methyl)piperidin-1-yl)carbonyl)-1H-pyrido[2,3-b][1,4]oxazin-2(3H)-one, and 7-((4-((2-methoxyphenoxy)methyl)piperidin-1-yl)carbonyl)-1H-pyrido[2,3-b][1,4]oxazin-2(3H)-one are excluded, or a salt thereof (hereinafter sometimes to be referred to as compound (I)).

[2] A compound represented by the formula (I):

(I)

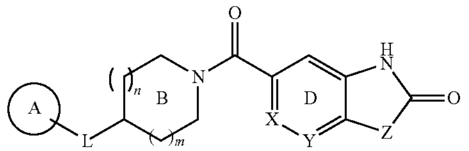

wherein m and n are each independently 0 or 1,

Ring A is an optionally further substituted cyclic group,

Ring B is an azetidine ring, a pyrrolidine ring or a piperidine ring, each of which is an optionally further substituted, Ring D is an optionally further substituted 6-membered aromatic ring, L is —$CH_2$—O—$CH_2$— or —O—$CH_2$—, X and Y are each independently a carbon atom or a nitrogen atom, Z is —O—$CH_2$—, —NR—$CH_2$—, —$CH_2$—$CH_2$—, —CH═CH—, —$CH_2$—, —O—, —S— or —NR—, and R is a substituent, provided that 7-((4-(phenoxymethyl)piperidin-1-yl)carbonyl)-1H-pyrido[2,3-b][1,4]oxazin-2(3H)-one, 7-((4-((3-methoxyphenoxy)methyl)piperidin-1-yl) carbonyl)-1H-pyrido[2,3-b][1,4]oxazin-2(3H)-one, and 7-((4-((2-methoxyphenoxy)methyl)piperidin-1-yl)carbonyl)-1H-pyrido[2,3-b][1,4]oxazin-2(3H)-one are excluded, or a salt thereof.

[3] The compound or salt of the above-mentioned [1] or [2], wherein Ring B is an optionally further substituted azetidine ring, or an optionally further substituted piperidine ring.

[4] The compound or salt of any of the above-mentioned [1] to [3], wherein Ring B is an optionally further substituted azetidine ring.

[4A] The compound or salt of any of the above-mentioned [1] to [4], wherein Ring B is an azetidine ring.

[5] The compound or salt of any of the above-mentioned [1] to [4] and [4A], wherein X and Y are both carbon atoms.

[6] The compound or salt of any of the above-mentioned [1] to [4], [4A] and [5], wherein Z is —O—$CH_2$— or —O—.

[6A] The compound or salt of any of the above-mentioned [1] to [4], [4A], [5] and [6], wherein Z is —O—$CH_2$—.

[7] The compound or salt of any of the above-mentioned [1], [3], [4], [4A], [5], [6] and [6A], wherein L is —O—$CH_2$— or —$CH_2$—O—.

[8] The compound or salt of any of the above-mentioned [1] to [4], [4A], [5], [6], [6A] and [7], wherein Ring A is (1) a $C_{6-14}$ aryl group which is optionally further substituted and optionally fused with a $C_{3-10}$ cycloalkane, (2) an optionally further substituted pyridyl group, (3) an optionally further substituted pyrimidinyl group, (4) an optionally further substituted imidazopyridyl group, (5) an optionally further substituted benzothiazolyl group, (6) an optionally further substituted indazolyl group, (7) an optionally further substituted pyrazolyl group, (8) an optionally further substituted benzoxazolyl group, (9) an optionally further substituted benzisoxazolyl group,

(10) an optionally further substituted quinoxalinyl group,

(11) an optionally further substituted quinolyl group,

(12) an optionally further substituted isoquinolyl group,

(13) an optionally further substituted pyrazolopyridyl group,

(14) an optionally further substituted $C_{3-10}$ cycloalkyl group,

(15) an optionally further substituted tetrahydropyranyl group,

(16) an optionally further substituted dihydrobenzofuryl group, or

(17) an optionally further substituted dihydropyranopyridyl group.

[9] The compound or salt of any of the above-mentioned [1] to [4], [4A], [5], [6], [6A], [7] and [8], wherein m and n are each independently 0 or 1;

Ring A is (1) a $C_{6-14}$ aryl group which is optionally fused with a $C_{3-10}$ cycloalkane wherein the $C_{6-14}$ aryl group is optionally further substituted by 1 to 3 substituents selected from (i) a halogen atom, (ii) an optionally halogenated $C_{1-6}$ alkoxy group, (iii) a cyano group, (iv) a $C_{1-6}$ alkyl group optionally substituted by 1 to 3 substituents selected from (a) a halogen atom, and
(b) a hydroxy group,
(v) a $C_{3-10}$ cycloalkyl group,
(vi) a $C_{2-6}$ alkenyl group,
(vii) a $C_{1-6}$ alkoxy-carbonyl group,
(viii) a $C_{1-6}$ alkylsulfonyl group,
(ix) a $C_{6-14}$ aryl group optionally substituted by 1 to 3 $C_{1-6}$ alkoxy groups,
(x) a $C_{6-14}$ aryloxy group,
(xi) a 5- to 14-membered aromatic heterocyclic group optionally substituted by 1 to 3 substituents selected from
(a) a halogen atom,
(b) a $C_{1-6}$ alkyl group optionally substituted by 1 to 3 halogen atoms, and
(c) a $C_{3-10}$ cycloalkyl group, and
(xii) a 3- to 14-membered non-aromatic heterocyclic group optionally substituted by 1 to 3 substituents selected from
(a) a $C_{1-6}$ alkyl group, and
(b) a halogen atom,
(2) a 5- to 14-membered aromatic heterocyclic group optionally further substituted by 1 to 3 substituents selected from
(i) a halogen atom,
(ii) a $C_{1-6}$ alkyl group,
(iii) an amino group,
(iv) a $C_{1-6}$ alkyl-carbonyl group,
(v) a $C_{6-14}$ aryl group optionally substituted by 1 to 3 halogen atoms, and
(vi) a 5- to 14-membered aromatic heterocyclic group optionally substituted by 1 to 3 $C_{1-6}$ alkyl groups,
(3) a $C_{3-10}$ cycloalkyl group optionally further substituted by 1 to 3 halogen atoms, or
(4) a 3- to 14-membered non-aromatic heterocyclic group optionally further substituted by 1 to 3 $C_{1-6}$ alkyl groups;
Ring B is
(1) an azetidine ring optionally further substituted by 1 to 3 substituents selected from
(i) a halogen atom, and
(ii) a $C_{1-6}$ alkyl group,
(2) a pyrrolidine ring, or
(3) a piperidine ring optionally further substituted by 1 to 3 substituents selected from
(i) a halogen atom,
(ii) a hydroxy group, and
(iii) a cyano group;
Ring D is
(1) a benzene ring optionally further substituted by 1 to 3 substituents selected from
(i) a halogen atom,
(ii) a $C_{1-6}$ alkyl group, and
(iii) a $C_{1-6}$ alkoxy group, or
(2) a pyridine ring optionally further substituted by 1 to 3 $C_{1-6}$ alkyl groups;
L is
(1) $—CH_2—O—CH_2—$,
(2) $—O—CR^1R^2—$ wherein $R^1$ and $R^2$ is each independently
(1) a hydrogen atom, or
(2) a $C_{1-6}$ alkyl group optionally substituted by one substituent selected from a hydroxy group and a $C_{1-6}$ alkoxy group,
(3) $—CH(R^1)—O—$ wherein $R^1$ is a hydrogen atom or a $C_{1-6}$ alkyl group,
(4) $—CF_2—CH_2—$, or
(5) $—CF_2—$;
X is a carbon atom or a nitrogen atom;
Y is a carbon atom or a nitrogen atom; and
Z is $—O—CH_2—$, $—CH_2—CH_2—$, $—CH{=}CH—$, $—CH_2—$ or $—O—$.

[9A] The compound or salt of any of the above-mentioned [1] to [4], [4A], [5], [6], [6A], [7], [8] and [9], wherein X and Y are both carbon atoms.

[9B] The compound or salt of any of the above-mentioned [1] to [4], [4A], [5], [6], [6A], [7], [8], [9] and [9A], wherein m and n are each independently 0 or 1;
Ring A is
(1) a phenyl group optionally further substituted by 1 to 3 substituents selected from
(i) a halogen atom,
(ii) an optionally halogenated $C_{1-6}$ alkoxy group,
(iii) a cyano group,
(iv) a $C_{1-6}$ alkyl group optionally substituted by 1 to 3 substituents selected from
(a) a halogen atom, and
(b) a hydroxy group,
(v) a $C_{3-10}$ cycloalkyl group,
(vi) a $C_{2-6}$ alkenyl group,
(vii) a $C_{1-6}$ alkoxy-carbonyl group,
(viii) a $C_{1-6}$ alkylsulfonyl group,
(ix) a phenyl group optionally substituted by 1 to 3 $C_{1-6}$ alkoxy groups,
(x) a phenoxy group,
(xi) a pyridyl group optionally substituted by 1 to 3 substituents selected from
(a) a halogen atom, and
(b) a $C_{1-6}$ alkyl group optionally substituted by 1 to 3 halogen atoms,
(xii) a pyrazolyl group optionally substituted by 1 to 3 substituents selected from
(a) a $C_{1-6}$ alkyl group optionally substituted by 1 to 3 halogen atoms, and
(b) a $C_{3-10}$ cycloalkyl group,
(xiii) a pyrrolyl group optionally substituted by 1 to 3 $C_{1-6}$ alkyl groups,
(xiv) a pyrimidinyl group optionally substituted by 1 to 3 $C_{1-6}$ alkyl groups optionally substituted by 1 to 3 halogen atoms,
(xv) a thiazolyl group optionally substituted by 1 to 3 $C_{1-6}$ alkyl groups,
(xvi) an oxadiazolyl group,
(xvii) a dihydropyranyl group,
(xviii) a dihydrobenzofuryl group,
(xix) a tetrahydropyridyl group optionally substituted by 1 to 3 $C_{1-6}$ alkyl groups, and
(xx) an azetidinyl group optionally substituted by 1 to 3 halogen atoms,
(2) a naphthyl group,
(3) an indanyl group,
(4) a tetrahydronaphthyl group optionally further substituted by 1 to 3 halogen atoms,
(5) a pyridyl group optionally further substituted by 1 to 3 substituents selected from
(i) a halogen atom,
(ii) a $C_{1-6}$ alkyl group,
(iii) an amino group, and
(iv) a pyridyl group optionally substituted by 1 to 3 $C_{1-6}$ alkyl groups,
(6) a pyrimidinyl group,
(7) an imidazopyridyl group optionally further substituted by 1 to 3 phenyl groups optionally substituted by 1 to 3 halogen atoms,
(8) a benzothiazolyl group optionally further substituted by 1 to 3 $C_{1-6}$ alkyl groups, (9) an indazolyl group optionally further substituted by 1 to 3 $C_{1-6}$ alkyl-carbonyl groups,
(10) a pyrazolyl group optionally further substituted by 1 to 3 substituents selected from
(i) a $C_{1-6}$ alkyl group, and
(ii) a pyridyl group,
(11) a benzoxazolyl group optionally further substituted by 1 to 3 $C_{1-6}$ alkyl groups,
(12) a benzisoxazolyl group optionally further substituted by 1 to 3 halogen atoms,
(13) a quinoxalinyl group,
(14) a quinolyl group,
(15) an isoquinolyl group,
(16) a pyrazolopyridyl group optionally further substituted by 1 to 3 phenyl groups,
(17) a $C_{3-10}$ cycloalkyl group optionally further substituted by 1 to 3 halogen atoms,
(18) a tetrahydropyranyl group,
(19) a dihydrobenzofuryl group optionally further substituted by 1 to 3 $C_{1-6}$ alkyl groups, or
(20) a dihydropyranopyridyl group;
Ring B is
(1) an azetidine ring optionally further substituted by 1 to 3 substituents selected from
(i) a halogen atom, and
(ii) a $C_{1-6}$ alkyl group,
(2) a pyrrolidine ring, or
(3) a piperidine ring optionally further substituted by 1 to 3 substituents selected from
(i) a halogen atom,
(ii) a hydroxy group, and
(iii) a cyano group;
Ring D is
(1) a benzene ring optionally further substituted by 1 to 3 substituents selected from
(i) a halogen atom,
(ii) a $C_{1-6}$ alkyl group, and
(iii) a $C_{1-6}$ alkoxy group, or
(2) a pyridine ring optionally further substituted by 1 to 3 $C_{1-6}$ alkyl groups;
L is
(1) —$CH_2$—O—$CH_2$—,
(2) —O—$CR^1R^2$— wherein $R^1$ and $R^2$ is each independently (1) a hydrogen atom, or (2) a $C_{1-6}$ alkyl group optionally substituted by one substituent selected from a hydroxy group and a $C_{1-6}$ alkoxy group,
(3) —CH($R^1$)—O— wherein $R^1$ is a hydrogen atom or a $C_{1-6}$ alkyl group,
(4) —$CF_2$—$CH_2$—, or
(5) —$CF_2$—;
X is a carbon atom or a nitrogen atom;
Y is a carbon atom or a nitrogen atom; and
Z is —O—$CH_2$—, —$CH_2$—$CH_2$—, —CH═CH—, —$CH_2$— or —O—.
[9C] The compound or salt of any of the above-mentioned [1] to [4], [4A], [5], [6], [6A], [7], [8], [9], [9A] and [9B], wherein
m and n are both 0 or both 1;
Ring A is
(1) a phenyl group optionally further substituted by 1 to 3 substituents selected from
(i) a halogen atom,
(ii) an optionally halogenated $C_{1-6}$ alkoxy group,
(iii) a cyano group,
(iv) a $C_{1-6}$ alkyl group optionally substituted by 1 to 3 substituents selected from
(a) a halogen atom, and
(b) a hydroxy group,
(v) a $C_{3-10}$ cycloalkyl group,
(vi) a $C_{2-6}$ alkenyl group,
(vii) a $C_{1-6}$ alkoxy-carbonyl group,
(viii) a $C_{1-6}$ alkylsulfonyl group,
(ix) a phenyl group optionally substituted by 1 to 3 $C_{1-6}$ alkoxy groups,
(x) a phenoxy group,
(xi) a pyridyl group optionally substituted by 1 to 3 substituents selected from
(a) a halogen atom, and
(b) a $C_{1-6}$ alkyl group optionally substituted by 1 to 3 halogen atoms,
(xii) a pyrazolyl group optionally substituted by 1 to 3 substituents selected from
(a) a $C_{1-6}$ alkyl group optionally substituted by 1 to 3 halogen atoms, and
(b) a $C_{3-10}$ cycloalkyl group,
(xiii) a pyrrolyl group optionally substituted by 1 to 3 $C_{1-6}$ alkyl groups,
(xiv) a pyrimidinyl group optionally substituted by 1 to 3 $C_{1-6}$ alkyl groups optionally substituted by 1 to 3 halogen atoms,
(xv) a thiazolyl group optionally substituted by 1 to 3 $C_{1-6}$ alkyl groups,
(xvi) an oxadiazolyl group,
(xvii) a dihydropyranyl group,
(xviii) a dihydrobenzofuryl group,
(xix) a tetrahydropyridyl group optionally substituted by 1 to 3 $C_{1-6}$ alkyl groups, and
(xx) an azetidinyl group optionally substituted by 1 to 3 halogen atoms,
(2) a naphthyl group,
(3) an indanyl group,
(4) a tetrahydronaphthyl group optionally further substituted by 1 to 3 halogen atoms,
(5) a pyridyl group optionally further substituted by 1 to 3 substituents selected from
(i) a halogen atom,
(ii) a $C_{1-6}$ alkyl group, and
(iii) a pyridyl group optionally substituted by 1 to 3 $C_{1-6}$ alkyl groups,
(6) an imidazopyridyl group optionally further substituted by 1 to 3 phenyl groups optionally substituted by 1 to 3 halogen atoms,
(7) a benzothiazolyl group optionally further substituted by 1 to 3 $C_{1-6}$ alkyl groups,
(8) an indazolyl group optionally further substituted by 1 to 3 $C_{1-6}$ alkyl-carbonyl groups,
(9) a pyrazolyl group optionally further substituted by 1 to 3 substituents selected from
(i) a $C_{1-6}$ alkyl group, and
(ii) a pyridyl group,
(10) a benzoxazolyl group optionally further substituted by 1 to 3 $C_{1-6}$ alkyl groups,
(11) a benzisoxazolyl group optionally further substituted by 1 to 3 halogen atoms,
(12) a quinoxalinyl group,
(13) a quinolyl group,
(14) an isoquinolyl group,
(15) a pyrazolopyridyl group optionally further substituted by 1 to 3 phenyl groups,
(16) a $C_{3-10}$ cycloalkyl group optionally further substituted by 1 to 3 halogen atoms,
(17) a tetrahydropyranyl group,

(18) a dihydrobenzofuryl group optionally further substituted by 1 to 3 $C_{1-6}$ alkyl groups, or
(19) a dihydropyranopyridyl group;
Ring B is
(1) an azetidine ring optionally further substituted by 1 to 3 substituents selected from
(i) a halogen atom, and
(ii) a $C_{1-6}$ alkyl group, or
(2) a piperidine ring optionally further substituted by 1 to 3 substituents selected from
(i) a halogen atom,
(ii) a hydroxy group, and
(iii) a cyano group;
Ring D is
(1) a benzene ring optionally further substituted by 1 to 3 substituents selected from
(i) a halogen atom,
(ii) a $C_{1-6}$ alkyl group, and
(iii) a $C_{1-6}$ alkoxy group, or
(2) a pyridine ring optionally further substituted by 1 to 3 $C_{1-6}$ alkyl groups;
L is
(1) $—CH_2—O—CH_2—$,
(2) $—O—CR^1R^2—$ wherein $R^1$ and $R^2$ is each independently (1) a hydrogen atom, or (2) a $C_{1-6}$ alkyl group optionally substituted by one $C_{1-6}$ alkoxy group,
(3) $—CH(R^1)—O—$ wherein $R^1$ is a hydrogen atom or a $C_{1-6}$ alkyl group,
(4) $—CF_2—CH_2—$, or
(5) $—CF_2—$;
X is a carbon atom or a nitrogen atom;
Y is a carbon atom or a nitrogen atom; and
Z is $—O—CH_2—$, $—CH{=}CH—$, $—CH_2—$ or $—O—$.
[10] The compound or salt of any of the above-mentioned [1] to [4], [4A], [5], [6], [6A], [7], [8], [9], [9A], [9B] and [9C],
wherein
m and n are both 0 or both 1;
Ring A is
(1) a phenyl group further substituted by 1 to 3 substituents selected from
(i) a halogen atom,
(ii) a cyano group,
(iii) an optionally halogenated $C_{1-6}$ alkyl group,
(iv) a $C_{2-6}$ alkenyl group,
(v) a pyridyl group optionally substituted by 1 to 3 substituents selected from
(a) a halogen atom, and
(b) a $C_{1-6}$ alkyl group, and
(vi) an azetidinyl group optionally substituted by 1 to 3 halogen atoms,
(2) an indanyl group,
(3) a tetrahydronaphthyl group, or
(4) a pyridyl group optionally further substituted by 1 to 3 halogen atoms;
Ring B is
(1) an azetidine ring, or
(2) a piperidine ring optionally further substituted by 1 to 3 hydroxy groups;
Ring D is
(1) a benzene ring optionally further substituted by 1 to 3 substituents selected from
(i) a halogen atom,
(ii) a $C_{1-6}$ alkyl group, and
(iii) a $C_{1-6}$ alkoxy group, or
(2) a pyridine ring;
L is $—O—CH_2—$ or $—CH_2—O—$;
X is a carbon atom;
Y is a carbon atom or a nitrogen atom; and
Z is $—O—CH_2—$ or $—O—$.
[10A] The compound or salt of any of the above-mentioned [1] to [4], [4A], [5], [6], [6A], [7], [8], [9], [9A], [9B], [9C] and [10], wherein
m and n are both 0 or both 1;
Ring A is
(1) a phenyl group further substituted by 1 to 3 substituents selected from
(i) a halogen atom,
(ii) a cyano group,
(iii) an optionally halogenated $C_{1-6}$ alkyl group,
(iv) a $C_{2-6}$ alkenyl group, and
(v) an azetidinyl group optionally substituted by 1 to 3 halogen atoms,
(2) an indanyl group,
(3) a tetrahydronaphthyl group, or
(4) a pyridyl group optionally further substituted by 1 to 3 halogen atoms;
Ring B is
(1) an azetidine ring, or
(2) a piperidine ring optionally further substituted by 1 to 3 hydroxy groups;
Ring D is
(1) a benzene ring optionally further substituted by 1 to 3 substituents selected from
(i) a halogen atom
(ii) a $C_{1-6}$ alkyl group, and
(iii) a $C_{1-6}$ alkoxy group, or
(2) a pyridine ring;
L is $—O—CH_2—$ or $—CH_2—O—$;
X is a carbon atom;
Y is a carbon atom or a nitrogen atom; and
Z is $—O—CH_2—$ or $—O—$.
[11] The compound or salt of any of the above-mentioned [1] to [4], [4A], [5], [6], [6A], [7], [8], [9], [9A], [9B], [9C], [10] and [10A], wherein
m and n are both 0 or both 1;
Ring A is
(1) a phenyl group further substituted by 1 to 3 substituents selected from
(i) a halogen atom,
(ii) a cyano group,
(iii) an optionally halogenated $C_{1-6}$ alkyl group,
(iv) a pyridyl group optionally substituted by 1 to 3 substituents selected from
(a) a halogen atom, and
(b) a $C_{1-6}$ alkyl group, and
(v) an azetidinyl group optionally substituted by 1 to 3 halogen atoms,
(2) a tetrahydronaphthyl group, or
(3) a pyridyl group optionally further substituted by 1 to 3 halogen atoms;
Ring B is an azetidine ring or a piperidine ring;
Ring D is
(1) a benzene ring optionally further substituted by 1 to 3 halogen atoms, or
(2) a pyridine ring;
L is $—O—CH_2—$ or $—CH_2—O—$;
X is a carbon atom;
Y is a carbon atom or a nitrogen atom; and
Z is $—O—CH_2—$.
[11A] The compound or salt of any of the above-mentioned [1] to [4], [4A], [5], [6], [6A], [7], [8], [9], [9A], [9B], [9C], [10], [10A] and [11], wherein
m and n are both 0 or both 1;

Ring A is
(1) a phenyl group further substituted by 1 to 3 substituents selected from
(i) a halogen atom,
(ii) a cyano group,
(iii) an optionally halogenated $C_{1-6}$ alkyl group, and
(iv) an azetidinyl group optionally substituted by 1 to 3 halogen atoms,
(2) a tetrahydronaphthyl group, or
(3) a pyridyl group optionally further substituted by 1 to 3 halogen atoms;
Ring B is an azetidine ring or a piperidine ring;
Ring D is
(1) a benzene ring optionally further substituted by 1 to 3 halogen atoms, or
(2) a pyridine ring;
L is —O—$CH_2$— or —$CH_2$—O—;
X is a carbon atom;
Y is a carbon atom or a nitrogen atom; and
Z is —O—$CH_2$—.
[12] The compound or salt of any of the above-mentioned [1] to [4], [4A], [5], [6], [6A], [7], [8], [9], [9A], [9B], [9C], [10], [10A], [11] and [11A], wherein
m and n are both 0;
Ring A is
(1) a phenyl group further substituted by 1 to 3 substituents selected from
(i) a pyridyl group optionally substituted by 1 to 3 substituents selected from
(a) a halogen atom, and
(b) a $C_{1-6}$ alkyl group, and
(ii) an azetidinyl group optionally substituted by 1 to 3 halogen atoms;
Ring B is an azetidine ring;
Ring D is a benzene ring further substituted by 1 to 3 halogen atoms;
L is —O—$CH_2$— or —$CH_2$—O—;
X is a carbon atom;
Y is a carbon atom; and
Z is —O—$CH_2$—.
[13] The compound or salt of any of the above-mentioned [1] to [4], [4A], [5], [6], [6A], [7], [8], [9], [9A], [9B], [9C], [10], [10A], [11], [11A] and [12], wherein
m and n are both 0;
Ring A is
(1) a phenyl group further substituted by 1 to 3 substituents selected from
(i) a halogen atom,
(ii) an optionally halogenated $C_{1-6}$ alkyl group, and
(iii) an azetidinyl group optionally substituted by 1 to 3 halogen atoms, or
(2) a tetrahydronaphthyl group;
Ring B is an azetidine ring;
Ring D is a benzene ring further substituted by 1 to 3 halogen atoms;
L is —O—$CH_2$— or —$CH_2$—O—;
X is a carbon atom;
Y is a carbon atom; and
Z is —O—$CH_2$—.
[14] 7-Fluoro-6-((3-((5,6,7,8-tetrahydronaphthalen-2-yloxy)methyl)azetidin-1-yl)carbonyl)-2H-1,4-benzoxazin-3(4H)-one, or a salt thereof.
[15] 7-Fluoro-6-((3-((2-fluoro-4-(trifluoromethyl)phenoxy)methyl)azetidin-1-yl)carbonyl)-2H-1,4-benzoxazin-3(4H)-one, or a salt thereof.
[16] 6-((3-((2-Chloro-4-(3-fluoroazetidin-1-yl)phenoxy)methyl)azetidin-1-yl)carbonyl)-7-fluoro-2H-1,4-benzoxazin-3(4H)-one, or a salt thereof.
[17] 6-((3-((2-Chloro-4-fluorobenzyl)oxy)azetidin-1-yl)carbonyl)-7-fluoro-2H-1,4-benzoxazin-3(4H)-one, or a salt thereof.
[18] A medicament comprising a compound represented by the formula (I):

(I)

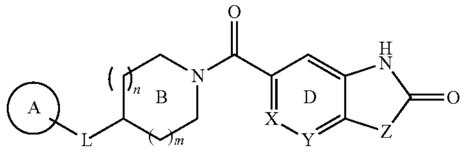

wherein
m and n are each independently 0 or 1,
Ring A is an optionally further substituted cyclic group,
Ring B is an azetidine ring, a pyrrolidine ring or a piperidine ring, each of which is an optionally further substituted,
Ring D is an optionally further substituted 6-membered aromatic ring,
L is —$CH_2$—O—$CH_2$—, —O—$CR^1R^2$—, —$CH(R^1)$—O—, —$CF_2$—$CH_2$—, —$CH_2$—$CF_2$— or —$CF_2$—,
$R^1$ and $R^2$ is each independently a hydrogen atom, or an optionally substituted $C_{1-6}$ alkyl group,
X and Y are each independently a carbon atom or a nitrogen atom,
Z is —O—$CH_2$—, —NR—$CH_2$—, —$CH_2$—$CH_2$—, —CH═CH—, —$CH_2$—, —O—, —S— or —NR—, and
R is a substituent,
or a salt thereof.
[18A] A medicament comprising a compound represented by the formula (I):

(I)

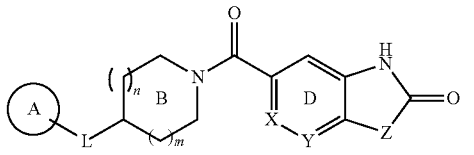

wherein
m and n are each independently 0 or 1,
Ring A is an optionally further substituted cyclic group,
Ring B is an azetidine ring, a pyrrolidine ring or a piperidine ring, each of which is an optionally further substituted,
Ring D is an optionally further substituted 6-membered aromatic ring,
L is —$CH_2$—O—$CH_2$— or —O—$CH_2$—,
X and Y are each independently a carbon atom or a nitrogen atom,
Z is —O—$CH_2$—, —NR—$CH_2$—, —$CH_2$—$CH_2$—, —CH═CH—, —$CH_2$—, —O—, —S— or —NR—, and
R is a substituent,
or a salt thereof.
[19] The medicament of the above-mentioned [18] or [18A], which is a monoacylglycerol lipase inhibitor.
[20] The medicament of the above-mentioned [18] or [18A], which is an agent for the prophylaxis or treatment of Alzheimer's disease, Parkinson's disease, Huntington's disease, amyotrophic lateral sclerosis, multiple sclerosis, anxiety disorder, pain, epilepsy or depression.

[21] A compound represented by the formula (I):

(I)

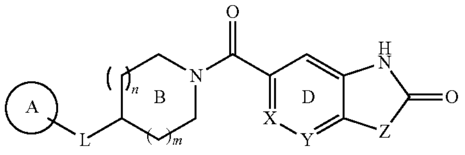

wherein m and n are each independently 0 or 1,

Ring A is an optionally further substituted cyclic group,

Ring B is an azetidine ring, a pyrrolidine ring or a piperidine ring, each of which is an optionally further substituted, Ring D is an optionally further substituted 6-membered aromatic ring, L is —$CH_2$—O—$CH_2$—, —O—$CR^1R^2$—, —$CH(R^1)$—O—, —$CF_2$—$CH_2$—, —$CH_2$—$CF_2$— or —$CF_2$—, $R^1$ and $R^2$ is each independently a hydrogen atom, or an optionally substituted $C_{1-6}$ alkyl group, X and Y are each independently a carbon atom or a nitrogen atom, Z is —O—$CH_2$—, —NR—$CH_2$—, —$CH_2$—$CH_2$—, —CH═CH—, —$CH_2$—, —O—, —S— or —NR—, and R is a substituent, or a salt thereof, for use in the prophylaxis or treatment of Alzheimer's disease, Parkinson's disease, Huntington's disease, amyotrophic lateral sclerosis, multiple sclerosis, anxiety disorder, pain, epilepsy or depression.

[22] A method of inhibiting monoacylglycerol lipase in a mammal, which comprises administering an effective amount of a compound represented by the formula (I):

(I)

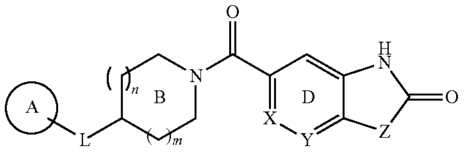

wherein m and n are each independently 0 or 1,

Ring A is an optionally further substituted cyclic group,

Ring B is an azetidine ring, a pyrrolidine ring or a piperidine ring, each of which is an optionally further substituted, Ring D is an optionally further substituted 6-membered aromatic ring, L is —$CH_2$—O—$CH_2$—, —O—$CR^1R^2$—, —$CH(R^1)$—O—, —$CF_2$—$CH_2$—, —$CH_2$—$CF_2$— or —$CF_2$—, $R^1$ and $R^2$ is each independently a hydrogen atom, or an optionally substituted $C_{1-6}$ alkyl group, X and Y are each independently a carbon atom or a nitrogen atom, Z is —O—$CH_2$—, —NR—$CH_2$—, —$CH_2$—$CH_2$—, —CH═CH—, —$CH_2$—, —O—, —S— or —NR—, and R is a substituent, or a salt thereof, to the mammal.

[23] A method for the prophylaxis or treatment of Alzheimer's disease, Parkinson's disease, Huntington's disease, amyotrophic lateral sclerosis, multiple sclerosis, anxiety disorder, pain, epilepsy or depression in a mammal, which comprises administering an effective amount of a compound represented by the formula (I):

(I)

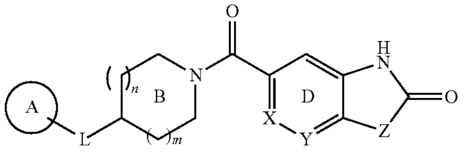

wherein m and n are each independently 0 or 1,

Ring A is an optionally further substituted cyclic group,

Ring B is an azetidine ring, a pyrrolidine ring or a piperidine ring, each of which is an optionally further substituted, Ring D is an optionally further substituted 6-membered aromatic ring, L is —$CH_2$—O—$CH_2$—, —O—$CR^1R^2$—, —$CH(R^1)$—O—, —$CF_2$—$CH_2$—, —$CH_2$—$CF_2$— or —$CF_2$—, $R^1$ and $R^2$ is each independently a hydrogen atom, or an optionally substituted $C_{1-6}$ alkyl group, X and Y are each independently a carbon atom or a nitrogen atom, Z is —O—$CH_2$—, —NR—$CH_2$—, —$CH_2$—$CH_2$—, —CH═CH—, —$CH_2$—, —O—, —S— or —NR—, and R is a substituent, or a salt thereof, to the mammal.

[24] Use of a compound represented by the formula (I):

(I)

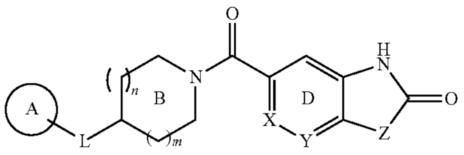

wherein m and n are each independently 0 or 1,

Ring A is an optionally further substituted cyclic group,

Ring B is an azetidine ring, a pyrrolidine ring or a piperidine ring, each of which is an optionally further substituted, Ring D is an optionally further substituted 6-membered aromatic ring, L is —$CH_2$—O—$CH_2$—, —O—$CR^1R^2$—, —$CH(R^1)$—O—, —$CF_2$—$CH_2$—, —$CH_2$—$CF_2$— or —$CF_2$—, $R^1$ and $R^2$ is each independently a hydrogen atom, or an optionally substituted $C_{1-6}$ alkyl group, X and Y are each independently a carbon atom or a nitrogen atom, Z is —O—$CH_2$—, —NR—$CH_2$—, —$CH_2$—$CH_2$—, —CH═CH—, —$CH_2$—, —O—, —S— or —NR—, and R is a substituent, or a salt thereof, for the production of an agent for the prophylaxis or treatment of Alzheimer's disease, Parkinson's disease, Huntington's disease, amyotrophic lateral sclerosis, multiple sclerosis, anxiety disorder, pain, epilepsy or depression.

Effect of the Invention

According to the present invention, a compound having a superior MAGL inhibitory action, which is expected to be useful as an agent for the prophylaxis or treatment of neurodegenerative diseases (e.g., Alzheimer's disease, Parkinson's disease, Huntington's disease, amyotrophic lateral sclerosis, traumatic brain injury, glaucoma, multiple sclerosis etc.), anxiety disorder, pains (e.g., inflammatory pain, cancerous pain, neurogenic pain etc.), epilepsy, depression and the like can be provided.

DETAILED DESCRIPTION OF THE INVENTION

Figure 1:
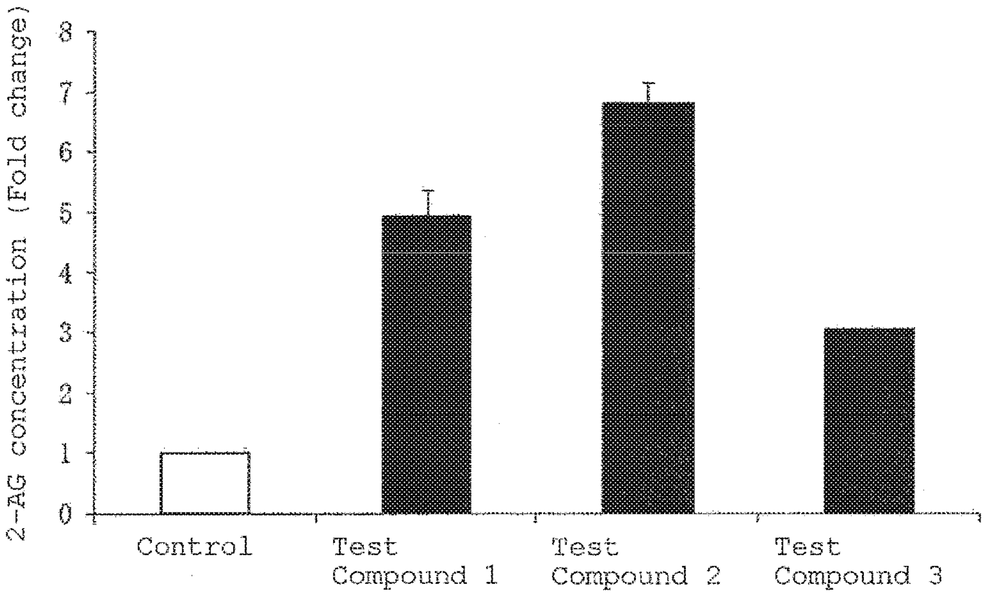
FIG. 1 shows changes in 2-AG concentrations of compounds 1 to 3 in Experimental Example 4.

The present invention is explained in detail in the following.

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ aryl-carbonyl group" include benzoyl, l-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following Substituent Group A.

[Substituent Group A]

(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl) amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,

(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group, and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 heteroatoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 heteroatoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 heteroatoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the above-mentioned Substituent Group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkylphosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent Group A".

Preferable examples of the optionally substituted amino group include an amino group, a mono- or di- (optionally halogenated $C_{1-6}$ alkyl) amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di- (optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl) amino group (e.g., methylcarbamoylamino), a (mono- or di-$C_{7-16}$ aralkyl-carbamoyl) amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl) ($C_{1-6}$ alkyl-carbonyl) amino group (e.g., N-acetyl-N-methylamino) and a ($C_{1-6}$ alkyl)($C_{6-14}$ aryl-carbonyl) amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_6$-14 aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent Group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent Group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_6$-14 aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent Group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxy group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent Group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from Substituent Group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-13}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from Substituent Group A".

Preferable examples of the optionally substituted silyl group include a tri-$C_{1-6}$ alkylsilyl group (e.g., trimethylsilyl, tert-butyl(dimethyl)silyl).

The definition of each symbol in the formula (I) is explained in detail in the following.

m and n are each independently 0 or 1.

m and n are preferably both 0 or both 1.

m and n are particularly preferably both 0.

Ring A is an optionally further substituted cyclic group.

Examples of the "cyclic group" of the "optionally further substituted cyclic group" represented by Ring A include a $C_{6-14}$ aryl group, a $C_{3-10}$ cycloalkyl group, a $C_{3-10}$ cycloalkenyl group and a heterocyclic group.

The "cyclic group" of the "optionally further substituted cyclic group" represented by Ring A is optionally further substituted, for example, by substituent(s) selected from the above-mentioned Substituent Group A. The number of the substituents is, for example, 1 to 3. When the number of the substituents is 2 or more, the respective substituents may be the same or different.

Ring A is preferably an optionally further substituted $C_{6-14}$ aryl group, an optionally further substituted 5- to 14-membered aromatic heterocyclic group (preferably a 5- or 6-membered monocyclic aromatic heterocyclic group or a 8- to 14-membered fused polycyclic (preferably bicyclic or tricyclic) aromatic heterocyclic group), an optionally further substituted $C_{3-10}$ cycloalkyl group, or an optionally further substituted 3- to 14-membered non-aromatic heterocyclic group (preferably a 3- to 8-membered monocyclic non-aromatic heterocyclic group).

Ring A is more preferably (1) a $C_{6-14}$ aryl group (e.g., phenyl, naphthyl) optionally further substituted by 1 to 3 substituents selected from (i) a halogen atom (e.g., a fluorine atom, a chlorine atom), (ii) an optionally halogenated $C_{1-6}$ alkoxy group (e.g., methoxy, trifluoromethoxy), (iii) a cyano group, (iv) an optionally halogenated $C_{1-6}$ alkyl group (e.g., methyl, trifluoromethyl), (v) a $C_{3-13}$ cycloalkyl group (e.g., cyclopropyl), (vi) a $C_{2-6}$ alkenyl group (e.g., propenyl), and (vii) a $C_{1-6}$ alkoxy-carbonyl group (e.g., methoxycarbonyl), (2) a 5- to 14-membered aromatic heterocyclic group (preferably a 5- or 6-membered monocyclic aromatic heterocyclic group or a 8- to 14-membered fused polycyclic (preferably bicyclic or tricyclic) aromatic heterocyclic group) (e.g., pyridyl, pyrimidinyl, imidazopyridyl, benzothiazolyl, indazolyl) optionally further substituted by 1 to 3 substituents selected from (i) a halogen atom (e.g., a chlorine atom), (ii) a $C_{1-6}$ alkyl group (e.g., methyl), (iii) an amino group, and (iv) a $C_{1-6}$ alkyl-carbonyl group (e.g., acetyl), (3) a $C_{3-10}$ cycloalkyl group (e.g., cyclohexyl), or (4) a 3- to 14-membered non-aromatic heterocyclic group (preferably a 3- to 8-membered monocyclic non-aromatic heterocyclic group) (e.g., tetrahydropyranyl).

Ring A is further more preferably (1) a phenyl group optionally further substituted by 1 to 3 substituents selected from (i) a halogen atom (e.g., a fluorine atom, a chlorine atom), (ii) an optionally halogenated $C_{1-6}$ alkoxy group (e.g., methoxy, trifluoromethoxy), (iii) a cyano group, (iv) an optionally halogenated $C_{1-6}$ alkyl group (e.g., methyl, trifluoromethyl), (v) a $C_{3-10}$ cycloalkyl group (e.g., cyclopropyl), (vi) a $C_{2-6}$ alkenyl group (e.g., propenyl), and (vii) a $C_{1-6}$ alkoxy-carbonyl group (e.g., methoxycarbonyl), (2) a naphthyl group, (3) a pyridyl group optionally further substituted by 1 to 3 substituents selected from (i) a halogen atom (e.g., a chlorine atom), (ii) a $C_{1-6}$ alkyl group (e.g., methyl), and (iii) an amino group, (4) a pyrimidinyl group, (5) an imidazopyridyl group, (6) a benzothiazolyl group, (7) an indazolyl group optionally further substituted by 1 to 3 $C_{1-6}$ alkyl-carbonyl groups (e.g., acetyl), (8) a $C_{3-10}$ cycloalkyl group (e.g., cyclohexyl), or (9) a tetrahydropyranyl group.

Ring A is still more preferably (1) a phenyl group optionally further substituted by 1 to 3 substituents selected from (i) a halogen atom (e.g., a fluorine atom, a chlorine atom), (ii) a cyano group, (iii) an optionally halogenated $C_{1-6}$ alkyl group (e.g., trifluoromethyl), and (iv) a $C_{2-6}$ alkenyl group (e.g., propenyl), or (2) a pyridyl group optionally further substituted by 1 to 3 halogen atoms (e.g., a chlorine atom).

Ring A is particularly preferably (1) a phenyl group optionally further substituted by 1 to 3 substituents selected from (i) a halogen atom (e.g., a fluorine atom, a chlorine atom), (ii) a cyano group, and (iii) an optionally halogenated $C_{1-6}$ alkyl group (e.g., trifluoromethyl), or (2) a pyridyl group optionally further substituted by 1 to 3 halogen atoms (e.g., a chlorine atom).

In another embodiment, Ring A is preferably a $C_{6-14}$ aryl group which is optionally further substituted and optionally fused with a $C_{3-10}$ cycloalkane, an optionally further substituted 5- to 14-membered aromatic heterocyclic group (preferably a 5- or 6-membered monocyclic aromatic heterocyclic group or a 8- to 14-membered fused polycyclic (preferably bicyclic or tricyclic) aromatic heterocyclic group), an optionally further substituted $C_{3-10}$ cycloalkyl group, or an optionally further substituted 3- to 14-membered non-aromatic heterocyclic group (preferably a 3- to 8-membered monocyclic non-aromatic heterocyclic group or a 9- to 14-membered fused polycyclic (preferably bicyclic or tricyclic) non-aromatic heterocyclic group).

In this embodiment, Ring A is more preferably (1) a $C_{6-14}$ aryl group optionally fused with a $C_{3-10}$ cycloalkane (e.g., cyclopentane, cyclohexane) (e.g., phenyl, naphthyl, indanyl (preferably 2,3-dihydroinden-5-yl), tetrahydronaphthyl (preferably 5,6,7,8-tetrahydronaphthalen-2-yl)) wherein the $C_{6-14}$ aryl group is optionally further substituted by 1 to 3 substituents selected from (i) a halogen atom (e.g., a fluorine atom, a chlorine atom, a bromine atom), (ii) an optionally halogenated $C_{1-6}$ alkoxy group (e.g., methoxy, trifluoromethoxy, difluoromethoxy, trifluoroethoxy), (iii) a cyano group, (iv) a $C_{1-6}$ alkyl group (e.g., methyl, isopropyl, tert-butyl) optionally substituted by 1 to 3 substituents selected from (a) a halogen atom (e.g., a fluorine atom), and (b) a hydroxy group, (v) a $C_{3-10}$ cycloalkyl group (e.g., cyclopropyl, cyclopentyl), (vi) a $C_{2-6}$ alkenyl group (e.g., propenyl), (vii) a $C_{1-6}$ alkoxy-carbonyl group (e.g., methoxycarbonyl), (viii) a $C_{6-14}$ aryl group (e.g., phenyl) optionally substituted by 1 to 3 $C_{1-6}$ alkoxy groups (e.g., methoxy), (ix) a $C_{6-14}$ aryloxy group (e.g., phenoxy), (x) a 5- to 14-membered aromatic heterocyclic group (preferably a 5- or 6-membered monocyclic aromatic heterocyclic group) (e.g., pyridyl, pyrazolyl, pyrrolyl, pyrimidinyl, thiazolyl, oxadiazolyl) optionally substituted by 1 to 3 substituents selected from (a) a halogen atom (e.g., a fluorine atom, a chlorine atom), (b) a $C_{1-6}$ alkyl group (e.g., methyl, ethyl, isobutyl) optionally substituted by 1 to 3 halogen atoms (e.g., a fluorine atom), and (c) a $C_{3-10}$ cycloalkyl group (e.g., cyclopropyl), and (xi) a 3- to 14-membered non-aromatic heterocyclic group (preferably a 3- to 8-membered monocyclic non-aromatic heterocyclic group or a 9- to 14-membered fused polycyclic (preferably bicyclic or tricyclic) non-aromatic heterocyclic group) (e.g., dihydropyranyl, dihydrobenzofuryl, tetrahydropyridyl) optionally substituted by 1 to 3 $C_{1-6}$ alkyl groups (e.g., methyl), (2) a 5- to 14-membered aromatic heterocyclic group (preferably a 5- or 6-membered monocyclic aromatic heterocyclic group or a 8- to 14-membered fused polycyclic (preferably bicyclic or tricyclic) aromatic heterocyclic group) (e.g., pyridyl, pyrimidinyl, imidazopyridyl, benzothiazolyl, indazolyl, pyrazolyl, benzoxazolyl, benzisoxazolyl, quinoxalinyl, quinolyl, isoquinolyl, pyrazolopyridyl) optionally further substituted by 1 to 3 substituents selected from (i) a halogen atom (e.g., a chlorine atom), (ii) a $C_{1-6}$ alkyl group (e.g., methyl), (iii) an amino group, (iv) a $C_{1-6}$ alkyl-carbonyl group (e.g., acetyl), (v) a $C_{6-14}$ aryl group (e.g., phenyl) optionally substituted by 1 to 3 halogen atoms (e.g., a fluorine atom), and (vi) a 5- to 14-membered aromatic heterocyclic group (preferably a 5- or 6-membered monocyclic aromatic heterocyclic group) (e.g., pyridyl) optionally substituted by 1 to 3 $C_{1-6}$ alkyl groups (e.g., ethyl), (3) a $C_{3-10}$ cycloalkyl group (e.g., cyclopropyl, cyclohexyl) optionally further substituted by 1 to 3 halogen atoms (e.g., a fluorine atom), or (4) a 3- to 14-membered non-aromatic heterocyclic group (preferably a 3- to 8-membered monocyclic non-aromatic heterocyclic group or a 9- to 14-membered fused polycyclic (preferably bicyclic or tricyclic) non-aromatic heterocyclic group) (e.g., tetrahydropyranyl, dihydrobenzofuryl, dihydropyranopyridyl) optionally further substituted by 1 to 3 $C_{1-6}$ alkyl groups (e.g., methyl).

In this embodiment, Ring A is further more preferably (1) a phenyl group optionally further substituted by 1 to 3 substituents selected from (i) a halogen atom (e.g., a fluorine atom, a chlorine atom, a bromine atom), (ii) an optionally halogenated $C_{1-6}$ alkoxy group (e.g., methoxy, trifluoromethoxy, difluoromethoxy, trifluoroethoxy), (iii) a cyano group, (iv) a $C_{1-6}$ alkyl group (e.g., methyl, isopropyl, tert-butyl) optionally substituted by 1 to 3 substituents selected from (a) a halogen atom (e.g., a fluorine atom), and (b) a hydroxy group, (v) a $C_{3-10}$ cycloalkyl group (e.g., cyclopropyl, cyclopentyl), (vi) a $C_{2-6}$ alkenyl group (e.g., propenyl), (vii) a $C_{1-6}$ alkoxy-carbonyl group (e.g., methoxycarbonyl), (viii) a phenyl group optionally substituted by 1 to 3 $C_{1-6}$ alkoxy groups (e.g., methoxy), (ix) a phenoxy group, (x) a pyridyl group optionally substituted by 1 to 3 substituents selected from (a) a halogen atom (e.g., a fluorine atom, a chlorine atom), and (b) a $C_{1-6}$ alkyl group (e.g., methyl, ethyl) optionally substituted by 1 to 3 halogen atoms (e.g., a fluorine atom), (xi) a pyrazolyl group optionally substituted by 1 to 3 substituents selected from (a) a $C_{1-6}$ alkyl group (e.g., methyl, isobutyl) optionally substituted by 1 to 3 halogen atoms (e.g., a fluorine atom), and (b) a $C_{3-10}$ cycloalkyl group (e.g., cyclopropyl), (xii) a pyrrolyl group optionally substituted by 1 to 3 $C_{1-6}$ alkyl groups (e.g., methyl), (xiii) a pyrimidinyl group optionally substituted by 1 to 3 $C_{1-6}$ alkyl groups (e.g., methyl) optionally substituted by 1 to 3 halogen atoms (e.g., a fluorine atom), (xiv) a thiazolyl group optionally substituted by 1 to 3 $C_{1-6}$ alkyl groups (e.g., methyl), (xv) an oxadiazolyl group, (xvi) a dihydropyranyl group, (xvii) a dihydrobenzofuryl group, and (xviii) a tetrahydropyridyl group optionally substituted by 1 to 3 $C_{1-6}$ alkyl groups (e.g., methyl), (2) a naphthyl group, (3) an indanyl group (preferably 2,3-dihydroinden-5-yl), (4) a tetrahydronaphthyl group (preferably 5,6,7,8-tetrahydronaphthalen-2-yl), (5) a pyridyl group optionally further substituted by 1 to 3 substituents selected from (i) a halogen atom (e.g., a chlorine atom), (ii) a $C_{1-6}$ alkyl group (e.g., methyl), (iii) an amino group, and (iv) a pyridyl group optionally substituted by 1 to 3 $C_{1-6}$ alkyl groups (e.g., ethyl), (6) a pyrimidinyl group, (7) an imidazopyridyl group optionally further substituted by 1 to 3 phenyl groups optionally substituted by 1 to 3 halogen atoms (e.g., a fluorine atom), (8) a benzothiazolyl group optionally further substituted by 1 to 3 $C_{1-6}$ alkyl groups (e.g., methyl), (9) an indazolyl group optionally further substituted by 1 to 3 $C_{1-6}$ alkyl-carbonyl groups (e.g., acetyl),

(10) a pyrazolyl group optionally further substituted by 1 to 3 substituents selected from (i) a $C_{1-6}$ alkyl group (e.g., methyl), and (ii) a pyridyl group,

(11) a benzoxazolyl group optionally further substituted by 1 to 3 $C_{1-6}$ alkyl groups (e.g., methyl),

(12) a benzisoxazolyl group optionally further substituted by 1 to 3 halogen atoms (e.g., a chlorine atom),

(13) a quinoxalinyl group,

(14) a quinolyl group,

(15) an isoquinolyl group,

(16) a pyrazolopyridyl group optionally further substituted by 1 to 3 phenyl groups,

(17) a $C_{3-10}$ cycloalkyl group (e.g., cyclopropyl, cyclohexyl) optionally further substituted by 1 to 3 halogen atoms (e.g., a fluorine atom),

(18) a tetrahydropyranyl group,

(19) a dihydrobenzofuryl group optionally further substituted by 1 to 3 $C_{1-6}$ alkyl groups (e.g., methyl), or

(20) a dihydropyranopyridyl group.

In this embodiment, Ring A is still more preferably (1) a phenyl group optionally further substituted by 1 to 3 substituents selected from (i) a halogen atom (e.g., a fluorine atom, a chlorine atom), (ii) a cyano group, (iii) an optionally halogenated $C_{1-6}$ alkyl group (e.g., methyl, trifluoromethyl), and (iv) a $C_{2-6}$ alkenyl group (e.g., propenyl), (2) an indanyl group (preferably 2,3-dihydroinden-5-yl), (3) a tetrahydronaphthyl group (preferably 5,6,7,8-tetrahydronaphthalen-2-yl), or (4) a pyridyl group optionally further substituted by 1 to 3 halogen atoms (e.g., a chlorine atom).

In this embodiment, Ring A is even more preferably (1) a phenyl group optionally further substituted by 1 to 3 substituents selected from (i) a halogen atom (e.g., a fluorine atom, a chlorine atom), (ii) a cyano group, and (iii) an optionally halogenated $C_{1-6}$ alkyl group (e.g., trifluoromethyl), (2) a tetrahydronaphthyl group (preferably 5,6,7,8-tetrahydronaphthalen-2-yl), or (3) a pyridyl group optionally further substituted by 1 to 3 halogen atoms (e.g., a chlorine atom).

In this embodiment, Ring A is particularly preferably a tetrahydronaphthyl group (preferably 5,6,7,8-tetrahydronaphthalen-2-yl).

In another embodiment, Ring A is more preferably (1) a $C_{6-14}$ aryl group which is optionally further substituted and optionally fused with a $C_{3-10}$ cycloalkane, (2) an optionally further substituted pyridyl group, (3) an optionally further substituted pyrimidinyl group, (4) an optionally further substituted imidazopyridyl group, (5) an optionally further substituted benzothiazolyl group, (6) an optionally further substituted indazolyl group, (7) an optionally further substituted pyrazolyl group, (8) an optionally further substituted benzoxazolyl group, (9) an optionally further substituted benzisoxazolyl group,

(10) an optionally further substituted quinoxalinyl group,

(11) an optionally further substituted quinolyl group,

(12) an optionally further substituted isoquinolyl group,

(13) an optionally further substituted pyrazolopyridyl group,

(14) an optionally further substituted $C_{3-10}$ cycloalkyl group,

(15) an optionally further substituted tetrahydropyranyl group,

(16) an optionally further substituted dihydrobenzofuryl group, or

(17) an optionally further substituted dihydropyranopyridyl group.

In another embodiment, Ring A is more preferably (1) a $C_{6-14}$ aryl group optionally fused with a $C_{3-10}$ cycloalkane (e.g., cyclopentane, cyclohexane) (e.g., phenyl, naphthyl, indanyl (preferably 2,3-dihydroinden-5-yl), tetrahydronaphthyl (preferably 5,6,7,8-tetrahydronaphthalen-2-yl)) wherein the $C_{6-14}$ aryl group is optionally further substituted by 1 to 3 substituents selected from (i) a halogen atom (e.g., a fluorine atom, a chlorine atom, a bromine atom), (ii) an optionally halogenated $C_{1-6}$ alkoxy group (e.g., methoxy, trifluoromethoxy, difluoromethoxy, trifluoroethoxy), (iii) a cyano group, (iv) a $C_{1-6}$ alkyl group (e.g., methyl, isopropyl, tert-butyl) optionally substituted by 1 to 3 substituents selected from (a) a halogen atom (e.g., a fluorine atom), and (b) a hydroxy group, (v) a $C_{3-10}$ cycloalkyl group (e.g., cyclopropyl, cyclopentyl), (vi) a $C_{2-6}$ alkenyl group (e.g., propenyl), (vii) a $C_{1-6}$ alkoxy-carbonyl group (e.g., methoxycarbonyl), (viii) a $C_{1-6}$ alkylsulfonyl group (e.g., methylsulfonyl), (ix) a $C_{6-14}$ aryl group (e.g., phenyl) optionally substituted by 1 to 3 $C_{1-6}$ alkoxy groups (e.g., methoxy), (x) a $C_{6-14}$ aryloxy group (e.g., phenoxy), (xi) a 5- to 14-membered aromatic heterocyclic group (preferably a 5- or 6-membered monocyclic aromatic heterocyclic group) (e.g., pyridyl, pyrazolyl, pyrrolyl, pyrimidinyl, thiazolyl, oxadiazolyl) optionally substituted by 1 to 3 substituents selected from (a) a halogen atom (e.g., a fluorine atom, a chlorine atom), (b) a $C_{1-6}$ alkyl group (e.g., methyl, ethyl, isobutyl) optionally substituted by 1 to 3 halogen atoms (e.g., a fluorine atom), and (c) a $C_{3-10}$ cycloalkyl group (e.g., cyclopropyl), and (xii) a 3- to 14-membered non-aromatic heterocyclic group (preferably a 3- to 8-membered monocyclic non-aromatic heterocyclic group or a 9- to 14-membered fused polycyclic (preferably bicyclic or tricyclic) non-aromatic heterocyclic group) (e.g., dihydropyranyl, dihydrobenzofuryl, tetrahydropyridyl, azetidinyl) optionally substituted by 1 to 3 substituents selected from (a) a $C_{1-6}$ alkyl group (e.g., methyl), and (b) a halogen atom (e.g., a fluorine atom), (2) a 5- to 14-membered aromatic heterocyclic group (preferably a 5- or 6-membered monocyclic aromatic heterocyclic group or a 8- to 14-membered fused polycyclic (preferably bicyclic or tricyclic) aromatic heterocyclic group) (e.g., pyridyl, pyrimidinyl, imidazopyridyl, benzothiazolyl, indazolyl, pyrazolyl, benzoxazolyl, benzisoxazolyl, quinoxalinyl, quinolyl, isoquinolyl, pyrazolopyridyl) optionally further substituted by 1 to 3 substituents selected from (i) a halogen atom (e.g., a chlorine atom), (ii) a $C_{1-6}$ alkyl group (e.g., methyl), (iii) an amino group, (iv) a $C_{1-6}$ alkyl-carbonyl group (e.g., acetyl), (v) a $C_{6-14}$ aryl group (e.g., phenyl) optionally substituted by 1 to 3 halogen atoms (e.g., a fluorine atom), and (vi) a 5- to 14-membered aromatic heterocyclic group (preferably a 5- or 6-membered monocyclic aromatic heterocyclic group) (e.g., pyridyl) optionally substituted by 1 to 3 $C_{1-6}$ alkyl groups (e.g., ethyl), (3) a $C_{3-10}$ cycloalkyl group (e.g., cyclopropyl, cyclohexyl) optionally further substituted by 1 to 3 halogen atoms (e.g., a fluorine atom), or (4) a 3- to 14-membered non-aromatic heterocyclic group (preferably a 3- to 8-membered monocyclic non-aromatic heterocyclic group or a 9- to 14-membered fused polycyclic (preferably bicyclic or tricyclic) non-aromatic heterocyclic group) (e.g., tetrahydropyranyl, dihydrobenzofuryl, dihydropyranopyridyl) optionally further substituted by 1 to 3 $C_{1-6}$ alkyl groups (e.g., methyl).

In this embodiment, Ring A is further more preferably (1) a phenyl group optionally further substituted by 1 to 3 substituents selected from (i) a halogen atom (e.g., a fluorine atom, a chlorine atom, a bromine atom), (ii) an optionally halogenated $C_{1-6}$ alkoxy group (e.g., methoxy, trifluoromethoxy, difluoromethoxy, trifluoroethoxy), (iii) a cyano group, (iv) a $C_{1-6}$ alkyl group (e.g., methyl, isopropyl, tert-butyl) optionally substituted by 1 to 3 substituents selected from (a) a halogen atom (e.g., a fluorine atom), and (b) a hydroxy group, (v) a $C_{3-10}$ cycloalkyl group (e.g., cyclopropyl, cyclopentyl), (vi) a $C_{2-6}$ alkenyl group (e.g., propenyl), (vii) a $C_{1-6}$ alkoxy-carbonyl group (e.g., methoxycarbonyl), (viii) a $C_{1-6}$ alkylsulfonyl group (e.g., methylsulfonyl), (ix) a phenyl group optionally substituted by 1 to 3 $C_{1-6}$ alkoxy groups (e.g., methoxy), (x) a phenoxy group, (xi) a pyridyl group optionally substituted by 1 to 3 substituents selected from (a) a halogen atom (e.g., a fluorine atom, a chlorine atom), and (b) a $C_{1-6}$ alkyl group (e.g., methyl, ethyl) optionally substituted by 1 to 3 halogen atoms (e.g., a fluorine atom), (xii) a pyrazolyl group optionally substituted by 1 to 3 substituents selected from (a) a $C_{1-6}$ alkyl group (e.g., methyl, isobutyl) optionally substituted by 1 to 3 halogen atoms (e.g., a fluorine atom), and (b) a $C_{3-10}$ cycloalkyl group (e.g., cyclopropyl), (xiii) a pyrrolyl group optionally substituted by 1 to 3 $C_{1-6}$ alkyl groups (e.g., methyl), (xiv) a pyrimidinyl group optionally substituted by 1 to 3 $C_{1-6}$ alkyl groups (e.g., methyl) optionally substituted by 1 to 3 halogen atoms (e.g., a fluorine atom), (xv) a thiazolyl group optionally substituted by 1 to 3 $C_{1-6}$ alkyl groups (e.g., methyl), (xvi) an oxadiazolyl group, (xvii) a dihydropyranyl group, (xviii) a dihydrobenzofuryl group, (xix) a tetrahydropyridyl group optionally substituted by 1 to 3 $C_{1-6}$ alkyl groups (e.g., methyl), and (xx) an azetidinyl group optionally substituted by 1 to 3 halogen atoms (e.g., a fluorine atom), (2) a naphthyl group, (3) an indanyl group (preferably 2,3-dihydroinden-5-yl), (4) a tetrahydronaphthyl group (preferably 5,6,7,8-tetrahydronaphthalen-2-yl) optionally further substituted by 1 to 3 halogen atoms (e.g., a bromine atom), (5) a pyridyl group optionally further substituted by 1 to 3 substituents selected from
(i) a halogen atom (e.g., a chlorine atom),
(ii) a $C_{1-6}$ alkyl group (e.g., methyl),
(iii) an amino group, and
(iv) a pyridyl group optionally substituted by 1 to 3 $C_{1-6}$ alkyl groups (e.g., ethyl),
(6) a pyrimidinyl group,
(7) an imidazopyridyl group optionally further substituted by 1 to 3 phenyl groups optionally substituted by 1 to 3 halogen atoms (e.g., a fluorine atom),
(8) a benzothiazolyl group optionally further substituted by 1 to 3 $C_{1-6}$ alkyl groups (e.g., methyl),
(9) an indazolyl group optionally further substituted by 1 to 3 $C_{1-6}$ alkyl-carbonyl groups (e.g., acetyl),
(10) a pyrazolyl group optionally further substituted by 1 to 3 substituents selected from
(i) a $C_{1-6}$ alkyl group (e.g., methyl), and
(ii) a pyridyl group,
(11) a benzoxazolyl group optionally further substituted by 1 to 3 $C_{1-6}$ alkyl groups (e.g., methyl),
(12) a benzisoxazolyl group optionally further substituted by 1 to 3 halogen atoms (e.g., a chlorine atom),
(13) a quinoxalinyl group,
(14) a quinolyl group,
(15) an isoquinolyl group,
(16) a pyrazolopyridyl group optionally further substituted by 1 to 3 phenyl groups,
(17) a $C_{3-10}$ cycloalkyl group (e.g., cyclopropyl, cyclohexyl) optionally further substituted by 1 to 3 halogen atoms (e.g., a fluorine atom),
(18) a tetrahydropyranyl group,
(19) a dihydrobenzofuryl group optionally further substituted by 1 to 3 $C_{1-6}$ alkyl groups (e.g., methyl), or
(20) a dihydropyranopyridyl group.

In this embodiment, Ring A is further more preferably
(1) a phenyl group optionally further substituted by 1 to 3 substituents selected from
(i) a halogen atom (e.g., a fluorine atom, a chlorine atom, a bromine atom),
(ii) an optionally halogenated $C_{1-6}$ alkoxy group (e.g., methoxy, trifluoromethoxy, difluoromethoxy, trifluoroethoxy),
(iii) a cyano group,
(iv) a $C_{1-6}$ alkyl group (e.g., methyl, isopropyl, tert-butyl) optionally substituted by 1 to 3 substituents selected from
(a) a halogen atom (e.g., a fluorine atom), and
(b) a hydroxy group,
(v) a $C_{3-10}$ cycloalkyl group (e.g., cyclopropyl, cyclopentyl),
(vi) a $C_{2-6}$ alkenyl group (e.g., propenyl),
(vii) a $C_{1-6}$ alkoxy-carbonyl group (e.g., methoxycarbonyl),
(viii) a $C_{1-6}$ alkylsulfonyl group (e.g., methylsulfonyl),
(ix) a phenyl group optionally substituted by 1 to 3 $C_{1-6}$ alkoxy groups (e.g., methoxy),
(x) a phenoxy group,
(xi) a pyridyl group optionally substituted by 1 to 3 substituents selected from
(a) a halogen atom (e.g., a fluorine atom, a chlorine atom), and
(b) a $C_{1-6}$ alkyl group (e.g., methyl, ethyl) optionally substituted by 1 to 3 halogen atoms (e.g., a fluorine atom),
(xii) a pyrazolyl group optionally substituted by 1 to 3 substituents selected from
(a) a $C_{1-6}$ alkyl group (e.g., methyl, isobutyl) optionally substituted by 1 to 3 halogen atoms (e.g., a fluorine atom), and
(b) a $C_{3-10}$ cycloalkyl group (e.g., cyclopropyl),
(xiii) a pyrrolyl group optionally substituted by 1 to 3 $C_{1-6}$ alkyl groups (e.g., methyl),
(xiv) a pyrimidinyl group optionally substituted by 1 to 3 $C_{1-6}$ alkyl groups (e.g., methyl) optionally substituted by 1 to 3 halogen atoms (e.g., a fluorine atom),
(xv) a thiazolyl group optionally substituted by 1 to 3 $C_{1-6}$ alkyl groups (e.g., methyl),
(xvi) an oxadiazolyl group,
(xvii) a dihydropyranyl group,
(xviii) a dihydrobenzofuryl group,
(xix) a tetrahydropyridyl group optionally substituted by 1 to 3 $C_{1-6}$ alkyl groups (e.g., methyl), and
(xx) an azetidinyl group optionally substituted by 1 to 3 halogen atoms (e.g., a fluorine atom),
(2) a naphthyl group,
(3) an indanyl group (preferably 2,3-dihydroinden-5-yl),
(4) a tetrahydronaphthyl group (preferably 5,6,7,8-tetrahydronaphthalen-2-yl) optionally further substituted by 1 to 3 halogen atoms (e.g., a bromine atom),
(5) a pyridyl group optionally further substituted by 1 to 3 substituents selected from
(i) a halogen atom (e.g., a chlorine atom),
(ii) a $C_{1-6}$ alkyl group (e.g., methyl), and
(iii) a pyridyl group optionally substituted by 1 to 3 $C_{1-6}$ alkyl groups (e.g., ethyl),
(6) an imidazopyridyl group optionally further substituted by 1 to 3 phenyl groups optionally substituted by 1 to 3 halogen atoms (e.g., a fluorine atom),
(7) a benzothiazolyl group optionally further substituted by 1 to 3 $C_{1-6}$ alkyl groups (e.g., methyl),
(8) an indazolyl group optionally further substituted by 1 to 3 $C_{1-6}$ alkyl-carbonyl groups (e.g., acetyl),
(9) a pyrazolyl group optionally further substituted by 1 to 3 substituents selected from
(i) a $C_{1-6}$ alkyl group (e.g., methyl), and
(ii) a pyridyl group,
(10) a benzoxazolyl group optionally further substituted by 1 to 3 $C_{1-6}$ alkyl groups (e.g., methyl),
(11) a benzisoxazolyl group optionally further substituted by 1 to 3 halogen atoms (e.g., a chlorine atom),
(12) a quinoxalinyl group,
(13) a quinolyl group,
(14) an isoquinolyl group,
(15) a pyrazolopyridyl group optionally further substituted by 1 to 3 phenyl groups,
(16) a $C_{3-10}$ cycloalkyl group (e.g., cyclopropyl, cyclohexyl) optionally further substituted by 1 to 3 halogen atoms (e.g., a fluorine atom),
(17) a tetrahydropyranyl group,
(18) a dihydrobenzofuryl group optionally further substituted by 1 to 3 $C_{1-6}$ alkyl groups (e.g., methyl), or
(19) a dihydropyranopyridyl group.

In this embodiment, Ring A is still more preferably
(1) a phenyl group further substituted by 1 to 3 substituents selected from
(i) a halogen atom (e.g., a fluorine atom, a chlorine atom),
(ii) a cyano group,
(iii) an optionally halogenated $C_{1-6}$ alkyl group (e.g., methyl, trifluoromethyl),
(iv) a $C_{2-6}$ alkenyl group (e.g., propenyl), (v) a pyridyl group optionally substituted by 1 to 3 substituents selected from (a) a halogen atom (e.g., a fluorine atom), and (b) a $C_{1-6}$ alkyl group (e.g., methyl), and (vi) an azetidinyl group optionally substituted by 1 to 3 halogen atoms (e.g., a fluorine atom), (2) an indanyl group (preferably 2,3-dihydroinden-5-yl), (3) a tetrahydronaphthyl group (preferably 5,6,7,8-tetrahydronaphthalen-2-yl), or (4) a pyridyl group optionally further substituted by 1 to 3 halogen atoms (e.g., a chlorine atom).

In this embodiment, Ring A is still more preferably (1) a phenyl group further substituted by 1 to 3 substituents selected from (i) a halogen atom (e.g., a fluorine atom, a chlorine atom), (ii) a cyano group, (iii) an optionally halogenated $C_{1-6}$ alkyl group (e.g., methyl, trifluoromethyl), (iv) a $C_{2-6}$ alkenyl group (e.g., propenyl), and (v) an azetidinyl group optionally substituted by 1 to 3 halogen atoms (e.g., a fluorine atom), (2) an indanyl group (preferably 2,3-dihydroinden-5-yl), (3) a tetrahydronaphthyl group (preferably 5,6,7,8-tetrahydronaphthalen-2-yl), or (4) a pyridyl group optionally further substituted by 1 to 3 halogen atoms (e.g., a chlorine atom).

In this embodiment, Ring A is even more preferably (1) a phenyl group further substituted by 1 to 3 substituents selected from (i) a halogen atom (e.g., a fluorine atom, a chlorine atom), (ii) a cyano group, (iii) an optionally halogenated $C_{1-6}$ alkyl group (e.g., trifluoromethyl), (iv) a pyridyl group optionally substituted by 1 to 3 substituents selected from (a) a halogen atom (e.g., a fluorine atom), and (b) a $C_{1-6}$ alkyl group (e.g., methyl), and (v) an azetidinyl group optionally substituted by 1 to 3 halogen atoms (e.g., a fluorine atom), (2) a tetrahydronaphthyl group (preferably 5,6,7,8-tetrahydronaphthalen-2-yl), or (3) a pyridyl group optionally further substituted by 1 to 3 halogen atoms (e.g., a chlorine atom).

In this embodiment, Ring A is even more preferably (1) a phenyl group further substituted by 1 to 3 substituents selected from (i) a halogen atom (e.g., a fluorine atom, a chlorine atom), (ii) a cyano group, (iii) an optionally halogenated $C_{1-6}$ alkyl group (e.g., trifluoromethyl), and (iv) an azetidinyl group optionally substituted by 1 to 3 halogen atoms (e.g., a fluorine atom), (2) a tetrahydronaphthyl group (preferably 5,6,7,8-tetrahydronaphthalen-2-yl), or (3) a pyridyl group optionally further substituted by 1 to 3 halogen atoms (e.g., a chlorine atom).

In this embodiment, Ring A is even more preferably (1) a phenyl group further substituted by 1 to 3 substituents selected from (i) a pyridyl group optionally substituted by 1 to 3 substituents selected from (a) a halogen atom (e.g., a fluorine atom), and (b) a $C_{1-6}$ alkyl group (e.g., methyl), and (ii) an azetidinyl group optionally substituted by 1 to 3 halogen atoms (e.g., a fluorine atom).

In this embodiment, Ring A is particularly preferably (1) a phenyl group further substituted by 1 to 3 substituents selected from (i) a halogen atom (e.g., a fluorine atom, a chlorine atom), (ii) an optionally halogenated $C_{1-6}$ alkyl group (e.g., trifluoromethyl), and (iii) an azetidinyl group optionally substituted by 1 to 3 halogen atoms (e.g., a fluorine atom), or (2) a tetrahydronaphthyl group (preferably 5,6,7,8-tetrahydronaphthalen-2-yl).

Ring B is an azetidine ring, a pyrrolidine ring or a piperidine ring, each of which is an optionally further substituted.

The "azetidine ring", "pyrrolidine ring" and "piperidine ring" of the "azetidine ring, pyrrolidine ring or piperidine ring, each of which is an optionally further substituted" represented by Ring B are each optionally further substituted, for example, by substituent(s) selected from the above-mentioned Substituent Group A. The number of the substituents is, for example, 1 to 3. When the number of the substituents is 2 or more, the respective substituents may be the same or different.

Ring B is preferably an azetidine ring, a pyrrolidine ring, or an optionally further substituted piperidine ring.

Ring B is more preferably (1) an azetidine ring, (2) a pyrrolidine ring, or (3) a piperidine ring optionally further substituted by 1 to 3 substituents selected from (i) a halogen atom (e.g., a fluorine atom), (ii) a hydroxy group, and (iii) a cyano group.

In another embodiment, Ring B is preferably an optionally further substituted azetidine ring, a pyrrolidine ring, or an optionally further substituted piperidine ring.

In this embodiment, Ring B is more preferably (1) an azetidine ring optionally further substituted by 1 to 3 substituents selected from (i) a halogen atom (e.g., a fluorine atom), and (ii) a $C_{1-6}$ alkyl group (e.g., methyl), (2) a pyrrolidine ring, or (3) a piperidine ring optionally further substituted by 1 to 3 substituents selected from (i) a halogen atom (e.g., a fluorine atom), (ii) a hydroxy group, and (iii) a cyano group.

In this embodiment, Ring B is further more preferably (1) an azetidine ring optionally further substituted by 1 to 3 substituents selected from (i) a halogen atom (e.g., a fluorine atom), and (ii) a $C_{1-6}$ alkyl group (e.g., methyl), or (2) a piperidine ring optionally further substituted by 1 to 3 substituents selected from (i) a halogen atom (e.g., a fluorine atom), (ii) a hydroxy group, and (iii) a cyano group.

In another embodiment, Ring B is more preferably an azetidine ring, or an optionally further substituted piperidine ring.

Ring B is still more preferably (1) an azetidine ring, or (2) a piperidine ring optionally further substituted by 1 to 3 hydroxy groups.

Ring B is even more preferably an azetidine ring or a piperidine ring.

In another embodiment, Ring B is more preferably an optionally further substituted azetidine ring, or an optionally further substituted piperidine ring.

In this embodiment, Ring B is further more preferably an optionally further substituted azetidine ring.

Ring B is particularly preferably an azetidine ring.

Ring D is an optionally further substituted 6-membered aromatic ring.

Examples of the "6-membered aromatic ring" of the "optionally further substituted 6-membered aromatic ring" represented by Ring D include a benzene ring and a 6-membered monocyclic aromatic heterocycle (preferably a pyridine ring).

Examples of the above-mentioned 6-membered monocyclic aromatic heterocycle include a 6-membered monocyclic group, from among the above-mentioned "aromatic heterocycle".

The "6-membered aromatic ring" of the "optionally further substituted 6-membered aromatic ring" represented by Ring D is optionally further substituted, for example, by substituent(s) selected from the above-mentioned Substituent Group A. The number of the substituents is, for example, 1 to 3. When the number of the substituents is 2 or more, the respective substituents may be the same or different.

Ring D is preferably an optionally further substituted benzene ring, or an optionally further substituted pyridine ring.

Ring D is more preferably (1) a benzene ring optionally further substituted by 1 to 3 substituents selected from (i) a halogen atom (e.g., a fluorine atom, a chlorine atom), and (ii) a $C_{1-6}$ alkyl group (e.g., methyl), or (2) a pyridine ring.

Ring D is further more preferably (1) a benzene ring optionally further substituted by 1 to 3 halogen atoms (e.g., a fluorine atom), or (2) a pyridine ring.

In another embodiment, Ring D is more preferably (1) a benzene ring optionally further substituted by 1 to 3 substituents selected from (i) a halogen atom (e.g., a fluorine atom, a chlorine atom), (ii) a $C_{1-6}$ alkyl group (e.g., methyl), and (iii) a $C_{1-6}$ alkoxy group (e.g., methoxy), or (2) a pyridine ring optionally further substituted by 1 to 3 $C_{1-6}$ alkyl groups (e.g., methyl).

In this embodiment, Ring D is further more preferably (1) a benzene ring optionally further substituted by 1 to 3 substituents selected from (i) a halogen atom (e.g., a fluorine atom, a chlorine atom), (ii) a $C_{1-6}$ alkyl group (e.g., methyl), and (iii) a $C_{1-6}$ alkoxy group (e.g., methoxy), or (2) a pyridine ring.

In this embodiment, Ring D is still more preferably (1) a benzene ring optionally further substituted by 1 to 3 halogen atoms (e.g., a fluorine atom), or (2) a pyridine ring.

Ring D is particularly preferably a benzene ring further substituted by 1 to 3 halogen atoms (e.g., a fluorine atom).

L is $-CH_2-O-CH_2-$, $-O-CR^1R^2-$, $-CH(R^1)-O-$, $-CF_2-CH_2-$, $-CH_2-CF_2-$ or $-CF_2-$.

$R^1$ and $R^2$ is each independently a hydrogen atom, or an optionally substituted $C_{1-6}$ alkyl group.

When L is $-O-CR^1R^2-$, the oxygen atom in the $-O-CR^1R^2-$ is bonded to Ring A, and the carbon atom in the $-O-CR^1R^2-$ is bonded to Ring B.

When L is $-CH(R^1)-O-$, the carbon atom in the $-CH(R^1)-O-$ is bonded to Ring A, and the oxygen atom in the $-CH(R^1)-O-$ is bonded to Ring B.

L is preferably $-CH_2-O-CH_2-$ or $-O-CH_2-$.

L is more preferably $-O-CH_2-$.

In another embodiment, L is preferably (1) $-CH_2-O-CH_2-$, (2) $-O-CR^1R^2-$ wherein $R^1$ and $R^2$ is each independently a hydrogen atom, or an optionally substituted $C_{1-6}$ alkyl group, (3) $-CH(R^1)-O-$ wherein $R^1$ is a hydrogen atom or a $C_{1-6}$ alkyl group (e.g., methyl), (4) $-CF_2-CH_2-$, or (5) $-CF_2-$.

In this embodiment, L is more preferably (1) $-CH_2-O-CH_2-$, (2) $-O-CR^1R^2-$ wherein $R^1$ and $R^2$ is each independently (1) a hydrogen atom, or (2) a $C_{1-6}$ alkyl group (e.g., methyl) optionally substituted by one substituent selected from a hydroxy group and a $C_{1-6}$ alkoxy group (e.g., methoxy), (3) $-CH(R^1)-O-$ wherein $R^1$ is a hydrogen atom or a $C_{1-6}$ alkyl group (e.g., methyl), (4) $-CF_2-CH_2-$, or (5) $-CF_2-$.

In this embodiment, L is further more preferably (1) $-CH_2-O-CH_2-$, (2) $-O-CR^1R^2-$ wherein $R^1$ and $R^2$ is each independently (1) a hydrogen atom, or (2) a $C_{1-6}$ alkyl group (e.g., methyl) optionally substituted by one $C_{1-6}$ alkoxy group (e.g., methoxy), (3) $-CH(R^1)-O-$ wherein $R^1$ is a hydrogen atom or a $C_{1-6}$ alkyl group (e.g., methyl), (4) $-CF_2-CH_2-$, or (5) $-CF_2-$.

In this embodiment, L is particularly preferably $-O-CH_2-$ or $-CH_2-O-$.

X and Y are each independently a carbon atom or a nitrogen atom.

X is preferably a carbon atom.

In another embodiment, X is preferably a carbon atom having substituent(s).

When X is a carbon atom having substituent(s), examples of the substituent include substituent(s) selected from the above-mentioned Substituent Group A, preferred are a halogen atom (e.g., a fluorine atom, a chlorine atom) and a $C_{1-6}$ alkyl group (e.g., methyl), and more preferred is a halogen atom (e.g., a fluorine atom).

In another embodiment, when X is a carbon atom having substituent(s), examples of the substituent include substituent(s) selected from the above-mentioned Substituent Group A, preferred are a halogen atom (e.g., a fluorine atom, a chlorine atom), a $C_{1-6}$ alkyl group (e.g., methyl) and a $C_{1-6}$ alkoxy group (e.g., methoxy), and more preferred is a halogen atom (e.g., a fluorine atom).

Y is preferably a carbon atom.

In another embodiment, X and Y are preferably both carbon atoms.

Z is $-O-CH_2-$, $-NR-CH_2-$, $-CH_2-CH_2-$, $-CH=CH-$, $-CH_2-$, $-O-$, $-S-$ or $-NR-$.

When Z is $-O-CH_2-$, the oxygen atom in the $-O-CH_2-$ is bonded to the adjacent carbon atom of Ring D, and the carbon atom of the methylene in the $-O-CH_2-$ is bonded to the adjacent carbon atom of the carbonyl group.

When Z is $-NR-CH_2-$, the nitrogen atom in the $-NR-CH_2-$ is bonded to the adjacent carbon atom of Ring D, and the carbon atom of the methylene in the $-NR-CH_2-$ is bonded to the adjacent carbon atom of the carbonyl group.

Z is preferably —O—$CH_2$—, —$CH_2$—$CH_2$—, —CH═CH—, —$CH_2$— or —O—.

Z is more preferably —O—$CH_2$—, —CH═CH—, —$CH_2$— or —O—.

Z is further more preferably —O—$CH_2$— or —O—.

Z is particularly preferably —O—$CH_2$—.

R is a substituent.

R is preferably an optionally halogenated $C_{1-6}$ alkyl group (e.g., methyl, difluoromethyl), an optionally halogenated $C_{3-10}$ cycloalkyl group (e.g., cyclopropyl, 3-fluorocyclobutyl), an optionally halogenated $C_{7-16}$ aralkyl group (e.g., benzyl, 4-fluorobenzyl), or an optionally halogenated $C_{6-14}$ aryl group (e.g., phenyl, 4-fluorophenyl).

In another embodiment, the present invention does not contain "7-((4-(phenoxymethyl)piperidin-1-yl)carbonyl)-1H-pyrido[2,3-b][1,4]oxazin-2(3H)-one, 7-((4-((3-methoxyphenoxy)methyl)piperidin-1-yl)carbonyl)-1H-pyrido[2,3-b][1,4]oxazin-2(3H)-one, and 7-((4-((2-methoxyphenoxy)methyl)piperidin-1-yl)carbonyl)-1H-pyrido[2,3-b][1,4]oxazin-2(3H)-one", preferably does not contain a "compound wherein one of X and Y is a nitrogen atom, and Ring A is i) a phenyl group further substituted by no substituent, or ii) a phenyl group substituted by one methoxy group".

Preferable examples of compound (I) include the following compounds.

[Compound A-1]

Compound (I) wherein m and n are each independently 0 or 1;

Ring A is an optionally further substituted $C_{6-14}$ aryl group, an optionally further substituted 5- to 14-membered aromatic heterocyclic group (preferably a 5- or 6-membered monocyclic aromatic heterocyclic group or a 8- to 14-membered fused polycyclic (preferably bicyclic or tricyclic) aromatic heterocyclic group), an optionally further substituted $C_{3-10}$ cycloalkyl group, or an optionally further substituted 3- to 14-membered non-aromatic heterocyclic group (preferably a 3- to 8-membered monocyclic non-aromatic heterocyclic group);

Ring B is an azetidine ring, a pyrrolidine ring, or an optionally further substituted piperidine ring;

Ring D is an optionally further substituted benzene ring, or an optionally further substituted pyridine ring;

L is —$CH_2$—O—$CH_2$— or —O—$CH_2$—;

X is a carbon atom;

Y is a carbon atom or a nitrogen atom; and

Z is —O—$CH_2$—, —$CH_2$—$CH_2$—, —CH═CH—, —$CH_2$— or —O—.

[Compound B-1]

Compound (I) wherein m and n are each independently 0 or 1;

Ring A is (1) a $C_{6-14}$ aryl group (e.g., phenyl, naphthyl) optionally further substituted by 1 to 3 substituents selected from (i) a halogen atom (e.g., a fluorine atom, a chlorine atom), (ii) an optionally halogenated $C_{1-6}$ alkoxy group (e.g., methoxy, trifluoromethoxy), (iii) a cyano group, (iv) an optionally halogenated $C_{1-6}$ alkyl group (e.g., methyl, trifluoromethyl), (v) a $C_{3-10}$ cycloalkyl group (e.g., cyclopropyl), (vi) a $C_{2-6}$ alkenyl group (e.g., propenyl), and (vii) a $C_{1-6}$ alkoxy-carbonyl group (e.g., methoxycarbonyl), (2) a 5- to 14-membered aromatic heterocyclic group (preferably a 5- or 6-membered monocyclic aromatic heterocyclic group or a 8- to 14-membered fused polycyclic (preferably bicyclic or tricyclic) aromatic heterocyclic group) (e.g., pyridyl, pyrimidinyl, imidazopyridyl, benzothiazolyl, indazolyl) optionally further substituted by 1 to 3 substituents selected from (i) a halogen atom (e.g., a chlorine atom), (ii) a $C_{1-6}$ alkyl group (e.g., methyl), (iii) an amino group, and (iv) a $C_{1-6}$ alkyl-carbonyl group (e.g., acetyl), (3) a $C_{3-10}$ cycloalkyl group (e.g., cyclohexyl), or (4) a 3- to 14-membered non-aromatic heterocyclic group (preferably a 3- to 8-membered monocyclic non-aromatic heterocyclic group) (e.g., tetrahydropyranyl);

Ring B is (1) an azetidine ring, (2) a pyrrolidine ring, or (3) a piperidine ring optionally further substituted by 1 to 3 substituents selected from (i) a halogen atom (e.g., a fluorine atom), (ii) a hydroxy group, and (iii) a cyano group;

Ring D is (1) a benzene ring optionally further substituted by 1 to 3 substituents selected from (i) a halogen atom (e.g., a fluorine atom, a chlorine atom), and (ii) a $C_{1-6}$ alkyl group (e.g., methyl), or (2) a pyridine ring;

L is —$CH_2$—O—$CH_2$— or —O—$CH_2$—;

X is a carbon atom;

Y is a carbon atom or a nitrogen atom; and

Z is —O—$CH_2$—, —$CH_2$—$CH_2$—, —CH═CH—, —$CH_2$— or —O—.

[Compound C-1]

Compound (I) wherein m and n are each independently 0 or 1;

Ring A is (1) a phenyl group optionally further substituted by 1 to 3 substituents selected from (i) a halogen atom (e.g., a fluorine atom, a chlorine atom), (ii) an optionally halogenated $C_{1-6}$ alkoxy group (e.g., methoxy, trifluoromethoxy), (iii) a cyano group, (iv) an optionally halogenated $C_{1-6}$ alkyl group (e.g., methyl, trifluoromethyl), (v) a $C_{3-10}$ cycloalkyl group (e.g., cyclopropyl), (vi) a $C_{2-6}$ alkenyl group (e.g., propenyl), and (vii) a $C_{1-6}$ alkoxy-carbonyl group (e.g., methoxycarbonyl), (2) a naphthyl group, (3) a pyridyl group optionally further substituted by 1 to 3 substituents selected from (i) a halogen atom (e.g., a chlorine atom), (ii) a $C_{1-6}$ alkyl group (e.g., methyl), and (iii) an amino group, (4) a pyrimidinyl group, (5) an imidazopyridyl group, (6) a benzothiazolyl group, (7) an indazolyl group optionally further substituted by 1 to 3 $C_{1-6}$ alkyl-carbonyl groups (e.g., acetyl), (8) a $C_{3-10}$ cycloalkyl group (e.g., cyclohexyl), or (9) a tetrahydropyranyl group;

Ring B is (1) an azetidine ring, (2) a pyrrolidine ring, or (3) a piperidine ring optionally further substituted by 1 to 3 substituents selected from (i) a halogen atom (e.g., a fluorine atom),
(ii) a hydroxy group, and
(iii) a cyano group;

Ring D is
(1) a benzene ring optionally further substituted by 1 to 3 substituents selected from
(i) a halogen atom (e.g., a fluorine atom, a chlorine atom), and
(ii) a $C_{1-6}$ alkyl group (e.g., methyl), or
(2) a pyridine ring;
L is —$CH_2$—O—$CH_2$— or —O—$CH_2$—;
X is a carbon atom;
Y is a carbon atom or a nitrogen atom; and
Z is —O—$CH_2$—, —$CH_2$—$CH_2$—, —CH═CH—, —$CH_2$— or —O—.

[Compound D-1]

Compound (I) wherein
m and n are both 0 or both 1;
Ring A is
(1) a phenyl group optionally further substituted by 1 to 3 substituents selected from
(i) a halogen atom (e.g., a fluorine atom, a chlorine atom),
(ii) a cyano group,
(iii) an optionally halogenated $C_{1-6}$ alkyl group (e.g., trifluoromethyl), and
(iv) a $C_{2-6}$ alkenyl group (e.g., propenyl), or
(2) a pyridyl group optionally further substituted by 1 to 3 halogen atoms (e.g., a chlorine atom); Ring B is
(1) an azetidine ring, or
(2) a piperidine ring optionally further substituted by 1 to 3 hydroxy groups;
Ring D is
(1) a benzene ring optionally further substituted by 1 to 3 substituents selected from
(i) a halogen atom (e.g., a fluorine atom, a chlorine atom), and
(ii) a $C_{1-6}$ alkyl group (e.g., methyl), or
(2) a pyridine ring;
L is —O—$CH_2$—;
X is a carbon atom;
Y is a carbon atom or a nitrogen atom; and
Z is —O—$CH_2$—.

[Compound E-1]

Compound (I) wherein
m and n are both 0 or both 1;
Ring A is
(1) a phenyl group optionally further substituted by 1 to 3 substituents selected from
(i) a halogen atom (e.g., a fluorine atom, a chlorine atom),
(ii) a cyano group, and
(iii) an optionally halogenated $C_{1-6}$ alkyl group (e.g., trifluoromethyl), or
(2) a pyridyl group optionally further substituted by 1 to 3 halogen atoms (e.g., a chlorine atom);
Ring B is an azetidine ring or a piperidine ring;
Ring D is
(1) a benzene ring optionally further substituted by 1 to 3 halogen atoms (e.g., a fluorine atom), or
(2) a pyridine ring;
L is —O—$CH_2$—;
X is a carbon atom;
Y is a carbon atom or a nitrogen atom; and
Z is —O—$CH_2$—.

[Compound A-2]

Compound (I) wherein
m and n are each independently 0 or 1;
Ring A is a $C_{6-14}$ aryl group which is optionally further substituted and optionally fused with a $C_{3-10}$ cycloalkane, an optionally further substituted 5- to 14-membered aromatic heterocyclic group (preferably a 5- or 6-membered monocyclic aromatic heterocyclic group or a 8- to 14-membered fused polycyclic (preferably bicyclic or tricyclic) aromatic heterocyclic group), an optionally further substituted $C_{3-10}$ cycloalkyl group, or an optionally further substituted 3- to 14-membered non-aromatic heterocyclic group (preferably a 3- to 8-membered monocyclic non-aromatic heterocyclic group or a 9- to 14-membered fused polycyclic (preferably bicyclic or tricyclic) non-aromatic heterocyclic group);
Ring B is an optionally further substituted azetidine ring, a pyrrolidine ring, or an optionally further substituted piperidine ring;
Ring D is an optionally further substituted benzene ring, or an optionally further substituted pyridine ring;
L is —$CH_2$—O—$CH_2$— or —O—$CH_2$—;
X is a carbon atom or a nitrogen atom;
Y is a carbon atom or a nitrogen atom; and
Z is —O—$CH_2$—, —$CH_2$—$CH_2$—, —CH═CH—, —$CH_2$— or —O—.

[Compound B-2]

Compound (I) wherein
m and n are each independently 0 or 1;
Ring A is
(1) a $C_{6-14}$ aryl group optionally fused with a $C_{3-10}$ cycloalkane (e.g., cyclopentane, cyclohexane) (e.g., phenyl, naphthyl, indanyl (preferably 2,3-dihydroinden-5-yl), tetrahydronaphthyl (preferably 5,6,7,8-tetrahydronaphthalen-2-yl)) wherein the $C_{6-14}$ aryl group is optionally further substituted by 1 to 3 substituents selected from
(i) a halogen atom (e.g., a fluorine atom, a chlorine atom, a bromine atom),
(ii) an optionally halogenated $C_{1-6}$ alkoxy group (e.g., methoxy, trifluoromethoxy, difluoromethoxy, trifluoroethoxy),
(iii) a cyano group,
(iv) a $C_{1-6}$ alkyl group (e.g., methyl, isopropyl, tert-butyl) optionally substituted by 1 to 3 substituents selected from
(a) a halogen atom (e.g., a fluorine atom), and
(b) a hydroxy group,
(v) a $C_{3-10}$ cycloalkyl group (e.g., cyclopropyl, cyclopentyl),
(vi) a $C_{2-6}$ alkenyl group (e.g., propenyl),
(vii) a $C_{1-6}$ alkoxy-carbonyl group (e.g., methoxycarbonyl),
(viii) a $C_{6-14}$ aryl group (e.g., phenyl) optionally substituted by 1 to 3 $C_{1-6}$ alkoxy groups (e.g., methoxy),
(ix) a $C_{6-14}$ aryloxy group (e.g., phenoxy),
(x) a 5- to 14-membered aromatic heterocyclic group (preferably a 5- or 6-membered monocyclic aromatic heterocyclic group) (e.g., pyridyl, pyrazolyl, pyrrolyl, pyrimidinyl, thiazolyl, oxadiazolyl) optionally substituted by 1 to 3 substituents selected from
(a) a halogen atom (e.g., a fluorine atom, a chlorine atom),
(b) a $C_{1-6}$ alkyl group (e.g., methyl, ethyl, isobutyl) optionally substituted by 1 to 3 halogen atoms (e.g., a fluorine atom), and
(c) a $C_{3-10}$ cycloalkyl group (e.g., cyclopropyl), and
(xi) a 3- to 14-membered non-aromatic heterocyclic group (preferably a 3- to 8-membered monocyclic non-aromatic heterocyclic group or a 9- to 14-membered fused polycyclic (preferably bicyclic or tricyclic) non-aromatic heterocyclic group) (e.g., dihydropyranyl, dihydrobenzofuryl, tetrahydropyridyl) optionally substituted by 1 to 3 $C_{1-6}$ alkyl groups (e.g., methyl), (2) a 5- to 14-membered aromatic heterocyclic group (preferably a 5- or 6-membered monocyclic aromatic heterocyclic group or a 8- to 14-membered fused polycyclic (preferably bicyclic or tricyclic) aromatic heterocyclic group) (e.g., pyridyl, pyrimidinyl, imidazopyridyl, benzothiazolyl, indazolyl, pyrazolyl, benzoxazolyl, benzisoxazolyl, quinoxalinyl, quinolyl, isoquinolyl, pyrazolopyridyl) optionally further substituted by 1 to 3 substituents selected from (i) a halogen atom (e.g., a chlorine atom), (ii) a $C_{1-6}$ alkyl group (e.g., methyl), (iii) an amino group, (iv) a $C_{1-6}$ alkyl-carbonyl group (e.g., acetyl), (v) a $C_{6-14}$ aryl group (e.g., phenyl) optionally substituted by 1 to 3 halogen atoms (e.g., a fluorine atom), and (vi) a 5- to 14-membered aromatic heterocyclic group (preferably a 5- or 6-membered monocyclic aromatic heterocyclic group) (e.g., pyridyl) optionally substituted by 1 to 3 $C_{1-6}$ alkyl groups (e.g., ethyl), (3) a $C_{3-10}$ cycloalkyl group (e.g., cyclopropyl, cyclohexyl) optionally further substituted by 1 to 3 halogen atoms (e.g., a fluorine atom), or (4) a 3- to 14-membered non-aromatic heterocyclic group (preferably a 3- to 8-membered monocyclic non-aromatic heterocyclic group or a 9- to 14-membered fused polycyclic (preferably bicyclic or tricyclic) non-aromatic heterocyclic group) (e.g., tetrahydropyranyl, dihydrobenzofuryl, dihydropyranopyridyl) optionally further substituted by 1 to 3 $C_{1-6}$ alkyl groups (e.g., methyl);

Ring B is (1) an azetidine ring optionally further substituted by 1 to 3 substituents selected from (i) a halogen atom (e.g., a fluorine atom), and (ii) a $C_{1-6}$ alkyl group (e.g., methyl), (2) a pyrrolidine ring, or (3) a piperidine ring optionally further substituted by 1 to 3 substituents selected from (i) a halogen atom (e.g., a fluorine atom), (ii) a hydroxy group, and (iii) a cyano group;

Ring D is (1) a benzene ring optionally further substituted by 1 to 3 substituents selected from (i) a halogen atom (e.g., a fluorine atom, a chlorine atom), (ii) a $C_{1-6}$ alkyl group (e.g., methyl), and (iii) a $C_{1-6}$ alkoxy group (e.g., methoxy), or (2) a pyridine ring optionally further substituted by 1 to 3 $C_{1-6}$ alkyl groups (e.g., methyl);

L is $-CH_2-O-CH_2-$ or $-O-CH_2-$;

X is a carbon atom or a nitrogen atom;

Y is a carbon atom or a nitrogen atom; and

Z is $-O-CH_2-$, $-CH_2-CH_2-$, $-CH=CH-$, $-CH_2-$ or $-O-$.

[Compound C-2]

Compound (I) wherein m and n are each independently 0 or 1;

Ring A is (1) a phenyl group optionally further substituted by 1 to 3 substituents selected from (i) a halogen atom (e.g., a fluorine atom, a chlorine atom, a bromine atom), (ii) an optionally halogenated $C_{1-6}$ alkoxy group (e.g., methoxy, trifluoromethoxy, difluoromethoxy, trifluoroethoxy), (iii) a cyano group, (iv) a $C_{1-6}$ alkyl group (e.g., methyl, isopropyl, tert-butyl) optionally substituted by 1 to 3 substituents selected from (a) a halogen atom (e.g., a fluorine atom), and (b) a hydroxy group, (v) a $C_{3-10}$ cycloalkyl group (e.g., cyclopropyl, cyclopentyl), (vi) a $C_{2-6}$ alkenyl group (e.g., propenyl), (vii) a $C_{1-6}$ alkoxy-carbonyl group (e.g., methoxycarbonyl), (viii) a phenyl group optionally substituted by 1 to 3 $C_{1-6}$ alkoxy groups (e.g., methoxy), (ix) a phenoxy group, (x) a pyridyl group optionally substituted by 1 to 3 substituents selected from (a) a halogen atom (e.g., a fluorine atom, a chlorine atom), and (b) a $C_{1-6}$ alkyl group (e.g., methyl, ethyl) optionally substituted by 1 to 3 halogen atoms (e.g., a fluorine atom), (xi) a pyrazolyl group optionally substituted by 1 to 3 substituents selected from (a) a $C_{1-6}$ alkyl group (e.g., methyl, isobutyl) optionally substituted by 1 to 3 halogen atoms (e.g., a fluorine atom), and (b) a $C_{3-10}$ cycloalkyl group (e.g., cyclopropyl), (xii) a pyrrolyl group optionally substituted by 1 to 3 $C_{1-6}$ alkyl groups (e.g., methyl), (xiii) a pyrimidinyl group optionally substituted by 1 to 3 $C_{1-6}$ alkyl groups (e.g., methyl) optionally substituted by 1 to 3 halogen atoms (e.g., a fluorine atom), (xiv) a thiazolyl group optionally substituted by 1 to 3 $C_{1-6}$ alkyl groups (e.g., methyl), (xv) an oxadiazolyl group, (xvi) a dihydropyranyl group, (xvii) a dihydrobenzofuryl group, and (xviii) a tetrahydropyridyl group optionally substituted by 1 to 3 $C_{1-6}$ alkyl groups (e.g., methyl), (2) a naphthyl group, (3) an indanyl group (preferably 2,3-dihydroinden-5-yl), (4) a tetrahydronaphthyl group (preferably 5,6,7,8-tetrahydronaphthalen-2-yl), (5) a pyridyl group optionally further substituted by 1 to 3 substituents selected from (i) a halogen atom (e.g., a chlorine atom), (ii) a $C_{1-6}$ alkyl group (e.g., methyl), (iii) an amino group, and (iv) a pyridyl group optionally substituted by 1 to 3 $C_{1-6}$ alkyl groups (e.g., ethyl), (6) a pyrimidinyl group, (7) an imidazopyridyl group optionally further substituted by 1 to 3 phenyl groups optionally substituted by 1 to 3 halogen atoms (e.g., a fluorine atom), (8) a benzothiazolyl group optionally further substituted by 1 to 3 $C_{1-6}$ alkyl groups (e.g., methyl), (9) an indazolyl group optionally further substituted by 1 to 3 $C_{1-6}$ alkyl-carbonyl groups (e.g., acetyl),

(10) a pyrazolyl group optionally further substituted by 1 to 3 substituents selected from (i) a $C_{1-6}$ alkyl group (e.g., methyl), and (ii) a pyridyl group,

(11) a benzoxazolyl group optionally further substituted by 1 to 3 $C_{1-6}$ alkyl groups (e.g., methyl),

(12) a benzisoxazolyl group optionally further substituted by 1 to 3 halogen atoms (e.g., a chlorine atom),
(13) a quinoxalinyl group,
(14) a quinolyl group,
(15) an isoquinolyl group,
(16) a pyrazolopyridyl group optionally further substituted by 1 to 3 phenyl groups,
(17) a $C_{3-10}$ cycloalkyl group (e.g., cyclopropyl, cyclohexyl) optionally further substituted by 1 to 3 halogen atoms (e.g., a fluorine atom),
(18) a tetrahydropyranyl group,
(19) a dihydrobenzofuryl group optionally further substituted by 1 to 3 $C_{1-6}$ alkyl groups (e.g., methyl), or
(20) a dihydropyranopyridyl group;
Ring B is
(1) an azetidine ring optionally further substituted by 1 to 3 substituents selected from
(i) a halogen atom (e.g., a fluorine atom), and
(ii) a $C_{1-6}$ alkyl group (e.g., methyl),
(2) a pyrrolidine ring, or
(3) a piperidine ring optionally further substituted by 1 to 3 substituents selected from
(i) a halogen atom (e.g., a fluorine atom),
(ii) a hydroxy group, and
(iii) a cyano group;
Ring D is
(1) a benzene ring optionally further substituted by 1 to 3 substituents selected from
(i) a halogen atom (e.g., a fluorine atom, a chlorine atom),
(ii) a $C_{1-6}$ alkyl group (e.g., methyl), and
(iii) a $C_{1-6}$ alkoxy group (e.g., methoxy), or
(2) a pyridine ring optionally further substituted by 1 to 3 $C_{1-6}$ alkyl groups (e.g., methyl);
L is $—CH_2—O—CH_2—$ or $—O—CH_2—$;
X is a carbon atom or a nitrogen atom;
Y is a carbon atom or a nitrogen atom; and
Z is $—O—CH_2—$, $—CH_2—CH_2—$, $—CH{=}CH—$, $—CH_2—$ or $—O—$.

[Compound D-2]

Compound (I) wherein
m and n are both 0 or both 1;
Ring A is
(1) a phenyl group optionally further substituted by 1 to 3 substituents selected from
(i) a halogen atom (e.g., a fluorine atom, a chlorine atom),
(ii) a cyano group,
(iii) an optionally halogenated $C_{1-6}$ alkyl group (e.g., methyl, trifluoromethyl), and
(iv) a $C_{2-6}$ alkenyl group (e.g., propenyl),
(2) an indanyl group (preferably 2,3-dihydroinden-5-yl),
(3) a tetrahydronaphthyl group (preferably 5,6,7,8-tetrahydronaphthalen-2-yl), or
(4) a pyridyl group optionally further substituted by 1 to 3 halogen atoms (e.g., a chlorine atom);
Ring B is
(1) an azetidine ring, or
(2) a piperidine ring optionally further substituted by 1 to 3 hydroxy groups;
Ring D is
(1) a benzene ring optionally further substituted by 1 to 3 substituents selected from
(i) a halogen atom (e.g., a fluorine atom, a chlorine atom),
(ii) a $C_{1-6}$ alkyl group (e.g., methyl), and
(iii) a $C_{1-6}$ alkoxy group (e.g., methoxy), or
(2) a pyridine ring;
L is $—O—CH_2—$;
X is a carbon atom;
Y is a carbon atom or a nitrogen atom; and
Z is $—O—CH_2—$ or $—O—$.

[Compound D-2(2)]

Compound (I) wherein
m and n are both 0 or both 1;
Ring A is
(1) a phenyl group optionally further substituted by 1 to 3 substituents selected from
(i) a halogen atom (e.g., a fluorine atom, a chlorine atom),
(ii) a cyano group,
(iii) an optionally halogenated $C_{1-6}$ alkyl group (e.g., methyl, trifluoromethyl), and
(iv) a $C_{2-6}$ alkenyl group (e.g., propenyl),
(2) an indanyl group (preferably 2,3-dihydroinden-5-yl),
(3) a tetrahydronaphthyl group (preferably 5,6,7,8-tetrahydronaphthalen-2-yl), or
(4) a pyridyl group optionally further substituted by 1 to 3 halogen atoms (e.g., a chlorine atom);
Ring B is
(1) an azetidine ring, or
(2) a piperidine ring optionally further substituted by 1 to 3 hydroxy groups;
Ring D is
(1) a benzene ring optionally further substituted by 1 to 3 substituents selected from
(i) a halogen atom (e.g., a fluorine atom, a chlorine atom),
(ii) a $C_{1-6}$ alkyl group (e.g., methyl), and
(iii) a $C_{1-6}$ alkoxy group (e.g., methoxy), or
(2) a pyridine ring;
L is $—O—CH_2—$;
X is a carbon atom;
Y is a carbon atom; and
Z is $—O—CH_2—$ or $—O—$.

[Compound E-2]

Compound (I) wherein
m and n are both 0 or both 1;
Ring A is
(1) a phenyl group optionally further substituted by 1 to 3 substituents selected from
(i) a halogen atom (e.g., a fluorine atom, a chlorine atom),
(ii) a cyano group, and
(iii) an optionally halogenated $C_{1-6}$ alkyl group (e.g., trifluoromethyl),
(2) a tetrahydronaphthyl group (preferably 5,6,7,8-tetrahydronaphthalen-2-yl), or
(3) a pyridyl group optionally further substituted by 1 to 3 halogen atoms (e.g., a chlorine atom);
Ring B is an azetidine ring or a piperidine ring;
Ring D is
(1) a benzene ring optionally further substituted by 1 to 3 halogen atoms (e.g., a fluorine atom), or
(2) a pyridine ring;
L is $—O—CH_2—$;
X is a carbon atom;
Y is a carbon atom or a nitrogen atom; and
Z is $—O—CH_2—$.

[Compound E-2(2)]

Compound (I) wherein
m and n are both 0 or both 1;
Ring A is
(1) a phenyl group optionally further substituted by 1 to 3 substituents selected from
(i) a halogen atom (e.g., a fluorine atom, a chlorine atom),
(ii) a cyano group, and
(iii) an optionally halogenated $C_{1-6}$ alkyl group (e.g., trifluoromethyl), (2) a tetrahydronaphthyl group (preferably 5,6,7,8-tetrahydronaphthalen-2-yl), or
(3) a pyridyl group optionally further substituted by 1 to 3 halogen atoms (e.g., a chlorine atom);
Ring B is an azetidine ring or a piperidine ring;
Ring D is
(1) a benzene ring optionally further substituted by 1 to 3 halogen atoms (e.g., a fluorine atom), or
(2) a pyridine ring;
L is —O—$CH_2$—;
X is a carbon atom;
Y is a carbon atom; and
Z is —O—$CH_2$—.

[Compound F-2]

Compound (I) wherein
m and n are both 0;
Ring A is a tetrahydronaphthyl group (preferably 5,6,7,8-tetrahydronaphthalen-2-yl);
Ring B is an azetidine ring;
Ring D is a benzene ring further substituted by 1 to 3 halogen atoms (e.g., a fluorine atom);
L is —O—$CH_2$—;
X is a carbon atom;
Y is a carbon atom; and
Z is —O—$CH_2$—.

[Compound A-3]

Compound (I) wherein
m and n are each independently 0 or 1;
Ring A is a $C_{6-14}$ aryl group which is optionally further substituted and optionally fused with a $C_{3-10}$ cycloalkane, an optionally further substituted 5- to 14-membered aromatic heterocyclic group (preferably a 5- or 6-membered monocyclic aromatic heterocyclic group or a 8- to 14-membered fused polycyclic (preferably bicyclic or tricyclic) aromatic heterocyclic group), an optionally further substituted $C_{3-10}$ cycloalkyl group, or an optionally further substituted 3- to 14-membered non-aromatic heterocyclic group (preferably a 3- to 8-membered monocyclic non-aromatic heterocyclic group or a 9- to 14-membered fused polycyclic (preferably bicyclic or tricyclic) non-aromatic heterocyclic group);
Ring B is an optionally further substituted azetidine ring, a pyrrolidine ring, or an optionally further substituted piperidine ring;
Ring D is an optionally further substituted benzene ring, or an optionally further substituted pyridine ring;
L is
(1) —$CH_2$—O—$CH_2$—,
(2) —O—$CR^1R^2$— wherein $R^1$ and $R^2$ is each independently a hydrogen atom, or an optionally substituted $C_{1-6}$ alkyl group,
(3) —CH($R^1$)—O— wherein $R^1$ is a hydrogen atom or a $C_{1-6}$ alkyl group (e.g., methyl),
(4) —$CF_2$—$CH_2$—, or
(5) —$CF_2$—;
X is a carbon atom or a nitrogen atom;
Y is a carbon atom or a nitrogen atom; and
Z is —O—$CH_2$—, —$CH_2$—$CH_2$—, —CH═CH—, —$CH_2$— or —O—; provided that
7-((4-(phenoxymethyl)piperidin-1-yl)carbonyl)-1H-pyrido[2,3-b][1,4]oxazin-2(3H)-one,
7-((4-((3-methoxyphenoxy)methyl)piperidin-1-yl)carbonyl)-1H-pyrido[2,3-b][1,4]oxazin-2(3H)-one, and
7-((4-((2-methoxyphenoxy)methyl)piperidin-1-yl)carbonyl)-1H-pyrido[2,3-b][1,4]oxazin-2(3H)-one
are excluded.

Preferably, [Compound A-3] wherein
X is a carbon atom; and
Y is a carbon atom.

In another embodiment, preferably, [Compound A-3] wherein Ring B is an optionally further substituted azetidine ring.

[Compound B-3]

Compound (I) wherein
m and n are each independently 0 or 1;
Ring A is
(1) a $C_{6-14}$ aryl group optionally fused with a $C_{3-10}$ cycloalkane (e.g., cyclopentane, cyclohexane) (e.g., phenyl, naphthyl, indanyl (preferably 2,3-dihydroinden-5-yl), tetrahydronaphthyl (preferably 5,6,7,8-tetrahydronaphthalen-2-yl)) wherein the $C_{6-14}$ aryl group is optionally further substituted by 1 to 3 substituents selected from
(i) a halogen atom (e.g., a fluorine atom, a chlorine atom, a bromine atom),
(ii) an optionally halogenated $C_{1-6}$ alkoxy group (e.g., methoxy, trifluoromethoxy, difluoromethoxy, trifluoroethoxy),
(iii) a cyano group,
(iv) a $C_{1-6}$ alkyl group (e.g., methyl, isopropyl, tert-butyl) optionally substituted by 1 to 3 substituents selected from
(a) a halogen atom (e.g., a fluorine atom), and
(b) a hydroxy group,
(v) a $C_{3-10}$ cycloalkyl group (e.g., cyclopropyl, cyclopentyl),
(vi) a $C_{2-6}$ alkenyl group (e.g., propenyl),
(vii) a $C_{1-6}$ alkoxy-carbonyl group (e.g., methoxycarbonyl),
(viii) a $C_{1-6}$ alkylsulfonyl group (e.g., methylsulfonyl),
(ix) a $C_{6-14}$ aryl group (e.g., phenyl) optionally substituted by 1 to 3 $C_{1-6}$ alkoxy groups (e.g., methoxy),
(x) a $C_{6-14}$ aryloxy group (e.g., phenoxy),
(xi) a 5- to 14-membered aromatic heterocyclic group (preferably a 5- or 6-membered monocyclic aromatic heterocyclic group) (e.g., pyridyl, pyrazolyl, pyrrolyl, pyrimidinyl, thiazolyl, oxadiazolyl) optionally substituted by 1 to 3 substituents selected from
(a) a halogen atom (e.g., a fluorine atom, a chlorine atom),
(b) a $C_{1-6}$ alkyl group (e.g., methyl, ethyl, isobutyl) optionally substituted by 1 to 3 halogen atoms (e.g., a fluorine atom), and
(c) a $C_{3-10}$ cycloalkyl group (e.g., cyclopropyl), and
(xii) a 3- to 14-membered non-aromatic heterocyclic group (preferably a 3- to 8-membered monocyclic non-aromatic heterocyclic group or a 9- to 14-membered fused polycyclic (preferably bicyclic or tricyclic) non-aromatic heterocyclic group) (e.g., dihydropyranyl, dihydrobenzofuryl, tetrahydropyridyl, azetidinyl) optionally substituted by 1 to 3 substituents selected from
(a) a $C_{1-6}$ alkyl group (e.g., methyl), and
(b) a halogen atom (e.g., a fluorine atom),
(2) a 5- to 14-membered aromatic heterocyclic group (preferably a 5- or 6-membered monocyclic aromatic heterocyclic group or a 8- to 14-membered fused polycyclic (preferably bicyclic or tricyclic) aromatic heterocyclic group) (e.g., pyridyl, pyrimidinyl, imidazopyridyl, benzothiazolyl, indazolyl, pyrazolyl, benzoxazolyl, benzisoxazolyl, quinoxalinyl, quinolyl, isoquinolyl, pyrazolopyridyl) optionally further substituted by 1 to 3 substituents selected from
(i) a halogen atom (e.g., a chlorine atom),
(ii) a $C_{1-6}$ alkyl group (e.g., methyl),
(iii) an amino group,
(iv) a $C_{1-6}$ alkyl-carbonyl group (e.g., acetyl), (v) a $C_{6-14}$ aryl group (e.g., phenyl) optionally substituted by 1 to 3 halogen atoms (e.g., a fluorine atom), and (vi) a 5- to 14-membered aromatic heterocyclic group (preferably a 5- or 6-membered monocyclic aromatic heterocyclic group) (e.g., pyridyl) optionally substituted by 1 to 3 $C_{1-6}$ alkyl groups (e.g., ethyl), (3) a $C_{3-10}$ cycloalkyl group (e.g., cyclopropyl, cyclohexyl) optionally further substituted by 1 to 3 halogen atoms (e.g., a fluorine atom), or (4) a 3- to 14-membered non-aromatic heterocyclic group (preferably a 3- to 8-membered monocyclic non-aromatic heterocyclic group or a 9- to 14-membered fused polycyclic (preferably bicyclic or tricyclic) non-aromatic heterocyclic group) (e.g., tetrahydropyranyl, dihydrobenzofuryl, dihydropyranopyridyl) optionally further substituted by 1 to 3 $C_{1-6}$ alkyl groups (e.g., methyl);

Ring B is (1) an azetidine ring optionally further substituted by 1 to 3 substituents selected from (i) a halogen atom (e.g., a fluorine atom), and (ii) a $C_{1-6}$ alkyl group (e.g., methyl), (2) a pyrrolidine ring, or (3) a piperidine ring optionally further substituted by 1 to 3 substituents selected from (i) a halogen atom (e.g., a fluorine atom), (ii) a hydroxy group, and (iii) a cyano group;

Ring D is (1) a benzene ring optionally further substituted by 1 to 3 substituents selected from (i) a halogen atom (e.g., a fluorine atom, a chlorine atom), (ii) a $C_{1-6}$ alkyl group (e.g., methyl), and (iii) a $C_{1-6}$ alkoxy group (e.g., methoxy), or (2) a pyridine ring optionally further substituted by 1 to 3 $C_{1-6}$ alkyl groups (e.g., methyl);

L is (1) $—CH_2—O—CH_2—$, (2) $—O—CR^1R^2—$ wherein $R^1$ and $R^2$ is each independently (1) a hydrogen atom, or (2) a $C_{1-6}$ alkyl group (e.g., methyl) optionally substituted by one substituent selected from a hydroxy group and a $C_{1-6}$ alkoxy group (e.g., methoxy), (3) $—CH(R^1)—O—$ wherein $R^1$ is a hydrogen atom or a $C_{1-6}$ alkyl group (e.g., methyl), (4) $—CF_2—CH_2—$, or (5) $—CF_2—$;

X is a carbon atom or a nitrogen atom;

Y is a carbon atom or a nitrogen atom; and

Z is $—O—CH_2—$, $—CH_2—CH_2—$, $—CH{=}CH—$, $—CH_2—$ or $—O—$; provided that 7-((4-(phenoxymethyl)piperidin-1-yl)carbonyl)-1H-pyrido[2,3-b][1,4]oxazin-2(3H)-one, 7-((4-((3-methoxyphenoxy)methyl)piperidin-1-yl)carbonyl)-1H-pyrido[2,3-b][1,4]oxazin-2(3H)-one, and 7-((4-((2-methoxyphenoxy)methyl)piperidin-1-yl) carbonyl)-1H-pyrido[2,3-b][1,4]oxazin-2(3H)-one are excluded.

Preferably, [Compound B-3] wherein

X is a carbon atom; and

Y is a carbon atom.

In another embodiment, preferably, [Compound B-3] wherein Ring B is (1) an azetidine ring optionally further substituted by 1 to 3 substituents selected from (i) a halogen atom (e.g., a fluorine atom), and (ii) a $C_{1-6}$ alkyl group (e.g., methyl).

[Compound C-3]

Compound (I) wherein m and n are each independently 0 or 1;

Ring A is (1) a phenyl group optionally further substituted by 1 to 3 substituents selected from (i) a halogen atom (e.g., a fluorine atom, a chlorine atom, a bromine atom), (ii) an optionally halogenated $C_{1-6}$ alkoxy group (e.g., methoxy, trifluoromethoxy, difluoromethoxy, trifluoroethoxy), (iii) a cyano group, (iv) a $C_{1-6}$ alkyl group (e.g., methyl, isopropyl, tert-butyl) optionally substituted by 1 to 3 substituents selected from (a) a halogen atom (e.g., a fluorine atom), and (b) a hydroxy group, (v) a $C_{3-10}$ cycloalkyl group (e.g., cyclopropyl, cyclopentyl), (vi) a $C_{2-6}$ alkenyl group (e.g., propenyl), (vii) a $C_{1-6}$ alkoxy-carbonyl group (e.g., methoxycarbonyl), (viii) a $C_{1-6}$ alkylsulfonyl group (e.g., methylsulfonyl), (ix) a phenyl group optionally substituted by 1 to 3 $C_{1-6}$ alkoxy groups (e.g., methoxy), (x) a phenoxy group, (xi) a pyridyl group optionally substituted by 1 to 3 substituents selected from (a) a halogen atom (e.g., a fluorine atom, a chlorine atom), and (b) a $C_{1-6}$ alkyl group (e.g., methyl, ethyl) optionally substituted by 1 to 3 halogen atoms (e.g., a fluorine atom), (xii) a pyrazolyl group optionally substituted by 1 to 3 substituents selected from (a) a $C_{1-6}$ alkyl group (e.g., methyl, isobutyl) optionally substituted by 1 to 3 halogen atoms (e.g., a fluorine atom), and (b) a $C_{3-10}$ cycloalkyl group (e.g., cyclopropyl), (xiii) a pyrrolyl group optionally substituted by 1 to 3 $C_{1-6}$ alkyl groups (e.g., methyl), (xiv) a pyrimidinyl group optionally substituted by 1 to 3 $C_{1-6}$ alkyl groups (e.g., methyl) optionally substituted by 1 to 3 halogen atoms (e.g., a fluorine atom), (xv) a thiazolyl group optionally substituted by 1 to 3 $C_{1-6}$ alkyl groups (e.g., methyl), (xvi) an oxadiazolyl group, (xvii) a dihydropyranyl group, (xviii) a dihydrobenzofuryl group, (xix) a tetrahydropyridyl group optionally substituted by 1 to 3 $C_{1-6}$ alkyl groups (e.g., methyl), and (xx) an azetidinyl group optionally substituted by 1 to 3 halogen atoms (e.g., a fluorine atom), (2) a naphthyl group, (3) an indanyl group (preferably 2,3-dihydroinden-5-yl), (4) a tetrahydronaphthyl group (preferably 5,6,7,8-tetrahydronaphthalen-2-yl) optionally further substituted by 1 to 3 halogen atoms (e.g., a bromine atom), (5) a pyridyl group optionally further substituted by 1 to 3 substituents selected from (i) a halogen atom (e.g., a chlorine atom), (ii) a $C_{1-6}$ alkyl group (e.g., methyl), (iii) an amino group, and (iv) a pyridyl group optionally substituted by 1 to 3 $C_{1-6}$ alkyl groups (e.g., ethyl), (6) a pyrimidinyl group,
(7) an imidazopyridyl group optionally further substituted by 1 to 3 phenyl groups optionally substituted by 1 to 3 halogen atoms (e.g., a fluorine atom),
(8) a benzothiazolyl group optionally further substituted by 1 to 3 $C_{1-6}$ alkyl groups (e.g., methyl),
(9) an indazolyl group optionally further substituted by 1 to 3 $C_{1-6}$ alkyl-carbonyl groups (e.g., acetyl),
(10) a pyrazolyl group optionally further substituted by 1 to 3 substituents selected from
(i) a $C_{1-6}$ alkyl group (e.g., methyl), and
(ii) a pyridyl group,
(11) a benzoxazolyl group optionally further substituted by 1 to 3 $C_{1-6}$ alkyl groups (e.g., methyl),
(12) a benzisoxazolyl group optionally further substituted by 1 to 3 halogen atoms (e.g., a chlorine atom),
(13) a quinoxalinyl group,
(14) a quinolyl group,
(15) an isoquinolyl group,
(16) a pyrazolopyridyl group optionally further substituted by 1 to 3 phenyl groups,
(17) a $C_{3-10}$ cycloalkyl group (e.g., cyclopropyl, cyclohexyl) optionally further substituted by 1 to 3 halogen atoms (e.g., a fluorine atom),
(18) a tetrahydropyranyl group,
(19) a dihydrobenzofuryl group optionally further substituted by 1 to 3 $C_{1-6}$ alkyl groups (e.g., methyl), or
(20) a dihydropyranopyridyl group;
Ring B is
(1) an azetidine ring optionally further substituted by 1 to 3 substituents selected from
(i) a halogen atom (e.g., a fluorine atom), and
(ii) a $C_{1-6}$ alkyl group (e.g., methyl),
(2) a pyrrolidine ring, or
(3) a piperidine ring optionally further substituted by 1 to 3 substituents selected from
(i) a halogen atom (e.g., a fluorine atom),
(ii) a hydroxy group, and
(iii) a cyano group;
Ring D is
(1) a benzene ring optionally further substituted by 1 to 3 substituents selected from
(i) a halogen atom (e.g., a fluorine atom, a chlorine atom),
(ii) a $C_{1-6}$ alkyl group (e.g., methyl), and
(iii) a $C_{1-6}$ alkoxy group (e.g., methoxy), or
(2) a pyridine ring optionally further substituted by 1 to 3 $C_{1-6}$ alkyl groups (e.g., methyl);
L is
(1) $—CH_2—O—CH_2—$,
(2) $—O—CR^1R^2—$ wherein $R^1$ and $R^2$ is each independently (1) a hydrogen atom, or (2) a $C_{1-6}$ alkyl group (e.g., methyl) optionally substituted by one substituent selected from a hydroxy group and a $C_{1-6}$ alkoxy group (e.g., methoxy),
(3) $—CH(R^1)—O—$ wherein $R^1$ is a hydrogen atom or a $C_{1-6}$ alkyl group (e.g., methyl),
(4) $—CF_2—CH_2—$, or
(5) $—CF_2—$;
X is a carbon atom or a nitrogen atom;
Y is a carbon atom or a nitrogen atom; and
Z is $—O—CH_2—$, $—CH_2—CH_2—$, $—CH{=}CH—$, $—CH_2—$ or $—O—$; provided that
7-((4-(phenoxymethyl)piperidin-1-yl)carbonyl)-1H-pyrido[2,3-b][1,4]oxazin-2(3H)-one,
7-((4-((3-methoxyphenoxy)methyl)piperidin-1-yl)carbonyl)-1H-pyrido[2,3-b][1,4]oxazin-2(3H)-one, and
7-((4-((2-methoxyphenoxy)methyl)piperidin-1-yl)carbonyl)-1H-pyrido[2,3-b][1,4]oxazin-2(3H)-one
are excluded.

Preferably, [Compound C-3] wherein
X is a carbon atom; and
Y is a carbon atom.

In another embodiment, preferably, [Compound C-3] wherein
Ring B is
(1) an azetidine ring optionally further substituted by 1 to 3 substituents selected from
(i) a halogen atom (e.g., a fluorine atom), and
(ii) a $C_{1-6}$ alkyl group (e.g., methyl).

[Compound C'-3]

Compound (I) wherein
m and n are both 0 or both 1;
Ring A is
(1) a phenyl group optionally further substituted by 1 to 3 substituents selected from
(i) a halogen atom (e.g., a fluorine atom, a chlorine atom, a bromine atom),
(ii) an optionally halogenated $C_{1-6}$ alkoxy group (e.g., methoxy, trifluoromethoxy, difluoromethoxy, trifluoroethoxy),
(iii) a cyano group,
(iv) a $C_{1-6}$ alkyl group (e.g., methyl, isopropyl, tert-butyl) optionally substituted by 1 to 3 substituents selected from
(a) a halogen atom (e.g., a fluorine atom), and
(b) a hydroxy group,
(v) a $C_{3-10}$ cycloalkyl group (e.g., cyclopropyl, cyclopentyl),
(vi) a $C_{2-6}$ alkenyl group (e.g., propenyl),
(vii) a $C_{1-6}$ alkoxy-carbonyl group (e.g., methoxycarbonyl),
(viii) a $C_{1-6}$ alkylsulfonyl group (e.g., methylsulfonyl),
(ix) a phenyl group optionally substituted by 1 to 3 $C_{1-6}$ alkoxy groups (e.g., methoxy),
(x) a phenoxy group,
(xi) a pyridyl group optionally substituted by 1 to 3 substituents selected from
(a) a halogen atom (e.g., a fluorine atom, a chlorine atom), and
(b) a $C_{1-6}$ alkyl group (e.g., methyl, ethyl) optionally substituted by 1 to 3 halogen atoms (e.g., a fluorine atom),
(xii) a pyrazolyl group optionally substituted by 1 to 3 substituents selected from
(a) a $C_{1-6}$ alkyl group (e.g., methyl, isobutyl) optionally substituted by 1 to 3 halogen atoms (e.g., a fluorine atom), and
(b) a $C_{3-10}$ cycloalkyl group (e.g., cyclopropyl),
(xiii) a pyrrolyl group optionally substituted by 1 to 3 $C_{1-6}$ alkyl groups (e.g., methyl),
(xiv) a pyrimidinyl group optionally substituted by 1 to 3 $C_{1-6}$ alkyl groups (e.g., methyl) optionally substituted by 1 to 3 halogen atoms (e.g., a fluorine atom),
(xv) a thiazolyl group optionally substituted by 1 to 3 $C_{1-6}$ alkyl groups (e.g., methyl),
(xvi) an oxadiazolyl group,
(xvii) a dihydropyranyl group,
(xviii) a dihydrobenzofuryl group,
(xix) a tetrahydropyridyl group optionally substituted by 1 to 3 $C_{1-6}$ alkyl groups (e.g., methyl), and
(xx) an azetidinyl group optionally substituted by 1 to 3 halogen atoms (e.g., a fluorine atom), (2) a naphthyl group,
(3) an indanyl group (preferably 2,3-dihydroinden-5-yl),
(4) a tetrahydronaphthyl group (preferably 5,6,7,8-tetrahydronaphthalen-2-yl) optionally further substituted by 1 to 3 halogen atoms (e.g., a bromine atom),
(5) a pyridyl group optionally further substituted by 1 to 3 substituents selected from
(i) a halogen atom (e.g., a chlorine atom),
(ii) a $C_{1-6}$ alkyl group (e.g., methyl), and
(iii) a pyridyl group optionally substituted by 1 to 3 $C_{1-6}$ alkyl groups (e.g., ethyl),
(6) an imidazopyridyl group optionally further substituted by 1 to 3 phenyl groups optionally substituted by 1 to 3 halogen atoms (e.g., a fluorine atom),
(7) a benzothiazolyl group optionally further substituted by 1 to 3 $C_{1-6}$ alkyl groups (e.g., methyl),
(8) an indazolyl group optionally further substituted by 1 to 3 $C_{1-6}$ alkyl-carbonyl groups (e.g., acetyl),
(9) a pyrazolyl group optionally further substituted by 1 to 3 substituents selected from
(i) a $C_{1-6}$ alkyl group (e.g., methyl), and
(ii) a pyridyl group,
(10) a benzoxazolyl group optionally further substituted by 1 to 3 $C_{1-6}$ alkyl groups (e.g., methyl),
(11) a benzisoxazolyl group optionally further substituted by 1 to 3 halogen atoms (e.g., a chlorine atom),
(12) a quinoxalinyl group,
(13) a quinolyl group,
(14) an isoquinolyl group,
(15) a pyrazolopyridyl group optionally further substituted by 1 to 3 phenyl groups,
(16) a $C_{3-10}$ cycloalkyl group (e.g., cyclopropyl, cyclohexyl) optionally further substituted by 1 to 3 halogen atoms (e.g., a fluorine atom),
(17) a tetrahydropyranyl group,
(18) a dihydrobenzofuryl group optionally further substituted by 1 to 3 $C_{1-6}$ alkyl groups (e.g., methyl), or
(19) a dihydropyranopyridyl group;
Ring B is
(1) an azetidine ring optionally further substituted by 1 to 3 substituents selected from
(i) a halogen atom (e.g., a fluorine atom), and
(ii) a $C_{1-6}$ alkyl group (e.g., methyl), or
(2) a piperidine ring optionally further substituted by 1 to 3 substituents selected from
(i) a halogen atom (e.g., a fluorine atom),
(ii) a hydroxy group, and
(iii) a cyano group;
Ring D is
(1) a benzene ring optionally further substituted by 1 to 3 substituents selected from
(i) a halogen atom (e.g., a fluorine atom, a chlorine atom),
(ii) a $C_{1-6}$ alkyl group (e.g., methyl), and
(iii) a $C_1$— alkoxy group (e.g., methoxy), or
(2) a pyridine ring optionally further substituted by 1 to 3 $C_{1-6}$ alkyl groups (e.g., methyl);
L is
(1) —$CH_2$—O—$CH_2$—,
(2) —O—$CR^1R^2$— wherein $R^1$ and $R^2$ is each independently (1) a hydrogen atom, or (2) a $C_{1-6}$ alkyl group (e.g., methyl) optionally substituted by one $C_{1-6}$ alkoxy group (e.g., methoxy),
(3) —CH($R^1$)—O— wherein $R^1$ is a hydrogen atom or a $C_{1-6}$ alkyl group (e.g., methyl),
(4) —$CF_2$—$CH_2$—, or
(5) —$CF_2$—;
X is a carbon atom or a nitrogen atom;
Y is a carbon atom or a nitrogen atom; and
Z is —O—$CH_2$—, —CH═CH—, —$CH_2$— or —O—;
provided that
7-((4-(phenoxymethyl)piperidin-1-yl)carbonyl)-1H-pyrido[2,3-b][1,4]oxazin-2(3H)-one,
7-((4-((3-methoxyphenoxy)methyl)piperidin-1-yl)carbonyl)-1H-pyrido[2,3-b][1,4]oxazin-2(3H)-one, and
7-((4-((2-methoxyphenoxy)methyl)piperidin-1-yl)carbonyl)-1H-pyrido[2,3-b][1,4]oxazin-2(3H)-one
are excluded.

Preferably, [Compound C'-3] wherein
X is a carbon atom; and
Y is a carbon atom.

In another embodiment, preferably, [Compound C'-3] wherein Ring B is
(1) an azetidine ring optionally further substituted by 1 to 3 substituents selected from
(i) a halogen atom (e.g., a fluorine atom), and
(ii) a $C_{1-6}$ alkyl group (e.g., methyl).

[Compound D'-3]

Compound (I) wherein
m and n are both 0 or both 1;
Ring A is
(1) a phenyl group further substituted by 1 to 3 substituents selected from
(i) a halogen atom (e.g., a fluorine atom, a chlorine atom),
(ii) a cyano group,
(iii) an optionally halogenated $C_{1-6}$ alkyl group (e.g., methyl, trifluoromethyl),
(iv) a $C_{2-6}$ alkenyl group (e.g., propenyl),
(v) a pyridyl group optionally substituted by 1 to 3 substituents selected from
(a) a halogen atom (e.g., a fluorine atom), and
(b) a $C_{1-6}$ alkyl group (e.g., methyl), and
(vi) an azetidinyl group optionally substituted by 1 to 3 halogen atoms (e.g., a fluorine atom),
(2) an indanyl group (preferably 2,3-dihydroinden-5-yl),
(3) a tetrahydronaphthyl group (preferably 5,6,7,8-tetrahydronaphthalen-2-yl), or
(4) a pyridyl group optionally further substituted by 1 to 3 halogen atoms (e.g., a chlorine atom);
Ring B is
(1) an azetidine ring, or
(2) a piperidine ring optionally further substituted by 1 to 3 hydroxy groups;
Ring D is
(1) a benzene ring optionally further substituted by 1 to 3 substituents selected from
(i) a halogen atom (e.g., a fluorine atom, a chlorine atom),
(ii) a $C_{1-6}$ alkyl group (e.g., methyl), and
(iii) a $C_{1-6}$ alkoxy group (e.g., methoxy), or
(2) a pyridine ring;
L is —O—$CH_2$— or —$CH_2$—O—;
X is a carbon atom;
Y is a carbon atom or a nitrogen atom; and
Z is —O—$CH_2$— or —O—.

Preferably, [Compound D'-3] wherein Y is a carbon atom.

In another embodiment, preferably, [Compound D'-3] wherein Ring B is (1) an azetidine ring.

[Compound D-3]

Compound (I) wherein
m and n are both 0 or both 1;
Ring A is
(1) a phenyl group further substituted by 1 to 3 substituents selected from
(i) a halogen atom (e.g., a fluorine atom, a chlorine atom),
(ii) a cyano group, (iii) an optionally halogenated $C_{1-6}$ alkyl group (e.g., methyl, trifluoromethyl),
(iv) a $C_{2-6}$ alkenyl group (e.g., propenyl), and
(v) an azetidinyl group optionally substituted by 1 to 3 halogen atoms (e.g., a fluorine atom),
(2) an indanyl group (preferably 2,3-dihydroinden-5-yl),
(3) a tetrahydronaphthyl group (preferably 5,6,7,8-tetrahydronaphthalen-2-yl), or
(4) a pyridyl group optionally further substituted by 1 to 3 halogen atoms (e.g., a chlorine atom);
Ring B is
(1) an azetidine ring, or
(2) a piperidine ring optionally further substituted by 1 to 3 hydroxy groups;
Ring D is
(1) a benzene ring optionally further substituted by 1 to 3 substituents selected from
(i) a halogen atom (e.g., a fluorine atom, a chlorine atom),
(ii) a $C_{1-6}$ alkyl group (e.g., methyl), and
(iii) a $C_{1-6}$ alkoxy group (e.g., methoxy), or
(2) a pyridine ring;
L is —O—$CH_2$— or —$CH_2$—O—;
X is a carbon atom;
Y is a carbon atom or a nitrogen atom; and
Z is —O—$CH_2$— or —O—.

Preferably, [Compound D-3] wherein Y is a carbon atom.

In another embodiment, preferably, [Compound D-3] wherein Ring B is (1) an azetidine ring.

[Compound E'-3]

Compound (I) wherein
m and n are both 0 or both 1;
Ring A is
(1) a phenyl group further substituted by 1 to 3 substituents selected from
(i) a halogen atom (e.g., a fluorine atom, a chlorine atom),
(ii) a cyano group,
(iii) an optionally halogenated $C_{1-6}$ alkyl group (e.g., trifluoromethyl),
(iv) a pyridyl group optionally substituted by 1 to 3 substituents selected from
(a) a halogen atom (e.g., a fluorine atom), and
(b) a $C_{1-6}$ alkyl group (e.g., methyl), and
(v) an azetidinyl group optionally substituted by 1 to 3 halogen atoms (e.g., a fluorine atom),
(2) a tetrahydronaphthyl group (preferably 5,6,7,8-tetrahydronaphthalen-2-yl), or
(3) a pyridyl group optionally further substituted by 1 to 3 halogen atoms (e.g., a chlorine atom);
Ring B is an azetidine ring or a piperidine ring;
Ring D is
(1) a benzene ring optionally further substituted by 1 to 3 halogen atoms (e.g., a fluorine atom), or
(2) a pyridine ring;
L is —O—$CH_2$— or —$CH_2$—O—;
X is a carbon atom;
Y is a carbon atom or a nitrogen atom; and
Z is —O—$CH_2$—.

Preferably, [Compound E'-3] wherein Y is a carbon atom.

In another embodiment, preferably, [Compound E'-3] wherein Ring B is an azetidine ring.

[Compound E-3]

Compound (I) wherein
m and n are both 0 or both 1;
Ring A is
(1) a phenyl group further substituted by 1 to 3 substituents selected from
(i) a halogen atom (e.g., a fluorine atom, a chlorine atom),
(ii) a cyano group,
(iii) an optionally halogenated $C_{1-6}$ alkyl group (e.g., trifluoromethyl), and
(iv) an azetidinyl group optionally substituted by 1 to 3 halogen atoms (e.g., a fluorine atom),
(2) a tetrahydronaphthyl group (preferably 5,6,7,8-tetrahydronaphthalen-2-yl), or
(3) a pyridyl group optionally further substituted by 1 to 3 halogen atoms (e.g., a chlorine atom);
Ring B is an azetidine ring or a piperidine ring;
Ring D is
(1) a benzene ring optionally further substituted by 1 to 3 halogen atoms (e.g., a fluorine atom), or
(2) a pyridine ring;
L is —O—$CH_2$— or —$CH_2$—O—;
X is a carbon atom;
Y is a carbon atom or a nitrogen atom; and
Z is —O—$CH_2$—.

Preferably, [Compound E-3] wherein Y is a carbon atom.

In another embodiment, preferably, [Compound E-3] wherein Ring B is an azetidine ring.

[Compound F-3]

Compound (I) wherein
m and n are both 0;
Ring A is
(1) a phenyl group further substituted by 1 to 3 substituents selected from
(i) a pyridyl group optionally substituted by 1 to 3 substituents selected from
(a) a halogen atom (e.g., a fluorine atom), and
(b) a $C_{1-6}$ alkyl group (e.g., methyl), and
(ii) an azetidinyl group optionally substituted by 1 to 3 halogen atoms (e.g., a fluorine atom);
Ring B is an azetidine ring;
Ring D is a benzene ring further substituted by 1 to 3 halogen atoms (e.g., a fluorine atom);
L is —O—$CH_2$— or —$CH_2$—O—;
X is a carbon atom;
Y is a carbon atom; and
Z is —O—$CH_2$—.

[Compound G-3]

Compound (I) wherein
m and n are both 0;
Ring A is
(1) a phenyl group further substituted by 1 to 3 substituents selected from
(i) a halogen atom (e.g., a fluorine atom, a chlorine atom),
(ii) an optionally halogenated $C_{1-6}$ alkyl group (e.g., trifluoromethyl), and
(iii) an azetidinyl group optionally substituted by 1 to 3 halogen atoms (e.g., a fluorine atom), or
(2) a tetrahydronaphthyl group (preferably 5,6,7,8-tetrahydronaphthalen-2-yl);
Ring B is an azetidine ring;
Ring D is a benzene ring further substituted by 1 to 3 halogen atoms (e.g., a fluorine atom);
L is —O—$CH_2$— or —$CH_2$—O—;
X is a carbon atom;
Y is a carbon atom; and
Z is —O—$CH_2$—.

[Compound H-3]

7-fluoro-6-((3-((5,6,7,8-tetrahydronaphthalen-2-yloxy)methyl)azetidin-1-yl)carbonyl)-2H-1,4-benzoxazin-3(4H)-one, or a salt thereof;
7-fluoro-6-((3-((2-fluoro-4-(trifluoromethyl)phenoxy)methyl)azetidin-1-yl)carbonyl)-2H-1,4-benzoxazin-3(4H)-one, or a salt thereof;

6-((3-((2-chloro-4-(3-fluoroazetidin-1-yl)phenoxy)methyl)azetidin-1-yl)carbonyl)-7-fluoro-2H-1,4-benzoxazin-3(4H)-one, or a salt thereof; and 6-((3-((2-chloro-4-fluorobenzyl)oxy)azetidin-1-yl)carbonyl)-7-fluoro-2H-1,4-benzoxazin-3(4H)-one, or a salt thereof.

Specific examples of compound (I) include the compounds of Examples 1 and 5 to 356.

When compound (I) is a salt, examples of the salt include metal salts, ammonium salts, salts with organic base, salts with inorganic acid, salts with organic acid, salts with basic or acidic amino acid, and the like. Preferable examples of the metal salt include alkali metal salts such as sodium salts, potassium salts and the like; alkali earth metal salts such as calcium salts, magnesium salts, barium salts and the like; and aluminum salts. Preferable examples of the salt with organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with inorganic acid include salts with hydrochloric acid, hydrobromic acid, nitric acid, sulfuric acid, phosphoric acid and the like. Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salts with basic amino acid include salts with arginine, lysine, ornithine and the like. Preferable examples of the salt with acidic amino acid include salts with aspartic acid, glutamic acid and the like. Among them, a pharmaceutically acceptable salt is preferable. For example, when a compound has an acidic functional group, examples of the salt include inorganic salts such as alkali metal salts (e.g., sodium salt, potassium salt etc.), alkaline earth metal salts (e.g., calcium salt, magnesium salt etc.) and the like, ammonium salt etc., and when a compound has a basic functional group, examples of the salt include salts with inorganic acid such as hydrochloric acid, hydrobromic acid, nitric acid, sulfuric acid, phosphoric acid and the like, and salts with organic acid such as acetic acid, phthalic acid, fumaric acid, oxalic acid, tartaric acid, maleic acid, citric acid, succinic acid, methanesulfonic acid, benzenesulfonic acid, p-toluenesulfonic acid and the like.

When compound (I) contains isomers such as tautomers, optical isomers, stereoisomers, position isomers and rotational isomers, any of isomers or mixture are also encompassed in the compound of the present invention. Further, when compound (I) contains an optical isomer, the optical isomer separated from the racemate is encompassed in compound (I).

Compound (I) can be obtained in the crystal form. Either single crystalline form or crystalline mixture can be encompassed in compound (I).

Compound (I) can be a pharmaceutically acceptable cocrystal or a co-crystal salt. The co-crystal or co-crystal salt as used herein means a crystalline material composed of two or more unique solids at room temperature, each of which has distinctive physical characteristics such as structure, melting point, and heats of fusion, hygroscopicity, solubility, and stability. A co-crystal or a co-crystal salt can be produced according to co-crystallization method known per se.

Compound (I) may be a solvate (e.g., a hydrate) or a non-solvate and both are encompassed in compound (I).

Compounds labeled with or substituted by isotopes (e.g., $^{2}H$, $^{3}H$, $^{11}C$, $^{14}C$, $^{18}F$, $^{35}S$, $^{125}I$, etc.) are also encompassed in compound (I). The compound labeled with or substituted by isotopes can be used as, for example, a tracer used for Positron Emission Tomography (PET) (PET tracer), and are expected to be useful in the field of medical diagnosis and the like.

The production method of the compound of the present invention is explained below.

The raw material compound and reagent used and the compound obtained in each step in the following production method may be each in a form of a salt, and examples of such salt include those similar to the salts of the compound of the present invention and the like.

When the compound obtained in each step is a free form, it can be converted to the objective salt according to a method known per se. When the compound obtained in each step is a salt, it can be converted to the objective free form or the other salt according to a method known per se.

The compound obtained in each step can be used directly as the reaction mixture or as a crude product for the next reaction. Alternatively, the compound obtained in each step can be isolated and purified from a reaction mixture according to a method known per se, for example, a separation means such as concentration, crystallization, recrystallization, distillation, solvent extraction, fractional distillation, column chromatography and the like.

When the raw material compound and reagent used in each step are commercially available, the commercially available product can also be used directly.

In the reaction in each step, while the reaction time varies depending on the kind of the reagent and solvent to be used, it is generally 1 min-48 hr, preferably 10 min-8 hr, unless otherwise specified.

In the reaction in each step, while the reaction temperature varies depending on the kind of the reagent and solvent to be used, it is generally −78° C.-300° C., preferably −78° C.-150° C., unless otherwise specified.

In the reaction in each step, while the pressure varies depending on the kind of the reagent and solvent to be used, it is generally 1 atm-20 atm, preferably 1 atm-3 atm, unless otherwise specified.

Microwave synthesizer such as Initiator manufactured by Biotage and the like may be used for the reaction in each step. While the reaction temperature varies depending on the kind of the reagent and solvent to be used, it is generally room temperature—300° C., preferably 50° C.-250° C., unless otherwise specified. While the reaction time varies depending on the kind of the reagent and solvent to be used, it is generally 1 min-48 hr, preferably 1 min-8 hr, unless otherwise specified.

In the reaction in each step, the reagent is used in an amount of 0.5 equivalents-20 equivalents, preferably 0.8 equivalents-5 equivalents, relative to the substrate, unless otherwise specified. When the reagent is used as a catalyst, the reagent is used in an amount of 0.001 equivalent-1 equivalent, preferably 0.01 equivalent-0.2 equivalent, relative to the substrate. When the reagent is used as a reaction solvent, the reagent is used in a solvent amount.

Unless otherwise specified, the reaction in each step is carried out without solvent, or by dissolving or suspending the raw material compound in a suitable solvent. Examples of the solvent include those described in Examples and the following solvents.

alcohols: methanol, ethanol, tert-butyl alcohol, 2-methoxyethanol and the like;

ethers: diethyl ether, diphenyl ether, tetrahydrofuran, 1,2-dimethoxyethane and the like;

aromatic hydrocarbons: chlorobenzene, toluene, xylene and the like;
saturated hydrocarbons: cyclohexane, hexane and the like;
amides: N,N-dimethylformamide, N-methylpyrrolidone and the like;
halogenated hydrocarbons: dichloromethane, carbon tetrachloride and the like;
nitriles: acetonitrile and the like;
sulfoxides: dimethyl sulfoxide and the like;
aromatic organic bases: pyridine and the like;
anhydrides: acetic anhydride and the like;
organic acids: formic acid, acetic acid, trifluoroacetic acid and the like;
inorganic acids: hydrochloric acid, sulfuric acid and the like;
esters: ethyl acetate and the like;
ketones: acetone, methyl ethyl ketone and the like; water.

The above-mentioned solvent can be used in a mixture of two or more kinds thereof in an appropriate ratio.

When a base is used for the reaction in each step, examples thereof include those described in Examples and the following bases.
inorganic bases: sodium hydroxide, magnesium hydroxide, sodium carbonate, calcium carbonate, sodium hydrogen carbonate and the like;
organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine and the like; metal alkoxides: sodium ethoxide, potassium tert-butoxide and the like;
alkali metal hydrides: sodium hydride and the like;
metal amides: sodium amide, lithium diisopropylamide, lithium hexamethyldisilazide and the like;
organic lithiums: n-butyllithium and the like.

When an acid or an acid catalyst is used for the reaction in each step, examples thereof include those described in Examples and the following acids and acid catalysts. inorganic acids: hydrochloric acid, sulfuric acid, nitric acid, hydrobromic acid, phosphoric acid and the like; organic acids: acetic acid, trifluoroacetic acid, citric acid, p-toluenesulfonic acid, 10-camphorsulfonic acid and the like; Lewis acid: boron trifluoride diethyl ether complex, zinc iodide, anhydrous aluminum chloride, anhydrous zinc chloride, anhydrous iron chloride and the like.

Unless otherwise specified, the reaction in each step is carried out according to a method known per se, for example, the method described in Jikken Kagaku Kouza, 5th Edition, vol. 13-19 (the Chemical Society of Japan ed.); Shin Jikken Kagaku Kouza, vol. 14-15 (the Chemical Society of Japan ed.); Fine Organic Chemistry, Revised 2nd Edition (L. F. Tietze, Th. Eicher, Nankodo); Organic Name Reactions, the Reaction Mechanism and Essence, Revised Edition (Hideo Togo, Kodansha); ORGANIC SYNTHESES Collective Volume I-VII (John Wiley & Sons Inc.); Modern Organic Synthesis in the Laboratory A Collection of Standard Experimental Procedures (Jie Jack Li, OXFORD UNIVERSITY); Comprehensive Heterocyclic Chemistry III, Vol. 1-Vol. 14 (Elsevier Japan); Strategic Applications of Named Reactions in Organic Synthesis (translated by Kiyoshi Tomioka, Kagakudojin); Comprehensive Organic Transformations (VCH Publishers Inc.), 1989, or the like, or the method described in Examples.

In each step, the protection or deprotection reaction of an functional group is carried out according to a method known per se, for example, the method described in "Protective Groups in Organic Synthesis, 4th Ed", Wiley-Interscience, Inc., 2007 (Theodora W. Greene, Peter G. M. Wuts); "Protecting Groups 3rd Ed." Thieme, 2004 (P. J. Kocienski), or the like, or the method described in Examples.

Examples of the protecting group for a hydroxy group of an alcohol and the like and a phenolic hydroxy group include ether-type protecting groups such as methoxymethyl ether, benzyl ether, tert-butyldimethylsilyl ether, tetrahydropyranyl ether and the like; carboxylate ester-type protecting groups such as acetate ester and the like; sulfonate ester-type protecting groups such as methanesulfonate ester and the like; carbonate ester-type protecting groups such as tert-butylcarbonate and the like, and the like.

Examples of the protecting group for a carbonyl group of an aldehyde include acetal-type protecting groups such as dimethylacetal and the like; cyclic acetal-type protecting groups such as 1,3-dioxane and the like, and the like.

Examples of the protecting group for a carbonyl group of a ketone include ketal-type protecting groups such as dimethylketal and the like; cyclic ketal-type protecting groups such as 1,3-dioxane and the like; oxime-type protecting groups such as O-methyloxime and the like; hydrazone-type protecting groups such as N,N-dimethylhydrazone and the like, and the like.

Examples of the protecting group for a carboxyl group include ester-type protecting groups such as methyl ester and the like; amide-type protecting groups such as N,N-dimethylamide and the like, and the like.

Examples of the protecting group for a thiol include ether-type protecting groups such as benzyl thioether and the like; ester-type protecting groups such as thioacetate ester, thiocarbonate, thiocarbamate and the like, and the like.

Examples of the protecting group for an amino group and an aromatic heterocycle such as imidazole, pyrrole, indole and the like include carbamate-type protecting groups such as benzyl carbamate and the like; amide-type protecting groups such as acetamide and the like; alkyl amine-type protecting groups such as N-triphenylmethylamine and the like; sulfonamide-type protecting groups such as methanesulfonamide and the like, and the like.

The protecting groups can be removed according to a method known per se, for example, by employing a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide) and the like, a reduction method, and the like.

When reduction reaction is carried out in each step, examples of the reducing agent to be used include metal hydrides such as lithium aluminum hydride, sodium triacetoxyborohydride, sodium cyanoborohydride, diisobutylaluminum hydride (DIBAL-H), sodium borohydride, tetramethylammonium triacetoxyborohydride and the like; boranes such as borane tetrahydrofuran complex and the like; Raney nickel; Raney cobalt; hydrogen; formic acid; triethylsilane and the like. When carbon-carbon double bond or triple bond is reduced, a method using a catalyst such as palladium-carbon, Lindlar's catalyst and the like may be employed.

When oxidation reaction is carried out in each step, examples of the oxidizing agent to be used include peroxides such as m-chloroperbenzoic acid (MCPBA), hydrogen peroxide, tert-butylhydroperoxide and the like; perchlorates such as tetrabutylammonium perchlorate and the like; chlorates such as sodium chlorate and the like; chlorites such as sodium chlorite and the like; periodates such as sodium periodate and the like; hypervalent iodine reagents such as iodosylbenzene and the like; reagents containing manganese such as manganese dioxide, potassium permanganate and the like; leads such as lead tetraacetate and the like; reagents containing chromium such as pyridinium chlorochromate (PCC), pyridinium dichromate (PDC), Jones reagent and the like; halogen compounds such as N-bromosuccinimide (NBS) and the like; oxygen; ozone; sulfur trioxide-pyridine complex; osmium tetroxide; selenium dioxide; 2,3-dichloro-5,6-dicyano-1,4-benzoquinone (DDQ) and the like.

When radical cyclization reaction is carried out in each step, examples of the radical initiator to be used include azo compounds such as azobisisobutyronitrile (AIBN) and the like; water-soluble radical initiators such as 4-4'-azobis-4-cyanopentanoic acid (ACPA) and the like; triethylboron in the presence of air or oxygen; benzoyl peroxide and the like. Examples of the radical reagent to be used include tributylstannane, tristrimethylsilylsilane, 1,1,2,2-tetraphenyldisilane, diphenylsilane, samarium iodide and the like.

When Wittig reaction is carried out in each step, examples of the Wittig reagent to be used include alkylidene phosphoranes and the like. The alkylidene phosphoranes can be prepared according to a method known per se, for example, by reacting a phosphonium salt with a strong base.

When Horner-Emmons reaction is carried out in each step, examples of the reagent to be used include phosphonoacetates such as methyl dimethylphosphonoacetate, ethyl diethylphosphonoacetate and the like; and bases such as alkali metal hydrides, organic lithiums and the like.

When Friedel-Crafts reaction is carried out in each step, a combination of a Lewis acid and an acid chloride or a combination of a Lewis acid and an alkylating agent (e.g., an alkyl halide, an alcohol, an olefin etc.) is used as a reagent. Alternatively, an organic acid or an inorganic acid can also be used instead of a Lewis acid, and an anhydride such as acetic anhydride and the like can also be used instead of an acid chloride.

When aromatic nucleophilic substitution reaction is carried out in each step, a nucleophile (e.g., an amine, imidazole etc.) and a base (e.g., an inorganic base, an organic base etc.) are used as a reagent.

When nucleophilic addition reaction by a carbo anion, nucleophilic 1,4-addition reaction (Michael addition reaction) by a carbo anion or nucleophilic substitution reaction by a carbo anion is carried out in each step, and examples of the base to be used for generation of the carbo anion include organic lithiums, metal alkoxides, inorganic bases, organic bases and the like.

When Grignard reagent is carried out in each step, examples of the Grignard reagent to be used include arylmagnesium halides such as phenylmagnesium bromide and the like; and alkylmagnesium halides such as methylmagnesium bromide and the like. The Grignard reagent can be prepared according to a method known per se, for example, by reacting an alkyl halide or an aryl halide with a metal magnesium in an ether or tetrahydrofuran as a solvent.

When Knoevenagel condensation reaction is carried out in each step, a compound having an activated methylene group with two electron withdrawing groups (e.g., malonic acid, diethyl malonate, malononitrile etc.) and a base (e.g., an organic base, a metal alkoxide, an inorganic base) are used as a reagent.

When Vilsmeier-Haack reaction is carried out in each step, phosphoryl chloride and an amide derivative (e.g., N,N-dimethylformamide etc.) are used as a reagent.

When azidation reaction of an alcohol, an alkyl halide or a sulfonate is carried out in each step, examples of the azidating agent to be used include diphenylphosphorylazide (DPPA), trimethylsilylazide, sodium azide and the like. For example, for the azidation reaction of an alcohol, a method using diphenylphosphorylazide and 1,8-diazabicyclo[5.4.0]undec-7-ene (DBU), a method using trimethylsilylazide and a Lewis acid, and the like are employed.

When reductive amination reaction is carried out in each step, examples of the reducing agent to be used include sodium triacetoxyborohydride, sodium cyanoborohydride, hydrogen, formic acid and the like. When the substrate is an amine compound, examples of the carbonyl compound to be used include paraformaldehyde, aldehydes such as acetaldehyde and the like, and ketones such as cyclohexanone and the like. When the substrate is a carbonyl compound, examples of the amine to be used include ammonia, primary amines such as methylamine and the like; secondary amines such as dimethylamine and the like, and the like.

When Mitsunobu reaction is carried out in each step, an azodicarboxylate (e.g., diethyl azodicarboxylate (DEAD), diisopropyl azodicarboxylate (DIAD) etc.), triphenylphosphine, tri-n-butylphosphine and the like are used as a reagent.

When esterification reaction, amidation reaction or urea formation reaction is carried out in each step, examples of the reagent to be used include acyl halides such as acid chlorides, acid bromides and the like; activated carboxylic acids such as anhydrides, activated esters, sulfates and the like. Examples of the activating agent of the carboxylic acid include carbodiimide condensing agents such as 1-ethyl-3-(3-dimethylaminopropyl)carbodiimide hydrochloride (EDCI) and the like; triazine condensing agents such as 4-(4,6-dimethoxy-1,3,5-triazin-2-yl)-4-methylmorpholinium chloride n-hydrate (DMT-MM) and the like; carbonate condensing agents such as 1,1-carbonyldiimidazole (CDI) and the like; diphenylphosphoryl azide (DPPA); benzotriazol-1-yloxy-trisdimethylaminophosphonium salt (BOP reagent); 2-chloro-1-methyl-pyridinium iodide (Mukaiyama reagent); thionyl chloride; lower alkyl haloformates such as ethyl chloroformate and the like; O-(7-azabenzotriazol-1-yl)-N,N,N',N'-tetramethyluronium hexafluorophosphorate (HATU); sulfuric acid; combinations thereof and the like. When carbodiimide condensing agent is used, an additive such as 1-hydroxybenzotriazole (HOBt), N-hydroxysuccinimide (HOSu), dimethylaminopyridine (DMAP) and the like may be added to the reaction system.

When coupling reaction is carried out in each step, examples of the metal catalyst to be used include palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocene palladium(II) chloride, palladium (II) acetate and the like; nickel compounds such as tetrakis(triphenylphosphine)nickel(0) and the like; rhodium compounds such as tris(triphenylphosphine)rhodium(III) chloride and the like; cobalt compounds; copper compounds such as copper oxide, copper(I) iodide and the like; platinum compounds and the like. In addition, a base can be added to the reaction system, and examples thereof include inorganic bases, metal alkoxides and the like.

When thiocarbonylation reaction is carried out in each step, phosphorus pentasulfide is typically used as the thiocarbonylating agent. Alternatively, a reagent having a 1,3,2,4-dithiadiphosphetane-2,4-disulfide structure (e.g., 2,4-bis(4-methoxyphenyl)-1,3,2,4-dithiadiphosphetane-2,4-disulfide (Lawesson reagent) etc.) can also be used instead of phosphorus pentasulfide.

When Wohl-Ziegler reaction is carried out in each step, examples of the halogenating agent to be used include N-iodosuccinimide, N-bromosuccinimide (NBS), N-chlorosuccinimide (NCS), bromine, sulfuryl chloride and the like. In addition, the reaction can be accelerated by subjecting a radical initiator such as heat, light, benzoyl peroxide, azobisisobutyronitrile and the like to the reaction system reaction.

When halogenation reaction of a hydroxy group is carried out in each step, examples of the halogenating agent to be used include hydrohalic acids and acid halides of inorganic acids, specifically, hydrochloric acid, thionyl chloride, phosphorus oxychloride and the like for chlorination, 48% hydrobromic acid and the like for bromination. In addition, a method of producing an alkyl halide by reacting an alcohol with triphenylphosphine and carbon tetrachloride or carbon tetrabromide or the like can be employed. Alternatively, a method of producing an alkyl halide via two step comprising converting an alcohol to the corresponding sulfonate, and then reacting the sulfonate with lithium bromide, lithium chloride or sodium iodide can also be employed.

When Arbuzov reaction is carried out in each step, examples of the reagent to be used include alkyl halides such as ethyl bromoacetate and the like; and phosphites such as triethyl phosphite, tri(isopropyl) phosphite and the like.

When sulfonate esterification reaction is carried out in each step, examples of the sulfonating agent to be used include methanesulfonyl chloride, p-toluenesulfonyl chloride, methanesulfonic anhydride, p-toluenesulfonic anhydride and the like.

When hydrolysis reaction is carried out in each step, an acid or a base is used as a reagent. For acid hydrolysis reaction of tert-butyl ester, formic acid, triethylsilane and the like may be added to reductively-trap tert-butyl cation which is by-produced.

When dehydration reaction is carried out in each step, examples of the dehydrating agent to be used include sulfuric acid, diphosphorus pentaoxide, phosphorus oxychloride, N,N'-dicyclohexylcarbodiimide, alumina, polyphosphoric acid and the like.

Compound (I) of the present invention can be produced according Production Methods A to H explained below.

Each symbol in the formulas of the schemes is as defined above, unless otherwise specified. In the formulas, $P^1$ to $P^7$ are each a protecting group, specifically, $P^1$ or $p^4$ to $P^7$: a "protecting group for an amino group", $P^2$: a "protecting group for a hydroxyl group", $P^3$: a "protecting group for a cyclic amido group". Examples of the "protecting group for an amino group" include tert-butoxycarbonyl group and the like, in addition to those exemplified as the above-mentioned protecting group for an amino group. Examples of the "protecting group for a cyclic amido group" include a methoxymethyl group, a 2-(trimethylsilyl)ethoxymethyl group and the like. $LG^1$ to $LG^8$ are each a "leaving group", and $R^a$ is an optionally substituted $C_{1-6}$ alkyl group. Examples of the "leaving group" include a halogen atom (e.g., a fluorine atom, a chlorine atom, a bromine atom, an iodine atom etc.), an optionally halogenated $C_{1-6}$ alkylsulfonyloxy group (e.g., methanesulfonyloxy, ethanesulfonyloxy, trifluoromethanesulfonyloxy etc.), an optionally substituted $C_{6-14}$ arylsulfonyloxy group [e.g., a $C_{6-14}$ arylsulfonyloxy group optionally having 1 to 3 substituents selected from a $C_{1-6}$ alkyl group (e.g., methyl, etc.), a $C_{1-6}$ alkoxy group (e.g., methoxy, etc.) and a nitro group, and the like, and specific examples thereof include benzenesulfonyloxy, m-nitrobenzenesulfonyloxy, p-toluenesulfonyloxy, naphthylsulfonyloxy and the like] and the like.

[Production Method A]

Compound (I) of the present invention can be produced from compound (2) according to the following method.

(Scheme 1)

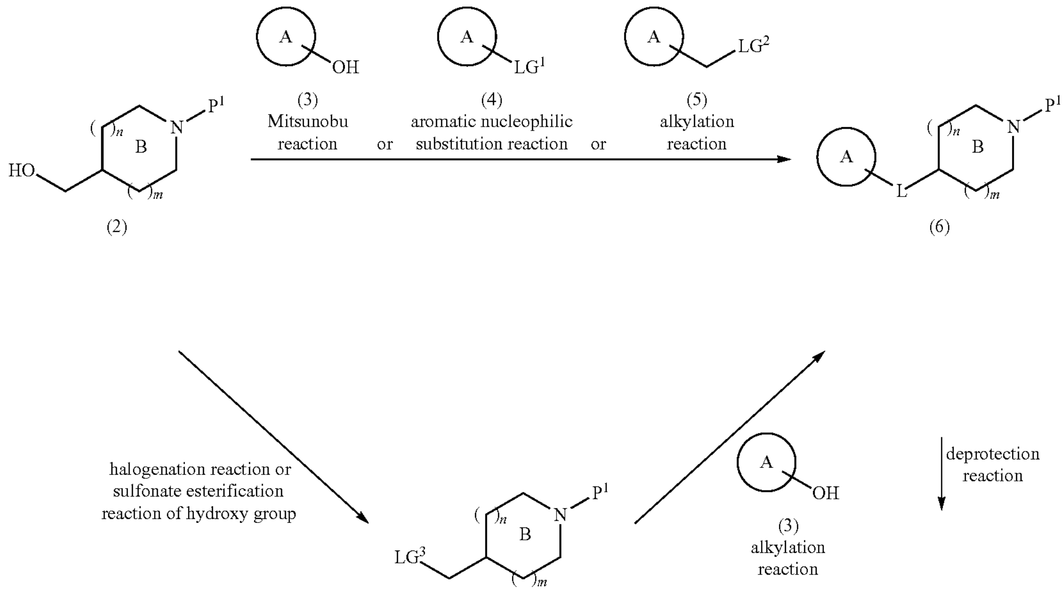

(3) (4) (5) (2) (6) (3) (7)

-continued

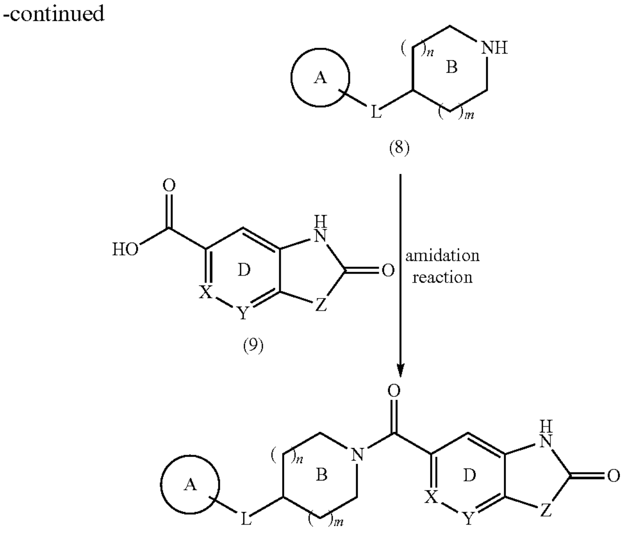

(8)

(9)

(I)

Compound (6) can be produced by subjecting compound (2) and compound (3), or compound (2) and compound (4) to the above-mentioned reaction. Alternatively, compound (6) can also be produced by subjecting compound (2) and compound (5), or compound (7) and compound (3) to an alkylation reaction in the presence of a base. Examples of the base include potassium carbonate, tripotassium phosphate, triethylamine, N,N-diisopropylethylamine, pyridine, sodium ethoxide, potassium tert-butoxide, sodium hydride, lithium hexamethyldisilazide, sodium hexamethyldisilazide, n-butyl lithium and the like.

[Production Method B]

Compound (I) of the present invention can be produced from compound (2) according to the following method.

(Scheme 2)

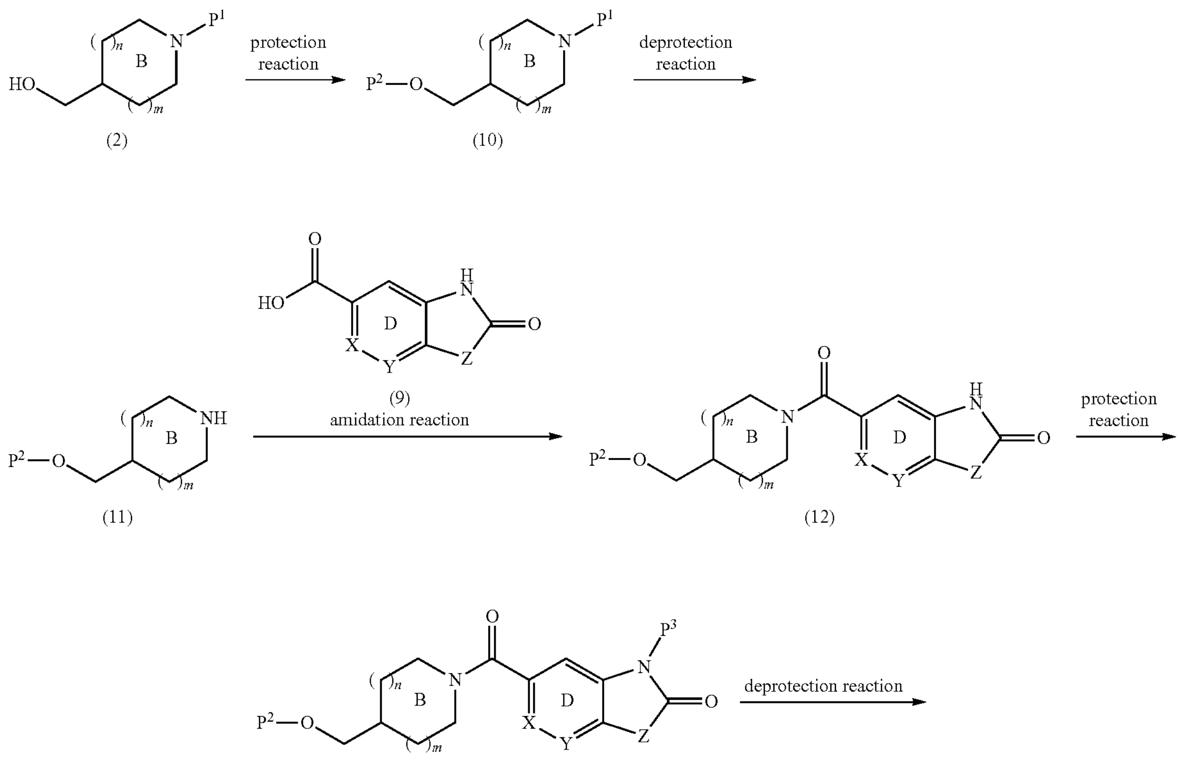

(2) (10) (9) (11) (12) (13)

-continued

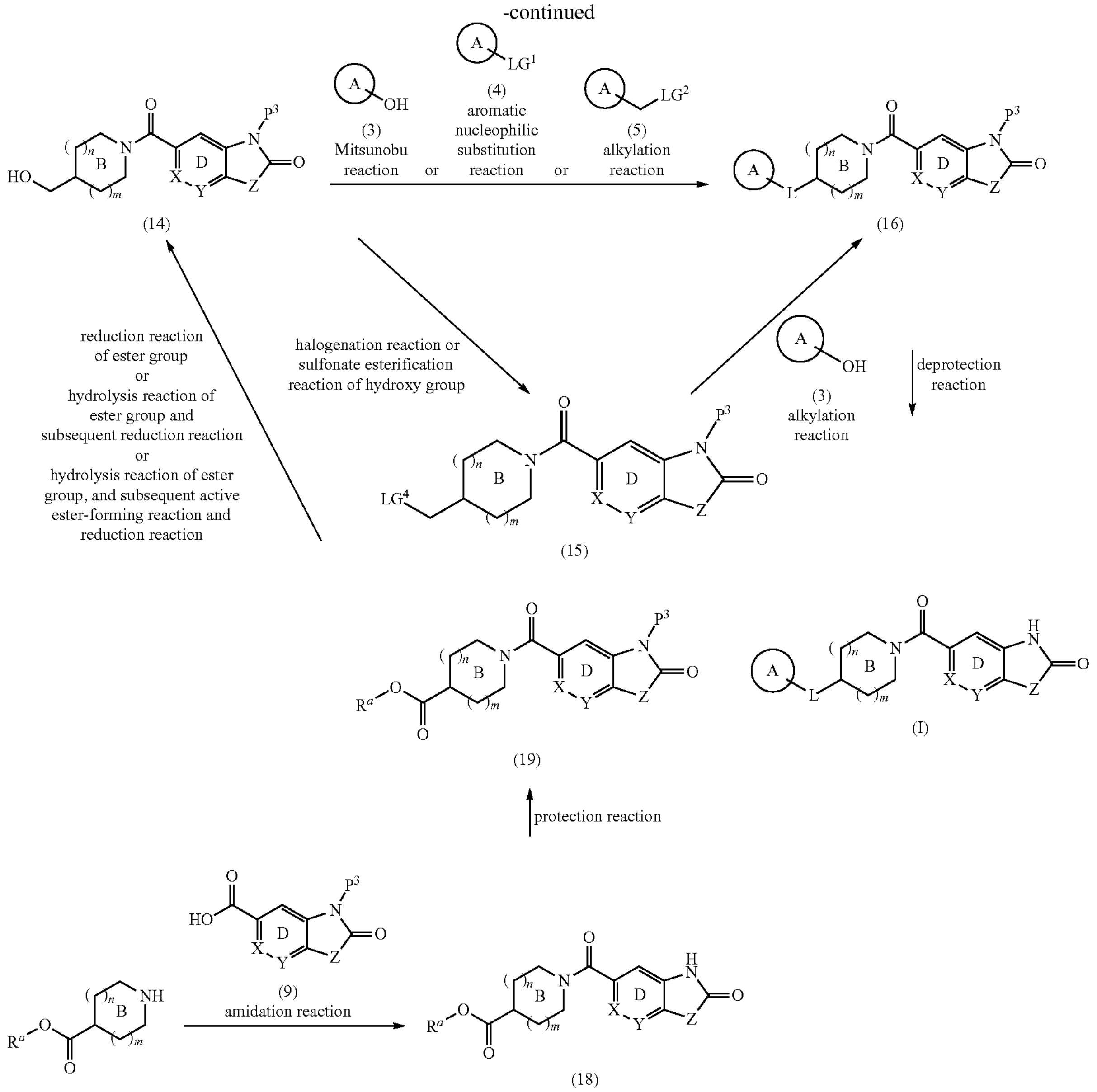

Compound (14) can be produced by subjecting the ester group of compound (19) to a reduction reaction. Alternatively, compound (14) can also be produced by subjecting the ester group of compound (19) to a hydrolysis reaction, followed by a reduction reaction. The hydrolysis reaction is carried out using an inorganic base or an inorganic acid, and the obtained carboxylic acid is subjected to a reduction reaction. The reduction reaction of the carboxylic acid is carried out using borane-tetrahydrofuran complex and the like. Alternatively, Compound (14) can also be produced by subjecting the ester group of compound (19) to a hydrolysis reaction, followed by an active ester-forming reaction and a reduction reaction. The hydrolysis reaction is carried out using an inorganic base or an inorganic acid, and the obtained carboxylic acid is converted to the active ester, and the active ester is subjected to a reduction reaction. The formation of the active ester is carried out using a base (triethylamine, N,N-diisopropylethylamine, etc.) and ethyl chloroformate, isopropyl chloroformate, isobutyl chloroformate and the like. The reduction reaction of the active ester is carried out using sodium borohydride and the like.

Compound (16) can be produced by subjecting compound (14) and compound (3), or compound (14) and compound (4) to the above-mentioned reaction. Alternatively, compound (16) can also be produced by subjecting compound (14) and compound (5), or compound (15) and compound (3) to an alkylation reaction in the presence of a base. Examples of the base include potassium carbonate, tripotassium phosphate, triethylamine, N,N-diisopropylethylamine, pyridine, sodium ethoxide, potassium tert-butoxide, sodium hydride, lithium hexamethyldisilazide, sodium hexamethyldisilazide, n-butyl lithium and the like.

[Production Method C]

Compound (I) of the present invention can be produced from compound (20) according to the following method.

(Scheme 3)

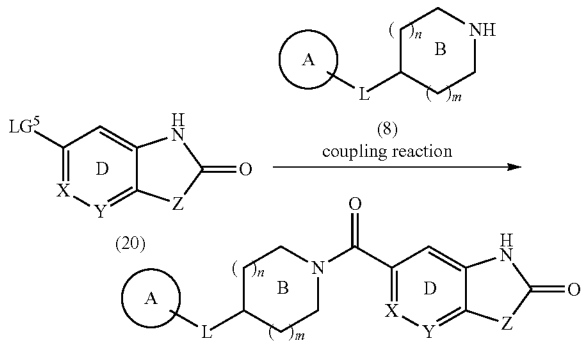

Compound (I) can be produced by subjecting compound (20) and compound (8) to a coupling reaction using a metal catalyst such as Pd and the like, in the presence of a carbon monoxide source. Examples of the carbon monoxide source include carbon monoxide gas, molybdenum hexacarbonyl (0), dicobalt ooctacarbonyl(0), N-formylsaccharine and the like.

[Production Method D]

Compound (I) of the present invention can be produced from compound (21) according to the following method.

(Scheme 4)

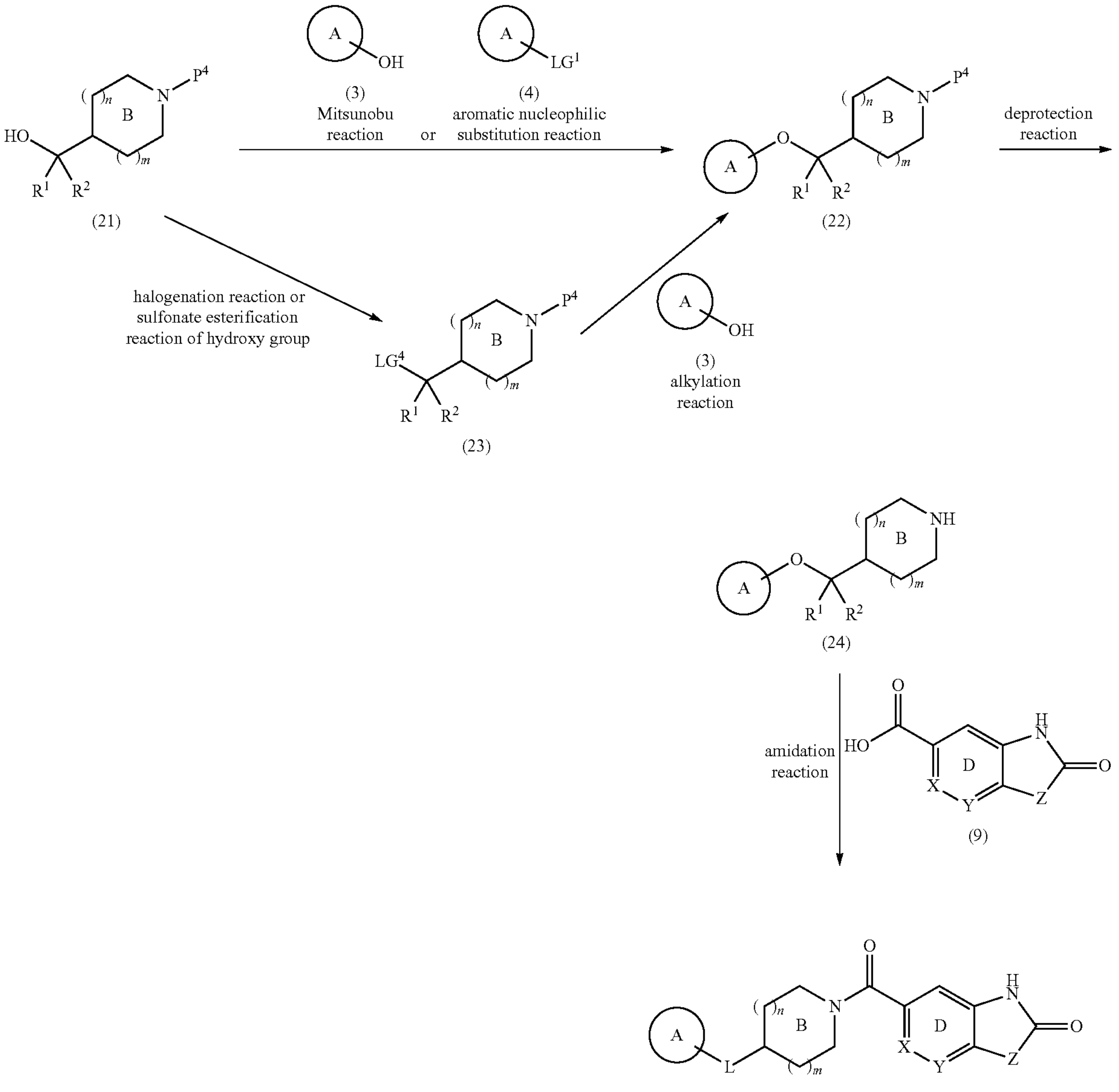

(I)

Compound (22) can be produced by subjecting compound (21) and compound (3), or compound (21) and compound (4) to the above-mentioned reaction. Alternatively, compound (22) can also be produced by subjecting compound (23) and compound (3) to an alkylation reaction in the presence of a base. Examples of the base include potassium carbonate, tripotassium phosphate, triethylamine, N,N-diisopropylethylamine, pyridine, sodium ethoxide, potassium tert-butoxide, sodium hydride, lithium hexamethyldisilazide, sodium hexamethyldisilazide, n-butyl lithium and the like.

[Production Method E]

Compound (I) of the present invention can be produced from compound (25) according to the following method.

Compound (27) can be produced by subjecting compound (25) and compound (26) to an alkylation reaction. Alternatively, compound (27) can also be produced by subjecting compound (28) and compound (29) to an alkylation reaction in the presence of a base. Examples of the base include potassium carbonate, tripotassium phosphate, triethylamine, N,N-diisopropylethylamine, pyridine, sodium ethoxide, potassium tert-butoxide, sodium hydride, lithium hexamethyldisilazide, sodium hexamethyldisilazide, n-butyl lithium and the like.

[Production Method F]

Compound (I) of the present invention can be produced from compound (31) according to the following method.

(Scheme 5)

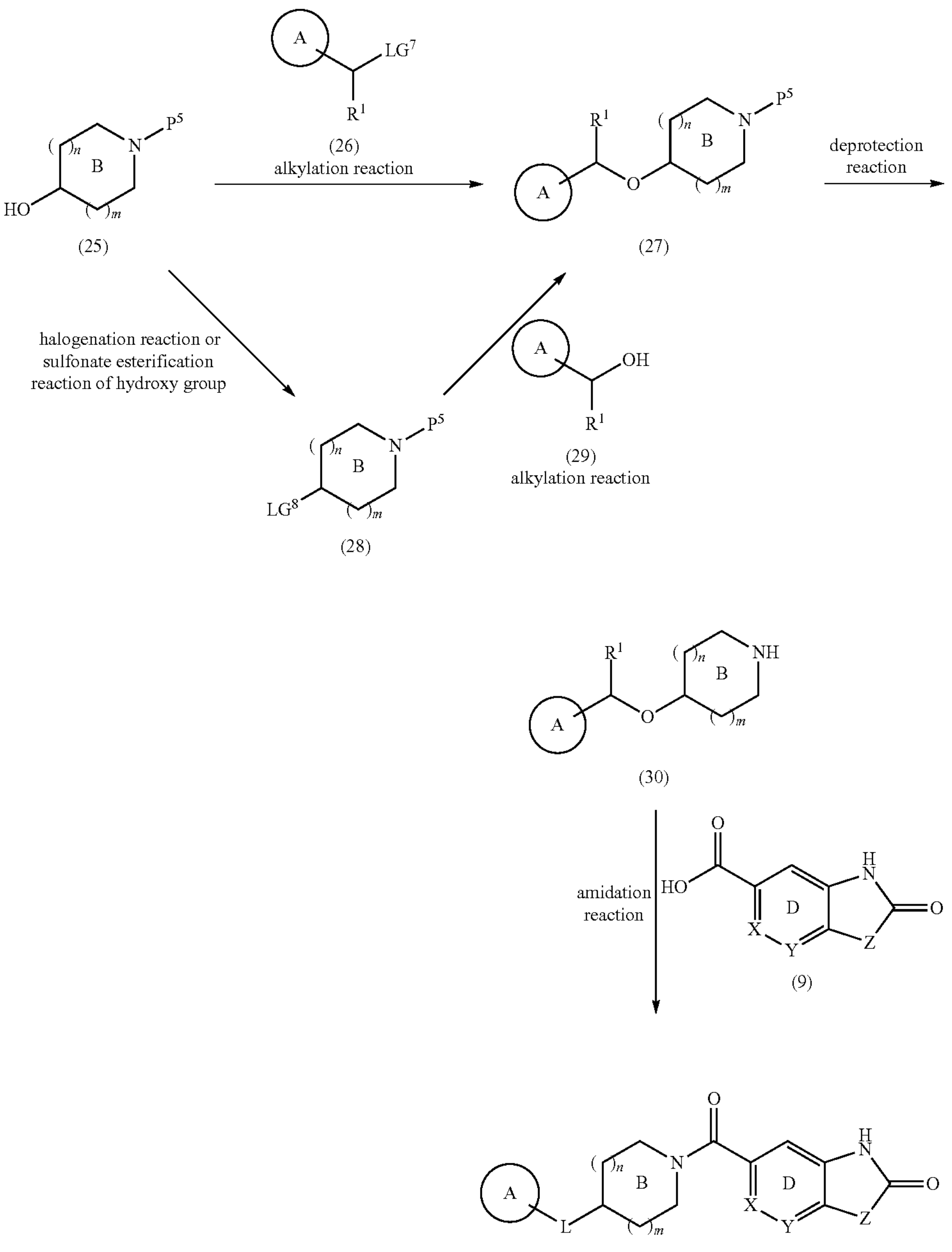

(I)

(Scheme 6)

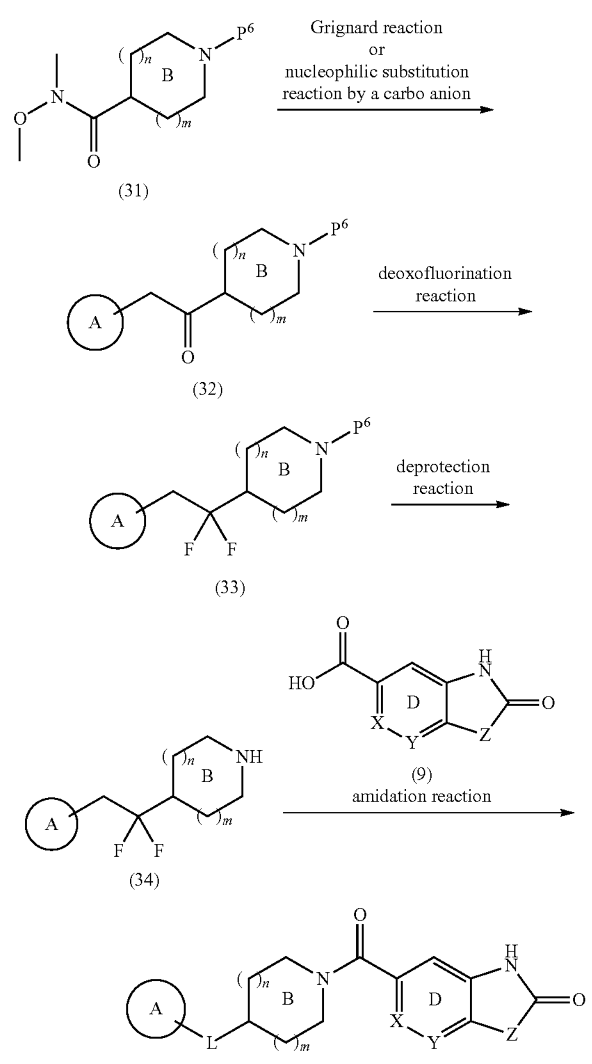

(31)

(32)

(33)

(9)

(34)

(I)

Compound (33) can be produced by subjecting compound (32) to a deoxyfluorination reaction. Examples of the fluorinating agent include bis(2-methoxyethyl)aminosulfur trifluoride, diethylaminosulfur trifluoride, 4-tert-butyl-2,6-dimethylphenylsulfur trifluoride, N,N-diethyl-S,S-difluorosulfiliminium tetrafluoroborate, difluoro-4-morpholinyl sulfonium tetrafluoroborate and the like.

[Production Method G]

Compound (I) of the present invention can be produced from compound (35) according to the following method.

(Scheme 7)

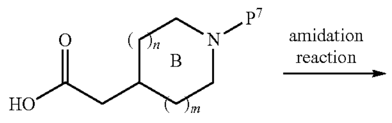

(35)

-continued

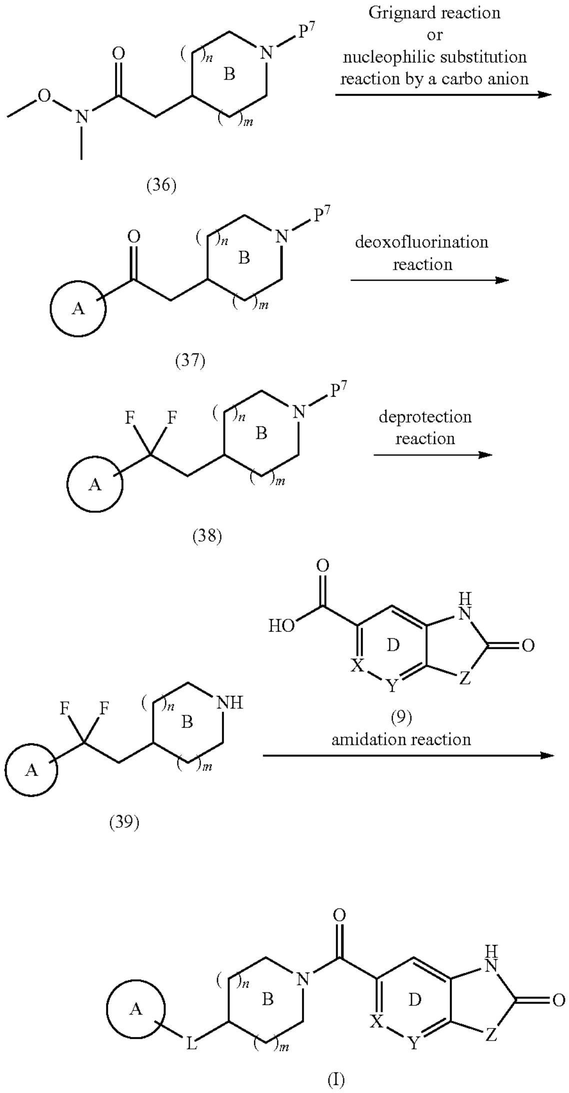

(36)

(37)

(38)

(9)

(39)

(I)

Compound (38) can be produced by subjecting compound (37) to a deoxyfluorination reaction. Examples of the fluorinating agent include bis(2-methoxyethyl)aminosulfur trifluoride, diethylaminosulfur trifluoride, 4-tert-butyl-2,6-dimethylphenylsulfur trifluoride, N,N-diethyl-S,S-difluorosulfiliminium tetrafluoroborate, difluoro-4-morpholinyl sulfonium tetrafluoroborate and the like.

[Production Method H]

Compound (I) of the present invention can be produced from compound (31) according to the following method.

(Scheme 8)

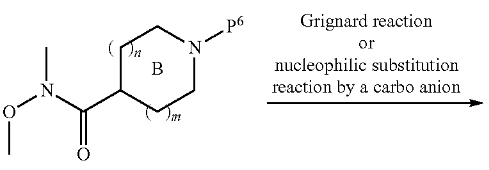

(31)

-continued

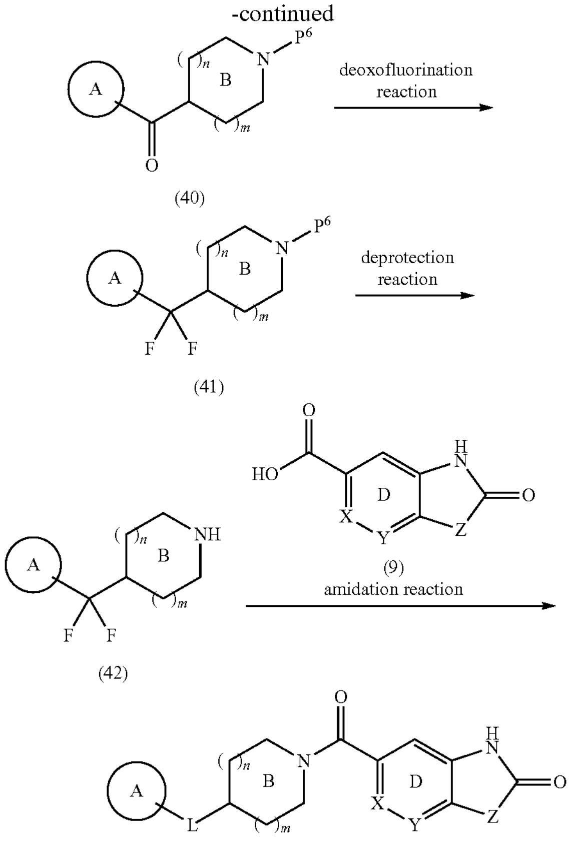

(40)

(41)

(9)

(42)

(I)

Compound (41) can be produced by subjecting compound (40) to a deoxyfluorination reaction. Examples of the fluorinating agent include bis(2-methoxyethyl)aminosulfur trifluoride, diethylaminosulfur trifluoride, 4-tert-butyl-2,6-dimethylphenylsulfur trifluoride, N,N-diethyl-S,S-difluorosulfiliminium tetrafluoroborate, difluoro-4-morpholinyl sulfonium tetrafluoroborate and the like.

Carboxylic acid (9) used in each production method may be commercially available products, or can be produced from commercially available or known starting materials according to methods known per se.

The starting compounds and/or production intermediates for compound (I) may form salts. While the salts are not particularly limited as long as the reaction can be performed, examples thereof include those similar to the salts optionally formed by compound (I) and the like, and the like.

As for the configurational isomers (E, Z forms) of compound (I), they can be isolated and purified when isomerization occurs, for example, according to a conventional separation means such as extraction, recrystallization, distillation, chromatography and the like to obtain a pure compound. In addition, the corresponding pure isomer can also be obtained by isomerizing a double bond using heating, an acid catalyst, a transition metal complex, a metal catalyst, a radical catalyst, light irradiation, a strong base catalyst and the like, according to the method described in Shin Jikken Kagaku Kouza 14 (The Chemical Society of Japan ed.), pages 251 to 253, 4th Edition Jikken Kagaku Kouza 19 (The Chemical Society of Japan ed.), pages 273 to 274 or a method analogous thereto.

Compound (I) contains a stereoisomer depending on the kind of a substituent, and each stereoisomer and a mixture thereof are encompassed in the present invention.

Compound (I) may be a hydrate or a non-hydrate.

When desired, compound (I) can be synthesized by performing deprotection reaction, acylation reaction, alkylation reaction, hydrogenation reaction, oxidation reaction, reduction reaction, reaction of carbon chain extension, halogenation reaction, substituent exchange reaction, coupling reaction, nucleophilic addition reaction by a carbo anion, and Grignard reagent singly or two or more thereof in combination.

When the objective product is obtained as a free form by the above-mentioned reaction, it can be converted to a salt according to a conventional method, or when the objective product is obtained as a salt, it can be converted to a free form or other salt according to a conventional method. The thus-obtained compound (I) can also be isolated and purified from a reaction mixture according to a known method such as phase transfer, concentration, solvent extraction, distillation, crystallization, recrystallization, chromatography and the like.

When compound (I) contains a configurational isomer, a diastereomer, a conformer and the like, each can be isolated according to the above-mentioned separation and purification methods, if desired. In addition, when compound (I) is racemic, d-form and 1-form can be isolated according to a conventional optical resolution.

The thus-obtained compound (I), other reaction intermediates therefor and starting compounds thereof can be isolated and purified from reaction mixtures according to methods known per se, for example, extraction, concentration, neutralization, filtration, distillation, recrystallization, column chromatography, thin layer chromatography, preparative high performance liquid chromatography (preparative HPLC), moderate-pressure preparative liquid chromatography (moderate-pressure preparative LC) and the like.

A salt of compound (I) can be produced according to a method known per se. For example, when compound (I) is a basic compound, it can be produced by adding an inorganic acid or organic acid, or when compound (I) is an acidic compound, by adding an organic base or inorganic base.

When compound (I) contains an optical isomer, each optical isomer and a mixture thereof are encompassed in the scope of the present invention, and these isomers can be subjected to optical resolution or can be produced respectively, according to a method known per se, if desired.

When compound (I) contains a configurational isomer, a diastereomer, a conformer and the like, each can be isolated according to the above-mentioned separation and purification methods, if desired. In addition, when compound (I) is racemic, S-form and R-form can be isolated according to a conventional optical resolution.

When compound (I) contains a stereoisomer, each isomer and a mixture thereof are encompassed in the present invention.

The compound of the present invention is expected to be useful for mammals (e.g., mouse, rat, hamster, rabbit, cat, dog, bovine, sheep, monkey, human etc.) as an agent for the prophylaxis or treatment of diseases, for example, (1) psychiatric diseases [e.g., depression, major depression, bipolar depression, dysthymic disorder, emotional disorder (seasonal affective disorder and the like), recurrent depression, postpartum depression, stress disorder, depression symptom, mania, anxiety, generalized anxiety disorder, anxiety syndrome, panic disorder, phobia, social phobia, social anxiety disorder, obsessive disorder, post-traumatic stress syndrome, post-traumatic stress disorder, Tourette syndrome, autism, fragile X syndrome, Rett syndrome, adjustment disorder, bipolar disorder, neurosis, schizophrenia (e.g., positive symptom, negative symptom, cognitive impairment), chronic fatigue syndrome, anxiety neurosis, compulsive neurosis, panic disorder, epilepsy, anxiety disorder, anxiety, anxious mental state, emotional abnormality, cyclothymia, nervous erethism, faint, addiction, low sex drive, attention deficit hyperactivity disorder (ADHD), psychotic major depression, refractory major depression, treatment-resistant depression], (2) neurodegenerative diseases [e.g., Alzheimer's disease, Alzheimer-type senile dementia, Parkinson's disease, Huntington's disease, multi-infarct dementia, frontotemporal dementia, dementia Parkinson's type, progressive supranuclear palsy, Pick's syndrome, Niemann-Pick syndrome, corticobasal degeneration, Down's disease, vascular dementia, postencephalitic parkinsonism, Lewy body dementia, HIV dementia, amyotrophic lateral sclerosis (ALS), motor neurogenesis disease (MND), Creutzfeldt-Jakob disease or prion disease, cerebral palsy, progressive supranuclear palsy, traumatic brain injury, glaucoma, multiple sclerosis, neuromyelitis optica (NMO)], (3) age-related cognition memory disorders [e.g., age-related memory disorders, senile dementia], (4) sleep disorders [e.g., intrinsic sleep disorders (e.g., psychophysiological insomnia and the like), extrinsic sleep disorder, circadian rhythm disorders (e.g., time zone change syndrome (jet lag), shift work sleep disorder, irregular sleep-wake pattern, delayed sleep phase syndrome, advanced sleep phase syndrome, non-24-hour sleep-wake and the like), parasomnia, sleep disorders associated with internal medical or psychiatric disorder (e.g., chronic obstructive pulmonary diseases, Alzheimer's disease, Parkinson's disease, cerebrovascular dementia, schizophrenia, depression, anxiety neurosis), stress insomnia, insomnia, insomniac neurosis, sleep apnea syndrome], (5) respiratory depression caused by anesthetics, traumatic disease, or neurodegenerative disease and the like, (6) traumatic brain injury, cerebral apoplexy, neurotic anorexia, eating disorder, anorexia nervosa, hyperorexia, other eating disorder, alcohol dependence, alcohol abuse, alcoholic amnesia, alcohol paranoia, alcohol preference, alcohol withdrawal, alcoholic insanity, alcohol poisoning, alcoholic jealousy, alcoholic mania, alcohol-dependent psychiatric disorder, alcoholic insanity, pharmacophilia, pharmacophobia, pharmacomania, drug withdrawal, stress headache, catatonic headache, diabetic neuropathy, obesity, diabetes, muscular spasm, Meniere's disease, autonomic ataxia, alopecia, glaucoma, hypertension, cardiac disease, tachycardia, congestive cardiac failure, hyperventilation, bronchial asthma, apnea, sudden infant death syndrome, inflammatory disease, allergic disease, impotence, climacteric disorder, infertility, cancer, immunodeficiency syndrome caused by HIV infection, immunodeficiency syndrome caused by stress, cerebrospinal meningitis, acromegaly, incontinence, metabolic syndrome, osteoporosis, peptic ulcer, irritable bowel syndrome, inflammatory bowel disease, ulcerative colitis, Crohn's disease, stress gastrointestinal disorder, stress vomiting, diarrhea, constipation, postoperative ileus and the like, (7) pain (e.g., inflammatory pain, cancerous pain, neuropathic pain etc.), (8) migraine, (9) cerebral edema,

(10) cerebral ischemia, and the like.

Since the compound of the present invention has a superior MAGL inhibitory action, a superior prophylactic or therapeutic effect for the above-mentioned diseases may be expected.

Since the compound of the present invention has a superior MAGL inhibitory action, a superior prophylactic or therapeutic effect for neurodegenerative diseases (e.g., Alzheimer's disease, Parkinson's disease, Huntington's disease, amyotrophic lateral sclerosis, traumatic brain injury, glaucoma, multiple sclerosis etc.), anxiety disorder, pains (e.g., inflammatory pain, cancerous pain, neurogenic pain etc.), epilepsy, depression and the like, particularly Alzheimer's disease, Parkinson's disease, Huntington's disease, amyotrophic lateral sclerosis, multiple sclerosis, anxiety disorder, pain, epilepsy or depression may be expected.

Since the compound of the present invention has a superior MAGL inhibitory action, a superior prophylactic or therapeutic effect for Alzheimer's disease, Parkinson's disease, Huntington's disease, amyotrophic lateral sclerosis, multiple sclerosis, anxiety disorder, pain, epilepsy or depression may be expected.

A prodrug of compound (I) means a compound which is converted to compound (I) with a reaction due to an enzyme, an gastric acid, etc. under the physiological condition in the living body, that is, a compound which is converted to compound (I) with oxidation, reduction, hydrolysis, etc. according to an enzyme; a compound which is converted to compound (I) by hydrolysis etc. due to gastric acid, etc.

A prodrug for compound (I) may be a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation, etc.); a compound obtained by subjecting a hydroxy group in compound (I) to an acylation, alkylation, phosphorylation or boration (e.g., a compound obtained by subjecting an hydroxy group in compound (I) to an acetylation, palmitoylation, propanoylation, pivaloylation, succinylation, fumarylation, alanylation or dimethylaminomethylcarbonylation, etc.); a compound obtained by subjecting a carboxyl group in compound (I) to an esterification or amidation (e.g., a compound obtained by subjecting a carboxyl group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation, etc.) and the like. Any of these compounds can be produced from compound (I) by a method known per se. The prodrug of compound (I) may be a compound that converts to compound (I) under physiological conditions as described in Development of Pharmaceutical Products, vol. 7, Molecule Design, 163-198, Hirokawa Shoten (1990).

The compound of the present invention is superior in vivo kinetics (e.g., plasma drug half-life, intracerebral transferability, metabolic stability), shows low toxicity (e.g., more superior as a medicament in terms of acute toxicity, chronic toxicity, genetic toxicity, reproductive toxicity, cardiotoxicity, drug interaction, carcinogenicity etc.). The compound of the present invention is directly used as a medicament or a pharmaceutical composition mixed with a pharmaceutically acceptable carrier or the like to be orally or parenterally administered to mammals (e.g., humans, monkeys, cows, horses, pigs, mice, rats, hamsters, rabbits, cats, dogs, sheep and goats) in safety. Examples of the "parenteral" include intravenous, intramuscular, subcutaneous, intra-organ, intranasal, intradermal, instillation, intracerebral, intrarectal, intravaginal, intraperitoneal and intratumor administrations, administration to the vicinity of tumor etc. and direct administration to the lesion.

While the dose of the compound of the present invention varies depending on the administration route, symptom and the like, when, for example, the compound is orally administered to a patient with Alzheimer's disease (adult, body weight 40-80 kg, for example, 60 kg), it is, for example, 0.001-1000 mg/kg body weight/day, preferably 0.01-100 mg/kg body weight/day, more preferably 0.1-10 mg/kg body weight/day. This amount can be administered in 1 to 3 portions per day.

A medicament containing the compound of the present invention can be used alone or as a pharmaceutical composition containing the compound of the present invention and a pharmaceutically acceptable carrier according to a method known per se as a production method of a pharmaceutical preparation (e.g., the method described in the Japanese Pharmacopoeia etc.). A medicament containing the compound of the present invention can be safely administered in the form of, for example, tablet (including sugar-coated tablet, film-coated tablet, sublingual tablet, orally disintegrating tablet, buccal and the like), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal administrations, and administration to the lesion).

As the aforementioned "pharmaceutically acceptable carrier", various organic or inorganic carriers conventionally used as preparation materials (starting materials) can be used. For example, excipient, lubricant, binder, disintegrant and the like are used for solid preparations, and solvent, solubilizing agent, suspending agent, isotonicity agent, buffer, soothing agent and the like are used for liquid preparations. Where necessary, preparation additives such as preservative, antioxidant, colorant, sweetening agent and the like can also be used.

Examples of the excipient include lactose, sucrose, D-mannitol, starch, corn starch, crystalline cellulose, light anhydrous silicic acid and the like.

Examples of the lubricant include magnesium stearate, calcium stearate, talc, colloidal silica and the like.

Examples of the binder include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, sodium carboxymethyl starch, L-hydroxypropylcellulose and the like.

Examples of the solvent include water for injection, alcohol, propylene glycol, Macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like. Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; and the like.

Examples of the isotonicity agent include glucose, D-sorbitol, sodium chloride, glycerin, D-mannitol and the like.

Examples of the buffer include buffer solutions such as phosphates, acetates, carbonates, citrates and the like.

Examples of the soothing agent include benzyl alcohol and the like.

Examples of the preservative include p-oxybenzoates, chlorobutanol, benzyl alcohol, phenylethyl alcohol, dehydroacetic acid, sorbic acid and the like.

Examples of the antioxidant include sulfite, ascorbic acid, α-tocopherol and the like.

While the pharmaceutical composition varies according to the dosage form, administration method, carrier and the like, it can be produced according to a conventional method by adding the compound of the present invention in a proportion of generally 0.01-100% (w/w), preferably 0.1-95% (w/w), of the total amount of the preparation.

The compound of the present invention can be used in combination with other active ingredients (hereinafter to be abbreviated as concomitant drug).

Examples of the concomitant drug include the following. benzodiazepine (chlordiazepoxide, diazepam, potassium clorazepate, lorazepam, clonazepam, alprazolam etc.), L-type calcium channel inhibitor (pregabalin etc.), tricyclic or tetracyclic antidepressant (imipramine hydrochloride, amitriptyline hydrochloride, desipramine hydrochloride, clomipramine hydrochloride etc.), selective serotonin reuptake inhibitor (fluvoxamine maleate, fluoxetine hydrochloride, citalopram hydrobromide, sertraline hydrochloride, paroxetine hydrochloride, escitalopram oxalate etc.), serotonin-noradrenaline reuptake inhibitor (venlafaxine hydrochloride, duloxetine hydrochloride, desvenlafaxine hydrochloride etc.), noradrenaline reuptake inhibitor (reboxetine mesylate etc.), noradrenaline-dopamine reuptake inhibitor (bupropion hydrochloride etc.), mirtazapine, trazodone hydrochloride, nefazodone hydrochloride, bupropion hydrochloride, setiptiline maleate, 5-HT agonist (buspirone hydrochloride, tandospirone citrate, osemozotan hydrochloride etc.), 5-$HT_3$ antagonist (Cyamemazine etc.), heart non-selective β inhibitor (propranolol hydrochloride, oxprenolol hydrochloride etc.), histamine $H_1$ antagonist (hydroxyzine hydrochloride etc.), therapeutic drug for schizophrenia (chlorpromazine, haloperidol, sulpiride, clozapine, trifluoperazine hydrochloride, fluphenazine hydrochloride, olanzapine, quetiapine fumarate, risperidone, aripiprazole etc.), CRF antagonist, other antianxiety drug (meprobamate etc.), tachykinin antagonist (MK-869, saredutant etc.), medicament that acts on metabotropic glutamate receptor, CCK antagonist, β3 adrenaline antagonist (amibegron hydrochloride etc.), GAT-1 inhibitor (tiagabine hydrochloride etc.), N-type calcium channel inhibitor, carbonic anhydrase II inhibitor, NMDA glycine moiety agonist, NMDA antagonist (memantine etc.), peripheral benzodiazepine receptor agonist, vasopressin antagonist, vasopressin V1b antagonist, vasopressin V1a antagonist, phosphodiesterase inhibitor, opioid antagonist, opioid agonist, uridine, nicotinic acid receptor agonist, thyroid hormone (T3, T4), TSH, TRH, MAO inhibitor (phenelzine sulfate, tranylcypromine sulfate, moclobemide etc.), 5-$HT_{2A}$ antagonist, 5-$HT_{2A}$ inverse agonist, COMT inhibitor (entacapone etc.), therapeutic drug for bipolar disorder (lithium carbonate, sodium valproate, lamotrigine, riluzole, felbamate etc.), cannabinoid CB1 antagonist (rimonabant etc.), FAAH inhibitor, sodium channel inhibitor, anti-ADHD drug (methylphenidate hydrochloride, methamphetamine hydrochloride etc.), therapeutic drug for alcoholism, therapeutic drug for autism, therapeutic drug for chronic fatigue syndrome, therapeutic drug for spasm, therapeutic drug for fibromyalgia syndrome, therapeutic drug for headache, therapeutic drug for insomnia (etizolam, zopiclone, triazolam, zolpidem, ramelteon, indiplon etc.), therapeutic drug for quitting smoking, therapeutic drug for myasthenia gravis, therapeutic drug for cerebral infarction, therapeutic drug for mania, therapeutic drug for hypersomnia, therapeutic drug for pain, therapeutic drug for dysthymia, therapeutic drug for autonomic ataxia, therapeutic drug for male and female sexual dysfunction, therapeutic drug for migraine, therapeutic drug for pathological gambler, therapeutic drug for restless legs syndrome, therapeutic drug for substance addiction, therapeutic drug for alcohol-related syndrome, therapeutic drug for irritable bowel syndrome, therapeutic drug for Alzheimer's disease (donepezil, galanthamine, memantine etc.), therapeutic drug for Parkinson's disease (levodopa, carbidopa, benserazide, selegiline, zonisamide, entacapone, amantadine, talipexole, pramipexole, apomorphine, cabergoline, bromocriptine, istradefylline, trihexyphenidyl, promethazine, pergolide, etc.), therapeutic drug for Huntington's disease (chlorpromazine hydrochloride, haloperidol, reserpine etc.), therapeutic drug for ALS (riluzole etc., neurotrophic factor etc.), therapeutic drug for multiple sclerosis (molecular target drug such as fingolimod, interferon beta 1b, natalizumab and the like, etc.), therapeutic drug for lipid abnormality such as cholesterol-lowering drug (statin series (pravastatin sodium, atrovastatin, simvastatin, rosuvastatin etc.), fibrate (clofibrate etc.), squalene synthetase inhibitor), therapeutic drug for abnormal behavior or suppressant of dromomania due to dementia (sedatives, antianxiety drug etc.), apoptosis inhibitor, antiobesity drug, therapeutic drug for diabetes, therapeutic drug for hypertension, therapeutic drug for hypotension, therapeutic drug for rheumatism (DMARD), anti-cancer agent, therapeutic drug for parathyroid (PTH), calcium receptor antagonist, sex hormone or a derivative thereof (progesterone, estradiol, estradiol benzoate etc.), neuronal differentiation promoter, nerve regeneration promoter, non-steroidal anti-inflammatory drug (meloxicam, tenoxicam, indomethacin, ibuprofen, celecoxib, rofecoxib, aspirin etc.), steroid (dexamethasone, cortisone acetate etc.), anti-cytokine drug (TNF inhibitor, MAP kinase inhibitor etc.), antibody medicament, nucleic acid or nucleic acid derivative, aptamer drug and the like.

By combining the compound of the present invention and a concomitant drug, a superior effect such as (1) the dose can be reduced as compared to single administration of the compound of the present invention or a concomitant drug, (2) the drug to be combined with the compound of the present invention can be selected according to the condition of patients (mild case, severe case and the like), (3) the period of treatment can be set longer by selecting a concomitant drug having different action and mechanism from the compound of the present invention, (4) a sustained treatment effect can be designed by selecting a concomitant drug having different action and mechanism from the compound of the present invention, (5) a synergistic effect can be afforded by a combined use of the compound of the present invention and a concomitant drug, and the like, can be achieved.

Hereinafter the compound of the present invention and a concomitant drug used in combination are referred to as the "combination agent of the present invention".

When using the combination agent of the present invention, the administration time of the compound of the present invention and the concomitant drug is not restricted, and the compound of the present invention or a pharmaceutical composition thereof and the concomitant drug or a pharmaceutical composition thereof can be administered to an administration subject simultaneously, or may be administered at different times. The dosage of the concomitant drug may be determined according to the dose clinically used, and can be appropriately selected depending on an administration subject, administration route, disease, combination and the like. The administration mode of the concomitant drug of the present invention is not particularly restricted, and it is sufficient that the compound of the present invention and the concomitant drug are combined in administration. Examples of such administration mode include the following methods: (1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (for example, administration in the order of the compound of the present invention and the concomitant drug, or in the reverse order) and the like.

The combination agent of the present invention exhibits low toxicity. For example, the compound of the present invention or(and) the aforementioned concomitant drug can be combined with a pharmacologically acceptable carrier according to the known method to prepare a pharmaceutical composition such as tablets (including sugar-coated tablet and film-coated tablet), powders, granules, capsules (including soft capsule), liquids, injections, suppositories, sustained-release agents, etc. These compositions can be administered safely orally or non-orally (e.g., topical, rectal, intravenous administration etc.). Injection can be administered intravenously, intramuscularly, subcutaneously, or by intraorgan administration or directly to the lesion.

Examples of the pharmacologically acceptable carriers usable for the production of a combination agent of the present invention, various organic or inorganic carrier substances conventionally used as preparation materials can be mentioned. For solid preparations, for example, excipient, lubricant, binder and disintegrant can be used. For liquid preparations, for example, solvent, solubilizing agent, suspending agent, isotonic agent, buffering agent, soothing agent and the like can be used. Where necessary, an appropriate amount of conventional preservative, antioxidant, colorant, sweetening agent, adsorbent, wetting agent and the like can be used as appropriate.

Examples of the excipient include lactose, sucrose, D-mannitol, starch, corn starch, crystalline cellulose, light anhydrous silicic acid and the like.

Examples of the lubricant include magnesium stearate, calcium stearate, talc, colloidal silica and the like.

Examples of the binder include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, sodium carboxymethyl starch, L-hydroxypropylcellulose and the like.

Examples of the solvent include water for injection, alcohol, propylene glycol, Macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffering agent include buffer solutions such as phosphates, acetates, carbonates, citrates and the like.

Examples of the soothing agent include benzyl alcohol and the like.

Examples of the preservative include p-oxybenzoates, chlorobutanol, benzyl alcohol, phenylethyl alcohol, dehydroacetic acid, sorbic acid and the like.

Examples of the antioxidant include sulfite, ascorbic acid, α-tocopherol and the like.

The mixing ratio of the compound of the present invention to the concomitant drug in the combination agent of the present invention can be appropriately selected depending on an administration subject, administration route, diseases and the like.

For example, the content of the compound of the present invention in the combination agent of the present invention differs depending on the form of a preparation, and usually from about 0.01 to about 100 wt %, preferably from about 0.1 to about 50 wt %, further preferably from about 0.5 to about 20 wt %, based on the preparation.

The content of the concomitant drug in the combination agent of the present invention differs depending on the form of a preparation, and usually from about 0.01 to about 100 wt %, preferably from about 0.1 to about 50 wt %, further preferably from about 0.5 to about 20 wt %, based on the preparation.

The content of additives such as a carrier and the like in the combination agent of the present invention differs depending on the form of a preparation, and usually from about 1 to about 99.99 wt %, preferably from about 10 to about 90 wt %, based on the preparation.

When the compound of the present invention and a concomitant drug are separately formulated into preparations, the contents thereof are similar to the above.

EXAMPLES

The present invention is explained in detail in the following by referring to Examples, Experimental Examples and Formulation Examples, which are not to be construed as limitative, and the invention may be changed within the scope of the present invention.

In the following Examples, the "room temperature" generally means about 10° C. to about 35° C. The ratios indicated for mixed solvents are volume mixing ratios, unless otherwise specified. % means wt %, unless otherwise specified.

In silica gel column chromatography, NH means use of aminopropylsilane-bonded silica gel. In HPLC (high performance liquid chromatography), C18 means use of octadecyl-bonded silica gel. The ratios of elution solvents are volume mixing ratios, unless otherwise specified.

In Examples, the following abbreviations are used.

mp: melting point
MS: mass spectrum
M: mol concentration
$CDCl_3$: deuterochloroform
DMSO-$d_6$: deuterodimethyl sulfoxide
$^1H$ NMR: proton nuclear magnetic resonance
LC/MS: liquid chromatograph mass spectrometer
ESI: Electron Spray Ionization
APCI: atmospheric pressure chemical ionization
ADDP: 1,1'-(azodicarbonyl)dipiperidine
DIPEA: N,N-diisopropylethylamine
DIAD: diisopropyl azodicarboxylate
DME: 1,2-dimethoxyethane
DMF: N,N-dimethylformamide
DMA: N,N-dimethylacetamide
DMSO: dimethyl sulfoxide
EDCI: 1-ethyl-3-(3-dimethylaminopropyl)carbodiimide hydrochloride
HATU: 2-(7-azabenzotriazol-1-yl)-1,1,3,3-tetramethyluronium hexafluorophosphate
HOBt-$H_2O$: 1-hydroxybenzotriazole monohydrate
IPA: 2-propanol
IPE: diisopropyl ether
p-TsOH—$H_2O$: p-toluenesulfonic acid monohydrate
TEA: triethylamine
THF: tetrahydrofuran $^1H$ NMR was measured by Fourier-transform type NMR. For the analysis, ACD/SpecManager (trade name) and the like were used. Peaks with very mild protons such as a hydroxy group, an amino group and the like are not described.

MS was measured by LC/MS. As ionization method, ESI method or APCI method was used. The data indicates actual measured value (found). Generally, molecular ion peaks ($[M+H]^+$, $[M-H]^-$ and the like) are observed. For example, in the case of a compound having a tert-butoxycarbonyl group, a peak after elimination of a tert-butoxycarbonyl group or a tert-butyl group may be observed as a fragment ion. In the case of a compound having a hydroxy group, a peak after elimination of $H_2O$ may be observed as a fragment ion. In the case of a salt, a molecular ion peak or fragment ion peak of free form is generally observed.

The unit of sample concentration (c) for optical rotation ($[\alpha]_D$) is g/100 mL.

Elemental analysis value (Anal.) was described as calculated value (Calcd) and actual measured value (Found).

Example 1

7-((4-(phenoxymethyl)piperidin-1-yl)carbonyl)-3,4-dihydroquinolin-2(1H)-one

To a mixture of 7-(4-(phenoxymethyl)piperidine-1-carbonyl)-3,4-dihydroquinolin-2(1H)-one (50.0 mg), 4-(phenoxymethyl)piperidine hydrochloride (40.0 mg) and DMF (1 mL) were added HATU (80.0 mg) and TEA (0.122 mL), and the mixture was stirred overnight at room temperature. The reaction mixture was diluted with ethyl acetate, water was added thereto, and the mixture was extracted with ethyl acetate. The organic layer was washed with water and saturated brine, dried over anhydrous sodium sulfate, and concentrated under reduced pressure. The residue was purified by silica gel column chromatography (ethyl acetate/hexane and methanol/ethyl acetate), and triturated with IPE/IPA to give the title compound (50.0 mg).

$^1$H NMR (300 MHz, $CDCl_3$) δ 1.19-1.52 (2H, m), 1.78-2.01 (2H, m), 2.03-2.21 (1H, m), 2.58-2.72 (2H, m), 2.77-2.93 (1H, m), 2.99 (3H, t, J=7.7 Hz), 3.72-4.05 (3H, m), 4.64-4.87 (1H, m), 6.78-7.07 (5H, m), 7.19 (1H, d, J=7.5 Hz), 7.28-7.35 (2H, m), 7.58-7.76 (1H, m).

Example 17

7-((4-((2,4-dichlorophenoxy)methyl)piperidin-1-yl)carbonyl)-1H-pyrido[2,3-b][1,4]oxazin-2 (3H)-one A) 4-((2,4-dichlorophenoxy)methyl)piperidine hydrochloride To a suspension of 60% sodium hydride (2.00 g) in DMF (25 mL) was added dropwise a solution of tert-butyl 4-(hydroxymethyl)piperidine-1-carboxylate (8.00 g) in DMF (25 mL) at 0° C., and then 2,4-dichloro-1-fluorobenzene (4.38 mL) was added thereto. The reaction mixture was stirred at room temperature for 18 hr. To the reaction mixture were added water and aqueous ammonium chloride solution, and the mixture was extracted with ethyl acetate. The organic layer was washed with saturated brine, dried over anhydrous magnesium sulfate, and concentrated under reduced pressure. The residue was purified by silica gel column chromatography (ethyl acetate/hexane) to give tert-butyl 4-((2,4-dichlorophenoxy)methyl)piperidine-1-carboxylate as a crude product.

To a solution of the obtained crude product in ethyl acetate (10 mL) was added 4M hydrogen chloride ethyl acetate solution (35 mL), and the reaction mixture was stirred at room temperature for 18 hr. The resulting precipitate was washed with ethyl acetate and hexane to give the title compound (9.72 g).

$^1$H NMR (300 MHz, DMSO-$d_6$) δ 1.43-1.64 (2H, m), 1.84-1.97 (2H, m), 2.01-2.18 (1H, m), 2.80-2.99 (2H, m), 3.29 (2H, d, J=12.5 Hz), 3.96 (2H, d, J=6.4 Hz), 7.19 (1H, d, J=9.1 Hz), 7.38 (1H, dd, J=8.9, 2.5 Hz), 7.57 (1H, d, J=2.3 Hz), 8.76 (1H, brs), 9.07 (1H, brs).

B) 7-((4-((2,4-dichlorophenoxy)methyl)piperidin-1-yl)carbonyl)-1H-pyrido[2,3-b][1,4]oxazin-2 (3H)-one A mixture of 4-((2,4-dichlorophenoxy)methyl)piperidine hydrochloride (764 mg), 2-oxo-2,3-dihydro-1H-pyrido[2,3-b][1,4]oxazine-7-carboxylic acid (500 mg), HOBt-$H_2O$ (473 mg), EDCI (592 mg), DIPEA (1.12 mL) and DMF (20 mL) was stirred at room temperature for 2 hr. To the reaction mixture was added water, and the resulting precipitate was collected, washed with water and ethyl acetate, dried under reduced pressure, and triturated with heated ethyl acetate to give the title compound (998 mg).

$^1$H NMR (300 MHz, DMSO-$d_6$) δ 1.15-1.41 (2H, m), 1.72-2.20 (3H, m), 2.75-3.23 (2H, m), 3.64-4.59 (4H, m), 4.83 (2H, s), 7.14-7.25 (2H, m), 7.37 (1H, dd, J=8.9, 2.6 Hz), 7.57 (1H, d, J=2.6 Hz), 7.83 (1H, d, J=2.1 Hz), 10.93 (1H, brs).

Example 24

6-((4-((2-chlorophenoxy)methyl)piperidin-1-yl)carbonyl)-2H-1,4-benzoxazin-3 (4H)-one A mixture of 4-((2-chlorophenoxy)methyl)piperidine hydrochloride (48.0 mg), 3-oxo-3,4-dihydro-2H-benzo[b][1,4]oxazine-6-carboxylic acid (50.0 mg), HOBt-$H_2O$ (47.6 mg), EDCI (59.5 mg), DIPEA (0.113 mL) and DMF (2 mL) was stirred at room temperature for 3 hr. To the reaction mixture was added water, and the resulting precipitate was collected, washed with water and ethyl acetate, dried under reduced pressure, and triturated with heated ethyl acetate to give the title compound (47.0 mg).

$^1$H NMR (300 MHz, DMSO-$d_6$) δ 1.19-1.40 (2H, m), 1.72-1.93 (2H, m), 2.01-2.17 (1H, m), 2.70-3.18 (2H, m), 3.49-4.52 (4H, m), 4.62 (2H, s), 6.89-7.02 (4H, m), 7.14 (1H, dd, J=8.3, 1.1 Hz), 7.25-7.34 (1H, m), 7.41 (1H, dd, J=7.9, 1.5 Hz), 10.80 (1H, s).

Example 26

6-((4-((2-chloro-4-fluorophenoxy)methyl)piperidin-1-yl)carbonyl)-2H-1, 4-benzoxazin-3 (4H)-one A) tert-butyl 4-((2-chloro-4-fluorophenoxy)methyl)piperidine-1-carboxylate To a solution of tert-butyl 4-(hydroxymethyl)piperidine-1-carboxylate (2.50 g), 2-chloro-4-fluorophenol (1.49 mL) and tributylphosphine (3.47 mL) in THF (50 mL) was added ADDP (3.52 g) at 0° C., and the reaction mixture was stirred at room temperature for 18 hr. The reaction mixture was passed through silica gel/NH silica gel pad, and the filtrate was concentrated under reduced pressure. The residue was purified by silica gel column chromatography (ethyl acetate/hexane) to give the title compound (3.81 g).

$^1$H NMR (300 MHz, $CDCl_3$) δ 1.21-1.38 (2H, m), 1.42-1.51 (9H, m), 1.78-2.11 (3H, m), 2.64-2.85 (2H, m), 3.75-3.97 (2H, m), 4.04-4.37 (2H, m), 6.80-7.00 (2H, m), 7.05-7.16 (1H, m).

B) 4-((2-chloro-4-fluorophenoxy)methyl)piperidine hydrochloride

To a solution of tert-butyl 4-((2-chloro-4-fluorophenoxy)methyl)piperidine-1-carboxylate (3.81 g) in ethyl acetate (30 mL) was added 4M hydrogen chloride ethyl acetate solution (22.2 mL), and the reaction mixture was stirred at room temperature for 14 hr. The resulting precipitate was collected, washed with ethyl acetate, and dried under reduced pressure to give the title compound (2.09 g).

$^1$H NMR (300 MHz, DMSO-$d_6$) δ 1.43-1.62 (2H, m), 1.84-1.98 (2H, m), 2.01-2.17 (1H, m), 2.83-2.97 (2H, m), 3.23-3.36 (2H, m), 3.93 (2H, d, J=6.2 Hz), 7.13-7.26 (2H, m), 7.39-7.48 (1H, m), 8.81 (2H, brs).

C) 6-((4-((2-chloro-4-fluorophenoxy)methyl)piperidin-1-yl) carbonyl)-2H-1,4-benzoxazin-3(4H)-one A mixture of 4-((2-chloro-4-fluorophenoxy)methyl)piperidine hydrochloride (725 mg), 3-oxo-3,4-dihydro-2H-benzo[b][1,4]oxazine-6-carboxylic acid (500 mg), HOBt-$H_2O$ (476 mg), EDCI (595 mg), DIPEA (1.13 mL) and DMF (20 mL) was stirred at room temperature for 3 hr. To the reaction mixture was added water, and the resulting precipitate was collected, washed with water and ethyl acetate, dried under reduced pressure, and triturated with heated ethyl acetate to give the title compound (886 mg).

$^1H$ NMR (300 MHz, DMSO-$d_6$) δ 1.17-1.42 (2H, m), 1.72-2.19 (3H, m), 2.76-3.15 (2H, m), 3.53-4.50 (4H, m), 4.62 (2H, s), 6.90-7.03 (3H, m), 7.17 (2H, dd, J=6.5, 1.6 Hz), 7.39-7.46 (1H, m), 10.80 (1H, s).

Example 66

6-((4-((2-chloro-4-fluorophenoxy)methyl)piperidin-1-yl)carbonyl)-7-fluoro-2H-1,4-benzoxazin-3(4H)-one A) 2-fluoro-4-hydroxy-5-nitrobenzonitrile To a solution of 2-fluoro-4-hydroxybenzonitrile (28.9 g) in acetic acid (160 mL) was added conc. sulfuric acid (0.65 mL), and the reaction mixture was stirred at 65° C. for 10 min. To the reaction mixture was added dropwise a solution of 69% nitric acid (19.2 g) in acetic acid (50 mL) over 30 min, and the reaction mixture was stirred at 65° C. for 1.5 hr. The reaction mixture was allowed to cool to room temperature, poured into ice-water (500 mL), and extracted with toluene. The organic layer was washed with water and saturated brine, and dried over anhydrous sodium sulfate, and the solvent was evaporated under reduced pressure. The obtained crude crystals were recrystallized from IPA/heptane to give the title compound (18.3 g).

$^1H$ NMR (300 MHz, $CDCl_3$) δ 7.03 (1H, d, J=9.4 Hz), 8.52 (1H, d, J=6.5 Hz), 11.10 (1H, s).

B) 7-fluoro-3-oxo-3,4-dihydro-2H-benzo[b][1,4]oxazine-6-carbonitrile

A mixture of 2-fluoro-4-hydroxy-5-nitrobenzonitrile (8.00 g), 10% palladium on carbon (0.800 g) and THF (200 mL) was stirred at room temperature for 6.5 hr under hydrogen atmosphere. The catalyst was removed by filtration, and the filtrate was concentrated under reduced pressure to give 5-amino-2-fluoro-4-hydroxybenzonitrile as a crude product.

To a mixture of the obtained crude product, benzyltriethylammonium chloride (10.0 g), sodium hydrogencarbonate (14.8 g) and THF (100 mL) was added dropwise chloroacetic chloride (4.02 mL) at 0° C. over 5 min, and the reaction mixture was stirred at room temperature for 1 hr, and then at 70° C. for 2 hr. The mixture was allowed to cool to room temperature, and the reaction mixture was diluted with ethyl acetate/water, and extracted with ethyl acetate. The organic layer was washed with water and saturated brine, dried over anhydrous sodium sulfate, and passed through silica gel pad, and the filtrate was concentrated under reduced pressure. The obtained crude crystals were recrystallized from ethyl acetate/IPA/heptane to give the title compound (5.36 g).

$^1H$ NMR (300 MHz, DMSO-$d_6$) δ 4.75 (2H, s), 7.19 (1H, d, J=6.5 Hz), 7.25 (1H, d, J=10.3 Hz), 11.00 (1H, s).

C) 7-fluoro-3-oxo-3,4-dihydro-2H-benzo[b][1,4]oxazine-6-carboxylic acid

A mixture of 7-fluoro-3-oxo-3,4-dihydro-2H-benzo[b][1,4]oxazine-6-carbonitrile (4.18 g), conc. hydrochloric acid (50 mL) and acetic acid (50 mL) was stirred at 90° C. for 36 hr. The mixture was allowed to cool to room temperature, and the resulting precipitate was collected, washed with water, dried under reduced pressure at 80° C. for 3 hr, and triturated with heated ethyl acetate to give the title compound (3.79 g).

$^1H$ NMR (300 MHz, DMSO-$d_6$) δ 4.69 (2H, s), 6.96 (1H, d, J=11.4 Hz), 7.40 (1H, d, J=7.3 Hz), 10.86 (1H, s), 13.06 (1H, s).

D) 6-((4-((2-chloro-4-fluorophenoxy)methyl)piperidin-1-yl) carbonyl)-7-fluoro-2H-1, 4-benzoxazin-3(4H)-one To a mixture of 7-fluoro-3-oxo-3,4-dihydro-2H-benzo[b][1,4]oxazine-6-carboxylic acid (80.0 mg), 4-((2-chloro-4-fluorophenoxy)methyl)piperidine hydrochloride (106 mg), EDCI (87.0 mg), HOBt-$H_2O$ (58.0 mg) and DMF (3 mL) was added TEA (0.126 mL) at room temperature, and the mixture was stirred overnight. The reaction mixture was diluted with saturated aqueous sodium hydrogencarbonate solution and water, and extracted with ethyl acetate. The organic layer was washed with water and saturated brine, dried over anhydrous sodium sulfate, and concentrated under reduced pressure. The residue was purified by silica gel column chromatography (ethyl acetate/hexane), and crystallized from ethyl acetate/IPE to give a crude product. The crude product was purified by silica gel column chromatography (NH, methanol/ethyl acetate), and crystallized from ethyl acetate/IPE to give the title compound (26.0 mg).

$^1H$ NMR (300 MHz, DMSO-$d_6$) δ 1.17-1.39 (2H, m), 1.69-1.82 (1H, m), 1.83-1.95 (1H, m), 2.08 (1H, brs), 2.76-2.91 (1H, m), 3.00-3.20 (1H, m), 3.42-3.62 (1H, m), 3.93 (2H, d, J=6.2 Hz), 4.45-4.56 (1H, m), 4.64 (2H, s), 6.82 (1H, d, J=6.8 Hz), 6.98 (1H, d, J=10.0 Hz), 7.17 (2H, dd, J=6.8, 1.7 Hz), 7.42 (1H, dt, J=8.3, 1.8 Hz), 10.81 (1H, brs).

Example 68

2-((1-((7-fluoro-3-oxo-3,4-dihydro-2H-1,4-benzoxazin-6-yl)carbonyl)piperidin-4-yl)methoxy)-5-(trifluoromethyl)benzonitrile A) tert-butyl 4-((2-cyano-4-(trifluoromethyl)phenoxy)methyl)piperidine-1-carboxylate To a solution of 2-hydroxy-5-(trifluoromethyl)benzonitrile (1.94 g), tert-butyl 4-(hydroxymethyl)piperidine-1-carboxylate (2.23 g) and tributylphosphine (3.10 mL) in THF (50 mL) was added ADDP (3.14 g) at 0° C., and the reaction mixture was stirred at room temperature for 4 hr. Then, the reaction mixture was heated under reflux for 14 hr. The reaction mixture was concentrated, and the residue was purified by silica gel column chromatography (NH, ethyl acetate/hexane) to give the title compound (1.41 g).

$^1H$ NMR (300 MHz, $CDCl_3$) δ 1.22-1.37 (2H, m), 1.47 (9H, s), 1.82-1.94 (2H, m), 2.00-2.19 (1H, m), 2.68-2.86

(2H, m), 3.96 (2H, d, J=6.6 Hz), 4.11-4.27 (2H, m), 7.05 (1H, d, J=8.9 Hz), 7.74-7.86 (2H, m).

B) 2-(piperidin-4-ylmethoxy)-5-(trifluoromethyl) benzonitrile hydrochloride

To a solution of tert-butyl 4-((2-cyano-4-(trifluoromethyl) phenoxy)methyl)piperidine-1-carboxylate (1.41 g) in ethyl acetate (15 mL) was added 4M hydrogen chloride ethyl acetate solution (15 mL), and the reaction mixture was stirred at room temperature for 1 hr. The resulting precipitate was collected, washed with ethyl acetate, and dried under reduced pressure to give the title compound (1.12 g).

$^1$H NMR (300 MHz, DMSO-$d_6$) δ 1.43-1.62 (2H, m), 1.86-2.02 (2H, m), 2.07-2.23 (1H, m), 2.82-3.02 (2H, m), 3.32 (2H, d, J=12.6 Hz), 4.15 (2H, d, J=6.4 Hz), 7.48 (1H, d, J=8.9 Hz), 8.05 (1H, dd, J=9.2, 2.1 Hz), 8.25 (1H, d, J=2.0 Hz), 8.56 (1H, brs), 8.88 (1H, brs).

C) 2-((1-((7-fluoro-3-oxo-3,4-dihydro-2H-1,4-benzoxazin-6-yl)carbonyl)piperidin-4-yl)methoxy)-5-(trifluoromethyl)benzonitrile A mixture of 2-(piperidin-4-ylmethoxy)-5-(trifluoromethyl)benzonitrile hydrochloride (76.0 mg), 7-fluoro-3-oxo-3,4-dihydro-2H-benzo[b][1,4]oxazine-6-carboxylic acid (50.0 mg), HOBt-$H_2O$ (43.5 mg), EDCI (54.5 mg), DIPEA (0.165 mL) and DMF (1.5 mL) was stirred at room temperature for 12 hr. To the reaction mixture was added water, and the resulting precipitate was collected, washed with water and ethyl acetate, and dried under reduced pressure. The obtained crude product was purified by silica gel column chromatography (ethyl acetate/hexane) to give the title compound (43.0 mg).

$^1$H NMR (300 MHz, $CDCl_3$) δ 1.42-1.62 (2H, m), 1.83-2.00 (2H, m), 2.13-2.31 (1H, m), 2.75-2.92 (1H, m), 3.05-3.24 (1H, m), 3.61-3.77 (1H, m), 3.94-4.08 (2H, m), 4.64 (2H, s), 4.76-4.90 (1H, m), 6.74 (1H, d, J=9.6 Hz), 6.98 (1H, d, J=6.2 Hz), 7.05 (1H, d, J=8.9 Hz), 7.75-7.88 (2H, m), 8.53 (1H, s).

Example 70

3-chloro-4-((1-((7-fluoro-3-oxo-3,4-dihydro-2H-1,4-benzoxazin-6-yl)carbonyl)piperidin-4-yl)methoxy) benzonitrile A) 3-chloro-4-(piperidin-4-ylmethoxy)benzonitrile hydrochloride To a solution of 3-chloro-4-hydroxybenzonitrile (2.14 g), tert-butyl 4-(hydroxymethyl)piperidine-1-carboxylate (3.00 g) and triphenylphosphine (4.39 g) in THF (50 mL) was added 1.9 M DIAD (toluene solution, 8.80 mL) at 0° C., and the reaction mixture was stirred at room temperature for 4 hr. The reaction mixture was concentrated, and the residue was purified by silica gel column chromatography (ethyl acetate/hexane) to give tert-butyl 4-((2-chloro-4-cyanophenoxy) methyl)piperidine-1-carboxylate as a crude product.

To a solution of the obtained crude product in ethyl acetate (20 mL) was added 4M hydrogen chloride ethyl acetate solution (60 mL), and the reaction mixture was stirred at room temperature for 1 hr. The resulting precipitate was collected, washed with ethyl acetate, and dried under reduced pressure to give the title compound (3.17 g).

$^1$H NMR (300 MHz, DMSO-$d_6$) δ 1.41-1.63 (2H, m), 1.86-1.99 (2H, m), 2.05-2.24 (1H, m), 2.81-3.03 (2H, m), 3.21-3.46 (2H, m), 4.08 (2H, d, J=6.2 Hz), 7.34 (1H, d, J=8.7 Hz), 7.84 (1H, dd, J=8.7, 2.1 Hz), 8.04 (1H, d, J=1.9 Hz), 8.54 (1H, brs), 8.86 (1H, brs).

B) 3-chloro-4-((1-((7-fluoro-3-oxo-3,4-dihydro-2H-1,4-benzoxazin-6-yl)carbonyl)piperidin-4-yl) methoxy)benzonitrile A mixture of 3-chloro-4-(piperidin-4-ylmethoxy)benzonitrile hydrochloride (95.0 mg), 7-fluoro-3-oxo-3,4-dihydro-2H-benzo[b][1,4]oxazine-6-carboxylic acid (70.0 mg), HOBt-$H_2O$ (60.9 mg), EDCI (76.0 mg), DIPEA (0.231 mL) and DMF (2 mL) was stirred at room temperature for 12 hr. To the reaction mixture was added water, and the resulting precipitate was collected, washed with water and ethyl acetate, and dried under reduced pressure. The obtained crude compound was purified by silica gel column chromatography (ethyl acetate/hexane and methanol/ethyl acetate), and triturated with heated ethyl acetate/heptane to give the title compound (55.0 mg).

$^1$H NMR (300 MHz, DMSO-$d_6$) δ 1.15-1.39 (2H, m), 1.70-1.94 (2H, m), 2.03-2.23 (1H, m), 2.77-2.94 (1H, m), 3.02-3.20 (1H, m), 3.45-3.60 (1H, m), 4.07 (2H, d, J=6.0 Hz), 4.45-4.55 (1H, m), 4.64 (2H, s), 6.81 (1H, d, J=6.8 Hz), 6.98 (1H, d, J=10.0 Hz), 7.32 (1H, d, J=8.7 Hz), 7.81 (1H, dd, J=8.6, 2.0 Hz), 8.02 (1H, d, J=1.9 Hz), 10.82 (1H, s).

Example 71

6-((4-(((2,6-dichloropyridin-3-yl)oxy)methyl)piperidin-1-yl)carbonyl)-7-fluoro-2H-1,4-benzoxazin-3 (4H)-one A) 2,6-dichloro-3-(piperidin-4-ylmethoxy)pyridine hydrochloride To a solution of 2,6-dichloropyridin-3-ol (1.06 g), tert-butyl 4-(hydroxymethyl)piperidine-1-carboxylate (1.39 g) and triphenylphosphine (2.03 g) in THF (30 mL) was added 1.9 M DIAD (toluene solution, 4.08 mL) at 0° C., and the reaction mixture was stirred at room temperature for 8 hr. The reaction mixture was concentrated, and the residue was purified by silica gel column chromatography (ethyl acetate/hexane) to give tert-butyl 4-(((2,6-dichloropyridin-3-yl)oxy) methyl)piperidine-1-carboxylate as a crude product.

To a solution of the obtained crude product in ethyl acetate (20 mL)/methanol (1 mL) was added 4M hydrogen chloride ethyl acetate solution (50 mL), and the reaction mixture was stirred at room temperature for 1 hr. The resulting precipitate was collected, washed with ethyl acetate, and dried under reduced pressure to give the title compound (1.44 g).

$^1$H NMR (300 MHz, DMSO-$d_6$) δ 1.42-1.60 (2H, m), 1.85-1.97 (2H, m), 2.02-2.19 (1H, m), 2.82-3.04 (2H, m), 3.27-3.37 (2H, m), 4.04 (2H, d, J=6.4 Hz), 7.55 (1H, d, J=8.5 Hz), 7.71 (1H, d, J=8.7 Hz), 8.46 (1H, brs), 8.76 (1H, brs).

B) 6-((4-(((2,6-dichloropyridin-3-yl)oxy)methyl) piperidin-1-yl)carbonyl)-7-fluoro-2H-1,4-benzoxazin-3(4H)-one A mixture of 2,6-dichloro-3-(piperidin-4-ylmethoxy)pyridine hydrochloride (70.5 mg), 7-fluoro-3-oxo-3,4-dihydro-2H-benzo[b][1,4]oxazine-6-carboxylic acid (50.0 mg), HOBt-$H_2O$ (43.5 mg), EDCI (54.5 mg), DIPEA (0.165 mL) and DMF (1.5 mL) was stirred at room temperature for 12 hr. To the reaction mixture was added water, and the mixture was extracted with ethyl acetate/IPA. The organic layer was washed with water and saturated brine, dried over anhydrous sodium sulfate, and concentrated under reduced pressure. The residue was purified by silica gel column chromatography (ethyl acetate/hexane and methanol/ethyl acetate), and recrystallized from ethyl acetate/heptane to give the title compound (84.0 mg).

$^1$H NMR (300 MHz, DMSO-$d_6$) δ 1.07-1.44 (2H, m), 1.69-1.94 (2H, m), 2.04-2.21 (1H, m), 2.75-2.91 (1H, m), 3.12 (1H, d, J=12.4 Hz), 3.44-3.60 (1H, m), 3.98-4.10 (2H, m), 4.43-4.56 (1H, m), 4.64 (2H, s), 6.81 (1H, d, J=7.0 Hz), 6.98 (1H, d, J=10.2 Hz), 7.52 (1H, d, J=8.5 Hz), 7.70 (1H, d, J=8.5 Hz), 10.82 (1H, s).

Example 72

5-chloro-2-((1-((7-fluoro-3-oxo-3, 4-dihydro-2H-1, 4-benzoxazin-6-yl)carbonyl)piperidin-4-yl)methoxy) benzonitrile

A) 5-chloro-2-(piperidin-4-ylmethoxy)benzonitrile hydrochloride

To a solution of 5-chloro-2-hydroxybenzonitrile (2.50 g), tert-butyl 4-(hydroxymethyl)piperidine-1-carboxylate (3.50 g) and triphenylphosphine (5.12 g) in THF (50 mL) was added 1.9 M DIAD (toluene solution, 10.3 mL) at 0° C., and the reaction mixture was stirred at room temperature for 12 hr. The reaction mixture was concentrated, and the residue was purified by silica gel column chromatography (ethyl acetate/hexane) to give tert-butyl 4-((4-chloro-2-cyanophenoxy)methyl)piperidine-1-carboxylate as a crude product.

To a solution of the obtained crude product in ethyl acetate (50 mL) was added 4M hydrogen chloride ethyl acetate solution (81 mL), and the reaction mixture was stirred at room temperature for 1.5 hr. The resulting precipitate was collected, washed with ethyl acetate, and dried under reduced pressure to give the title compound (3.56 g).

$^1$H NMR (300 MHz, DMSO-$d_6$) δ 1.40-1.62 (2H, m), 1.84-1.98 (2H, m), 2.05-2.20 (1H, m), 2.80-3.03 (2H, m), 3.23-3.43 (2H, m), 4.05 (2H, d, J=6.4 Hz), 7.31 (1H, d, J=9.2 Hz), 7.74 (1H, dd, J=9.1, 2.7 Hz), 7.92 (1H, d, J=2.6 Hz), 8.71 (1H, brs), 9.01 (1H, brs).

B) 5-chloro-2-((1-((7-fluoro-3-oxo-3,4-dihydro-2H-1,4-benzoxazin-6-yl)carbonyl)piperidin-4-yl) methoxy)benzonitrile A mixture of 5-chloro-2-(piperidin-4-ylmethoxy)benzonitrile hydrochloride (40.8 mg), 7-fluoro-3-oxo-3,4-dihydro-2H-benzo[b][1,4]oxazine-6-carboxylic acid (30.0 mg), HOBt-$H_2O$ (26.1 mg), EDCI (32.7 mg), DIPEA (0.0990 mL) and DMF (1.5 mL) was stirred at room temperature for 12 hr. To the reaction mixture was added water, and the resulting precipitate was collected, washed with water and ethyl acetate, and dried under reduced pressure. The obtained crude product was purified by silica gel column chromatography (ethyl acetate/hexane and methanol/ethyl acetate), and triturated with heated ethyl acetate/heptane to give the title compound (50.0 mg).

$^1$H NMR (300 MHz, DMSO-$d_6$) δ 1.14-1.35 (2H, m), 1.70-1.93 (2H, m), 2.04-2.22 (1H, m), 2.76-2.91 (1H, m), 3.02-3.20 (1H, m), 3.44-3.60 (1H, m), 4.01-4.10 (2H, m), 4.45-4.57 (1H, m), 4.64 (2H, s), 6.82 (1H, d, J=6.8 Hz), 6.98 (1H, d, J=10.2 Hz), 7.29 (1H, d, J=9.2 Hz), 7.72 (1H, dd, J=9.0, 2.8 Hz), 7.91 (1H, d, J=2.6 Hz), 10.82 (1H, s).

Example 74

6-((4-((2,4-dichlorophenoxy)methyl)-4-hydroxypiperidin-1-yl)carbonyl)-7-fluoro-2H-1,4-benzoxazin-3 (4H)-one

A) 4-((2,4-dichlorophenoxy)methyl)piperidin-4-ol hydrochloride

A mixture of 2,4-dichlorophenol (0.841 g), tert-butyl 1-oxa-6-azaspiro[2.5]octane-6-carboxylate (1.00 g), potassium carbonate (1.52 g) and DMF (10 mL) was stirred at 80° C. for 4 hr. The reaction mixture was diluted with water, and extracted with ethyl acetate. The organic layer was washed with water and saturated brine, dried over anhydrous sodium sulfate, and passed through NH silica gel pad, and the filtrate was concentrated under reduced pressure to give tert-butyl 4-((2,4-dichlorophenoxy)methyl)-4-hydroxypiperidine-1-carboxylate as a crude product.

To a solution of the obtained crude product in ethyl acetate (20 mL) was added 4M hydrogen chloride ethyl acetate solution (17.5 mL), and the reaction mixture was stirred at room temperature for 12 hr. The resulting precipitate was collected, washed with ethyl acetate, and dried under reduced pressure to give the title compound (1.36 g).

$^1$H NMR (300 MHz, DMSO-$d_6$) δ 1.69-1.81 (2H, m), 1.85-2.01 (2H, m), 2.98-3.27 (4H, m), 3.91 (2H, s), 4.43 (1H, brs), 7.20 (1H, d, J=9.0 Hz), 7.38 (1H, dd, J=8.9, 2.6 Hz), 7.58 (1H, d, J=2.5 Hz), 8.69 (1H, brs), 8.99 (1H, brs).

B) 6-((4-((2,4-dichlorophenoxy)methyl)-4-hydroxypiperidin-1-yl)carbonyl)-7-fluoro-2H-1,4-benzoxazin-3(4H)-one A mixture of 4-((2,4-dichlorophenoxy)methyl)piperidin-4-ol hydrochloride (53.3 mg), 7-fluoro-3-oxo-3,4-dihydro-2H-benzo[b][1,4]oxazine-6-carboxylic acid (30.0 mg), HOBt-$H_2O$ (28.3 mg), EDCI (35.4 mg), DIPEA (0.0990 mL) and DMF (1.5 mL) was stirred at room temperature for 12 hr. To the reaction mixture was added water, and the mixture was extracted with ethyl acetate/IPA. The organic layer was washed with water and saturated brine, dried over anhydrous sodium sulfate, and concentrated under reduced pressure. The residue was purified by silica gel column chromatography (ethyl acetate/hexane and methanol/ethyl acetate) to give the title compound (59.0 mg).

$^1$H NMR (300 MHz, DMSO-$d_6$) δ 1.46-1.82 (4H, m), 3.08-3.22 (1H, m), 3.31-3.42 (2H, m), 3.87 (2H, s), 4.22-4.37 (1H, m), 4.64 (2H, s), 4.93 (1H, s), 6.82 (1H, d, J=6.7 Hz), 6.98 (1H, d, J=10.1 Hz), 7.18 (1H, d, J=9.0 Hz), 7.36 (1H, dd, J=8.9, 2.5 Hz), 7.57 (1H, d, J=2.6 Hz), 10.83 (1H, s).

Example 76

6-((3-((2,4-dichlorophenoxy)methyl)azetidin-1-yl) carbonyl)-7-fluoro-2H-1,4-benzoxazin-3(4H)-one

A) tert-butyl 3-((2,4-dichlorophenoxy)methyl)azetidine-1-carboxylate

To a solution of 2,4-dichlorophenol (3.48 g), tert-butyl 3-(hydroxymethyl)azetidine-1-carboxylate (4.00 g) and triphenylphosphine (6.72 g) in THF (60 mL) was added 1.9 M DIAD (toluene solution, 13.5 mL), and the reaction mixture was stirred at room temperature for 12 hr. The reaction mixture was concentrated, and the residue was purified by silica gel column chromatography (ethyl acetate/hexane) to give the title compound (6.69 g).

$^1$H NMR (300 MHz, DMSO-$d_6$) δ 1.37 (9H, s), 2.85-3.06 (1H, m), 3.60-3.80 (2H, m), 3.86-4.04 (2H, m), 4.18 (2H, d, J=6.0 Hz), 7.20 (1H, d, J=8.9 Hz), 7.38 (1H, dd, J=8.8, 2.6 Hz), 7.58 (1H, d, J=2.5 Hz).

B) 6-((3-((2,4-dichlorophenoxy)methyl)azetidin-1-yl)carbonyl)-7-fluoro-2H-1,4-benzoxazin-3(4H)-one To a solution of tert-butyl 3-((2,4-dichlorophenoxy) methyl)azetidine-1-carboxylate (500 mg) in toluene (5 mL) was added trifluoroacetic acid (1 mL), and the reaction mixture was stirred at room temperature for 2 hr. The reaction mixture was concentrated, and the residue was diluted with ethyl acetate. The organic layer was washed with aqueous sodium hydrogencarbonate solution and saturated brine, dried over anhydrous sodium sulfate, and concentrated under reduced pressure to give 3-((2,4-dichlorophenoxy)methyl)azetidine as a crude product.

To a solution of a part (39.6 mg) of the obtained crude product, HOBt-$H_2O$ (26.1 mg), 7-fluoro-3-oxo-3,4-dihydro-2H-benzo[b][1,4]oxazine-6-carboxylic acid (30.0 mg) and TEA (0.0590 mL) in DMF (5 mL) was added EDCI (40.9 mg). The reaction mixture was stirred overnight at room temperature. The reaction was quenched with saturated aqueous sodium hydrogencarbonate solution, and the mixture was extracted with ethyl acetate. The organic layer was washed with water and saturated brine, dried over anhydrous magnesium sulfate, and concentrated under reduced pressure. The residue was purified by silica gel column chromatography (ethyl acetate/hexane and methanol/ethyl acetate) to give the title compound (24.0 mg).

$^1$H NMR (300 MHz, DMSO-$d_6$) δ 2.95-3.16 (1H, m), 3.80-3.99 (2H, m), 4.04-4.28 (4H, m), 4.65 (2H, s), 6.88-7.06 (2H, m), 7.20 (1H, d, J=9.0 Hz), 7.38 (1H, dd, J=8.8, 2.6 Hz), 7.58 (1H, d, J=2.6 Hz), 10.85 (1H, s).

Example 82

6-((4-((2-chloro-4-(prop-1-en-2-yl)phenoxy)methyl) piperidin-1-yl) carbonyl)-7-fluoro-2H-1,4-benzoxazin-3(4H)-one A) tert-butyl 4-((2-chloro-4-(methoxycarbonyl)phenoxy)methyl)piperidine-1-carboxylate To a solution of methyl 3-chloro-4-hydroxybenzoate (3.00 g), tert-butyl 4-(hydroxymethyl)piperidine-1-carboxylate (3.46 g) and triphenylphosphine (5.06 g) in THF (50 mL) was added 1.9 M DIAD (toluene solution, 10.2 mL) at 0° C., and the reaction mixture was stirred at room temperature for 96 hr. The reaction mixture was concentrated, and the residue was purified by silica gel column chromatography (ethyl acetate/hexane) to give the title compound (5.24 g).

$^1$H NMR (300 MHz, $CDCl_3$) δ 1.47 (9H, s), 1.81-1.93 (2H, m), 1.81-1.93 (2H, m), 1.97-2.15 (1H, m), 2.66-2.88 (2H, m), 3.87-3.97 (5H, m), 4.08-4.28 (2H, m), 6.91 (1H, d, J=8.7 Hz), 7.91 (1H, dd, J=8.7, 2.1 Hz), 8.05 (1H, d, J=2.1 Hz).

B) tert-butyl 4-((2-chloro-4-(2-hydroxypropan-2-yl) phenoxy)methyl)piperidine-1-carboxylate To a solution of tert-butyl 4-((2-chloro-4-(methoxycarbonyl)phenoxy)methyl)piperidine-1-carboxylate (270 mg) in THF (10 mL) was added 1 M methylmagnesium bromide (THF solution, 2.11 mL) at 0° C., and the reaction mixture was stirred at room temperature for 5 hr. To the reaction mixture was added again 1 M methylmagnesium bromide (THF solution, 2.11 mL), and the mixture was stirred overnight at 60° C. The reaction was quenched with saturated aqueous ammonium chloride solution, and the mixture was extracted with ethyl acetate. The organic layer was washed with water and saturated brine, dried over anhydrous magnesium sulfate, and concentrated under reduced pressure. The residue was purified by silica gel column chromatography (ethyl acetate/hexane) to give the title compound (230 mg).

$^1$H NMR (300 MHz, DMSO-$d_6$) δ 1.14-1.27 (2H, m), 1.38 (6H, s), 1.40 (9H, s), 1.67-1.81 (2H, m), 1.85-1.98 (1H, m), 2.56-2.91 (2H, m), 3.90 (2H, d, J=6.3 Hz), 3.93-4.02 (2H, m), 5.04 (1H, s), 7.04 (1H, d, J=8.6 Hz), 7.32 (1H, dd, J=8.6, 2.3 Hz), 7.46 (1H, d, J=2.3 Hz).

C) 6-((4-((2-chloro-4-(prop-1-en-2-yl)phenoxy) methyl)piperidin-1-yl)carbonyl)-7-fluoro-2H-1,4-benzoxazin-3(4H)-one tert-Butyl 4-((2-chloro-4-(2-hydroxypropan-2-yl)phenoxy)methyl)piperidine-1-carboxylate (160 mg) was dissolved in 4M hydrogen chloride ethyl acetate solution (3 mL). The reaction mixture was stirred at room temperature for 3 hr, and concentrated, and the resulting precipitate was collected, and washed with ethyl acetate/hexane to give 4-((2-chloro-4-(prop-1-en-2-yl)phenoxy)methyl)piperidine hydrochloride as a crude product. To a solution of a part (65.0 mg) of the obtained crude product, HOBt-$H_2O$ (36.2 mg), 7-fluoro-3-oxo-3,4-dihydro-2H-benzo[b][1,4]oxazine-6-carboxylic acid (45.4 mg) and TEA (0.120 mL) in DMF (2 mL) was added EDCI (53.6 mg). The reaction mixture was stirred overnight at room temperature. The reaction was quenched with saturated aqueous sodium hydrogencarbonate solution, and the mixture was extracted with ethyl acetate. The organic layer was washed with water and saturated brine, dried over anhydrous magnesium sulfate, and concentrated under reduced pressure. The residue was purified by silica gel column chromatography (ethyl acetate/hexane) to give the title compound (26.0 mg).

$^1$H NMR (300 MHz, DMSO-$d_6$) δ 1.18-1.43 (2H, m), 1.77 (1H, d, J=12.2 Hz), 1.89 (1H, d, J=12.5 Hz), 2.07 (3H, s), 2.08-2.16 (1H, m), 2.76-2.90 (1H, m), 3.10 (1H, t, J=12.7 Hz), 3.52 (1H, d, J=14.1 Hz), 3.97 (2H, d, J=6.1 Hz), 4.51 (1H, d, J=13.4 Hz), 4.64 (2H, s), 5.04 (1H, t, J=1.4 Hz), 5.38 (1H, s), 6.82 (1H, d, J=6.7 Hz), 6.99 (1H, d, J=10.1 Hz), 7.12 (1H, d, J=8.8 Hz), 7.42 (1H, dd, J=8.5, 2.3 Hz), 7.54 (1H, d, J=2.3 Hz), 10.83 (1H, s).

Example 87

7-chloro-6-((3-((2-chloro-4-fluorophenoxy)methyl) azetidin-1-yl)carbonyl)-2H-1,4-benzoxazin-3(4H)-one A) 7-chloro-3-oxo-3,4-dihydro-2H-benzo[b][1,4] oxazine-6-carbonitrile To a mixture of 5-amino-2-chloro-4-hydroxybenzonitrile (106 mg), benzyltriethylammonium chloride (143 mg), sodium hydrogencarbonate (211 mg) and THF (1.5 mL) was added chloroacetic chloride (0.0550 mL) at 0° C., and the reaction mixture was stirred at room temperature for 1 hr. Then, the reaction mixture was stirred at 70° C. for 2 hr. The reaction mixture was diluted with ethyl acetate/water, and extracted with ethyl acetate. The organic layer was washed with water and saturated brine, dried over anhydrous sodium sulfate, and concentrated under reduced pressure. The obtained crude crystals were triturated with ethyl acetate/hexane to give the title compound (91.0 mg).

MS: $[M-H]^-$ 206.9.

B) 7-chloro-3-oxo-3,4-dihydro-2H-benzo[b][1,4]oxazine-6-carboxylic acid

A mixture of 7-chloro-3-oxo-3,4-dihydro-2H-benzo[b][1,4]oxazine-6-carbonitrile (91.0 mg) and conc. sulfuric acid (1 mL) was stirred overnight at 90° C. The mixture was allowed to cool to room temperature, and the reaction mixture was carefully poured into water. The resulting precipitate was collected, and washed with water and ethyl acetate to give the title compound (62.0 mg).

$^1$H NMR (300 MHz, DMSO-$d_6$) δ 4.69 (2H, s), 7.13 (1H, s), 7.42 (1H, s), 10.93 (1H, s).

C) 7-chloro-6-((3-((2-chloro-4-fluorophenoxy)methyl)azetidin-1-yl)carbonyl)-2H-1,4-benzoxazin-3(4H)-one To a mixture of 3-((2-chloro-4-fluorophenoxy)methyl)azetidine (28.4 mg) and 7-chloro-3-oxo-3,4-dihydro-2H-benzo[b][1,4]oxazine-6-carboxylic acid (20.0 mg) in DMF (0.5 mL) were added HATU (50.1 mg) and TEA (0.0610 mL), and the mixture was stirred overnight at room temperature. The reaction mixture was diluted with ethyl acetate/water, and extracted with ethyl acetate. The organic layer was washed with water and saturated brine, dried over anhydrous sodium sulfate, and concentrated under reduced pressure. The residue was purified by silica gel column chromatography (ethyl acetate/hexane and methanol/ethyl acetate), and crystallized from ethyl acetate/hexane to give the title compound (9.70 mg).

$^1$H NMR (300 MHz, DMSO-$d_6$) δ 3.00-3.16 (1H, m), 3.80 (1H, dd, J=8.6, 5.8 Hz), 3.92 (1H, dd, J=10.0, 5.4 Hz), 4.00-4.08 (1H, m), 4.09-4.14 (1H, m), 4.16-4.22 (2H, m), 4.65 (2H, s), 6.87 (1H, s), 7.13 (1H, s), 7.17-7.23 (2H, m), 7.44 (1H, dd, J=7.8, 1.9 Hz), 10.93 (1H, s).

Example 88

6-((3-((2-chloro-4-fluorophenoxy)methyl)azetidin-1-yl) carbonyl)-7-methyl-2H-1,4-benzoxazin-3 (4H)-one A) methyl 4-(2-ethoxy-2-oxoethoxy)-2-methyl-5-nitrobenzoate To a solution of methyl 4-fluoro-2-methyl-5-nitrobenzoate (500 mg) and ethyl glycolate (0.266 mL) in DMF (5 mL) was added potassium carbonate (713 mg) at 0° C., and the reaction mixture was stirred overnight at 80° C. The reaction mixture was diluted with ethyl acetate/water, and extracted with ethyl acetate. The organic layer was washed with water and saturated brine, dried over anhydrous sodium sulfate, and concentrated under reduced pressure. The residue was purified by silica gel column chromatography (ethyl acetate/hexane) to give the title compound (460 mg).

$^1$H NMR (300 MHz, DMSO-$d_6$) δ 1.21 (3H, t, J=7.1 Hz), 2.59 (3H, s), 3.83 (3H, s), 4.18 (2H, q, J=7.1 Hz), 5.11 (2H, s), 7.33 (1H, s), 8.37 (1H, s).

B) methyl 7-methyl-3-oxo-3,4-dihydro-2H-benzo[b][1,4]oxazine-6-carboxylate

A mixture of methyl 4-(2-ethoxy-2-oxoethoxy)-2-methyl-5-nitrobenzoate (400 mg), 10% palladium on carbon (40.0 mg) and THF (3 mL)/methanol (1 mL) was stirred at room temperature for 5 hr under hydrogen atmosphere. The reaction atmosphere was replaced with nitrogen gas, and the mixture was stirred overnight at 60° C. The catalyst was removed by filtration, the filtrate was concentrated under reduced pressure, and the residue was triturated with IPE to give the title compound (284 mg).

MS: $[M+H]^+$222.1.

C) 7-methyl-3-oxo-3,4-dihydro-2H-benzo[b][1,4]oxazine-6-carboxylic acid

To a solution of methyl 7-methyl-3-oxo-3,4-dihydro-2H-benzo[b][1,4]oxazine-6-carboxylate (250 mg) in THF (2 mL)/methanol (1 mL)/water (1 mL) was added lithium hydroxide monohydrate (56.9 mg) at room temperature. The mixture was stirred at room temperature for 1 hr, and lithium hydroxide monohydrate (37.9 mg) was added thereto again. The reaction was quenched with 2 M hydrochloric acid (1.13 mL), and the mixture was extracted with ethyl acetate. The organic layer was washed with water and saturated brine, dried over anhydrous sodium sulfate, and concentrated under reduced pressure. The residue was triturated with ethyl acetate/hexane to give the title compound (52.0 mg).

MS: $[M+H]^+$ 208.0.

D) 6-((3-((2-chloro-4-fluorophenoxy)methyl)azetidin-1-yl)carbonyl)-7-methyl-2H-1,4-benzoxazin-3(4H)-one To a mixture of 3-((2-chloro-4-fluorophenoxy)methyl)azetidine (31.2 mg) and 7-methyl-3-oxo-3,4-dihydro-2H-benzo[b][1,4]oxazine-6-carboxylic acid (20.0 mg) in DMF (0.5 mL) were added HATU (55.1 mg) and TEA (0.0670 mL), and the mixture was stirred overnight at room temperature. The reaction mixture was diluted with ethyl acetate/water, and extracted with ethyl acetate. The organic layer was washed with water and saturated brine, dried over anhydrous sodium sulfate, and concentrated under reduced pressure. The residue was purified by silica gel column chromatography (ethyl acetate/hexane and methanol/ethyl acetate), and crystallized from ethyl acetate/hexane to give the title compound (10.4 mg).

$^1$H NMR (300 MHz, DMSO-$d_6$) δ 2.22 (3H, s), 2.99-3.12 (1H, m), 3.74-3.83 (1H, m), 3.92 (1H, dd, J=9.8, 5.7 Hz), 3.97-4.05 (1H, m), 4.07-4.15 (1H, m), 4.18 (2H, d, J=5.7 Hz), 4.58 (2H, s), 6.79 (1H, s), 6.84 (1H, s), 7.16-7.24 (2H, m), 7.40-7.48 (1H, m), 10.69 (1H, s).

The compounds of Examples 5 to 16, 18 to 23, 25, 27 to 65, 67, 69, 73, 75, 77 to 81, 83 to 86 and 89 in the following tables were produced according to the methods described in the above-mentioned Examples, or methods analogous thereto. The compounds of Examples are shown in the following Tables 1-1 to 1-10. MS in the tables means actual measured value.

TABLE 1-1

| Ex. No. | IUPAC NAME | STRUCTURE | MS |
|---|---|---|---|
| 1 | 7-((4-(phenoxymethyl)piperidin-1-yl)carbonyl)3,4-dihydroquinolin-2(1H)-one | 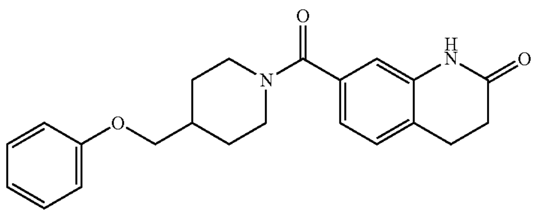 [SMILES: O=C1CCc2ccc(C(=O)N3CCC(COc4ccccc4)CC3)cc2N1] | 365.2 |
| 5 | 7-((4-((4-methoxyphenoxy)methyl)piperidin-1-yl)carbonyl)-1H-pyrido[2,3-b][1,4]oxazin-2(3H)-one | 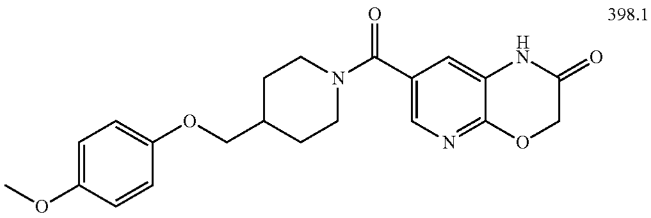 | 398.1 |
| 6 | 7-((4-((4-chlorophenoxy)methyl)piperidin-1-yl)carbonyl)-1H-pyrido[2,3-b][1,4]oxazin-2(3H)-one | 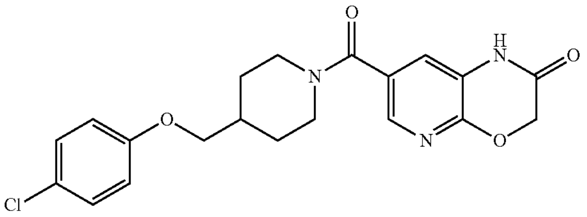 [SMILES: O=C1COc2ncc(C(=O)N3CCC(COc4ccc(Cl)cc4)CC3)cc2N1] | 402.0 |
| 7 | 7-((4-((2-chlorophenoxy)methyl)piperidin-1-yl)carbonyl)-1H-pyrido[2,3-b][1,4]oxazin-2(3H)-one | 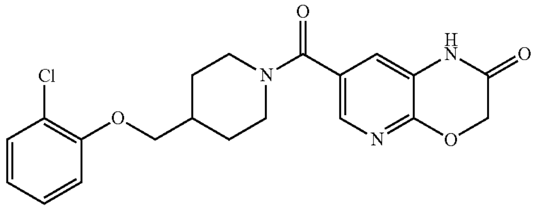 [SMILES: O=C1COc2ncc(C(=O)N3CCC(COc4ccccc4Cl)CC3)cc2N1] | 402.0 |
| 8 | 7-((3-(phenoxymethyl)pyrrolidin-1-yl)carbonyl)-1H-pyrido[2,3-b][1,4]oxazin-2(3H)-one | 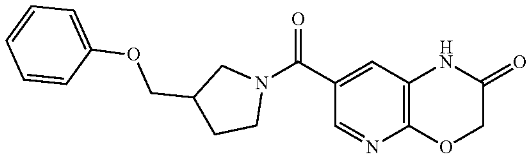 [SMILES: O=C1COc2ncc(C(=O)N3CCC(COc4ccccc4)C3)cc2N1] | 354.1 |
| 9 | 7-((4-((pyridin-2-yloxy)methyl)piperidin-1-yl)carbonyl)-1H-pyrido[2,3-b][1,4]oxazin-2(3H)-one | 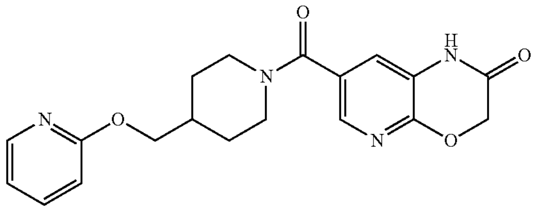 [SMILES: O=C1COc2ncc(C(=O)N3CCC(COc4ccccn4)CC3)cc2N1] | 369.1 |
| 10 | 7-((4-((pyrimidin-2-yloxy)methyl)piperidin-1-yl)carbonyl)-1H-pyrido[2,3-b][1,4]oxazin-2(3H)-one | 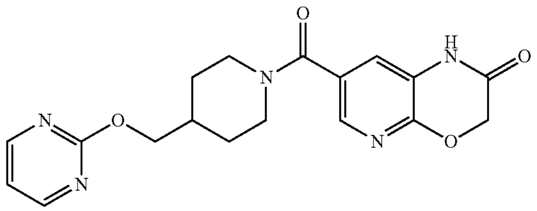 [SMILES: O=C1COc2ncc(C(=O)N3CCC(COc4ncccn4)CC3)cc2N1] | 370.1 |

TABLE 1-1-continued

| Ex. No. | IUPAC NAME | STRUCTURE | MS |
|---|---|---|---|
| 11 | 7-((4-((benzyloxy)methyl)piperidin-1-yl)carbonyl)-1H-pyrido[2,3-b][1,4]oxazin-2(3H)-one | 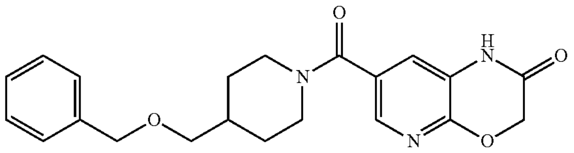 [SMILES: O=C1COc2ncc(C(=O)N3CCC(COCc4ccccc4)CC3)cc2N1] | 382.2 |
| 12 | 6-((4-(phenoxymethyl)piperidin-1-yl)carbonyl)-2H-1,4-benzoxazin-3(4H)-one | 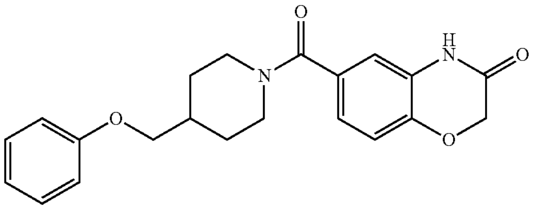 [SMILES: O=C1COc2ccc(C(=O)N3CCC(COc4ccccc4)CC3)cc2N1] | 367.2 |

TABLE 1-2

| | | | |
|---|---|---|---|
| 13 | 7-((4-((3-chlorophenoxy)methyl)piperidin-1-yl)carbonyl)-1H-pyrido[2,3-b][1,4]oxazin-2(3H)-one | 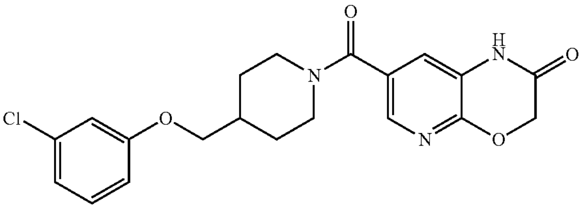 [SMILES: O=C1COc2ncc(C(=O)N3CCC(COc4cccc(Cl)c4)CC3)cc2N1] | 402.0 |
| 14 | 7-((3-((benzyloxy)methyl)azetidin-1-yl)carbonyl)-1H-pyrido[2.3-b][1,4]oxazin-2(3H)-one | 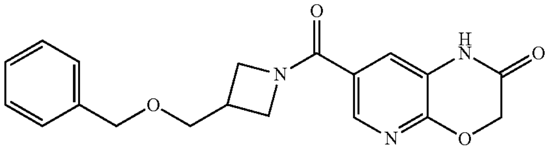 [SMILES: O=C1COc2ncc(C(=O)N3CC(COCc4ccccc4)C3)cc2N1] | 354.1 |
| 15 | 7-((3-((benzyloxy)methyl)pyrrolidin-1-yl)carbonyl)-1H-pyrido[2,3-b][1,4]oxazin-2(3H)-one | 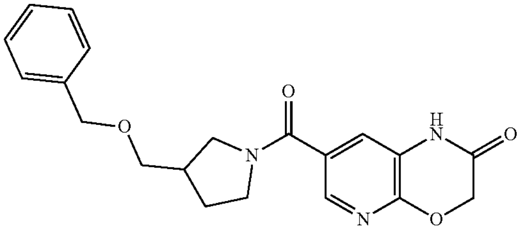 [SMILES: O=C1COc2ncc(C(=O)N3CCC(COCc4ccccc4)C3)cc2N1] | 368.1 |
| 16 | 7-((3-(phenoxymethyl)azetidin-1-yl)carbonyl)-1H-pyrido[2,3-b][1,4]oxazin-2(3H)-one | 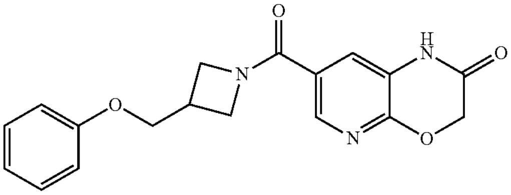 [SMILES: O=C1COc2ncc(C(=O)N3CC(COc4ccccc4)C3)cc2N1] | 340.1 |
| 17 | 7-((4-((2,4-dichlorophenoxy)methyl)piperidin-1-yl)carbonyl)-1H-pyrido[2,3-b][1,4]oxazin-2(3H)-one | 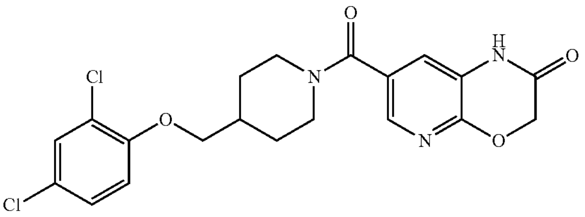 [SMILES: O=C1COc2ncc(C(=O)N3CCC(COc4ccc(Cl)cc4Cl)CC3)cc2N1] | 435.9 |

TABLE 1-2-continued

| | | | |
|---|---|---|---|
| 18 | 7-((4-((2,5-dichlorophenoxy)methyl)piperidin-1-yl)carbonyl)-1H-pyrido[2,3-b][1,4]oxazin-2(3H)-one | 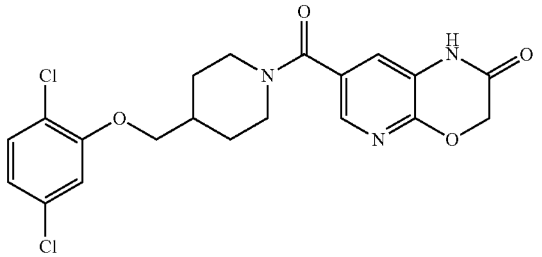 [SMILES: O=C1COc2ncc(C(=O)N3CCC(COc4cc(Cl)ccc4Cl)CC3)cc2N1] | 435.9 |
| 19 | 7-((4-((2-(trifluoromethyl)phenoxy)methyl) piperidin-1-yl)carbonyl)-1H-pyrido [2,3-b][1,4]oxazin-2(3H)-one | 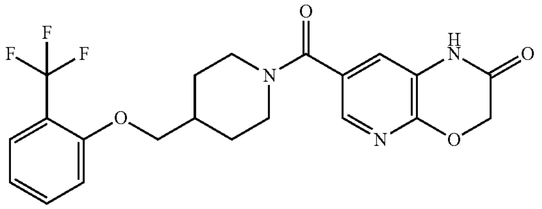 [SMILES: O=C1COc2ncc(C(=O)N3CCC(COc4ccccc4C(F)(F)F)CC3)cc2N1] | 436.0 |
| 20 | 7-((4-((2-chloro-4-fluorophenoxy)methyl)piperidin-1-yl)carbonyl)-1H-pyrido[2,3-b][1,4]oxazin-2(3H)-one | 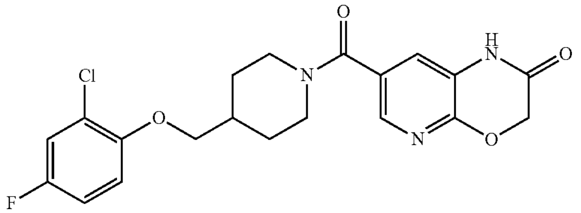 [SMILES: O=C1COc2ncc(C(=O)N3CCC(COc4ccc(F)cc4Cl)CC3)cc2N1] | 420.0 |
| 21 | 7-((4-((2-chloro-5-fluorophenoxy)methyl)piperidin-1-yl)carbonyl)-1H-pyrido[2,3-b][1,4]oxazin-2(3H)-one | 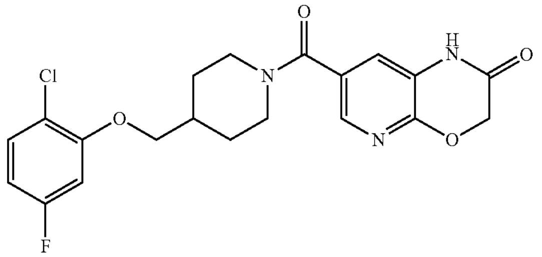 [SMILES: O=C1COc2ncc(C(=O)N3CCC(COc4cc(F)ccc4Cl)CC3)cc2N1] | 419.9 |

TABLE 1-3

| | | | |
|---|---|---|---|
| 22 | 7-((4-((2-chloro-6-fluorophenoxy)methyl)piperidin-1-yl)carbonyl)-1H-pyrido[2,3-b][1,4]oxazin-2(3H)-one | 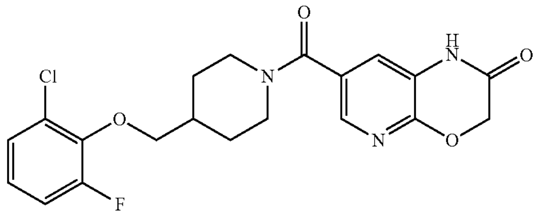 [SMILES: O=C1COc2ncc(C(=O)N3CCC(COc4c(F)cccc4Cl)CC3)cc2N1] | 420.0 |
| 23 | 6-((4-((2,4-dichlorophenoxy)methyl)piperidin-1-yl)carbonyl)-2H-1,4-benzoxazin-3(4H)-one | 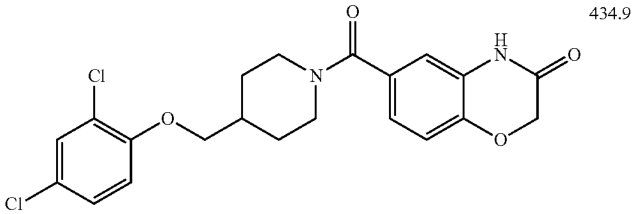 | 434.9 |

TABLE 1-3-continued

| | | | |
|---|---|---|---|
| 24 | 6-((4-((2-chlorophenoxy)methyl)piperidin-1-yl)carbonyl)-2H-1,4-benzoxazin-3(4H)-one | 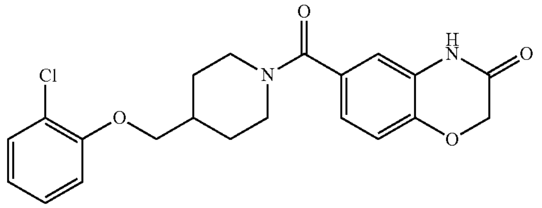 [SMILES: O=C1COc2ccc(C(=O)N3CCC(COc4ccccc4Cl)CC3)cc2N1] | 401.0 |
| 25 | 7-((4-((2,3-dichlorophenoxy)methyl)piperidin-1-yl)carbonyl)-1H-pyrido[2,3-b][1,4]oxazin-2(3H)-one | 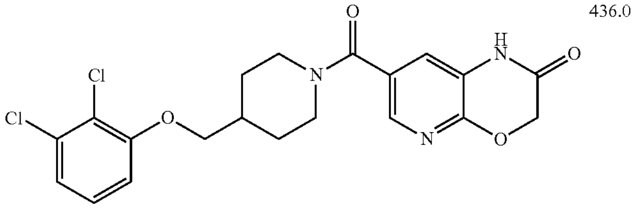 | 436.0 |
| 26 | 6-((4-((2-chloro-4-fluorophenoxy)methyl)piperidin-1-yl)carbonyl)-2H-1,4-benzoxazin-3(4H)-one | 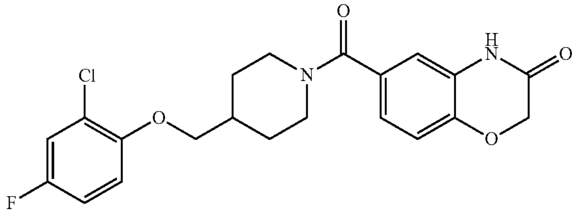 [SMILES: O=C1COc2ccc(C(=O)N3CCC(COc4ccc(F)cc4Cl)CC3)cc2N1] | 419.0 |
| 27 | 6-((4-((2-chloro-4-fluorophenoxy)methyl)-4-fluoropiperidin-1-yl)carbonyl)-2H-1,4-benzoxazin-3(4H)-one | 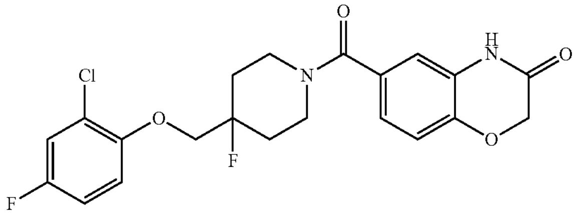 [SMILES: O=C1COc2ccc(C(=O)N3CCC(F)(COc4ccc(F)cc4Cl)CC3)cc2N1] | 436.9 |
| 28 | 6-(4-((2-chlorophenoxy)methyl)piperidin-1-yl)carbonyl)-1,3-dihydro-2H-indol-2-one | 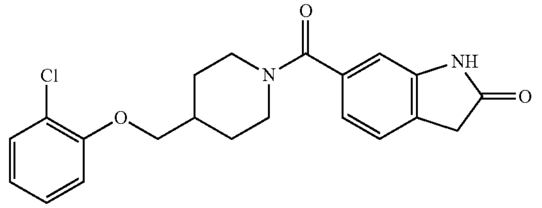 [SMILES: O=C1Cc2ccc(C(=O)N3CCC(COc4ccccc4Cl)CC3)cc2N1] | 385.0 |
| 29 | 5-((4-((2-chlorophenoxy)methyl)piperidin-1-yl)carbonyl)-1,3-benzoxazol-2(3H)-one | 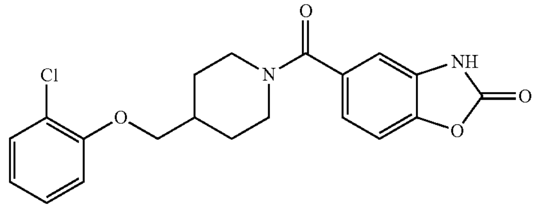 [SMILES: O=C(c1ccc2oc(=O)[nH]c2c1)N1CCC(COc2ccccc2Cl)CC1] | 387.0 |
| 30 | 2-((1-((3-oxo-3,4-dihydro-2H-1,4-benzoxazin-6-yl)carbonyl)piperidin-4-yl)methoxy)benzonitriie | 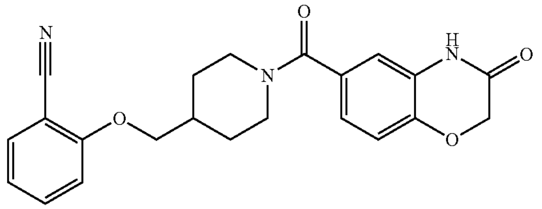 [SMILES: N#Cc1ccccc1OCC1CCN(C(=O)c2ccc3c(c2)NC(=O)CO3)CC1] | 392.0 |

TABLE 1-4

| | | | |
|---|---|---|---|
| 31 | 6-((4-((2-chloro-5-fluorophenoxy)methyl)piperidin-1-yl)carbonyl)-2H-1,4-benzoxazin-3(4H)-one | 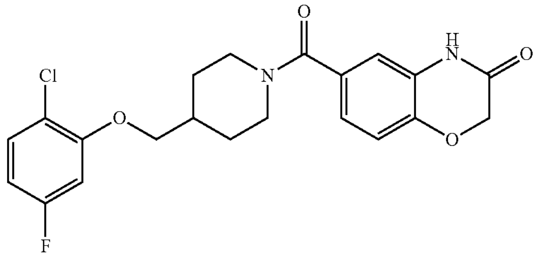 [SMILES: O=C1COc2ccc(C(=O)N3CCC(COc4cc(F)ccc4Cl)CC3)cc2N1] | 419.0 |
| 32 | 6-((4-((2-chloro-4-fluorophenoxy)methyl)piperidin-1-yl)carbonyl)-8-fluoro-2H-1,4-benzoxazin-3(4H)-one | 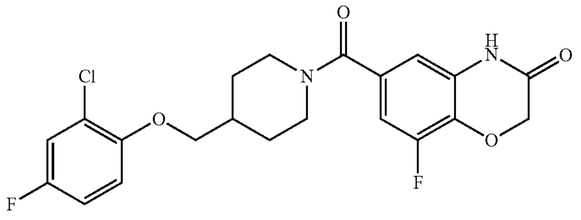 [SMILES: O=C1COc2c(F)cc(C(=O)N3CCC(COc4ccc(F)cc4Cl)CC3)cc2N1] | 437.0 |
| 33 | 5-chloro-2-((1-((3-oxo-3,4-dihydro-2H-1,4-benzoxazin-6-yl)carbonyl)piperidin-4-yl)methoxy)benzonitrile | 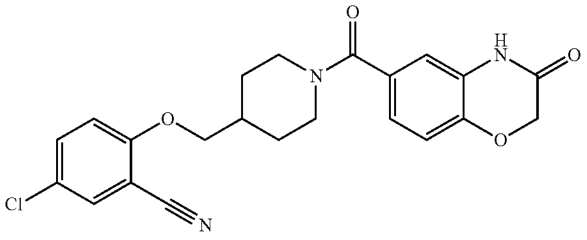 [SMILES: N#Cc1cc(Cl)ccc1OCC1CCN(C(=O)c2ccc3c(c2)NC(=O)CO3)CC1] | 426.0 |
| 34 | 6-((4-((2-methylphenoxy)methyl)piperidin-1-yl)carbonyl)-2H-1,4-benzoxazin-3(4H)-one | 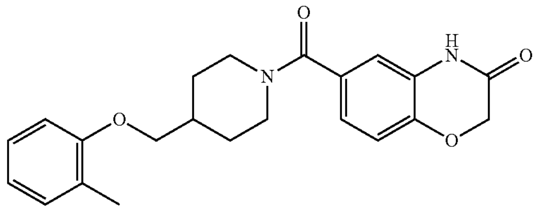 [SMILES: Cc1ccccc1OCC1CCN(C(=O)c2ccc3c(c2)NC(=O)CO3)CC1] | 381.0 |
| 35 | 6-((4-((2,4-dimethylphenoxy)methyl)piperidin-1-yl)carbonyl)-2H-1,4-benzoxazin-3(4H)-one | 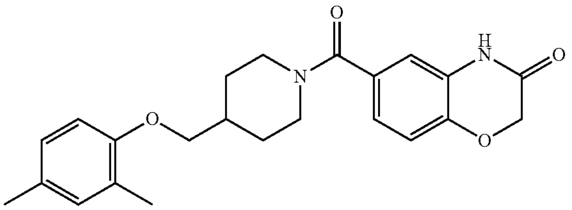 | 395.1 |
| 36 | 6-((4-((2-chloro-4-methylphenoxy)methyl)piperdin-1-yl)carbonyl)-2H-1,4-benzoxazin-3(4H)-one | 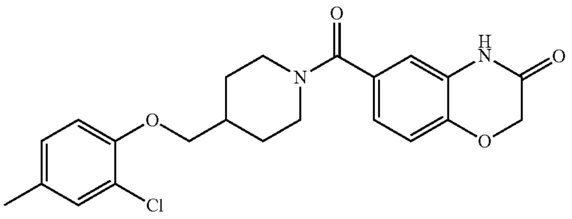 [SMILES: Cc1ccc(OCC2CCN(C(=O)c3ccc4c(c3)NC(=O)CO4)CC2)c(Cl)c1] | 415.0 |
| 37 | 6-((4-((4-chloro-2-methylphenoxy)methyl)piperidin-1-yl)carbonyl)-2H-1,4-benzoxazin-3(4H)-one | 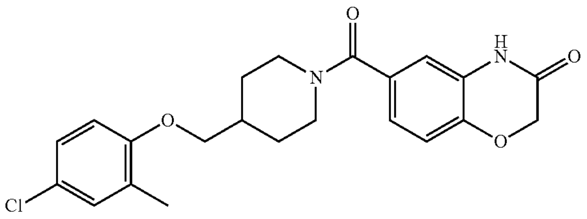 [SMILES: Cc1cc(Cl)ccc1OCC1CCN(C(=O)c2ccc3c(c2)NC(=O)CO3)CC1] | 415.0 |

TABLE 1-4-continued

| | | | |
|---|---|---|---|
| 38 | 6-((4-(((2,6-dimethylpyridin-3-yl)oxy)methyl)piperidin-1-yl)carbonyl)-2H-1,4-benzoxazin-3(4H)-one | 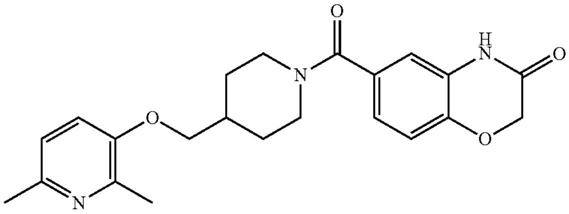 [SMILES: Cc1ccc(OCC2CCN(C(=O)c3ccc4c(c3)NC(=O)CO4)CC2)c(C)n1] | 396.1 |
| 39 | 6-((4(-(((4,6-dimethylpyridin-3-yl)oxy)methyl)piperidin-1-yl)carbonyl)-2H-1,4-benzoxazin-3(4H)-one | 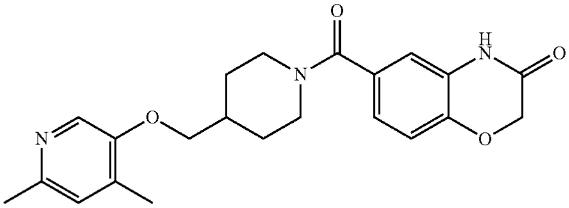 [SMILES: Cc1cc(C)c(OCC2CCN(C(=O)c3ccc4c(c3)NC(=O)CO4)CC2)cn1] | 396.1 |

TABLE 1-5

| | | | |
|---|---|---|---|
| 40 | 6-((4-(((2-chloro-6-methylpyridin-3-yl)oxy)methyl)piperidin-1-yl)carbonyl)-2H-1,4-benzoxazin-3(4H)-one | 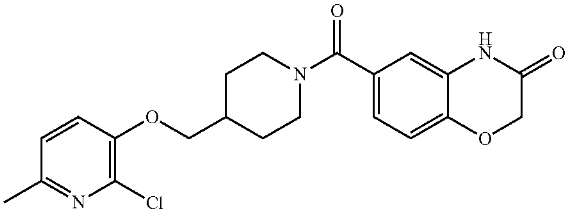 [SMILES: Cc1ccc(OCC2CCN(C(=O)c3ccc4c(c3)NC(=O)CO4)CC2)c(Cl)n1] | 416.0 |
| 41 | 6-((4-(((2,6-dichloropyridin-3-yl)oxy)methyl)piperidin-1-yl)carbonyl)-2H-1,4-benzoxazin-3(4H)-one | 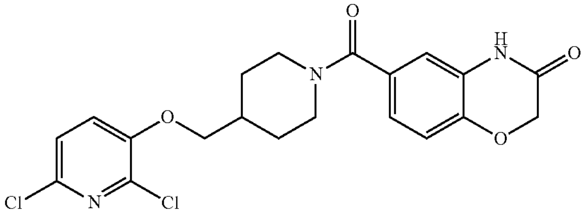 [SMILES: O=C1COc2ccc(C(=O)N3CCC(COc4ccc(Cl)nc4Cl)CC3)cc2N1] | 435.9 |
| 42 | 6-((4-((4-chloro-3-fluorophenoxy)methyl)piperidin-1-yl)carbonyl)-2H-1,4-benzoxazin-3(4H)-one | 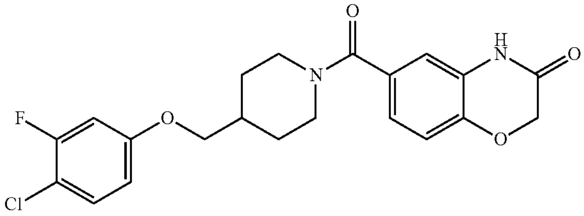 [SMILES: O=C1COc2ccc(C(=O)N3CCC(COc4ccc(Cl)c(F)c4)CC3)cc2N1] | 419.0 |
| 43 | 6-((4-((3,4-dichlorophenoxy)methyl)piperidin-1-yl)carbonyl)-2H-1,4-benzoxazin-3(4H)-one | 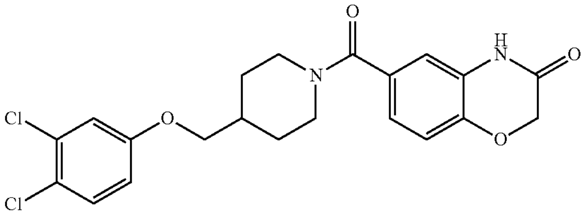 [SMILES: O=C1COc2ccc(C(=O)N3CCC(COc4ccc(Cl)c(Cl)c4)CC3)cc2N1] | 434.9 |
| 44 | 6-((4-(((6-chloropyridin-3-yl)oxy)methyl)piperidin-1-yl)carbonyl)-2H-1,4-benzoxazin-3(4H)-one | 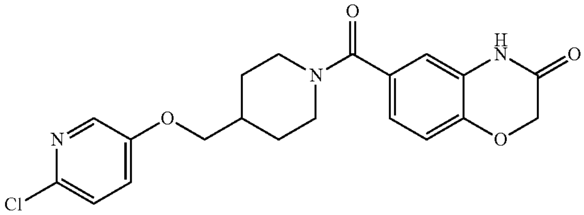 [SMILES: O=C1COc2ccc(C(=O)N3CCC(COc4ccc(Cl)nc4)CC3)cc2N1] | 402.0 |

TABLE 1-5-continued

| | | | |
|---|---|---|---|
| 45 | 6-((4-((3,5-dichlorophenoxy)methyl)piperidin-1-yl)carbonyl)-2H-1,4-benzoxazin-3(4H)-one | 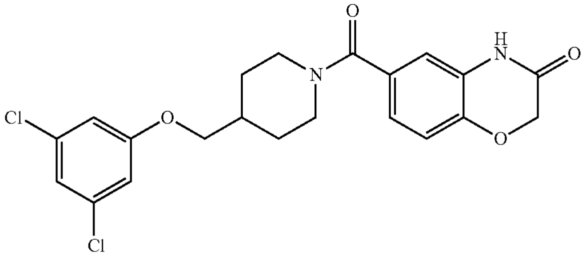 [SMILES: O=C1COc2ccc(C(=O)N3CCC(COc4cc(Cl)cc(Cl)c4)CC3)cc2N1] | 434.9 |
| 46 | 6-((4-(((2,3-dichloropyridin-4-yl)oxy)methyl)piperidin-1-yl)carbonyl)-2H-1,4-benzoxazin-3(4H)-one | 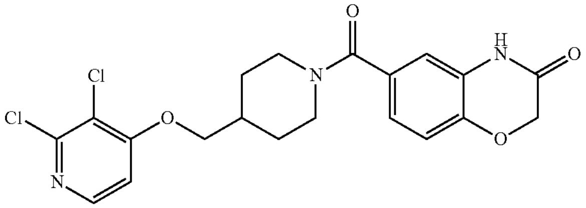 [SMILES: O=C1COc2ccc(C(=O)N3CCC(COc4ccnc(Cl)c4Cl)CC3)cc2N1] | 436.2 |
| 47 | 6-((4-(((2,5-dichloropyridin-4-yl)oxy)methyl)piperidin-1-yl)carbonyl)-2H-1,4-benzoxazin-3(4H)-one | 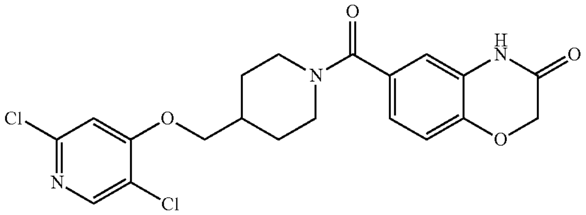 [SMILES: O=C1COc2ccc(C(=O)N3CCC(COc4cc(Cl)ncc4Cl)CC3)cc2N1] | 436.0 |
| 48 | 3-((1-((3-oxo-3,4-dihydro-2H-1,4-benzoxazin-6-yl)carbonyl)piperidin-4-yl)methoxy)benzonitrile | 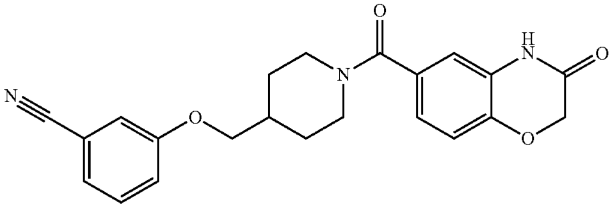 [SMILES: N#Cc1cccc(OCC2CCN(C(=O)c3ccc4c(c3)NC(=O)CO4)CC2)c1] | 392.0 |

TABLE 1-6

| | | | |
|---|---|---|---|
| 49 | 4-((1-((3-oxo-3,4-dihydro-2H-1,4-benzoxazin-6-yl)carbonyl)piperidin-4-yl)methoxy)benzonitrile | 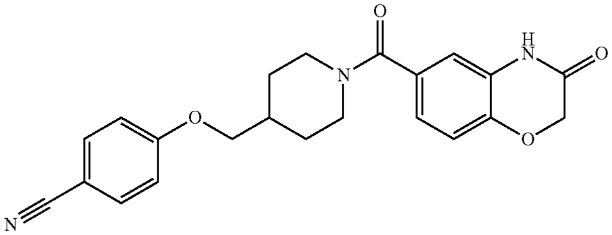 [SMILES: N#Cc1ccc(OCC2CCN(C(=O)c3ccc4c(c3)NC(=O)CO4)CC2)cc1] | 391.9 |
| 50 | 6-((4-((imidazo[1,2-a]pyridin-8-yloxy)methyl)piperidin-1-yl)carbonyl)-2H-1,4-benzoxazin-3(4H)-one | 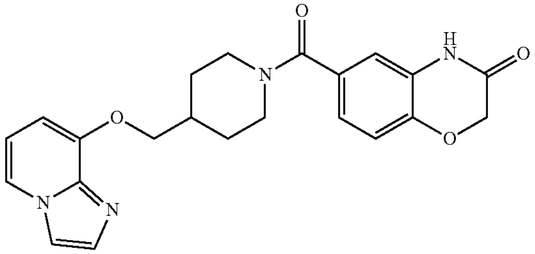 [SMILES: O=C1COc2ccc(C(=O)N3CCC(COc4cccn5ccnc45)CC3)cc2N1] | 407.0 |

TABLE 1-6-continued

| | | | |
|---|---|---|---|
| 51 | 6-((4-(((2-aminopyridin-3-yl)oxy)methyl)piperidin-1-yl)carbonyl)-2H-1,4-benzoxazin-3(4H)-one | 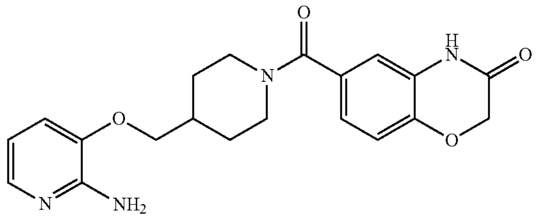 [SMILES: Nc1ncccc1OCC1CCN(C(=O)c2ccc3c(c2)NC(=O)CO3)CC1] | 383.0 |
| 52 | 3-chloro-4-((1-((3-oxo-3,4-dihydro-2H-1,4-benzoxazin-6-yl)carbonyl)piperidin-4-yl)methoxy)benzonitrile | 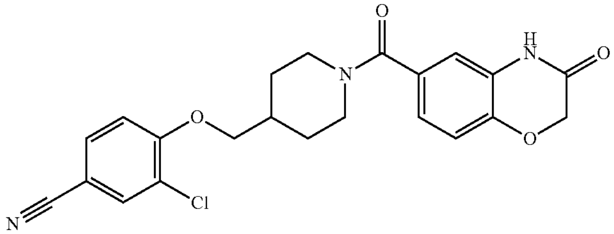 [SMILES: N#Cc1ccc(OCC2CCN(C(=O)c3ccc4c(c3)NC(=O)CO4)CC2)c(Cl)c1] | 426.0 |
| 53 | 6-((4-((2-(trifluoromethoxy)phenoxy)methyl) piperidin-1-yl)carbonyl)-2H-1,4-benzoxazin-3(4H)-one | 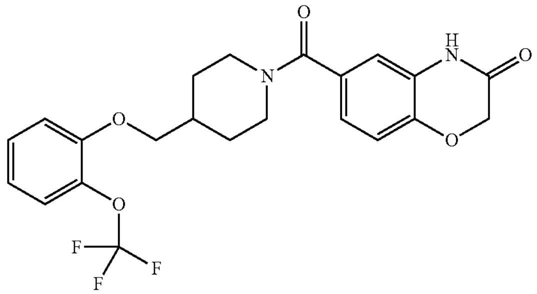 [SMILES: O=C1COc2ccc(C(=O)N3CCC(COc4ccccc4OC(F)(F)F)CC3)cc2N1] | 451.0 |
| 54 | 6-((4-((3-(trifluoromethoxy)phenoxy)methyl) piperidin-1-yl)carbonyl)-2H-1,4-benzoxazin-3(4H)-one | 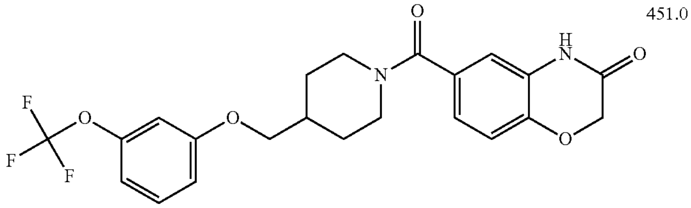 | 451.0 |
| 55 | 6-((4-((4-(trifluoromethoxy)phenoxy)methyl) piperidin-1-yl)carbonyl)-2H-1,4-benzoxazin-3(4H)-one | 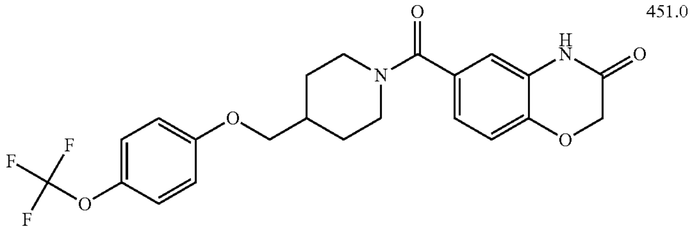 | 451.0 |
| 56 | 6-((4-((2-chloro-3-fluorophenoxy)methyl)piperidin-1-yl)carbonyl)-2H-1,4-benzoxazin-3(4H)-one | 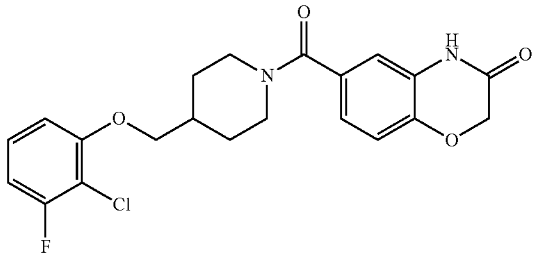 [SMILES: O=C1COc2ccc(C(=O)N3CCC(COc4cccc(F)c4Cl)CC3)cc2N1] | 418.9 |

TABLE 1-6-continued

| | | | |
|---|---|---|---|
| 57 | 6-((4-((3-(trifluoromethyl)phenoxy)methyl)piperidin-1-yl)carbonyl)-2H-1,4-benzoxazin-3(4H)-one | 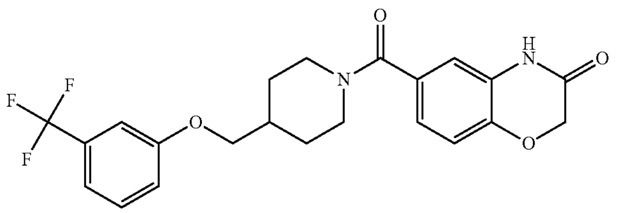 [SMILES: O=C1COc2ccc(C(=O)N3CCC(COc4cccc(C(F)(F)F)c4)CC3)cc2N1] | 435.0 |

TABLE 1-7

| | | | |
|---|---|---|---|
| 58 | 6-((4-((4-(trifluoromethyl)phenoxy)methyl)piperidin-1-yl)carbonyl)-2H-1,4-benzoxazin-3(4H)-one | 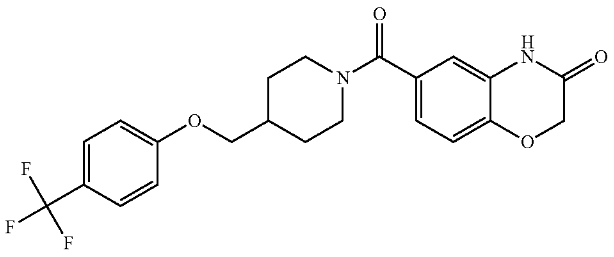 [SMILES: O=C1COc2ccc(C(=O)N3CCC(COc4ccc(C(F)(F)F)cc4)CC3)cc2N1] | 435.0 |
| 59 | 6-((4-((1-naphthyloxy)methyl)piperidin-1-yl)carbonyl)-2H-1,4-benzoxazin-3(4H)-one | 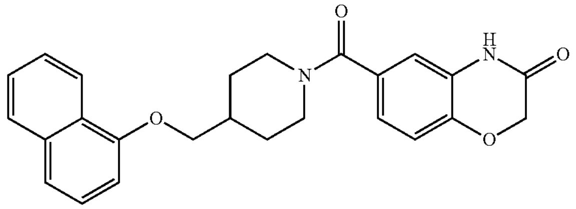 [SMILES: O=C1COc2ccc(C(=O)N3CCC(COc4cccc5ccccc45)CC3)cc2N1] | 417.0 |
| 60 | 6-((4-((2-naphthyloxy)methyl)piperidin-1-yl)carbonyl)-2H-1,4-benzoxazin-3(4H)-one | 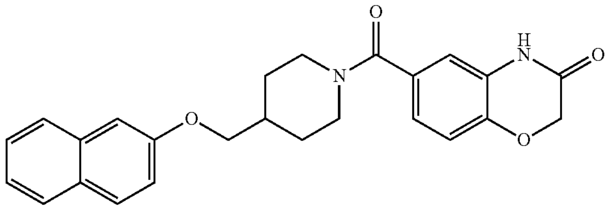 [SMILES: O=C1COc2ccc(C(=O)N3CCC(COc4ccc5ccccc5c4)CC3)cc2N1] | 415.1 |
| 61 | 6-((4-((1H-indazol-5-yloxy)methyl)piperidin-1-yl)carbonyl)-2H-1,4-benzoxazin-3(4H)-one | 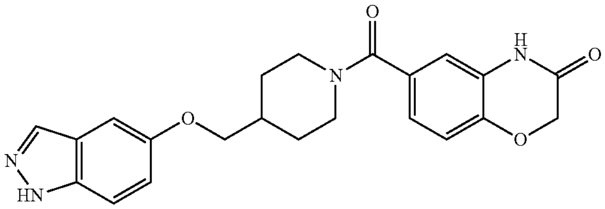 [SMILES: O=C1COc2ccc(C(=O)N3CCC(COc4ccc5[nH]ncc5c4)CC3)cc2N1] | 407.0 |
| 62 | 6-((4-((1,3-benzothiazol-2-yloxy)methyl)piperidin-1-yl)carbonyl)-2H-1,4-benzoxazin-3(4H)-one | 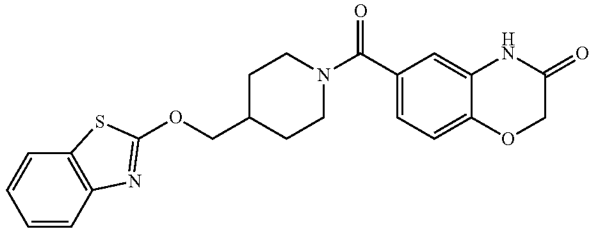 [SMILES: O=C1COc2ccc(C(=O)N3CCC(COc4nc5ccccc5s4)CC3)cc2N1] | 424.0 |

TABLE 1-7-continued

| | | | |
|---|---|---|---|
| 63 | 6-((4-(((1-acetyl-1H-indazol-4-yl)oxy)methyl)piperidin-1-yl)carbonyl)-2H-1,4-benzoxazin-3(4H)-one | 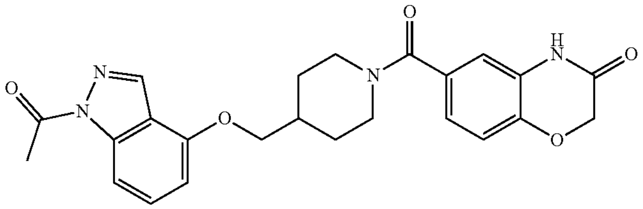 [SMILES: CC(=O)n1ncc2c(OCC3CCN(C(=O)c4ccc5c(c4)NC(=O)CO5)CC3)cccc21] | 449.0 |
| 64 | 6-((4-((1H-indazol-4-yloxy)methyl)piperidin-1-yl)carbonyl)-2H-1,4-benzoxazin-3(4H)-one | 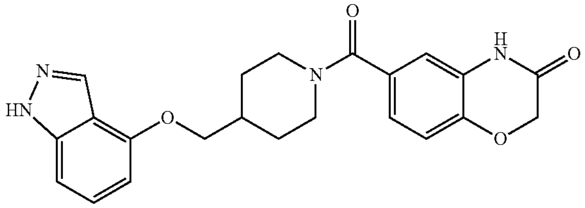 [SMILES: O=C1COc2ccc(C(=O)N3CCC(COc4cccc5[nH]ncc45)CC3)cc2N1] | 407.0 |
| 65 | 6-((4-((2-cyclopropylphenoxy)methyl)piperidin-1-yl)carbonyl)-2H-1,4-benzoxazin-3(4H)-one | 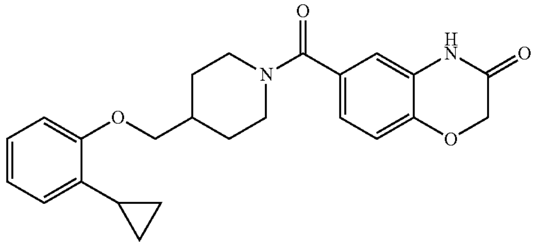 [SMILES: O=C1COc2ccc(C(=O)N3CCC(COc4ccccc4C4CC4)CC3)cc2N1] | 405.1 |
| 66 | 6-((4-((2-chloro-4-fluorophenoxy)methyl)piperidin-1-yl)carbonyl)-7-fluoro-2H-1,4-benzoxazin-3(4H)-one | 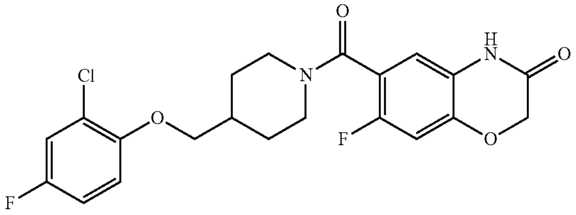 | 437.0 |

TABLE 1-8

| | | | |
|---|---|---|---|
| 67 | 2-(1-((3-oxo-3,4-dihydro-2H-1,4-benzoxazin-6-yl)carbonyl)piperidin-4-yl)methoxy)-5-(trifluoromethyl)benzonitrile | 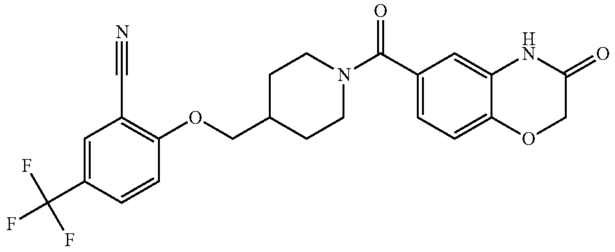 [SMILES: N#Cc1cc(C(F)(F)F)ccc1OCC1CCN(C(=O)c2ccc3c(c2)NC(=O)CO3)CC1] | 460.1 |
| 68 | 2-((1-((7-fluoro-3-oxo-3,4-dihydro-2H-1,4-benzoxazin-6-yl)carbonyl)piperidin-4-yl)methoxy)-5-(trifluoromethyl)benzonitrile | 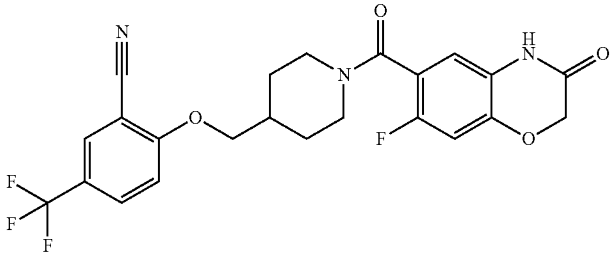 [SMILES: N#Cc1cc(C(F)(F)F)ccc1OCC1CCN(C(=O)c2cc3c(cc2F)OCC(=O)N3)CC1] | 478.1 |

TABLE 1-8-continued

| | | | |
|---|---|---|---|
| 69 | 2-((1-((2-oxo-2,3-dihydro-1H-indol-6-yl)carbonyl)piperidin-4-yl)methoxy)-5-(trifluoromethyl)benzonitrile | 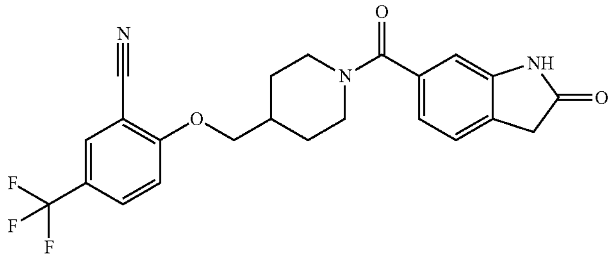 [SMILES: N#Cc1cc(C(F)(F)F)ccc1OCC1CCN(C(=O)c2ccc3c(c2)NC(=O)C3)CC1] | 444.4 |
| 70 | 3-chloro-4-((1-((7-fluoro-3-oxo-3,4-dihydro-2H-1,4-benzoxazin-6-yl)carbonyl)piperidin-4-yl)methoxy)benzonitrile | 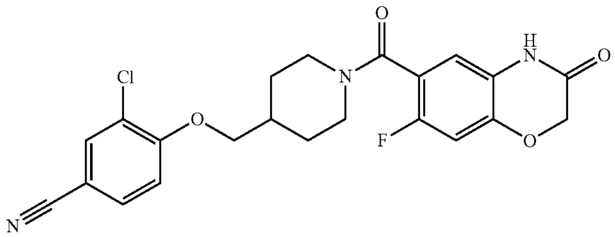 [SMILES: N#Cc1ccc(OCC2CCN(C(=O)c3cc4c(cc3F)OCC(=O)N4)CC2)c(Cl)c1] | 444.2 |
| 71 | 6-((4-(((2,6-dichloropyridin-3-yl)oxy)methyl)piperidin-1-yl)carbonyl)-7-fluoro-2H-1,4-benzoxazin-3(4H)-one | 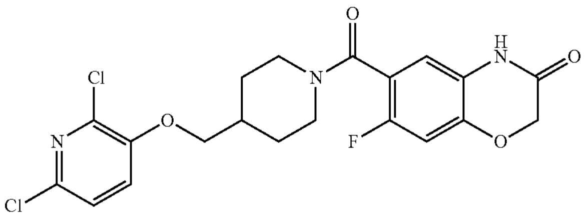 [SMILES: O=C1COc2cc(F)c(C(=O)N3CCC(COc4ccc(Cl)nc4Cl)CC3)cc2N1] | 454.0 |
| 72 | 5-chloro-2-((1-((7-fluoro-3-oxo-3,4-dihydro-2H-1,4-benzoxazin-6-yl)carbonyl)piperidin-4-yl)methoxy)benzonitrile | 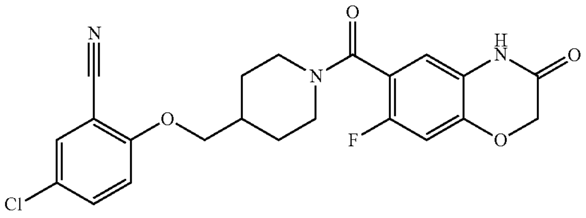 [SMILES: N#Cc1cc(Cl)ccc1OCC1CCN(C(=O)c2cc3c(cc2F)OCC(=O)N3)CC1] | 444.2 |
| 73 | 6-((4-((2-chloro-4-fluorophenoxy)methyl)-4-hydroxypiperidin-1-yl)carbonyl)-7-fluoro-2H-1,4-benzoxazin-3(4H)-one | 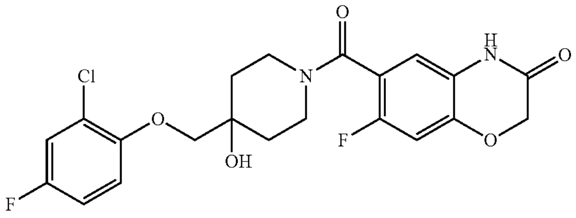 [SMILES: O=C1COc2cc(F)c(C(=O)N3CCC(O)(COc4ccc(F)cc4Cl)CC3)cc2N1] | 453.1 |
| 74 | 6-((4-((2,4-dichlorophenoxy)methyl)-4-hydroxypiperidin-1-yl)carbonyl)-7-fluoro-2H-1,4-benzoxazin-3(4H)-one | 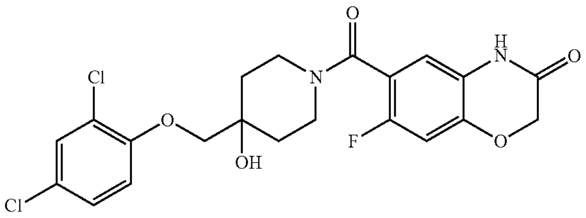 [SMILES: O=C1COc2cc(F)c(C(=O)N3CCC(O)(COc4ccc(Cl)cc4Cl)CC3)cc2N1] | 469.1 |
| 75 | 2-chloro-3-((1-((7-fluoro-3-oxo-3,4-dihydro-2H-1,4-benzoxazin-6-yl)carbonyl)piperidin-4-yl)methoxy)benzonitrile | 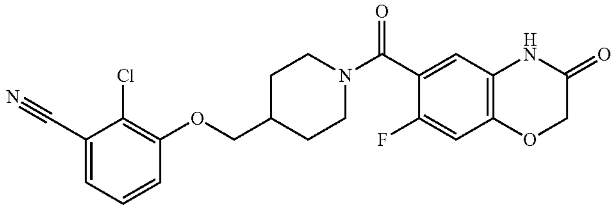 [SMILES: N#Cc1cccc(OCC2CCN(C(=O)c3cc4c(cc3F)OCC(=O)N4)CC2)c1Cl] | 444.2 |

TABLE 1-9

| | | | |
|---|---|---|---|
| 76 | 6-((3-((2,4-dichlorophenoxy)methyl)azetidin-1-yl)carbonyl)-7-fluoro-2H-1,4-benzoxazin-3(4H)-one | 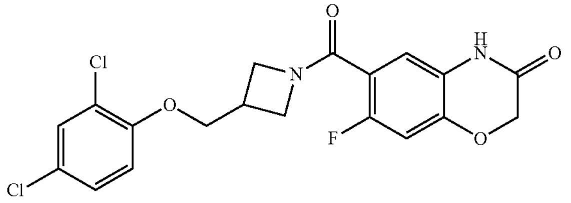 [SMILES: O=C1COc2cc(F)c(C(=O)N3CC(COc4ccc(Cl)cc4Cl)C3)cc2N1] | 425.0 |
| 77 | 6-((3-((2-chloro-4-fluorophenoxy)methyl)azetidin-1-yl)carbonyl)-7-fluoro-2H-1,4-benzoxazin-3(4H)-one | 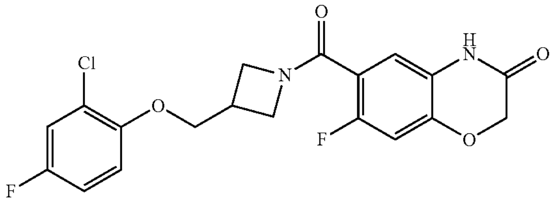 [SMILES: O=C1COc2cc(F)c(C(=O)N3CC(COc4ccc(F)cc4Cl)C3)cc2N1] | 409.0 |
| 78 | 6-((3-((2-chloro-4-fluorophenoxy)methyl)azetidin-1-yl)carbonyl)-2H-1,4-benzoxazin-3(4H)-one | 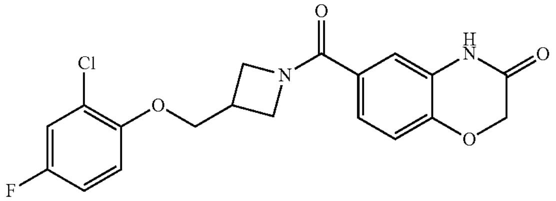 [SMILES: O=C1COc2ccc(C(=O)N3CC(COc4ccc(F)cc4Cl)C3)cc2N1] | 391.0 |
| 79 | 7-((4-((2-chloro-4-fluorophenoxy)methyl)piperidin-1-yl)carbonyl)quinolin-2(1H)-one | 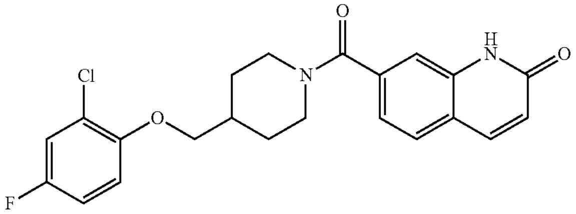 [SMILES: O=C(c1ccc2ccc(=O)[nH]c2c1)N1CCC(COc2ccc(F)cc2Cl)CC1] | 415.0 |
| 80 | 6-((4-((cyclohexyloxy)methyl)piperidin-1-yl)carbonyl)-7-fluoro-2H-1,4-benzoxazin-3(4H)-one | 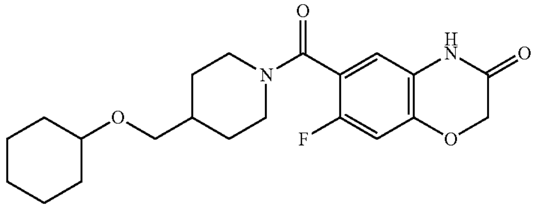 [SMILES: O=C1COc2cc(F)c(C(=O)N3CCC(COC4CCCCC4)CC3)cc2N1] | 391.2 |
| 81 | 4-((2-chloro-4-fluorophenoxy)methyl)-1-((7-fluoro-3-oxo-3,4-dihydro-2H-1,4-benzoxazin-6-yl)carbonyl)piperidine-4-carbonitrile | 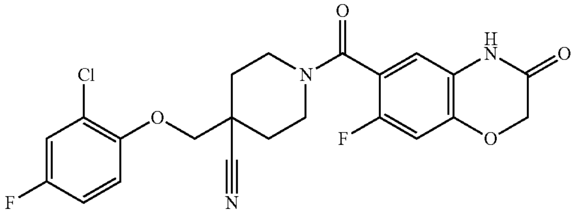 [SMILES: N#CC1(COc2ccc(F)cc2Cl)CCN(C(=O)c2cc3c(cc2F)OCC(=O)N3)CC1] | 462.1 |
| 82 | 6-((4-((2-chloro-4-(prop-1-en-2-yl)phenoxy)methyl)piperidin-1-yl)carbonyl)-7-fluoro-2H-1,4-benzoxazin-3(4H)-one | 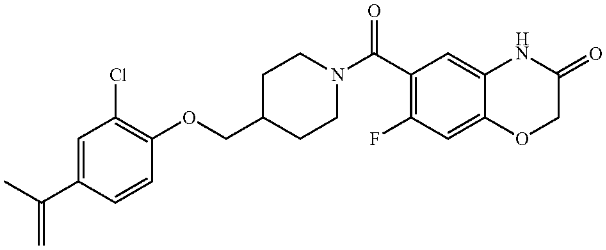 [SMILES: C=C(C)c1ccc(OCC2CCN(C(=O)c3cc4c(cc3F)OCC(=O)N4)CC2)c(Cl)c1] | 459.2 |

TABLE 1-9-continued

| | | | |
|---|---|---|---|
| 83 | 7-fluoro-6-((4-((tetrahydro-2H-pyran-4-yloxy)methyl)piperidin-1-yl)carbonyl)-2H-1,4-benzoxazin-3(4H)-one | 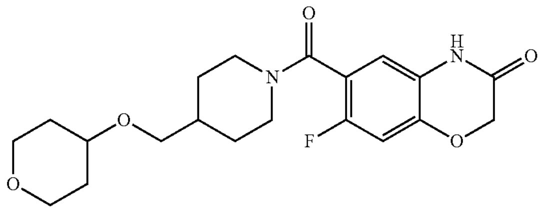 [SMILES: O=C1COc2cc(F)c(C(=O)N3CCC(COC4CCOCC4)CC3)cc2N1] | 393.2 |
| 84 | methyl-3-chloro-4-((1-((7-fluoro-3-oxo-3,4-dihydro-2H-1,4-benzoxazin-6-yl)carbony)piperidin-4-yl)methoxy)benzoate | 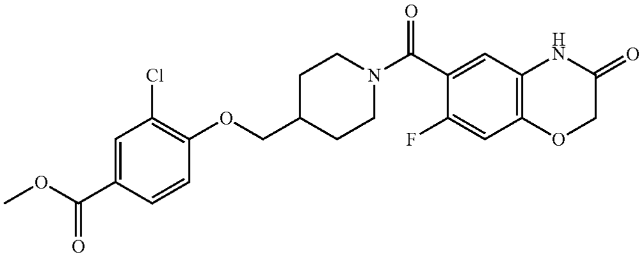 [SMILES: COC(=O)c1ccc(OCC2CCN(C(=O)c3cc4c(cc3F)OCC(=O)N4)CC2)c(Cl)c1] | 477.1 |

TABLE 1-10

| | | | |
|---|---|---|---|
| 85 | methyl 5-fluoro-2-((1-((7-fluoro-3-oxo-3,4-dihydro-2H-1,4-benzoxazin-6-yl)carbonyl)piperidin-4-yl)methoxy)benzoate | 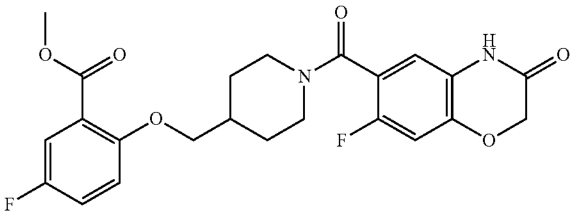 [SMILES: COC(=O)c1cc(F)ccc1OCC1CCN(C(=O)c2cc3c(cc2F)OCC(=O)N3)CC1] | 461.1 |
| 86 | 7-chloro-6-((4-((2-chloro-4-fluorophenoxy)methyl)piperidin-1-yl)carbonyl)-2H-1,4-benzoxazin-3(4H)-one | 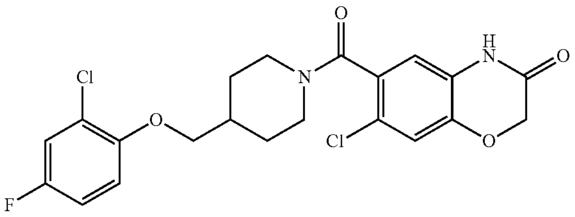 | 453.0 |
| 87 | 7-chloro-6-((3-((2-chloro-4-fluorophenoxy)methyl)azetidin-1-yl)carbonyl)-2H-1,4-benzoxazin-3(4H)-one | 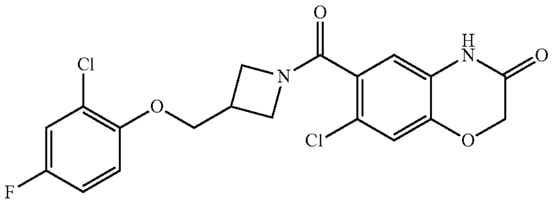 [SMILES: O=C1COc2cc(Cl)c(C(=O)N3CC(COc4ccc(F)cc4Cl)C3)cc2N1] | 425.0 |
| 88 | 6-((3-((2-chloro-4-fluorophenoxy)methyl)azetidin-1-yl)carbonyl)-7-methyl-2H-1,4-benzoxazin-3(4H)-one | 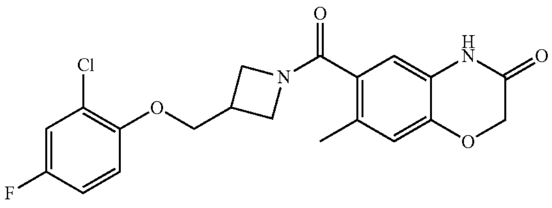 [SMILES: Cc1cc2c(cc1C(=O)N1CC(COc3ccc(F)cc3Cl)C1)NC(=O)CO2] | 405.1 |

TABLE 1-10-continued

| | | | |
|---|---|---|---|
| 89 | 6-((4-((2-chloro-4-fluorophenoxy)methyl)piperidin-1-yl)carbonyl)-7-methyl-2H-1,4-benzoxazin-3(4H)-one | 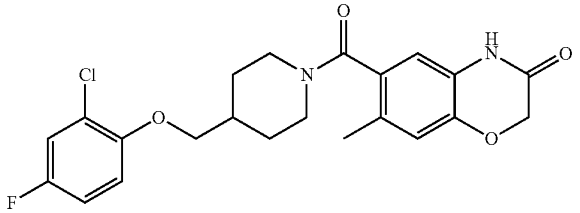 | 433.1 |

Example 97

6-((4-((2-chloro-4-fluorophenoxy)methyl)piperidin-1-yl) carbonyl)-7-methoxy-2H-1, 4-benzoxazin-3 (4H)-one A) 4-(1,3-dioxolan-2-yl)-5-methoxy-2-nitrophenol To a solution of 4-hydroxy-2-methoxy-5-nitrobenzaldehyde (1.00 g) and ethylene glycol (0.837 mL) in toluene (10 mL) was added p-TsOH—$H_2O$ (0.097 g) at room temperature, and the mixture was heated under reflux overnight using Dean-Stark apparatus. The mixture was diluted with water/ethyl acetate/THF, and the mixture was extracted with ethyl acetate/THF. The organic layer was washed with water and saturated brine, dried over anhydrous sodium sulfate, and concentrated under reduced pressure. The residue was triturated with ethyl acetate/hexane to give the title compound (0.900 g).

$^1$H NMR (300 MHz, DMSO-$d_6$) δ3.88 (3H, s), 3.89-3.97 (2H, m), 3.98-4.09 (2H, m), 5.87 (1H, s), 6.71 (1H, s), 8.03 (1H, s), 11.15 (1H, s).

B) 7-methoxy-3-oxo-3,4-dihydro-2H-benzo[b][1,4]oxazine-6-carbaldehyde

A mixture of 4-(1,3-dioxolan-2-yl)-5-methoxy-2-nitrophenol (0.900 g), 10% palladium on carbon (0.090 g) and THF (10 mL) was stirred under hydrogen atmosphere at room temperature for 5 hr. The catalyst was removed by filtration, and the filtrate was concentrated under reduced pressure to give 2-amino-4-(1,3-dioxolan-2-yl)-5-methoxyphenol as a crude product.

To a mixture of the obtained crude product, benzyltriethylammonium chloride (0.833 g), sodium hydrogencarbonate (1.23 g) and DMF (8 mL) was added chloroacetic chloride (0.319 mL) at 0° C., and the mixture was stirred at room temperature for 1 hr, and then stirred overnight at 70° C. The mixture was allowed to cool to room temperature, and the reaction mixture was diluted with ethyl acetate/THF/water, and extracted with ethyl acetate/THF. The organic layer was washed with water and saturated brine, dried over anhydrous sodium sulfate, and concentrated under reduced pressure. The obtained crude crystals were recrystallized from ethyl acetate/hexane to give the title compound (0.434 g).

$^1$H NMR (300 MHz, DMSO-$d_6$) δ3.86 (3H, s), 4.69 (2H, s), 6.84 (1H, s), 7.23 (1H, s), 10.18 (1H, s), 10.76 (1H, s).

C) 7-methoxy-3-oxo-3,4-dihydro-2H-benzo[b][1,4]oxazine-6-carboxylic acid

To a solution of 7-methoxy-3-oxo-3,4-dihydro-2H-benzo[b][1,4]oxazine-6-carbaldehyde (0.100 g), sodium dihydrogenphosphate (0.174 g) and 2-methyl-2-butene (0.255 mL) in tert-butanol (3 mL)/water (1 mL)/acetone (1 mL) was added sodium chlorite (0.166 g) at room temperature, and the mixture was stirred overnight. The reaction was quenched with aqueous sodium thiosulfate solution, and the reaction solution was acidified with 1M hydrochloric acid. The resulting precipitate was collected, and washed with water and ethyl acetate/hexane to give the title compound (0.052 g).

$^1$H NMR (300 MHz, DMSO-$d_6$) δ 3.76 (3H, s), 4.63 (2H, s), 6.74 (1H, s), 7.32 (1H, s), 10.66 (1H, s), 12.35 (1H, brs).

D) 6-((4-((2-chloro-4-fluorophenoxy)methyl)piperidin-1-yl) carbonyl)-7-methoxy-2H-1,4-benzoxazin-3 (4H)-one To a mixture of 7-methoxy-3-oxo-3,4-dihydro-2H-benzo[b][1,4]oxazine-6-carboxylic acid (20.0 mg) and 4-((2-chloro-4-fluorophenoxy)methyl)piperidine hydrochloride (28.0 mg) in DMF (0.5 mL) were added HATU (51.1 mg) and TEA (0.0620 mL), and the mixture was stirred overnight at room temperature. The reaction mixture was diluted with ethyl acetate/water, and the resulting precipitate was collected, and washed with ethyl acetate and water to give the title compound (25.6 mg).

$^1$H NMR (300 MHz, DMSO-$d_6$) δ 1.09-1.41 (2H, m), 1.66-1.75 (1H, m), 1.79-1.91 (1H, m), 1.95-2.12 (1H, m), 2.71-2.82 (1H, m), 2.91-3.13 (1H, m), 3.34-3.45 (1H, m), 3.73 (3H, s), 3.86-3.98 (2H, m), 4.44-4.56 (1H, m), 4.58 (2H, s), 6.68 (1H, d, J=13.5 Hz), 6.72 (1H, s), 7.17 (2H, d, J=6.6 Hz), 7.42 (1H, d, J=8.7 Hz), 10.61 (1H, brs).

Example 101

5-((4-((2-chloro-4-fluorophenoxy)methyl)piperidin-1-yl)carbonyl)-6-fluoro-1,3-benzoxazol-2(3H)-one A) methyl 5-amino-2-fluoro-4-hydroxybenzoate To a solution of 5-amino-2-fluoro-4-hydroxybenzoic acid (3.00 g) in methanol (30.0 mL) was added acetyl chloride (4.10 g), and the mixture was heated under reflux overnight. The mixture was allowed to cool to room temperature, and the mixture was concentrated under reduced pressure. The obtained crude product was washed with diethyl ether, and dried to give the title compound (4.20 g).

$^1$H NMR (400 MHz, DMSO-$d_6$) δ 3.75 (3H, s), 6.51 (1H, d, J=12.4 Hz), 7.10 (1H, d, J=7.6 Hz).

B) methyl 6-fluoro-2-oxo-2,3-dihydrobenzo[d]oxazole-5-carboxylate

To a solution of methyl 5-amino-2-fluoro-4-hydroxybenzoate (2.70 g) in THF (30 mL) was added 1,1'-carbonyldiimidazole (11.8 g), and the mixture was heated under reflux for 2 hr. The mixture was allowed to cool to room temperature, and the mixture was poured into water, and extracted with ethyl acetate. The organic layer was washed with saturated brine, and concentrated under reduced pressure to give the title compound (2.80 g).

$^1$H NMR (400 MHz, DMSO-$d_6$) δ 3.85 (3H, s), 7.42-7.49 (2H, m).

C) 6-fluoro-2-oxo-2,3-dihydrobenzo[d]oxazole-5-carboxylic acid

To a solution of methyl 6-fluoro-2-oxo-2,3-dihydrobenzo[d]oxazole-5-carboxylate (1.00 g) in THF (10 mL)/water (10 mL) was added lithium hydroxide monohydrate (1.09 g), and the mixture was stirred overnight at room temperature. The reaction solution was acidified (pH<5) with 1M hydrochloric acid, and extracted with ethyl acetate. The organic layer was washed with saturated brine, and concentrated under reduced pressure to give the title compound (0.840 g).

$^1$H NMR (400 MHz, DMSO-$d_6$) δ 7.42-7.46 (2H, m), 11.92 (1H, brs), 13.25 (1H, brs).

D) 5-((4-((2-chloro-4-fluorophenoxy)methyl)piperidin-1-yl)carbonyl)-6-fluoro-1,3-benzoxazol-2 (3H)-one A solution of 6-fluoro-2-oxo-2,3-dihydrobenzo[d]oxazole-5-carboxylic acid (0.110 g), EDCI (0.161 g), HOBt-$H_2O$ (0.114 g) and DIPEA (0.217 g) in dichloromethane (5 mL)/DMF (5 mL) was stirred for 30 min, 4-((2-chloro-4-fluorophenoxy)methyl)piperidine (0.136 g) was added thereto, and the mixture was stirred overnight. To the mixture was added water, and the mixture was extracted with ethyl acetate. The organic layer was washed with saturated brine, dried over anhydrous magnesium sulfate, and concentrated under reduced pressure. The crude product was purified by HPLC (C18, mobile phase: water/acetonitrile (containing 10 mM ammonium carbonate) to give the title compound (0.105 g).

$^1$H NMR (400 MHz, DMSO-$d_6$) δ 1.15-1.41 (2H, m), 1.65-1.82 (1H, m), 1.87-1.90 (1H, m), 1.99-2.18 (1H, m), 2.81-2.87 (1H, m), 2.98-3.22 (1H, m), 3.46-3.49 (1H, m), 3.88-4.01 (2H, m), 4.52-4.55 (1H, m), 7.04 (1H, d, J=5.6 Hz), 7.16-7.18 (2H, m), 7.41-7.47 (2H, m), 11.86 (1H, s).

Example 102

7-fluoro-6-((3-((5, 6,7,8-tetrahydronaphthalen-2-yloxy)methyl)azetidin-1-yl)carbonyl)-2H-1,4-benzoxazin-3 (4H)-one A) tert-butyl 3-(((5,6,7,8-tetrahydronaphthalen-2-yl)oxy)methyl) azetidine-1-carboxylate To a solution of 5,6,7,8-tetrahydronaphthalen-2-ol (1.60 g) and tert-butyl 3-(((methylsulfonyl)oxy)methyl)azetidine-1-carboxylate (2.86 g) in DMF (30 mL) was added potassium carbonate (2.24 g) at room temperature, and the mixture was stirred overnight at 80° C. The mixture was poured into saturated aqueous sodium hydrogencarbonate solution, and extracted with ethyl acetate. The organic layer was washed with saturated brine, dried over anhydrous magnesium sulfate, and concentrated under reduced pressure. The residue was purified by silica gel column chromatography (NH, ethyl acetate/hexane) to give the title compound (2.80 g).

$^1$H NMR (300 MHz, DMSO-$d_6$) δ1.38 (9H, s), 1.61-1.76 (4H, m), 2.55-2.73 (4H, m), 2.82-2.98 (1H, m), 3.55-3.73 (2H, m), 3.86-3.99 (2H, m), 3.99-4.09 (2H, m), 6.57-6.72 (2H, m), 6.94 (1H, d, J=8.2 Hz).

B) 3-(((5,6,7,8-tetrahydronaphthalen-2-yl)oxy) methyl)azetidine tosylate

A mixture of tert-butyl 3-(((5,6,7,8-tetrahydronaphthalen-2-yl)oxy)methyl) azetidine-1-carboxylate (2.80 g), p-TsOH—$H_2O$ (1.85 g) and ethyl acetate (30 mL) was heated under reflux for 1.5 hr. The mixture was allowed to cool to room temperature, and the resulting precipitate was collected, washed with ethyl acetate, and dried under reduced pressure to give the title compound (3.11 g).

$^1$H NMR (300 MHz, DMSO-$d_6$) δ1.62-1.79 (4H, m), 2.29 (3H, s), 2.55-2.77 (4H, m), 3.04-3.24 (1H, m), 3.74-3.89 (2H, m), 3.97-4.13 (4H, m), 6.58-6.75 (2H, m), 6.97 (1H, d, J=8.3 Hz), 7.06-7.15 (2H, m), 7.38-7.54 (2H, m), 8.50 (2H, brs).

C) 7-fluoro-6-((3-((5,6,7,8-tetrahydronaphthalen-2-yloxy)methyl)azetidin-1-yl)carbonyl)-2H-1,4-benzoxazin-3(4H)-one To a solution of EDCI (1.18 g), HOBt-H2O (0.944 g), 3-(((5, 6,7,8-tetrahydronaphthalen-2-yl)oxy)methyl) azetidine tosylate (2.00 g) and 7-fluoro-3-oxo-3,4-dihydro-2H-benzo[b][1,4]oxazine-6-carboxylic acid (1.08 g) in DMF (20 mL) was added TEA (2.14 mL) at room temperature, and the mixture was stirred for 21 hr. To the reaction mixture was added dropwise water, and the mixture was stirred for additional 1 hr. The resulting precipitate was collected, washed successively with water, 50% hydrous ethanol and ethanol to give crude crystals (1.97 g). The obtained crude crystals (1.00 g) were dissolved in DMSO (6 mL)/ethanol (6 mL) at 60° C. The solution was filtered on hot, with washing with DMSO/ethanol (4 mL, 1:1 v/v). To the filtrate was added dropwise water (4 mL), and the mixture was stirred at the internal temperature of 50-55° C. for 1 hr. The mixture was allowed to cool to room temperature, and the resulting precipitate was collected, washed with 50% hydrous ethanol, and dried under reduced pressure at 60° C. for 2 hr to give the title compound (0.930 g).

1H NMR (300 MHz, DMSO-$d_6$) δ1.62-1.77 (4H, m), 2.56-2.74 (4H, m), 2.94-3.11 (1H, m), 3.83 (2H, dd, J=9.4, 5.3 Hz), 4.00-4.21 (4H, m), 4.65 (2H, s), 6.57-6.73 (2H, m), 6.86-7.07 (3H, m), 10.84 (1H, s).

Example 188

7-fluoro-6-((3-((2-fluoro-4-(trifluoromethyl)phenoxy)methyl)azetidin-1-yl)carbonyl)-2H-1,4-benzoxazin-3(4H)-one A) tert-butyl 3-((2-fluoro-4-(trifluoromethyl)phenoxy)methyl)azetidine-1-carboxylate To a mixture of 1,2-difluoro-4-(trifluoromethyl)benzene (10.1 g), tert-butyl 3-(hydroxymethyl)azetidine-1-carboxylate (10.4 g) and THF (100 mL) was added potassium tert-butoxide (7.16 g) at 0° C., and the mixture was stirred at room temperature for 5 hr. The mixture was diluted with aqueous ammonium chloride solution, and extracted with ethyl acetate. The organic layer was washed with water and saturated brine, dried over anhydrous sodium sulfate, and filtered through NH silica gel/silica gel (1:1 v/v), and the filtrate was concentrated under reduced pressure. The crude crystals were recrystallized from ethyl acetate/heptane (1:15 v/v) to give the title compound (12.5 g).

$^1$H NMR (300 MHz, $CDCl_3$) δ1.45 (9H, s), 2.94-3.11 (1H, m), 3.80 (2H, dd, J=8.9, 5.1 Hz), 4.07-4.15 (2H, m), 4.21 (2H, d, J=6.8 Hz), 6.99-7.09 (1H, m), 7.31-7.41 (2H, m).

B) 3-((2-fluoro-4-(trifluoromethyl)phenoxy)methyl) azetidine tosylate

A mixture of tert-butyl 3-((2-fluoro-4-(trifluoromethyl) phenoxy)methyl)azetidine-1-carboxylate (13.4 g), p-TsOH—$H_2O$ (8.03 g) and ethyl acetate (150 mL) was heated under reflux for 1.5 hr. The mixture was cooled to 0° C., and the resulting precipitate was collected, washed with ethyl acetate, and dried under reduced pressure to give the title compound (14.7 g).

$^1$H NMR (300 MHz, DMSO-$d_6$) δ2.29 (3H, s), 3.19-3.38 (1H, m), 3.84-3.93 (2H, m), 4.02-4.12 (2H, m), 4.31 (2H, d, J=6.1 Hz), 7.06-7.15 (2H, m), 7.35-7.44 (1H, m), 7.45-7.51 (2H, m), 7.55-7.63 (1H, m), 7.72 (1H, dd, J=11.5, 2.0 Hz), 8.59 (2H, brs).

C) 7-fluoro-6-((3-((2-fluoro-4-(trifluoromethyl)phenoxy)methyl)azetidin-1-yl)carbonyl)-2H-1,4-benzoxazin-3(4H)-one A mixture of 3-((2-fluoro-4-(trifluoromethyl)phenoxy) methyl)azetidine tosylate (12.6 g), 7-fluoro-3-oxo-3, 4-dihydro-2H-benzo[b][1, 4]oxazine-6-carboxylic acid (6.31 g), HOBt-H2O (5.49 g), EDCI (6.88 g), DIPEA (12.5 mL) and DMF (50 mL) was stirred at room temperature for 14 hr. To the mixture was added water at 0° C., and the resulting precipitate was collected, washed with water, and dried under reduced pressure at 80° C. for 3 hr. The crude crystals were recrystallized from ethyl acetate/IPA/heptane (1:3:5 v/v/v) to give the title compound (10.8 g).

$^1$H NMR (300 MHz, DMSO-$d_6$) δ3.04-3.20 (1H, m), 3.82-3.94 (2H, m), 4.11-4.23 (2H, m), 4.33 (2H, d, J=6.3 Hz), 4.65 (2H, s), 6.93-7.04 (2H, m), 7.34-7.44 (1H, m), 7.51-7.60 (1H, m), 7.68 (1H, dd, J=11.4, 1.9 Hz), 10.84 (1H, s).

The compounds of Examples 90 to 96, 98 to 100, 103 to 187 and 189 to 283 in the following tables were produced according to the methods described in the above-mentioned Examples, or methods analogous thereto. The compounds of Examples are shown in the following Tables 2-1 to 2-22. MS in the tables means actual measured value.

TABLE 2-1

| Ex. No. | IUPAC NAME | STRUCTURE | MS |
|---|---|---|---|
| 90 | 6-((4-((2-chloro-4-(2-hydroxypropan-2-yl)phenoxy)methyl)piperidin-1-yl)carbonyl)-7-fluoro-2H-1,4-benzoxazin-3(4H)-one | 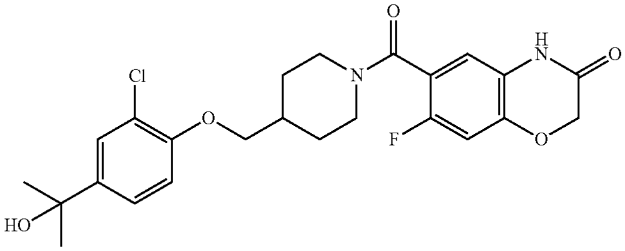 [SMILES: CC(C)(O)c1ccc(OCC2CCN(C(=O)c3cc4c(cc3F)OCC(=O)N4)CC2)c(Cl)c1] | 459.1 |
| 91 | 7-fluoro-6-((4-((4-fluoro-2-(2-hydroxypropan-2-yl)phenoxy)methyl)piperidin-1-yl)carbonyl)-2H-1,4-benzoxazin-3(4H)-one | 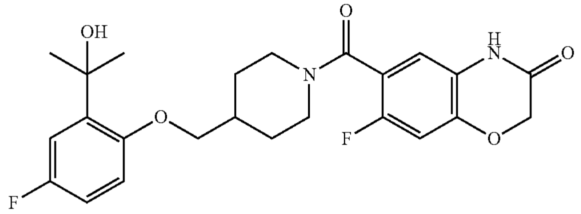 [SMILES: CC(C)(O)c1cc(F)ccc1OCC1CCN(C(=O)c2cc3c(cc2F)OCC(=O)N3)CC1] | 459.1 |
| 92 | 3-chloro-4-((1-((7-fluoro-3-oxo-3,4-dihydro-2H-1,4-benzoxazin-6-yl)carbonyl)azetidin-3-yl)methoxy)benzonitrile | 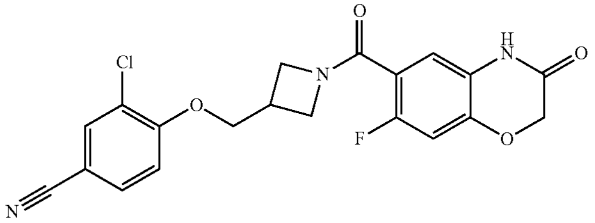 [SMILES: N#Cc1ccc(OCC2CN(C(=O)c3cc4c(cc3F)OCC(=O)N4)C2)c(Cl)c1] | 416.0 |
| 93 | 7-((4-((2-chloro-4-fluorophenoxy)methyl)piperidin-1-yl)carbonyl)-1H-pyrido[3,4-b][1,4]oxazin-2(3H)-one | 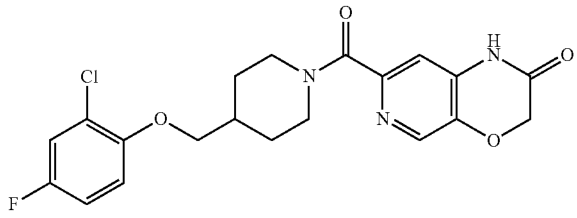 [SMILES: O=C1COc2cnc(C(=O)N3CCC(COc4ccc(F)cc4Cl)CC3)cc2N1] | 420.1 |

TABLE 2-1-continued

| Ex. No. | IUPAC NAME | STRUCTURE | MS |
|---|---|---|---|
| 94 | 6-((4-((2-fluorophenoxy)methyl)piperidin-1-yl)carbonyl)-2H-1,4-benzoxazin-3(4H)-one | 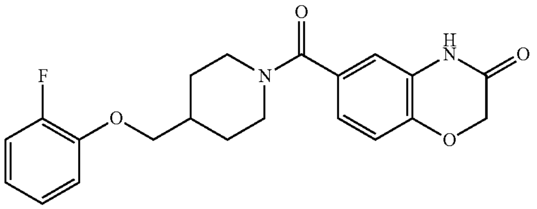 [SMILES: O=C1COc2ccc(C(=O)N3CCC(COc4ccccc4F)CC3)cc2N1] | 385.1 |
| 95 | 6-((4-(((4,4-difluorocyclohexyl)oxy)methyl) piperidin-1-yl)carbonyl)-7-fluoro-2H-1,4-benzoxazin-3(4H)-one | 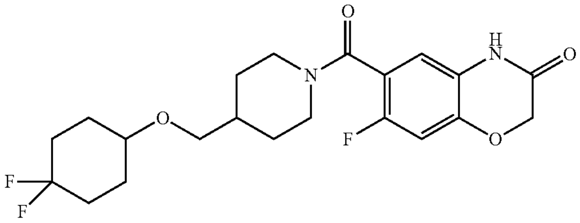 [SMILES: O=C1COc2cc(F)c(C(=O)N3CCC(COC4CCC(F)(F)CC4)CC3)cc2N1] | 427.2 |
| 96 | 6-((3-((2-chloro-4-fluorophenoxy)methyl)-3-fluoroazetidin-1-yl)carbonyl)-7-fluoro-2H-1,4-benzoxazin-3(4H)-one | 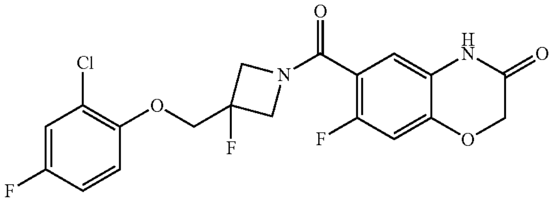 [SMILES: O=C1COc2cc(F)c(C(=O)N3CC(F)(COc4ccc(F)cc4Cl)C3)cc2N1] | 427.1 |
| 97 | 6-((4-((2-chloro-4-fluorophenoxy)methyl)piperidin-1-yl)carbonyl)-7-methoxy-2H-1,4-benzoxazin-3(4H)-one | 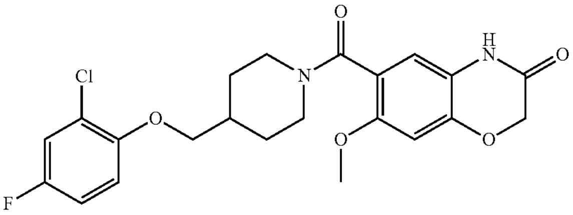 [SMILES: COc1cc2c(cc1C(=O)N1CCC(COc3ccc(F)cc3Cl)CC1)NC(=O)CO2] | 449.1 |
| 98 | 6-((3-((2-chloro-4-fluorophenoxy)methyl)azetidin-1-yl)carbonyl)-7-methoxy-2H-1,4-benzoxazin-3(4H)-one | 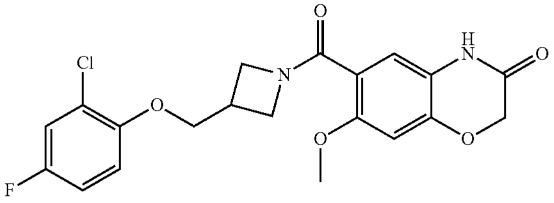 [SMILES: COc1cc2c(cc1C(=O)N1CC(COc3ccc(F)cc3Cl)C1)NC(=O)CO2] | 421.1 |

TABLE 2-2

| | | | |
|---|---|---|---|
| 99 | 6-((4-((2-bromo-4-fluorophenoxy)methyl)piperidin-1-yl)carbonyl)-7-fluoro-2H-1,4-benzoxazin-3(4H)-one | 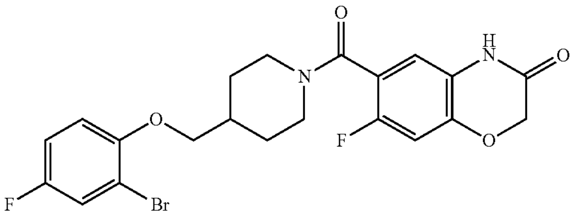 [SMILES: O=C1COc2cc(F)c(C(=O)N3CCC(COc4ccc(F)cc4Br)CC3)cc2N1] | 481.0 |

TABLE 2-2-continued

| | | | |
|---|---|---|---|
| 100 | 7-fluoro-6-((4-(((5-fluorobiphenyl-2-yl)oxy)methyl)piperidin-1-yl)carbonyl)-2H-1,4-benzoxazin-3(4H)-one | 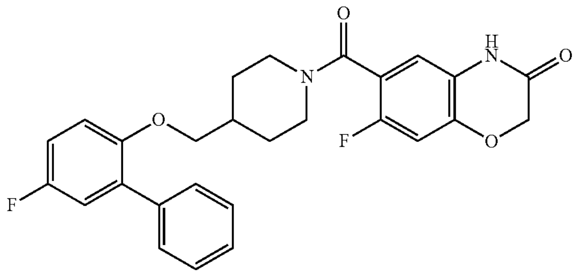 [SMILES: O=C1COc2cc(F)c(C(=O)N3CCC(COc4ccc(F)cc4-c4ccccc4)CC3)cc2N1] | 479.2 |
| 101 | 5-((4-((2-chloro-4-fluorophenoxy)methyl)piperidin-1-yl)carbonyl)-6-fluoro-1,3-benzoxazol-2(3H)-one | 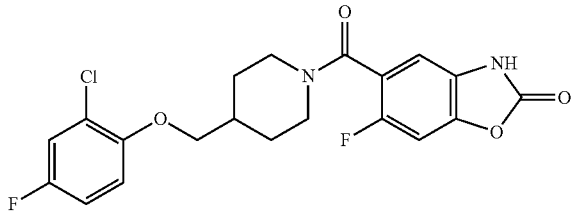 [SMILES: O=C(c1cc2[nH]c(=O)oc2cc1F)N1CCC(COc2ccc(F)cc2Cl)CC1] | 423.1 |
| 102 | 7-fluoro-6-((3-((5,6,7,8-tetrahydronaphthalen-2-yloxy)methyl)azetidin-1-yl)carbonyl)-2H-1,4-benzoxazin-3(4H)-one | 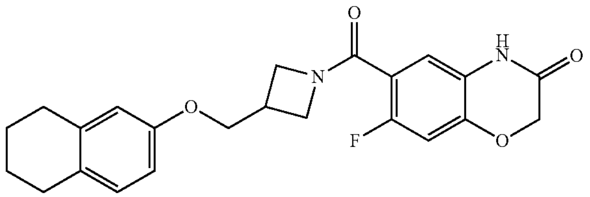 [SMILES: O=C1COc2cc(F)c(C(=O)N3CC(COc4ccc5c(c4)CCCC5)C3)cc2N1] | 411.2 |
| 103 | 6-((3-(((2,2-dimethyl-2,3-dihydro-1-benzofuran-7-yl)oxy)methyl)azetidin-1-yl)carbonyl)-7-fluoro-2H-1,4-benzoxazin-3(4H)-one | 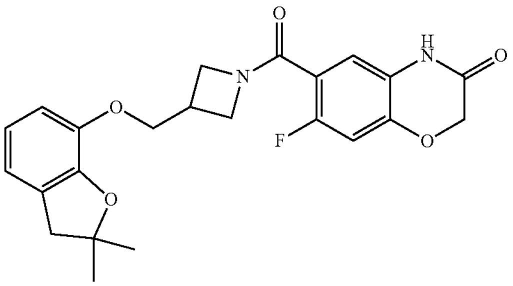 [SMILES: CC1(C)Cc2cccc(OCC3CN(C(=O)c4cc5c(cc4F)OCC(=O)N5)C3)c2O1] | 427.2 |
| 104 | 6-((3-((1,3-benzothiazol-5-yloxy)methyl)azetidin-1-yl)carbonyl)-7-fluoro-2H-1,4-benzoxazin-3(4H)-one | 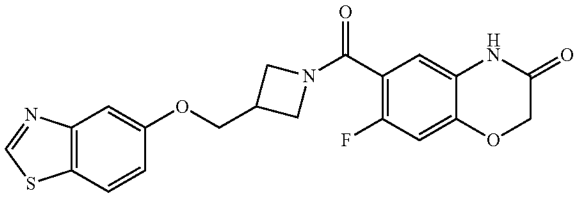 [SMILES: O=C1COc2cc(F)c(C(=O)N3CC(COc4ccc5scnc5c4)C3)cc2N1] | 414.1 |
| 105 | 6-((3-((1,3-benzothiazol-4-yloxy)methyl)azetidin-1-yl)carbonyl)-7-fluoro-2H-1,4-benzoxazin-3(4H)-one | 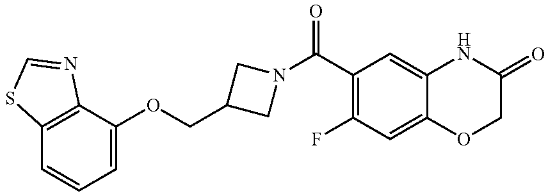 [SMILES: O=C1COc2cc(F)c(C(=O)N3CC(COc4cccc5scnc45)C3)cc2N1] | 414.1 |
| 106 | 6-((3-((1,3-benzoxazol-4-yloxy)methyl)azetidin-1-yl)carbonyl)-7-fluoro-2H-1,4-benzoxazin-3(4H)-one | 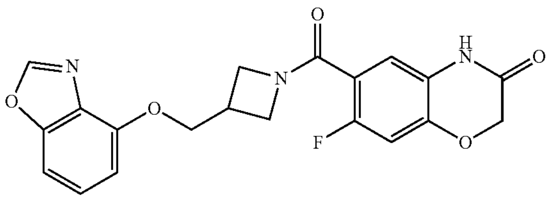 [SMILES: O=C1COc2cc(F)c(C(=O)N3CC(COc4cccc5ocnc45)C3)cc2N1] | 398.1 |

TABLE 2-2-continued

| | | | |
|---|---|---|---|
| 107 | 7-fluoro-6-((3-((1H-indazol-4-yloxy)methyl)azetidin-1-yl)carbonyl)-2H-1,4-benzoxazin-3(4H)-one | 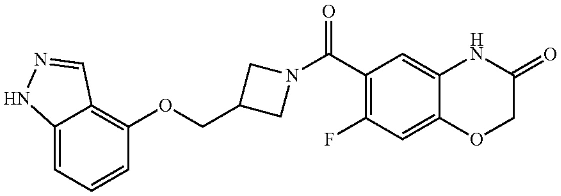 [SMILES: O=C1COc2cc(F)c(C(=O)N3CC(COc4cccc5[nH]ncc45)C3)cc2N1] | 397.1 |

TABLE 2-3

| | | | |
|---|---|---|---|
| 108 | 6-((3-((biphenyl-4-yloxy)methyl)azetidin-1-yl)carbonyl)-7-fluoro-2H-1,4-benzoxazin-3(4H)-one | 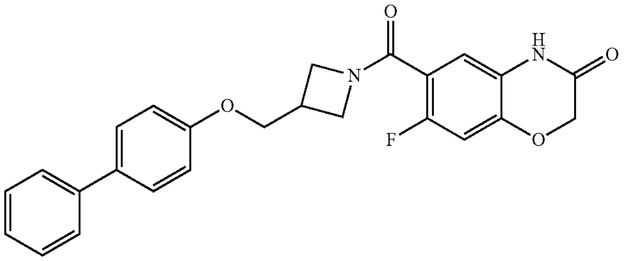 [SMILES: O=C1COc2cc(F)c(C(=O)N3CC(COc4ccc(-c5ccccc5)cc4)C3)cc2N1] | 433.1 |
| 109 | 6-((3-((biphenyl-2-yloxy)methyl)azetidin-1-yl)carbonyl)-7-fluoro-2H-1,4-benzoxazin-3(4H)-one | 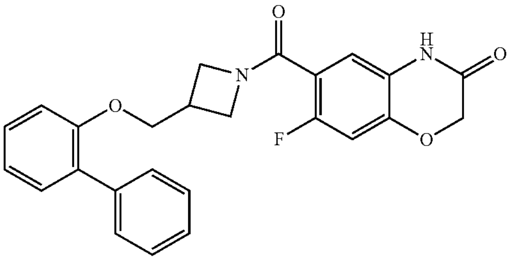 [SMILES: O=C1COc2cc(F)c(C(=O)N3CC(COc4ccccc4-c4ccccc4)C3)cc2N1] | 433.1 |
| 110 | 6-((3-((biphenyl-3-yloxy)methyl)azetidin-1-yl)carbonyl)-7-fluoro-2H-1,4-benzoxazin-3(4H)-one | 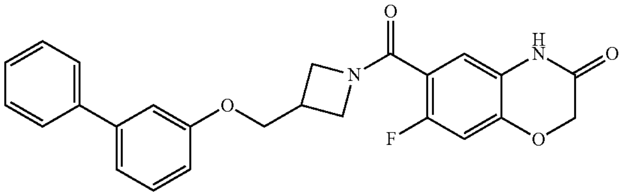 [SMILES: O=C1COc2cc(F)c(C(=O)N3CC(COc4cccc(-c5ccccc5)c4)C3)cc2N1] | 433.1 |
| 111 | 6-((3-((4-chlorophenoxy)methyl)azetidin-1-yl)carbonyl)-7-fluoro-2H-1,4-benzoxazin-3(4H)-one | 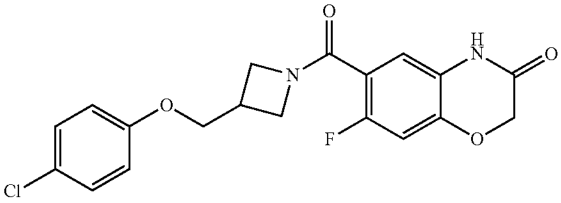 [SMILES: O=C1COc2cc(F)c(C(=O)N3CC(COc4ccc(Cl)cc4)C3)cc2N1] | 391.0 |
| 112 | 6-((3-((3-chlorophenoxy)methyl)azetidin-1-yl)carbonyl)-7-fluoro-2H-1,4-benzoxazin-3(4H)-one | 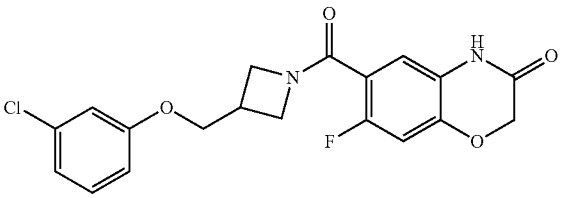 [SMILES: O=C1COc2cc(F)c(C(=O)N3CC(COc4cccc(Cl)c4)C3)cc2N1] | 391.0 |

TABLE 2-3-continued

| | | | |
|---|---|---|---|
| 113 | 6-((3-((2-chlorophenoxy)methyl)azetidin-1-yl)carbonyl)-7-fluoro-2H-1,4-benzoxazin-3(4H)-one | 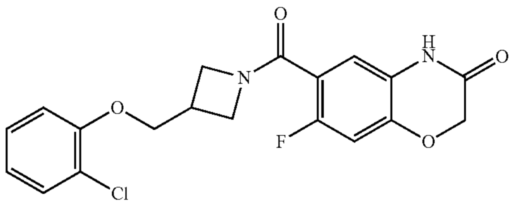 [SMILES: O=C1COc2cc(F)c(C(=O)N3CC(COc4ccccc4Cl)C3)cc2N1] | 391.0 |
| 114 | 7-fluoro-6-((3-((4-(2,2,2-trifluoroethoxy)phenoxy)methyl) azetidin-1-yl)carbonyl)-2H-1,4-benzoxazin-3(4H)-one | 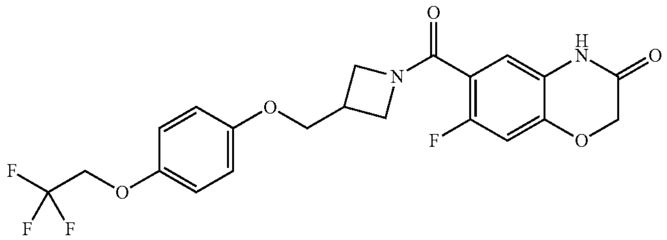 [SMILES: O=C1COc2cc(F)c(C(=O)N3CC(COc4ccc(OCC(F)(F)F)cc4)C3)cc2N1] | 455.1 |
| 115 | 6-((3-((4-chloro-2-methoxyphenoxy)methyl)azetidin-1-yl)carbonyl)-7-fluoro-2H-1,4-benzoxazin-3(4H)-one | 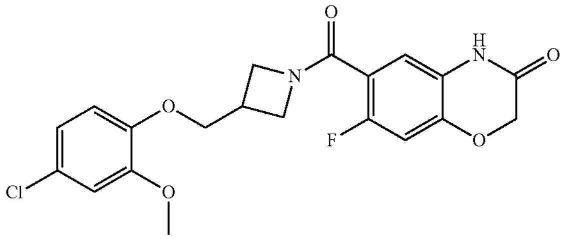 [SMILES: COc1cc(Cl)ccc1OCC1CN(C(=O)c2cc3c(cc2F)OCC(=O)N3)C1] | 421.0 |
| 116 | 6-((3-((2-chloro-4-(trifluoromethyl)phenoxy)methyl) azetidin-1-yl)carbonyl)-7-fluoro-2H-1,4-benzoxazin-3(4H)-one | 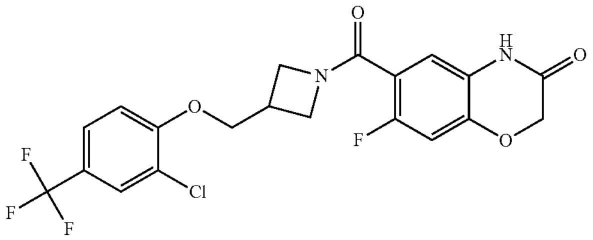 [SMILES: O=C1COc2cc(F)c(C(=O)N3CC(COc4ccc(C(F)(F)F)cc4Cl)C3)cc2N1] | 459.0 |

TABLE 2-4

| | | | |
|---|---|---|---|
| 117 | 6-((3-((2-chloro-4-methylphenoxy)methyl)azetidin-1-yl)carbonyl)-7-fluoro-2H-1,4-benzoxazin-3(4H)-one | 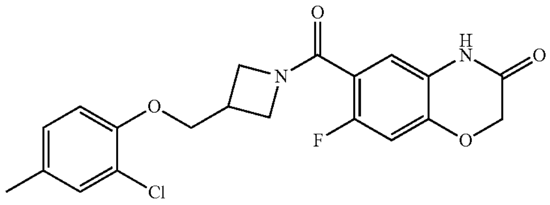 [SMILES: Cc1ccc(OCC2CN(C(=O)c3cc4c(cc3F)OCC(=O)N4)C2)c(Cl)c1] | 405.1 |
| 118 | 6-((3-((4-tert-butyl-2-chlorophenoxy)methyl)azetidin-1-yl)carbonyl)-7-fluoro-2H-1,4-benzoxazin-3(4H)-one | 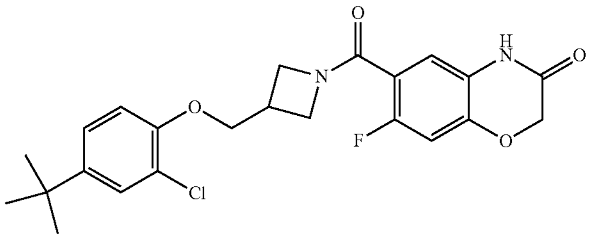 [SMILES: CC(C)(C)c1ccc(OCC2CN(C(=O)c3cc4c(cc3F)OCC(=O)N4)C2)c(Cl)c1] | 447.1 |

TABLE 2-4-continued

| | | | |
|---|---|---|---|
| 119 | 5-chloro-2-((1-((7-fluoro-3-oxo-3,4-dihydro-2H-1,4-benzoxazin-6-yl)carbonyl)azetidin-3-yl)methoxy)benzonitrile | 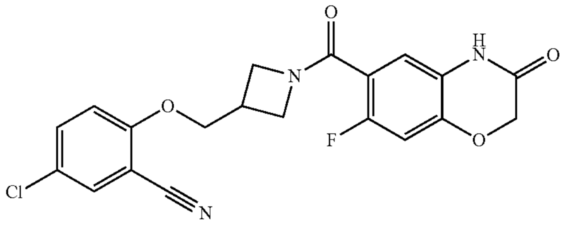 [SMILES: N#Cc1cc(Cl)ccc1OCC1CN(C(=O)c2cc3c(cc2F)OCC(=O)N3)C1] | 416.0 |
| 120 | 7-fluoro-6-((3-((4-fluoro-2-methylphenoxy)methyl)azetidin-1-yl)carbonyl)-2H-1,4-benzoxazin-3(4H)-one | 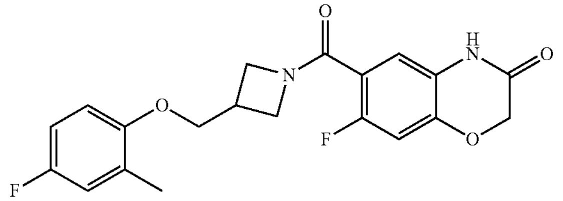 [SMILES: Cc1cc(F)ccc1OCC1CN(C(=O)c2cc3c(cc2F)OCC(=O)N3)C1] | 389.1 |
| 121 | 7-fluoro-6-((3-((4-fluoro-2-methoxyphenoxy)methyl)azetidin-1-yl)carbonyl)-2H-1,4-benzoxazin-3(4H)-one | 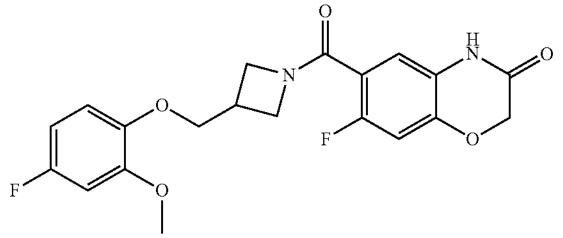 [SMILES: COc1cc(F)ccc1OCC1CN(C(=O)c2cc3c(cc2F)OCC(=O)N3)C1] | 405.1 |
| 122 | 6-((3-((2,6-dichlorophenoxy)methyl)azetidin-1-yl)carbonyl)-7-fluoro-2H-1,4-benzoxazin-3(4H)-one | 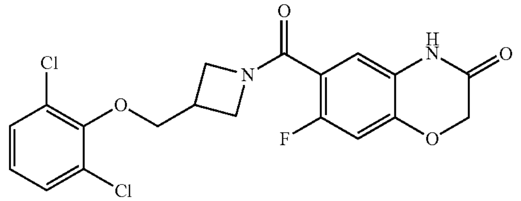 [SMILES: O=C1COc2cc(F)c(C(=O)N3CC(COc4c(Cl)cccc4Cl)C3)cc2N1] | 425.0 |
| 123 | 6-((3-((2,3-dichlorophenoxy)methyl)azetidin-1-yl)carbonyl)-7-fluoro-2H-1,4-benzoxazin-3(4H)-one | 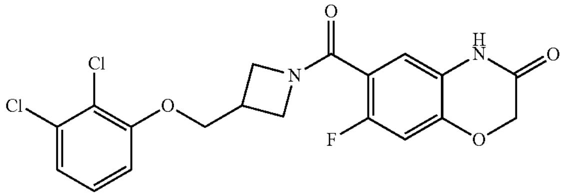 [SMILES: O=C1COc2cc(F)c(C(=O)N3CC(COc4cccc(Cl)c4Cl)C3)cc2N1] | 425.0 |
| 124 | 6-((3-((3,4-dichlorophenoxy)methyl)azetidin-1-yl)carbonyl)-7-fluoro-2H-1,4-benzoxazin-3(4H)-one | 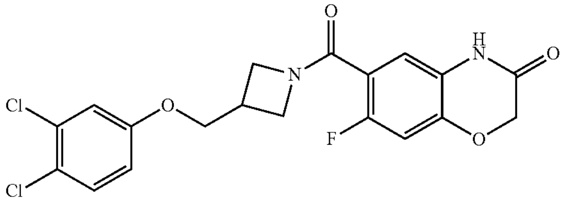 [SMILES: O=C1COc2cc(F)c(C(=O)N3CC(COc4ccc(Cl)c(Cl)c4)C3)cc2N1] | 425.0 |
| 125 | 6-((3-((2,5-dichlorophenoxy)methyl)azetidin-1-yl)carbonyl)-7-fluoro-2H-1,4-benzoxazin-3(4H)-one | 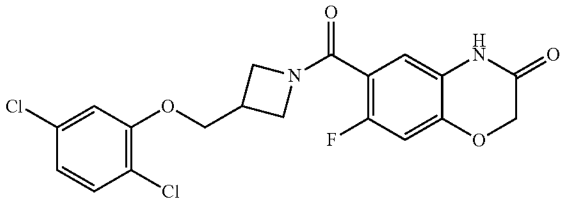 [SMILES: O=C1COc2cc(F)c(C(=O)N3CC(COc4cc(Cl)ccc4Cl)C3)cc2N1] | 425.0 |

TABLE 2-5

| | | | |
|---|---|---|---|
| 126 | 6-((3-((4-chloro-2-fluorophenoxy)methyl)azetidin-1-yl)carbonyl)-7-fluoro-2H-1,4-benzoxazin-3(4H)-one | 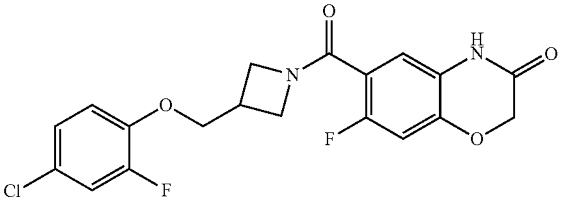 | 409.0 |
| 127 | 6-((3-((3,5-dichlorophenoxy)methyl)azetidin-1-yl)carbonyl)-7-fluoro-2H-1,4-benzoxazin-3(4H)-one | 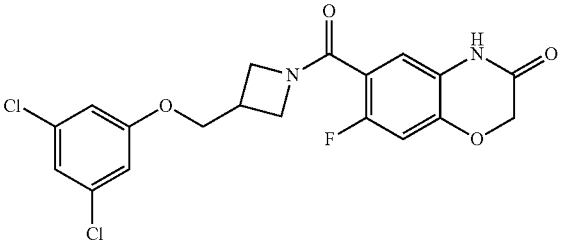 [SMILES: O=C1COc2cc(F)c(C(=O)N3CC(COc4cc(Cl)cc(Cl)c4)C3)cc2N1] | 425.1 |
| 128 | 7-fluoro-6-((3-((4-phenoxyphenoxy)methyl)azetidin-1-yl)carbonyl)-2H-1,4-benzoxazin-3(4H)-one | 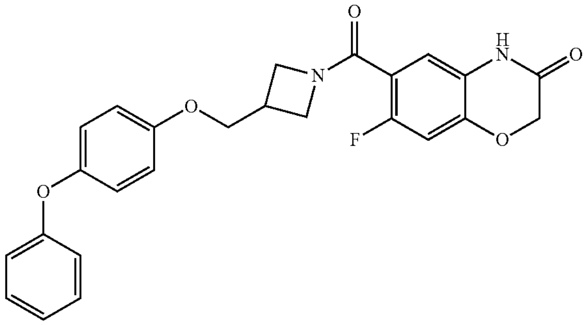 [SMILES: O=C1COc2cc(F)c(C(=O)N3CC(COc4ccc(Oc5ccccc5)cc4)C3)cc2N1] | 449.1 |
| 129 | 7-fluoro-6-((3-((3-phenoxyphenoxy)methyl)azetidin-1-yl)carbonyl)-2H-1,4-benzoxazin-3(4H)-one | 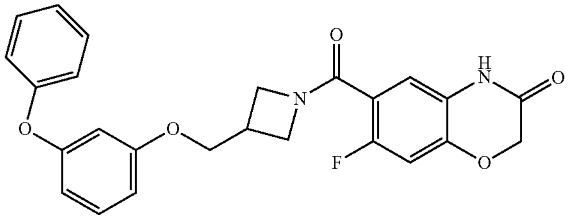 [SMILES: O=C1COc2cc(F)c(C(=O)N3CC(COc4cccc(Oc5ccccc5)c4)C3)cc2N1] | 449.1 |
| 130 | 6-((3-((4-chloro-3-fluorophenoxy)methyl)azetidin-1-yl)carbonyl)-7-fluoro-2H-1,4-benzoxazin-3(4H)-one | 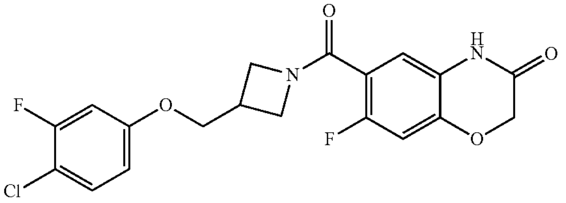 [SMILES: O=C1COc2cc(F)c(C(=O)N3CC(COc4ccc(Cl)c(F)c4)C3)cc2N1] | 409.0 |
| 131 | 6-((3-((3-chloro-4-fluorophenoxy)methyl)azetidin-1-yl)carbonyl)-7-fluoro-2H-1,4-benzoxazin-3(4H)-one | 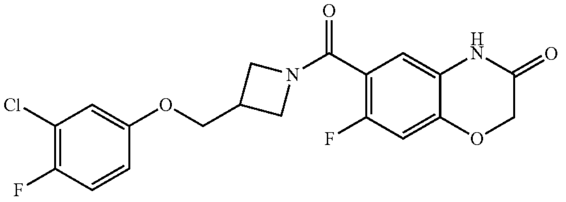 [SMILES: O=C1COc2cc(F)c(C(=O)N3CC(COc4ccc(F)c(Cl)c4)C3)cc2N1] | 409.0 |

TABLE 2-5-continued

| | | | |
|---|---|---|---|
| 132 | 6-((3-((2-chloro-5-fluorophenoxy)methyl)azetidin-1-yl)carbonyl)-7-fluoro-2H-1,4-benzoxazin-3(4H)-one | 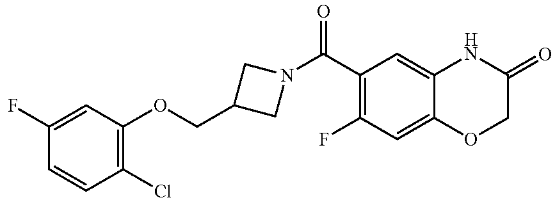 [SMILES: O=C1COc2cc(F)c(C(=O)N3CC(COc4cc(F)ccc4Cl)C3)cc2N1] | 409.0 |
| 133 | 2-chloro-5-((1-((7-fluoro-3-oxo-3,4-dihydro-2H-1,4-benzoxazin-6-yl)carbonyl)azetidin-3-yl)methoxy)benzonitrile | 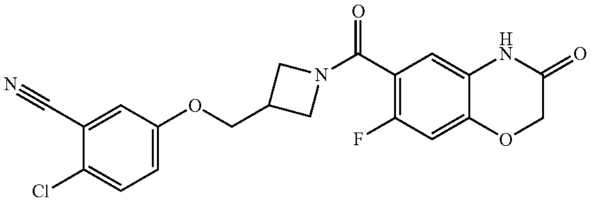 [SMILES: N#Cc1cc(OCC2CN(C(=O)c3cc4c(cc3F)OCC(=O)N4)C2)ccc1Cl] | 416.0 |
| 134 | 6-((3-((3-chloro-5-fluorophenoxy)methyl)azetidin-1-yl)carbonyl)-7-fluoro-2H-1,4-benzoxazin-3(4H)-one | 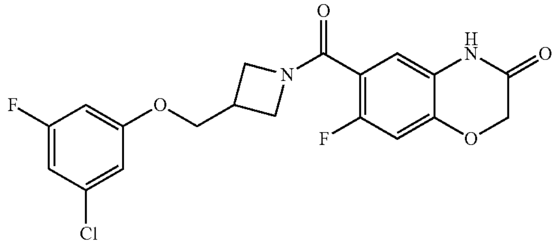 [SMILES: O=C1COc2cc(F)c(C(=O)N3CC(COc4cc(F)cc(Cl)c4)C3)cc2N1] | 409.0 |

TABLE 2-6

| | | | |
|---|---|---|---|
| 135 | 6-((3-((3-chloro-2-fluorophenoxy)methyl)azetidin-1-yl)carbonyl)-7-fluoro-2H-1,4-benzoxazin-3(4H)-one | 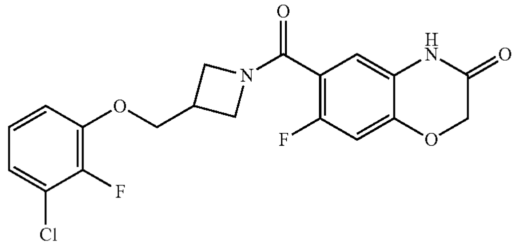 [SMILES: O=C1COc2cc(F)c(C(=O)N3CC(COc4cccc(Cl)c4F)C3)cc2N1] | 409.0 |
| 136 | 6-((3-((2-chloro-6-fluorophenoxy)methyl)azetidin-1-yl)carbonyl)-7-fluoro-2H-1,4-benzoxazin-3(4H)-one | 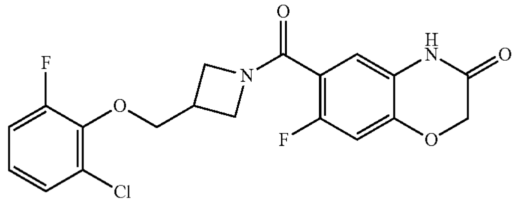 [SMILES: O=C1COc2cc(F)c(C(=O)N3CC(COc4c(F)cccc4Cl)C3)cc2N1] | 409.0 |
| 137 | 4-chloro-2-((1-((7-fluoro-3-oxo-3,4-dihydro-2H-1,4-benzoxazin-6-yl)carbonyl)azetidin-3-yl)methoxy)benzonitrile | 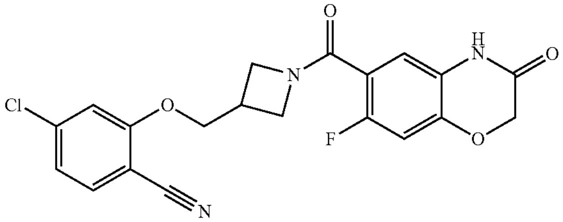 [SMILES: N#Cc1ccc(Cl)cc1OCC1CN(C(=O)c2cc3c(cc2F)OCC(=O)N3)C1] | 416.0 |

TABLE 2-6-continued

| | | | |
|---|---|---|---|
| 138 | 2-chloro-4-((1-((7-fluoro-3-oxo-3,4-dihydro-2H-1,4-benzoxazin-6-yl)carbonyl)azetidin-3-yl)methoxy)benzonitrile | 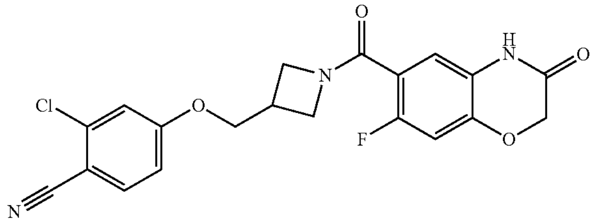 [SMILES: N#Cc1ccc(OCC2CN(C(=O)c3cc4c(cc3F)OCC(=O)N4)C2)cc1Cl] | 416.0 |
| 139 | 7-fluoro-6-((3-((quinoxalin-5-yloxy)methyl)azetidin-1-yl)carbonyl)-2H-1,4-benzoxazin-3(4H)-one | 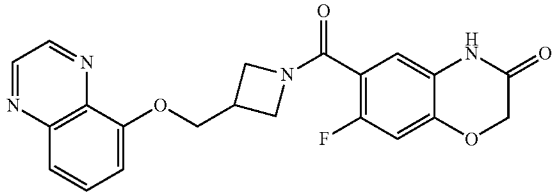 [SMILES: O=C1COc2cc(F)c(C(=O)N3CC(COc4cccc5nccnc45)C3)cc2N1] | 409.1 |
| 140 | 7-fluoro-6-((3-(phenoxymethyl)azetidin-1-yl)carbonyl)-2H-1,4-benzoxazin-3(4H)-one | 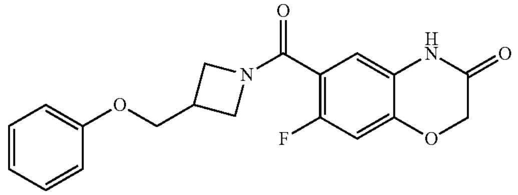 [SMILES: O=C1COc2cc(F)c(C(=O)N3CC(COc4ccccc4)C3)cc2N1] | 357.1 |
| 141 | 6-((3-(((2,6-dimethylpyridin-3-yl)oxy)methyl)azetidin-1-yl)carbonyl)-7-fluoro-2H-1,4-benzoxazin-3(4H)-one | 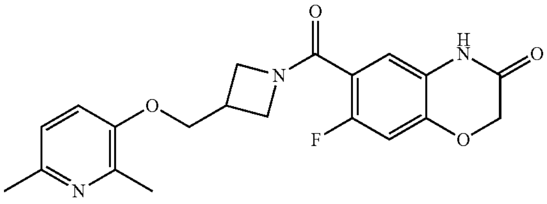 [SMILES: Cc1ccc(OCC2CN(C(=O)c3cc4c(cc3F)OCC(=O)N4)C2)c(C)n1] | 386.1 |
| 142 | 6-((3-(((4,6-dimethylpyridin-3-yl)oxy)methyl)azetidin-1-yl)carbonyl)-7-fluoro-2H-1,4-benzoxazin-3(4H)-one | 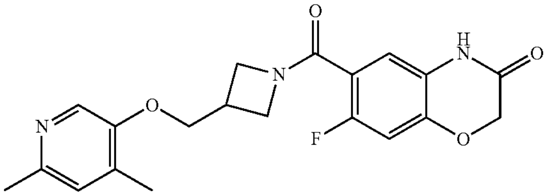 [SMILES: Cc1cc(C)c(OCC2CN(C(=O)c3cc4c(cc3F)OCC(=O)N4)C2)cn1] | 386.1 |
| 143 | 7-fluoro-6-((3-((4-(trifluoromethoxy)phenoxy)methyl) azetidin-1-yl)carbonyl)-2H-1,4-benzoxazin-3(4H)-one | 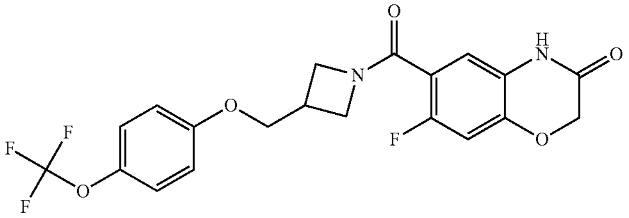 [SMILES: O=C1COc2cc(F)c(C(=O)N3CC(COc4ccc(OC(F)(F)F)cc4)C3)cc2N1] | 441.1 |

TABLE 2-7

| | | | |
|---|---|---|---|
| 144 | 7-((4-((2-chloro-4-(trifluoromethyl)phenoxy)methyl) piperidin-1-yl)carbonyl)-1H-pyrido[3,4-b][1,4]oxazin-2(3H)-one | 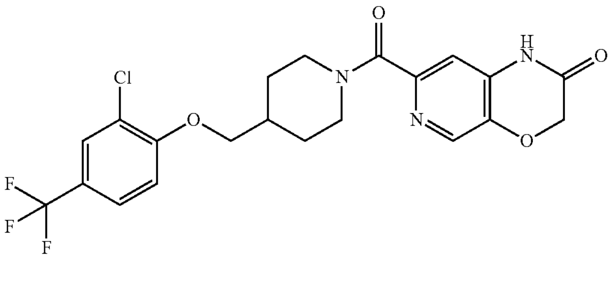 [SMILES: O=C1COc2cnc(C(=O)N3CCC(COc4ccc(C(F)(F)F)cc4Cl)CC3)cc2N1] | 470.1 |

TABLE 2-7-continued

| | | | |
|---|---|---|---|
| 145 | 7-((4-((2-chloro-4-fluorophenoxy)methyl)piperidin-1-yl)carbonyl)-6-methyl-1H-pyrido[2,3-b][1,4]oxazin-2(3H)-one | 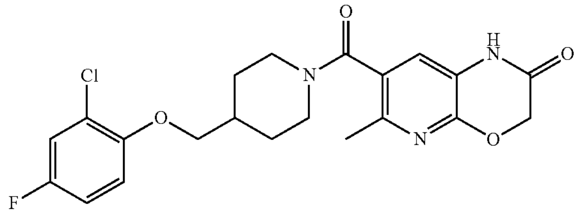 [SMILES: Cc1nc2c(cc1C(=O)N1CCC(COc3ccc(F)cc3Cl)CC1)NC(=O)CO2] | 434.1 |
| 146 | 6-((3-((2-tert-butylphenoxy)methyl)azetidin-1-yl)carbonyl)-2H-1,4-benzoxazin-3(4H)-one | 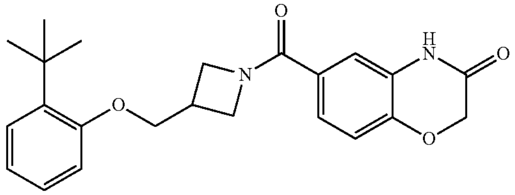 [SMILES: CC(C)(C)c1ccccc1OCC1CN(C(=O)c2ccc3c(c2)NC(=O)CO3)C1] | 395.3 |
| 147 | 6-((3-(((4-chlorobenzyl)oxy)methyl)azetidin-1-yl)carbonyl)-7-fluoro-2H-1,4-benzoxazin-3(4H)-one | 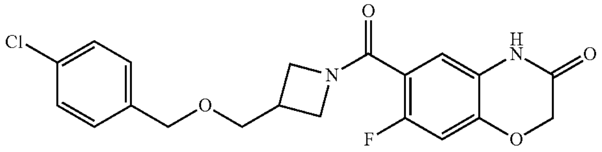 [SMILES: O=C1COc2cc(F)c(C(=O)N3CC(COCc4ccc(Cl)cc4)C3)cc2N1] | 405.1 |
| 148 | 6-((3-(((2-chlorobenzyl)oxy)methyl)azetidin-1-yl)carbonyl)-7-fluoro-2H-1,4-benzoxazin-3(4H)-one | 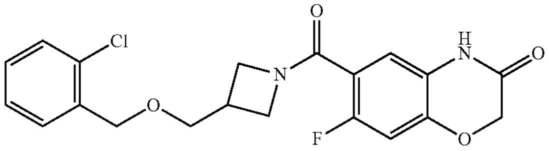 [SMILES: O=C1COc2cc(F)c(C(=O)N3CC(COCc4ccccc4Cl)C3)cc2N1] | 405.1 |
| 149 | 6-((4-((biphenyl-4-yloxy)methyl)piperidin-1-yl)carbonyl)-7-fluoro-2H-1,4-benzoxazin-3(4H)-one | 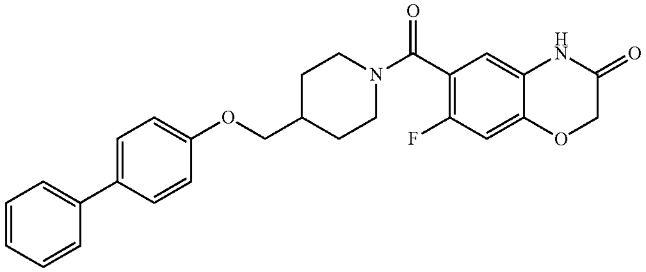 [SMILES: O=C1COc2cc(F)c(C(=O)N3CCC(COc4ccc(-c5ccccc5)cc4)CC3)cc2N1] | 461.2 |
| 150 | 6-((4-((biphenyl-3-yloxy)methyl)piperidin-1-yl)carbonyl)-7-fluoro-2H-1,4-benzoxazin-3(4H)-one | 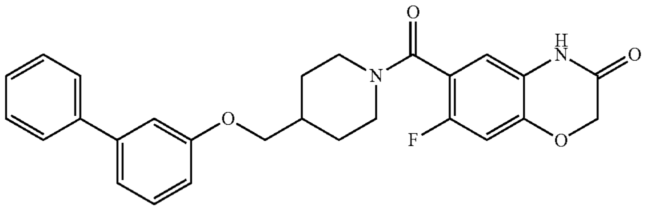 [SMILES: O=C1COc2cc(F)c(C(=O)N3CCC(COc4cccc(-c5ccccc5)c4)CC3)cc2N1] | 461.2 |
| 151 | 7-fluoro-6-((3-(((2-methyl-1,3-benzothiazol-5-yl)oxy)methyl)azetidin-1-yl)carbonyl)-2H-1,4-benzoxazin-3(4H)-one | 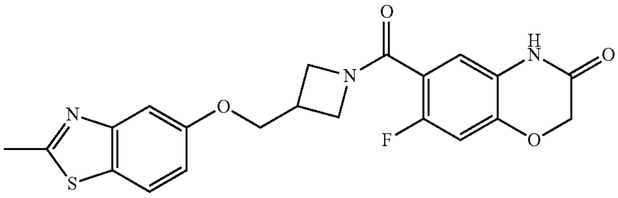 [SMILES: Cc1nc2cc(OCC3CN(C(=O)c4cc5c(cc4F)OCC(=O)N5)C3)ccc2s1] | 428.1 |

TABLE 2-7-continued

| | | | |
|---|---|---|---|
| 152 | 7-fluoro-6-((3-(((2-methyl-1,3-benzothiazol-6-yl)oxy)methyl)azetidin-1-yl)carbonyl)-2H-1,4-benzoxazin-3(4H)-one | 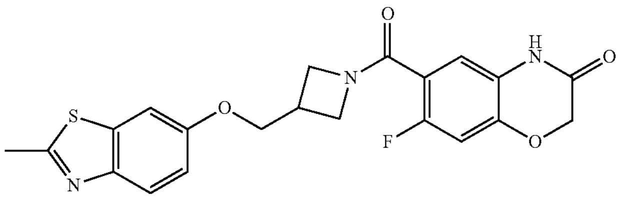 | 428.1 |

TABLE 2-8

| | | | |
|---|---|---|---|
| 153 | 7-fluoro-6-((3-(((2-methyl-1,3-benzoxazol-6-yl)oxy)methyl)azetidin-1-yl)carbonyl)-2H-1,4-benzoxazin-3(4H)-one | 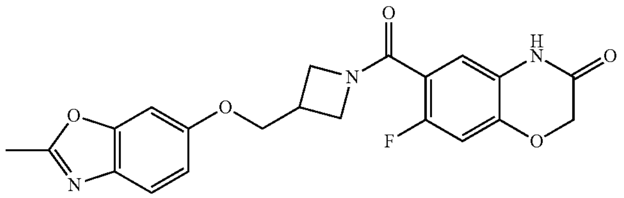 [SMILES: Cc1nc2ccc(OCC3CN(C(=O)c4cc5c(cc4F)OCC(=O)N5)C3)cc2s1] | 412.1 |
| 154 | 6-((3-((2,3-dihydro-1H-inden-5-yloxy)methyl)azetidin-1-yl)carbonyl)-7-fluoro-2H-1,4-benzoxazin-3(4H)-one | 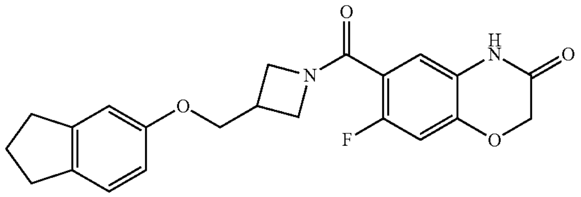 [SMILES: O=C1COc2cc(F)c(C(=O)N3CC(COc4ccc5c(c4)CCC5)C3)cc2N1] | 397.2 |
| 155 | 6-((3-((2,3-dihydro-1-benzofuran-5-yloxy)methyl)azetidin-1-yl)carbonyl)-7-fluoro-2H-1,4-benzoxazin-3(4H)-one | 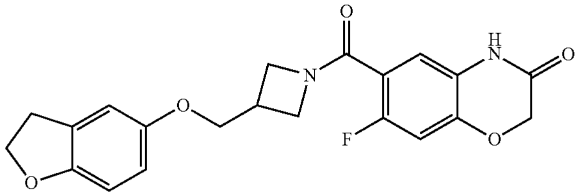 [SMILES: O=C1COc2cc(F)c(C(=O)N3CC(COc4ccc5c(c4)CCO5)C3)cc2N1] | 399.1 |
| 156 | 7-fluoro-6-((3-((1H-indazol-5-yloxy)methyl)azetidin-1-yl)carbonyl)-2H-1,4-benzoxazin-3(4H)-one | 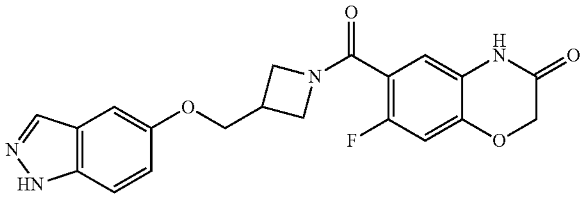 [SMILES: O=C1COc2cc(F)c(C(=O)N3CC(COc4ccc5[nH]ncc5c4)C3)cc2N1] | 397.1 |
| 157 | 7-fluoro-6-((3-((1H-indazol-6-yloxy)methyl)azetidin-1-yl)carbonyl)-2H-1,4-benzoxazin-3(4H)-one | 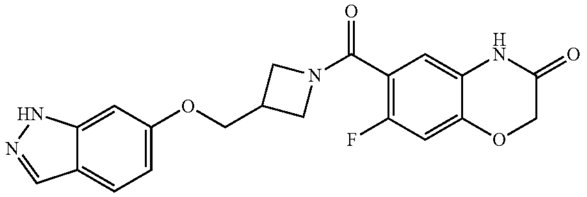 [SMILES: O=C1COc2cc(F)c(C(=O)N3CC(COc4ccc5cn[nH]c5c4)C3)cc2N1] | 397.1 |
| 158 | 6-((3-((3,4-difluorophenoxy)methyl)azetidin-1-yl)carbonyl)-7-fluoro-2H-1,4-benzoxazin-3(4H)-one | 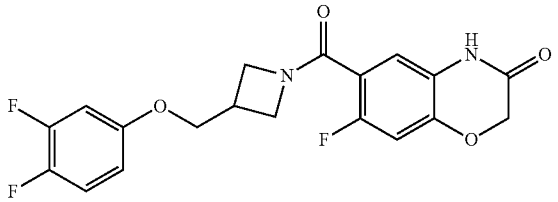 [SMILES: O=C1COc2cc(F)c(C(=O)N3CC(COc4ccc(F)c(F)c4)C3)cc2N1] | 393.1 |

TABLE 2-8-continued

| | | | |
|---|---|---|---|
| 159 | 7-fluoro-6-((3-((4-isopropylphenoxy)methyl)azetidin-1-yl)carbonyl)-2H-1,4-benzoxazin-3(4H)-one | 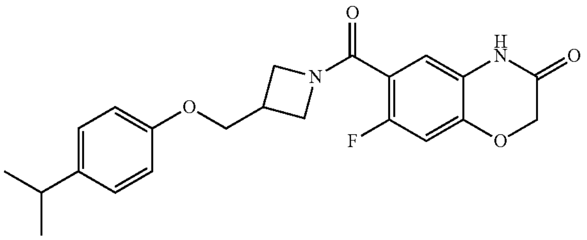 [SMILES: CC(C)c1ccc(OCC2CN(C(=O)c3cc4c(cc3F)OCC(=O)N4)C2)cc1] | 399.1 |
| 160 | 7-fluoro-6-((3-((2-isopropylphenoxy)methyl)azetidin-1-yl)carbonyl)-2H-1,4-benzoxazin-3(4H)-one | 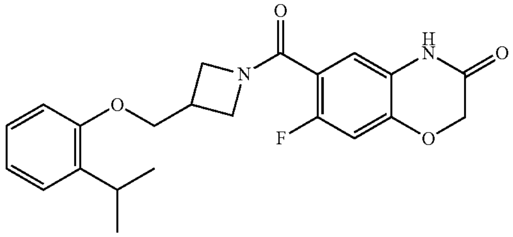 [SMILES: CC(C)c1ccccc1OCC1CN(C(=O)c2cc3c(cc2F)OCC(=O)N3)C1] | 399.1 |
| 161 | 7-fluoro-6-((3-((4-methylphenoxy)methyl)azetidin-1-yl)carbonyl)-2H-1,4-benzoxazin-3(4H)-one | 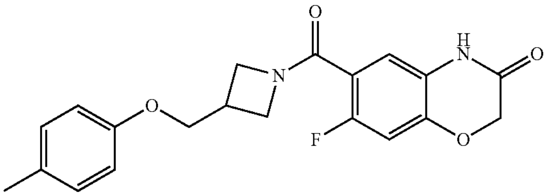 [SMILES: Cc1ccc(OCC2CN(C(=O)c3cc4c(cc3F)OCC(=O)N4)C2)cc1] | 371.1 |

TABLE 2-9

| | | | |
|---|---|---|---|
| 162 | 7-fluoro-6-((3-((3-methylphenoxy)methyl)azetidin-1-yl)carbonyl)-2H-1,4-benzoxazin-3(4H)-one | 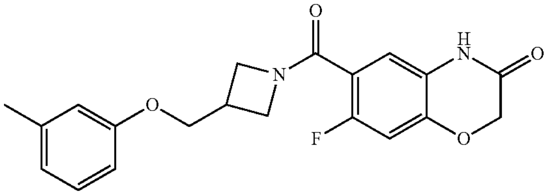 [SMILES: Cc1cccc(OCC2CN(C(=O)c3cc4c(cc3F)OCC(=O)N4)C2)c1] | 371.1 |
| 163 | 6-((3-((3,4-dimethylphenoxy)methyl)azetidin-1-yl)carbonyl)-7-fluoro-2H-1,4-benzoxazin-3(4H)-one | 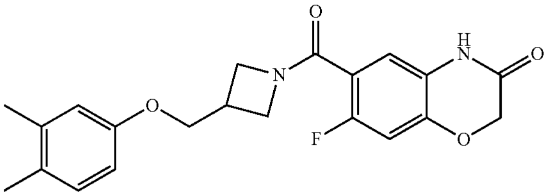 [SMILES: Cc1ccc(OCC2CN(C(=O)c3cc4c(cc3F)OCC(=O)N4)C2)cc1C] | 385.1 |
| 164 | 7-fluoro-6-((3-((2-fluoro-4-methylphenoxy)methyl)azetidin-1-yl)carbonyl)-2H-1,4-benzoxazin-3(4H)-one | 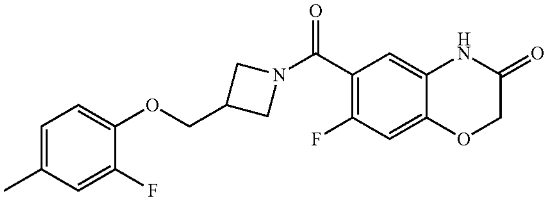 | 389.1 |
| 165 | 6-((3-((2,4-dimethylphenoxy)methyl)azetidin-1-yl)carbonyl)-7-fluoro-2H-1,4-benzoxazin-3(4H)-one | 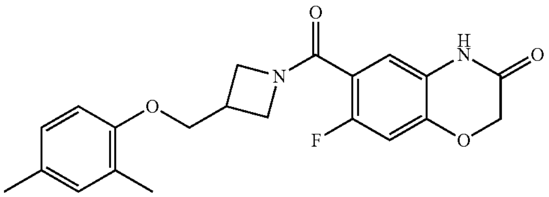 [SMILES: Cc1ccc(OCC2CN(C(=O)c3cc4c(cc3F)OCC(=O)N4)C2)c(C)c1] | 385.1 |

TABLE 2-9-continued

| | | | |
|---|---|---|---|
| 166 | 6-((3-((2-cyclopentylphenoxy)methyl)azetidin-1-yl)carbonyl)-7-fluoro-2H-1,4-benzoxazin-3(4H)-one | 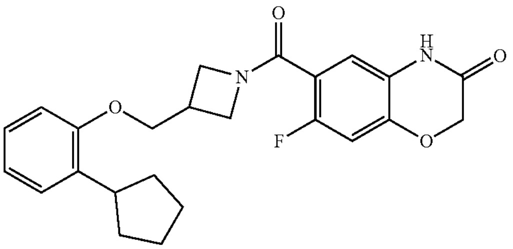 [SMILES: O=C1COc2cc(F)c(C(=O)N3CC(COc4ccccc4C4CCCC4)C3)cc2N1] | 425.2 |
| 167 | 6-((3-((2-tert-butylphenoxy)methyl)azetidin-1-yl)carbonyl)-7-fluoro-2H-1,4-benzoxazin-3(4H)-one | 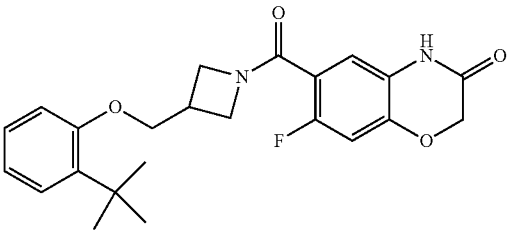 [SMILES: CC(C)(C)c1ccccc1OCC1CN(C(=O)c2cc3c(cc2F)OCC(=O)N3)C1] | 413.2 |
| 168 | 6-((3-((2-cyclopropylphenoxy)methyl)azetidin-1-yl)carbonyl)-7-fluoro-2H-1,4-benzoxazin-3(4H)-one | 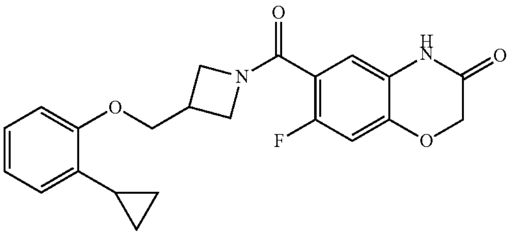 [SMILES: O=C1COc2cc(F)c(C(=O)N3CC(COc4ccccc4C4CC4)C3)cc2N1] | 397.2 |
| 169 | 7-fluoro-6-((3-((2-naphthyloxy)methyl)azetidin-1-yl)carbonyl)-2H-1,4-benzoxazin-3(4H)-one | 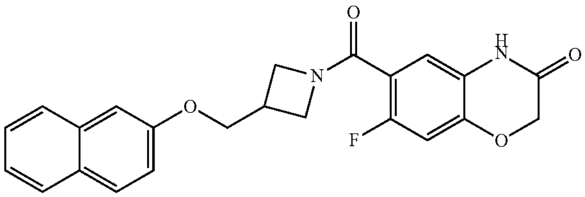 [SMILES: O=C1COc2cc(F)c(C(=O)N3CC(COc4ccc5ccccc5c4)C3)cc2N1] | 407.1 |
| 170 | 7-fluoro-6-((3-((quinolin-6-yloxy)methyl)azetidin-1-yl)carbonyl)-2H-1,4-benzoxazin-3(4H)-one | 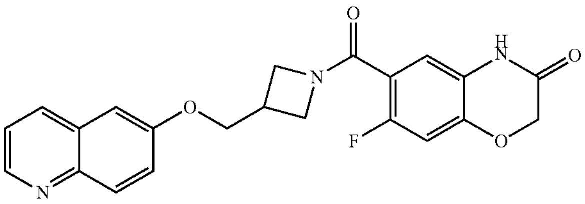 [SMILES: O=C1COc2cc(F)c(C(=O)N3CC(COc4ccc5ncccc5c4)C3)cc2N1] | 408.1 |

TABLE 2-10

| | | | |
|---|---|---|---|
| 171 | 7-fluoro-6-((3-((quinolin-7-yloxy)methyl)azetidin-1-yl)carbonyl)-2H-1,4-benzoxazin-3(4H)-one | 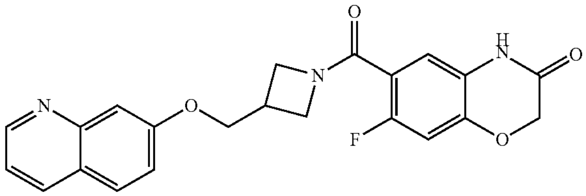 [SMILES: O=C1COc2cc(F)c(C(=O)N3CC(COc4ccc5cccnc5c4)C3)cc2N1] | 408.1 |

TABLE 2-10-continued

| | | | |
|---|---|---|---|
| 172 | 7-fluoro-6-((3-((isoquinolin-7-yloxy)methyl)azetidin-1-yl)carbonyl)-2H-1,4-benzoxazin-3(4H)-one | 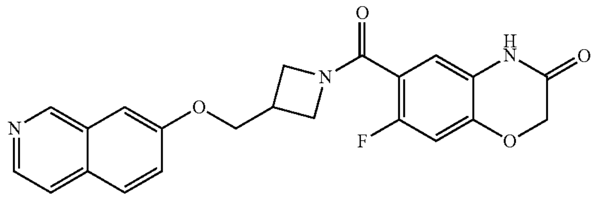 [SMILES: O=C1COc2cc(F)c(C(=O)N3CC(COc4ccc5ccncc5c4)C3)cc2N1] | 408.1 |
| 173 | 7-fluoro-6-((3-((isoquinolin-6-yloxy)methyl)azetidin-1-yl)carbonyl)-2H-1,4-benzoxazin-3(4H)-one | 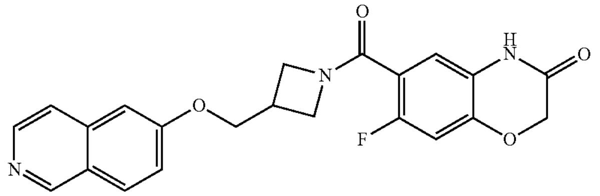 [SMILES: O=C1COc2cc(F)c(C(=O)N3CC(COc4ccc5cnccc5c4)C3)cc2N1] | 408.1 |
| 174 | 7-fluoro-6-((3-(((2'-methoxybiphenyl-2-yl)oxy)methyl)azetidin-1-yl)carbonyl)-2H-1,4-benzoxazin-3(4H)-one | 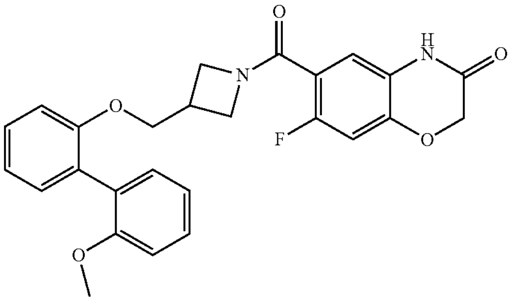 [SMILES: COc1ccccc1-c1ccccc1OCC1CN(C(=O)c2cc3c(cc2F)OCC(=O)N3)C1] | 463.1 |
| 175 | 6-((3-((4-chloro-2-(1,3,4-oxadiazol-2-yl)phenoxy)methyl)azetidin-1-yl)carbonyl)-7-fluoro-2H-1,4-benzoxazin-3(4H)-one | 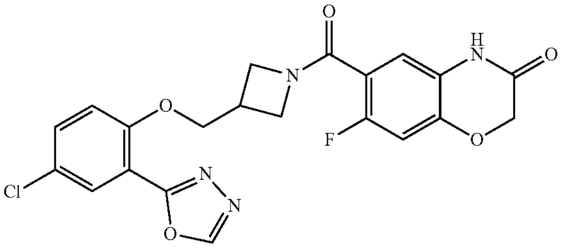 [SMILES: O=C1COc2cc(F)c(C(=O)N3CC(COc4ccc(Cl)cc4-c4nnco4)C3)cc2N1] | 459.2 |
| 176 | 6-((3-(((5-ethyl-2'-methyl-2,4'-bipyridin-3'-yl)oxy)methyl)azetidin-1-yl)carbonyl)-7-fluoro-2H-1,4-benzoxazin-3(4H)-one | 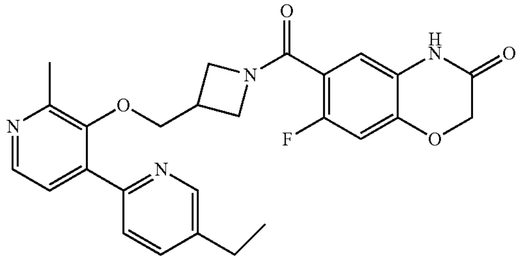 [SMILES: CCc1ccc(-c2ccnc(C)c2OCC2CN(C(=O)c3cc4c(cc3F)OCC(=O)N4)C2)nc1] | 477.2 |
| 177 | 7-fluoro-6-((3-(((2'-methyl-2,4'-bipyridin-3'-yl)oxy)methyl)azetidin-1-yl)carbonyl)-2H-1,4-benzoxazin-3(4H)-one | 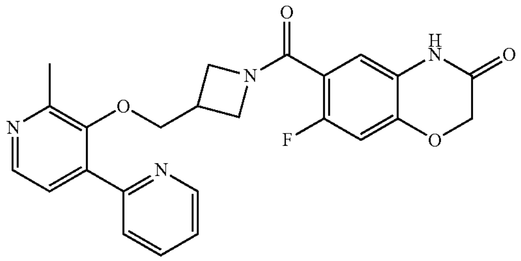 [SMILES: Cc1nccc(-c2ccccn2)c1OCC1CN(C(=O)c2cc3c(cc2F)OCC(=O)N3)C1] | 449.1 |

TABLE 2-10-continued

| | | | |
|---|---|---|---|
| 178 | 7-fluoro-6-((3-(((3-methyl-1-(pyridin-2-yl)-1H-pyrazol-5-yl)oxy)methyl)azetidin-1-yl)carbonyl)-2H-1,4-benzoxazin-3(4H)-one | 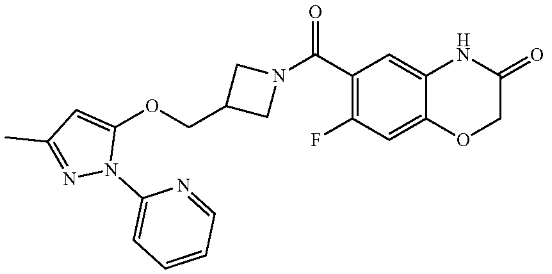 [SMILES: Cc1cc(OCC2CN(C(=O)c3cc4c(cc3F)OCC(=O)N4)C2)n(-c2ccccn2)n1] | 438.1 |
| 179 | 7-fluoro-6-((3-(((2-phenylpyrazolo[1,5-a]pyridin-3-yl)oxy)methyl)azetidin-1-yl)carbonyl)-2H-1,4-benzoxazin-3(4H)-one | 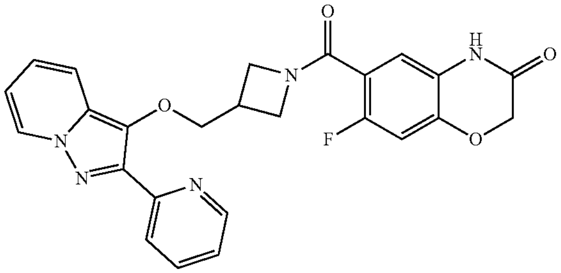 [SMILES: O=C1COc2cc(F)c(C(=O)N3CC(COc4c(-c5ccccn5)nn5ccccc45)C3)cc2N1] | 473.1 |

TABLE 2-11

| | | | |
|---|---|---|---|
| 180 | 6-((3-(((5-chloro-1,2-benzoxazol-3-yl)oxy)methyl)azetidin-1-yl)carbonyl)-7-fluoro-2H-1,4-benzoxazin-3(4H)-one | 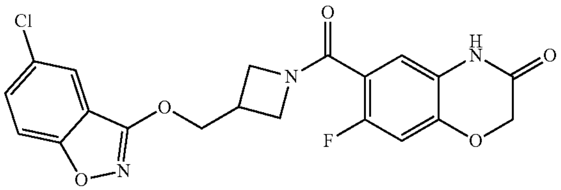 [SMILES: O=C1COc2cc(F)c(C(=O)N3CC(COc4noc5ccc(Cl)cc45)C3)cc2N1] | 432.0 |
| 181 | 7-fluoro-6-((3-(((5-(4-fluorophenyl)imidazo[1,2-a]pyridin-6-yl)oxy)methyl)azetidin-1-yl)carbonyl)-2H-1,4-benzoxazin-3(4H)-one | 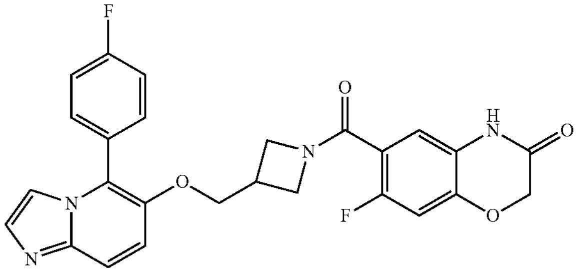 [SMILES: O=C1COc2cc(F)c(C(=O)N3CC(COc4ccc5nccn5c4-c4ccc(F)cc4)C3)cc2N1] | 491.1 |
| 182 | 6-((3-((4-bromophenoxy)methyl)azetidin-1-yl)carbonyl)-7-fluoro-2H-1,4-benzoxazin-3(4H)-one | 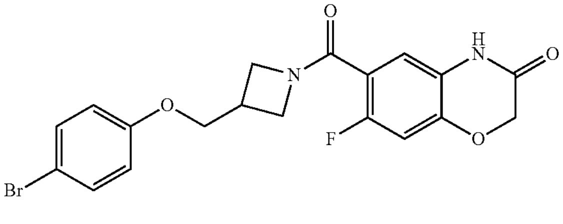 [SMILES: O=C1COc2cc(F)c(C(=O)N3CC(COc4ccc(Br)cc4)C3)cc2N1] | 435.0 |
| 183 | 6-((3-((3-chloro-4-methylphenoxy)methyl)azetidin-1-yl)carbonyl)-7-fluoro-2H-1,4-benzoxazin-3(4H)-one | 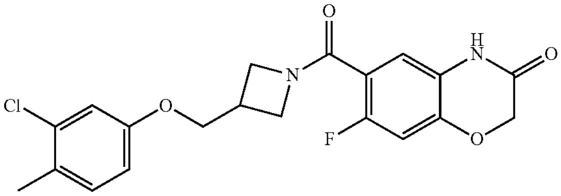 [SMILES: Cc1ccc(OCC2CN(C(=O)c3cc4c(cc3F)OCC(=O)N4)C2)cc1Cl] | 405.1 |

TABLE 2-11-continued

| | | | |
|---|---|---|---|
| 184 | 6-((3-((4-chloro-3-methylphenoxy)methyl)azetidin-1-yl)carbonyl)-7-fluoro-2H-1,4-benzoxazin-3(4H)-one | 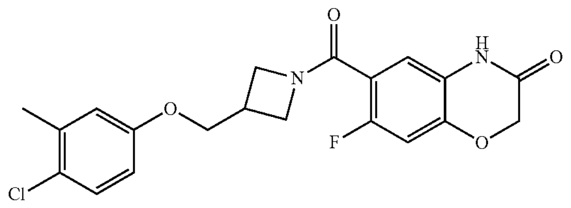 [SMILES: Cc1cc(OCC2CN(C(=O)c3cc4c(cc3F)OCC(=O)N4)C2)ccc1Cl] | 405.1 |
| 185 | 6-((3-((2-bromo-4-chlorophenoxy)methyl)azetidin-1-yl)carbonyl)-7-fluoro-2H-1,4-benzoxazin-3(4H)-one | 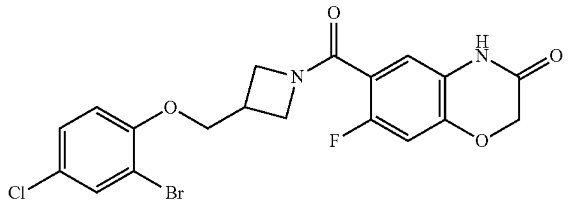 [SMILES: O=C1COc2cc(F)c(C(=O)N3CC(COc4ccc(Cl)cc4Br)C3)cc2N1] | 469.0 |
| 186 | 6-((4-((1,3-benzothiazol-4-yloxy)methyl)piperidin-1-yl)carbonyl)-7-fluoro-2H-1,4-benzoxazin-3(4H)-one | 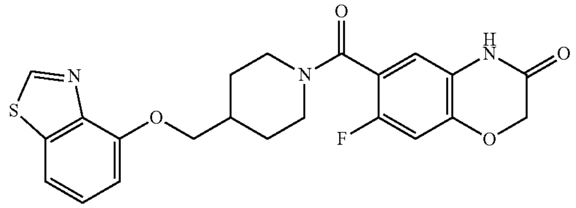 [SMILES: O=C1COc2cc(F)c(C(=O)N3CCC(COc4cccc5scnc45)CC3)cc2N1] | 442.1 |
| 187 | 7-fluoro-6-((4-(((2-methyl-1,3-benzothiazol-4-yl)oxy)methyl)piperidin-1-yl)carbonyl)-2H-1,4-benzoxazin-3(4H)-one | 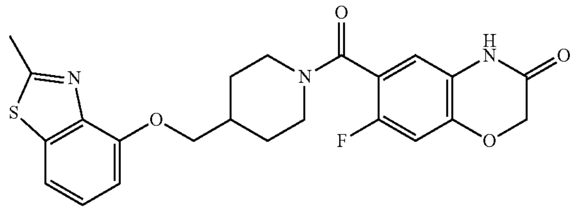 [SMILES: Cc1nc2c(OCC3CCN(C(=O)c4cc5c(cc4F)OCC(=O)N5)CC3)cccc2s1] | 456.1 |
| 188 | 7-fluoro-6-((3-((2-fluoro-4-(trifluoromethyl)phenoxy)methyl)azetidin-1-yl)carbonyl)-2H-1,4-benzoxazin-3(4H)-one | 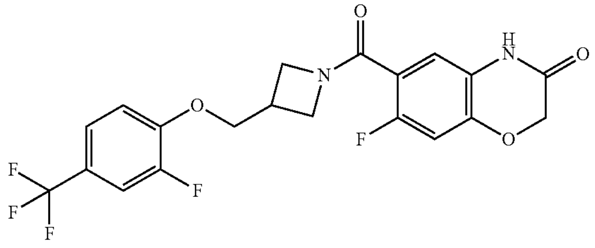 [SMILES: O=C1COc2cc(F)c(C(=O)N3CC(COc4ccc(C(F)(F)F)cc4F)C3)cc2N1] | 443.1 |

TABLE 2-12

| | | | |
|---|---|---|---|
| 189 | 6-((3-((4-chloro-2-(pyridin-2-yl)phenoxy)methyl)azetidin-1-yl)carbonyl)-7-fluoro-2H-1,4-benzoxazin-3(4H)-one | 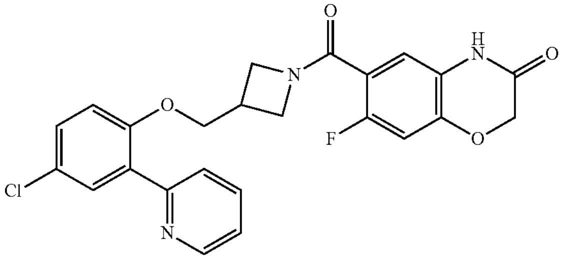 [SMILES: O=C1COc2cc(F)c(C(=O)N3CC(COc4ccc(Cl)cc4-c4ccccn4)C3)cc2N1] | 468.1 |

TABLE 2-12-continued

| | | | |
|---|---|---|---|
| 190 | 6-((3-((4-chloro-2-(6-methylpyridin-3-yl)phenoxy)methyl)azetidin-1-yl)carbonyl)-7-fluoro-2H-1,4-benzoxazin-3(4H)-one | 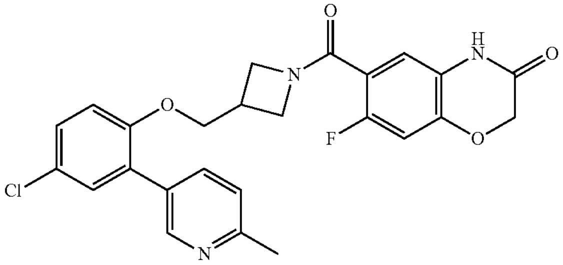 | 482.1 |
| 191 | 6-((3-((4-chloro-2-(2-methylpyridin-3-yl)phenoxy)methyl)azetidin-1-yl)carbonyl)-7-fluoro-2H-1,4-benzoxazin-3(4H)-one | 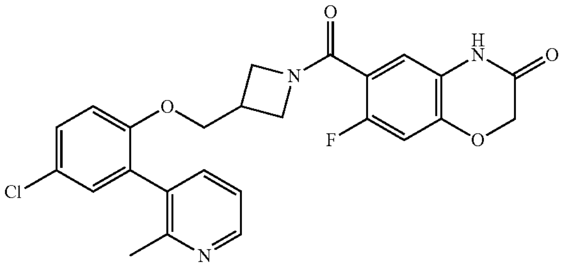 [SMILES: Cc1ncccc1-c1cc(Cl)ccc1OCC1CN(C(=O)c2cc3c(cc2F)OCC(=O)N3)C1] | 482.1 |
| 192 | 6-((3-((4-chloro-2-(pyridin-3-yl)phenoxy)methyl)azetidin-1-yl)carbonyl)-7-fluoro-2H-1,4-benzoxazin-3(4H)-one | 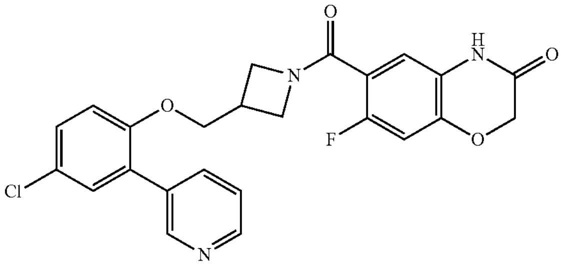 [SMILES: O=C1COc2cc(F)c(C(=O)N3CC(COc4ccc(Cl)cc4-c4cccnc4)C3)cc2N1] | 468.1 |
| 193 | 6-((3-((4-chloro-2-(2-methylpyridin-4-yl)phenoxy)methyl)azetidin-1-yl)carbonyl)-7-fluoro-2H-1,4-benzoxazin-3(4H)-one | 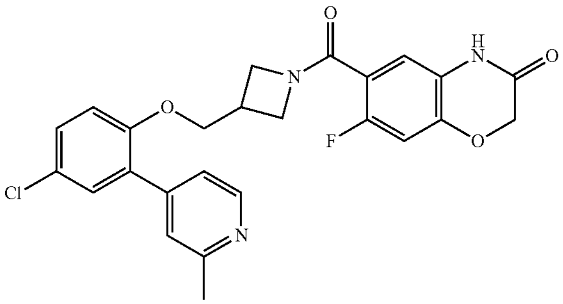 [SMILES: Cc1cc(-c2cc(Cl)ccc2OCC2CN(C(=O)c3cc4c(cc3F)OCC(=O)N4)C2)ccn1] | 482.1 |
| 194 | 6-((3-((4-bromo-2-fluorophenoxy)methyl)azetidin-1-yl)carbonyl)-7-fluoro-2H-1,4-benzoxazin-3(4H)-one | 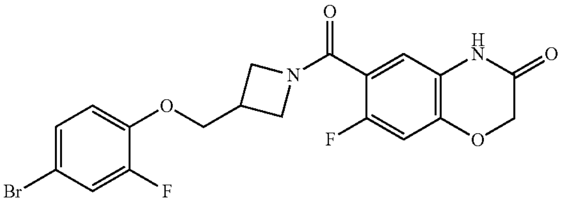 [SMILES: O=C1COc2cc(F)c(C(=O)N3CC(COc4ccc(Br)cc4F)C3)cc2N1] | 453.0 |
| 195 | 6-((3-((4-chloro-2-(5-fluoropyridin-2-yl)phenoxy)methyl)azetidin-1-yl)carbonyl)-7-fluoro-2H-1,4-benzoxazin-3(4H)-one | 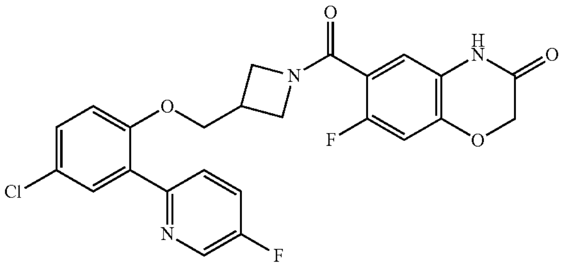 | 486.1 |

TABLE 2-12-continued

| | | | |
|---|---|---|---|
| 196 | 6-((3-((4-chloro-2-(5-chloropyridin-2-yl)phenoxy)methyl)azetidin-1-yl)carbonyl)-7-fluoro-2H-1,4-benzoxazin-3(4H)-one | 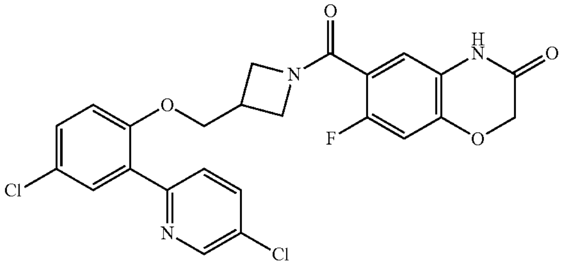 [SMILES: O=C1COc2cc(F)c(C(=O)N3CC(COc4ccc(Cl)cc4-c4ccc(F)cn4)C3)cc2N1] | 502.1 |
| 197 | 6-((3-((4-chloro-2-(6-methylpyridin-2-yl)phenoxy)methyl)azetidin-1-yl)carbonyl)-7-fluoro-2H-1,4-benzoxazin-3(4H)-one | 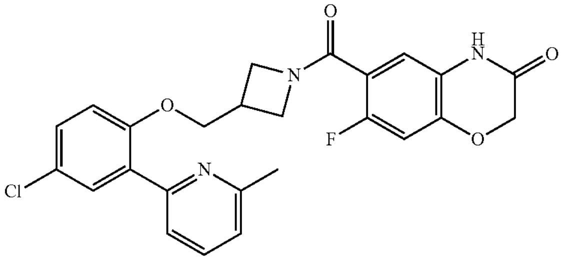 [SMILES: Cc1cccc(-c2cc(Cl)ccc2OCC2CN(C(=O)c3cc4c(cc3F)OCC(=O)N4)C2)n1] | 482.1 |

TABLE 2-13

| | | | |
|---|---|---|---|
| 198 | 6-((3-((4-chloro-2-(2-chloropyridin-3-yl)phenoxy)methyl)azetidin-1-yl)carbonyl)-7-fluoro-2H-1,4-benzoxazin-3(4H)-one | 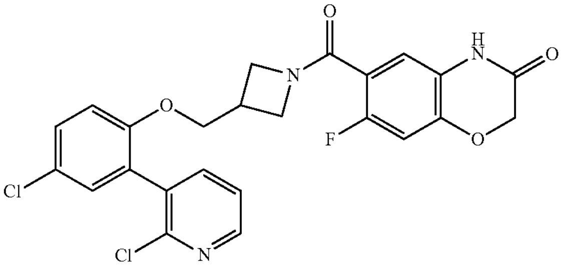 [SMILES: O=C1COc2cc(F)c(C(=O)N3CC(COc4ccc(Cl)cc4-c4cccnc4Cl)C3)cc2N1] | 502.1 |
| 199 | 6-((3-((4-chloro-2-(2-ethylpyridin-3-yl)phenoxy)methyl)azetidin-1-yl)carbonyl)-7-fluoro-2H-1,4-benzoxazin-3(4H)-one | 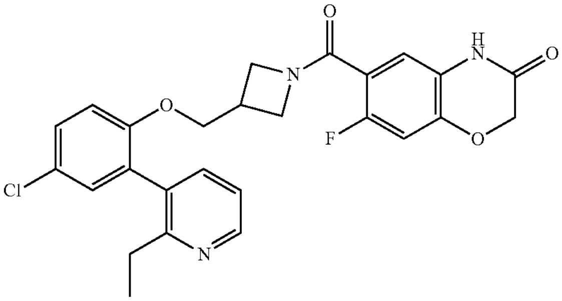 [SMILES: CCc1ncccc1-c1cc(Cl)ccc1OCC1CN(C(=O)c2cc3c(cc2F)OCC(=O)N3)C1] | 496.1 |
| 200 | 6-((3-((4-chloro-2-(5-fluoropyridin-3-yl)phenoxy)methyl)azetidin-1-yl)carbonyl)-7-fluoro-2H-1,4-benzoxazin-3(4H)-one | 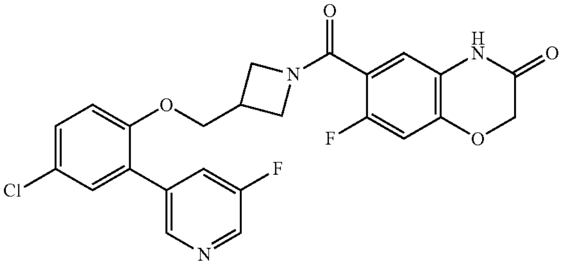 [SMILES: O=C1COc2cc(F)c(C(=O)N3CC(COc4ccc(Cl)cc4-c4cncc(F)c4)C3)cc2N1] | 486.1 |

TABLE 2-13-continued

| | | | |
|---|---|---|---|
| 201 | 6-((3-((4-chloro-2-(5-chloropyridin-3-yl)phenoxy)methyl)azetidin-1-yl)carbonyl)-7-fluoro-2H-1,4-benzoxazin-3(4H)-one | 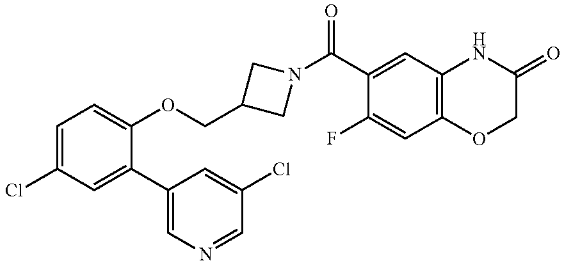 [SMILES: O=C1COc2cc(F)c(C(=O)N3CC(COc4ccc(Cl)cc4-c4cncc(Cl)c4)C3)cc2N1] | 502.1 |
| 202 | 6-((3-((4-chloro-2-(5-methylpyridin-3-yl)phenoxy)methyl)azetidin-1-yl)carbonyl)-7-fluoro-2H-1,4-benzoxazin-3(4H)-one | 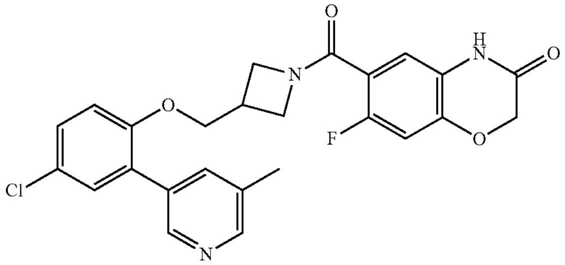 [SMILES: Cc1cncc(-c2cc(Cl)ccc2OCC2CN(C(=O)c3cc4c(cc3F)OCC(=O)N4)C2)c1] | 482.1 |
| 203 | 6-((3-((4-chloro-2-(4-methylpyridin-3-yl)phenoxy)methyl)azetidin-1-yl)carbonyl)-7-fluoro-2H-1,4-benzoxazin-3(4H)-one | 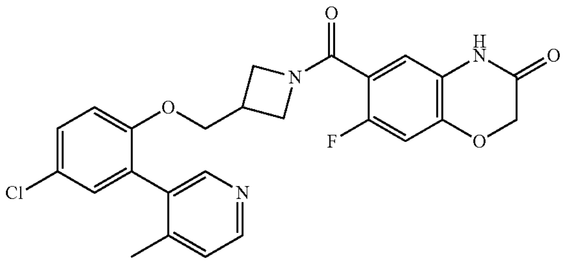 [SMILES: Cc1ccncc1-c1cc(Cl)ccc1OCC1CN(C(=O)c2cc3c(cc2F)OCC(=O)N3)C1] | 482.1 |
| 204 | 6-((3-((4-chloro-2-(6-fluoropyridin-3-yl)phenoxy)methyl)azetidin-1-yl)carbonyl)-7-fluoro-2H-1,4-benzoxazin-3(4H)-one | 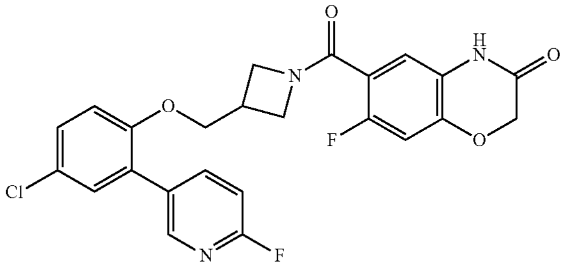 [SMILES: O=C1COc2cc(F)c(C(=O)N3CC(COc4ccc(Cl)cc4-c4ccc(F)nc4)C3)cc2N1] | 486.1 |
| 205 | 6-((3-((4-chloro-2-(6-chloropyridin-3-yl)phenoxy)methyl)azetidin-1-yl)carbonyl)-7-fluoro-2H-1,4-benzoxazin-3(4H)-one | 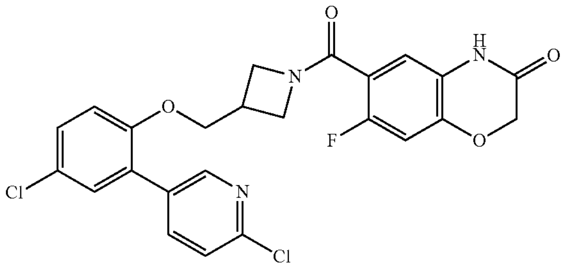 [SMILES: O=C1COc2cc(F)c(C(=O)N3CC(COc4ccc(Cl)cc4-c4ccc(Cl)nc4)C3)cc2N1] | 502.1 |
| 206 | 6-((3-((4-chloro-2-(pyridin-4-yl)phenoxy)methyl)azetidin-1-yl)carbonyl)-7-fluoro-2H-1,4-benzoxazin-3(4H)-one | 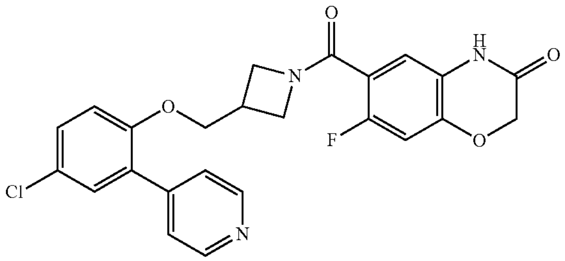 [SMILES: O=C1COc2cc(F)c(C(=O)N3CC(COc4ccc(Cl)cc4-c4ccncc4)C3)cc2N1] | 468.1 |

TABLE 2-14

| | | | |
|---|---|---|---|
| 207 | 6-((3-((4-chloro-2-(2-fluoropyridin-4-yl)phenoxy)methyl)azetidin-1-yl)carbonyl)-7-fluoro-2H-1,4-benzoxazin-3(4H)-one | 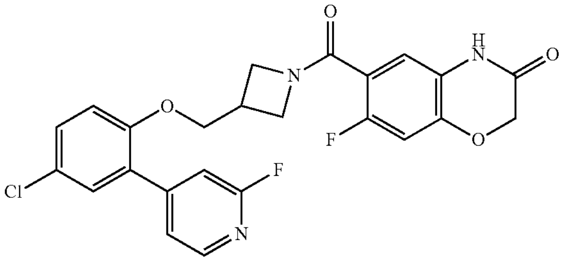 | 486.1 |
| 208 | 6-((3-((4-chloro-2-(2-chloropyridin-4-yl)phenoxy)methyl)azetidin-1-yl)carbonyl)-7-fluoro-2H-1,4-benzoxazin-3(4H)-one | 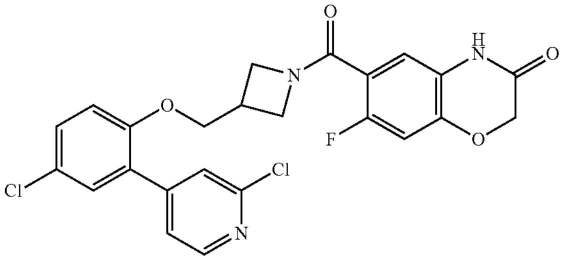 [SMILES: O=C1COc2cc(F)c(C(=O)N3CC(COc4ccc(Cl)cc4-c4ccnc(F)c4)C3)cc2N1] | 502.1 |
| 209 | 6-((3-((4-chloro-2-(3-fluoropyridin-4-yl)phenoxy)methyl)azetidin-1-yl)carbonyl)-7-fluoro-2H-1,4-benzoxazin-3(4H)-one | 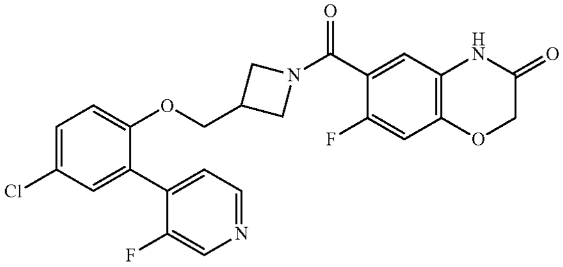 [SMILES: O=C1COc2cc(F)c(C(=O)N3CC(COc4ccc(Cl)cc4-c4ccncc4F)C3)cc2N1] | 486.1 |
| 210 | 6-((3-((4-chloro-2-(3-chloropyridin-4-yl)phenoxy)methyl)azetidin-1-yl)carbonyl)-7-fluoro-2H-1,4-benzoxazin-3(4H)-one | 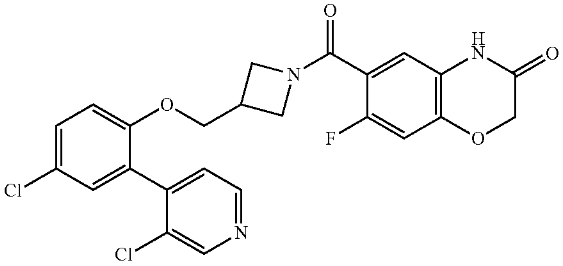 [SMILES: O=C1COc2cc(F)c(C(=O)N3CC(COc4ccc(Cl)cc4-c4ccncc4Cl)C3)cc2N1] | 502.1 |
| 211 | 6-((3-((4-chloro-2-(3,6-dihydro-2H-pyran-4-yl)phenoxy)methyl)azetidin-1-yl)carbonyl)-7-fluoro-2H-1,4-benzoxazin-3(4H)-one | 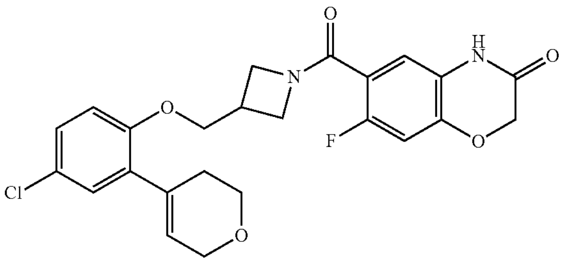 [SMILES: O=C1COc2cc(F)c(C(=O)N3CC(COc4ccc(Cl)cc4C4=CCOCC4)C3)cc2N1] | 473.1 |
| 212 | 6-((3-((4-chloro-2-(1-methyl-1,2,3,6-tetrahydropyridin-4-yl)phenoxy)methyl)azetidin-1-yl)carbonyl)-7-fluoro-2H-1,4-benzoxazin-3(4H)-one | 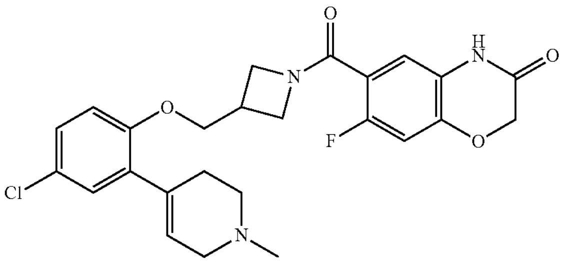 [SMILES: CN1CC=C(c2cc(Cl)ccc2OCC2CN(C(=O)c3cc4c(cc3F)OCC(=O)N4)C2)CC1] | 486.2 |

TABLE 2-14-continued

| | | | |
|---|---|---|---|
| 213 | 6-((3-((4-chloro-2-(1-methyl-1H-pyrazol-4-yl)phenoxy)methyl)azetidin-1-yl)carbonyl)-7-fluoro-2H-1,4-benzoxazin-3(4H)-one | 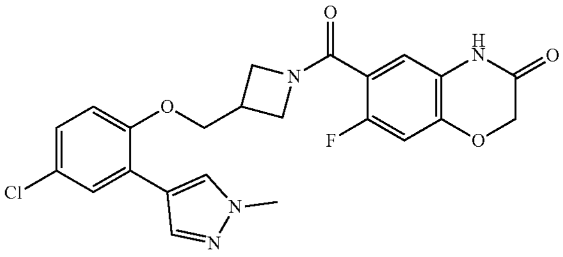 [SMILES: Cn1cc(-c2cc(Cl)ccc2OCC2CN(C(=O)c3cc4c(cc3F)OCC(=O)N4)C2)cn1] | 471.1 |
| 214 | 6-((3-((4-chloro-2-(1-(difluoromethyl)-1H-pyrazol-4-yl)phenoxy)methyl)azetidin-1-yl)carbonyl)-7-fluoro-2H-1,4-benzoxazin-3(4H)-one | 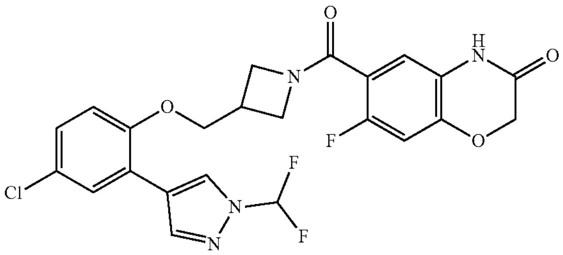 [SMILES: O=C1COc2cc(F)c(C(=O)N3CC(COc4ccc(Cl)cc4-c4cnn(C(F)F)c4)C3)cc2N1] | 507.1 |
| 215 | 6-((3-((4-chloro-2-(1-cyclopropyl-1H-pyrazol-4-yl)phenoxy)methyl)azetidin-1-yl)carbonyl)-7-fluoro-2H-1,4-benzoxazin-3(4H)-one | 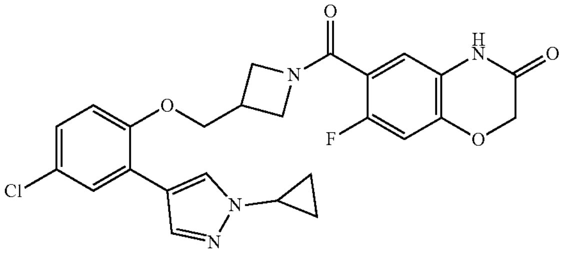 [SMILES: O=C1COc2cc(F)c(C(=O)N3CC(COc4ccc(Cl)cc4-c4cnn(C5CC5)c4)C3)cc2N1] | 497.1 |

TABLE 2-15

| | | | |
|---|---|---|---|
| 216 | 6-((3-((4-chloro-2-(1-methyl-1H-pyrazol-3-yl)phenoxy)methyl)azetidin-1-yl)carbonyl)-7-fluoro-2H-1,4-benzoxazin-3(4H)-one | 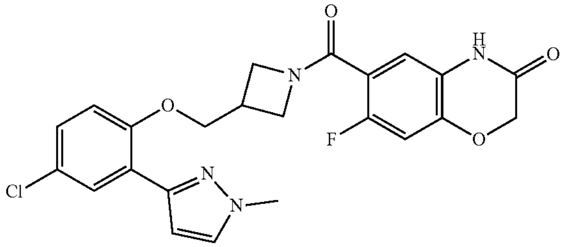 [SMILES: Cn1ccc(-c2cc(Cl)ccc2OCC2CN(C(=O)c3cc4c(cc3F)OCC(=O)N4)C2)n1] | 471.1 |
| 217 | 6-((3-((4-chloro-2-(1,5-dimethyl-1H-pyrazol-3-yl)phenoxy)methyl)azetidin-1-yl)carbonyl)-7-fluoro-2H-1,4-benzoxazin-3(4H)-one | 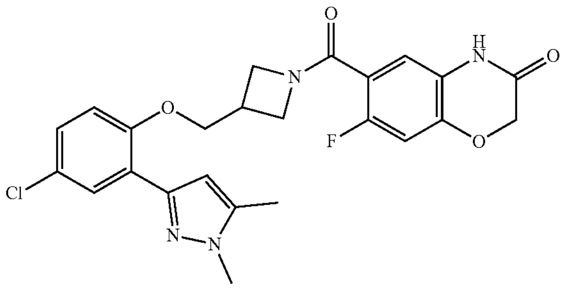 [SMILES: Cc1cc(-c2cc(Cl)ccc2OCC2CN(C(=O)c3cc4c(cc3F)OCC(=O)N4)C2)nn1C] | 485.2 |

TABLE 2-15-continued

| | | | |
|---|---|---|---|
| 218 | 6-((3-((4-chloro-2-(1-methyl-1H-pyrazol-5-yl)phenoxy)methyl)azetidin-1-yl)carbonyl)-7-fluoro-2H-1,4-benzoxazin-3(4H)-one | 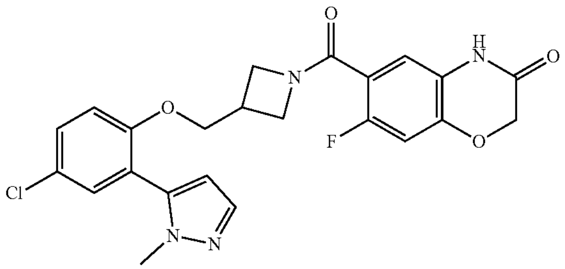 [SMILES: Cn1nccc1-c1cc(Cl)ccc1OCC1CN(C(=O)c2cc3c(cc2F)OCC(=O)N3)C1] | 471.1 |
| 219 | 6-((3-((4-chloro-2-(1-methyl-1H-pyrrol-2-yl)phenoxy)methyl)azetidin-1-yl)carbonyl)-7-fluoro-2H-1,4-benzoxazin-3(4H)-one | 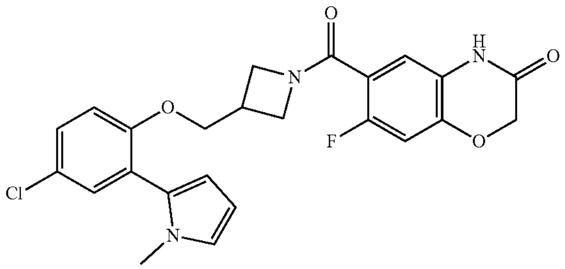 [SMILES: Cn1cccc1-c1cc(Cl)ccc1OCC1CN(C(=O)c2cc3c(cc2F)OCC(=O)N3)C1] | 470.1 |
| 220 | 6-((3-((4-chloro-2-(6-(trifluoromethyl)pyridin-3-yl)phenoxy)methyl)azetidin-1-yl)carbonyl)-7-fluoro-2H-1,4-benzoxazin-3(4H)-one | 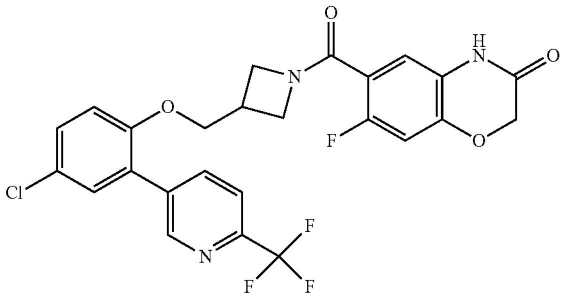 [SMILES: O=C1COc2cc(F)c(C(=O)N3CC(COc4ccc(Cl)cc4-c4ccc(C(F)(F)F)nc4)C3)cc2N1] | 536.1 |
| 221 | 6-((3-((4-chloro-2-(2,3-dihydro-1-benzofuran-5-yl)phenoxy)methyl)azetidin-1-yl)carbonyl)-7-fluoro-2H-1,4-benzoxazin-3(4H)-one | 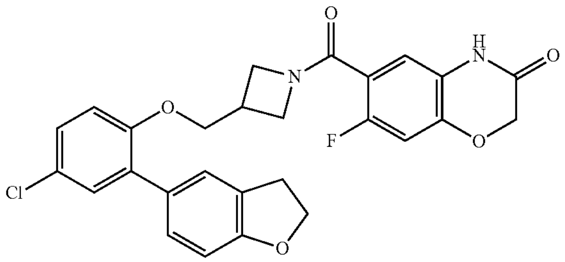 [SMILES: O=C1COc2cc(F)c(C(=O)N3CC(COc4ccc(Cl)cc4-c4ccc5c(c4)CCO5)C3)cc2N1] | 509.2 |
| 222 | 6-((3-((4-chloro-2-(2-(trifluoromethyl)pyrimidin-5-yl)phenoxy)methyl)azetidin-1-yl)carbonyl)-7-fluoro-2H-1,4-benzoxazin-3(4H)-one | 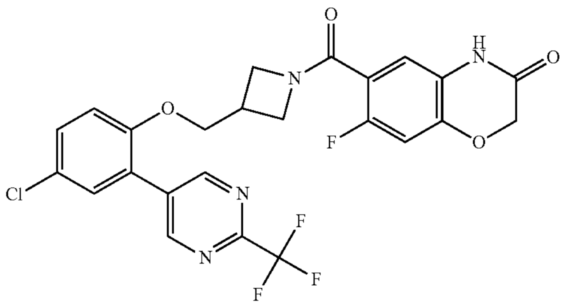 [SMILES: O=C1COc2cc(F)c(C(=O)N3CC(COc4ccc(Cl)cc4-c4cnc(C(F)(F)F)nc4)C3)cc2N1] | 537.1 |

TABLE 2-15-continued

| | | | |
|---|---|---|---|
| 223 | 6-((3-((4-chloro-2-(1,3-dimethyl-1H-pyrazol-5-yl)phenoxy)methyl)azetidin-1-yl)carbonyl)-7-fluoro-2H-1,4-benzoxazin-3(4H)-one | 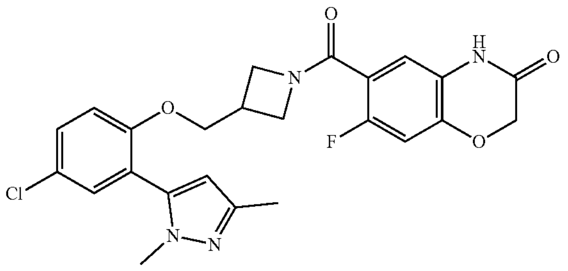 [SMILES: Cc1cc(-c2cc(Cl)ccc2OCC2CN(C(=O)c3cc4c(cc3F)OCC(=O)N4)C2)n(C)n1] | 485.2 |
| 224 | 6-((3-((4-chloro-2-(1-isobutyl-1H-pyrazol-4-yl)phenoxy)methyl)azetidin-1-yl)carbonyl)-7-fluoro-2H-1,4-benzoxazin-3(4H)-one | 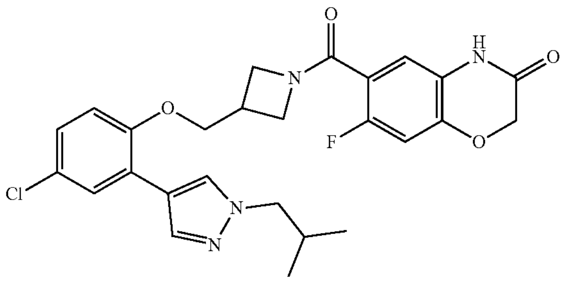 [SMILES: CC(C)Cn1cc(-c2cc(Cl)ccc2OCC2CN(C(=O)c3cc4c(cc3F)OCC(=O)N4)C2)cn1] | 513.1 |

TABLE 2-16

| | | | |
|---|---|---|---|
| 225 | 6-((3-((cyclopropylmethoxy)methyl)azetidin-1-yl)carbonyl)-7-fluoro-2H-1,4-benzoxazin-3(4H)-one | 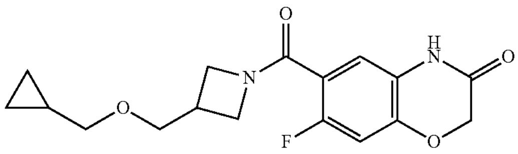 [SMILES: O=C1COc2cc(F)c(C(=O)N3CC(COCC4CC4)C3)cc2N1] | 335.1 |
| 226 | 6-((3-((4-chloro-2-methylphenoxy)methyl)azetidin-1-yl)carbonyl)-7-fluoro-2H-1,4-benzoxazin-3(4H)-one | 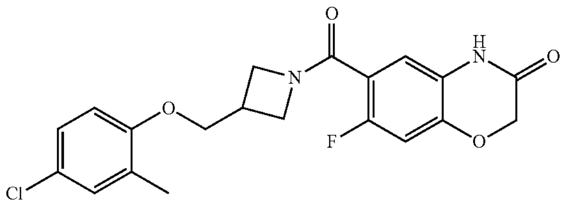 [SMILES: Cc1cc(Cl)ccc1OCC1CN(C(=O)c2cc3c(cc2F)OCC(=O)N3)C1] | 405.1 |
| 227 | 7-fluoro-6-((3-((2-fluoro-4-(pyridin-2-yl)phenoxy)methyl)azetidin-1-yl)carbonyl)-2H-1,4-benzoxazin-3(4H)-one | 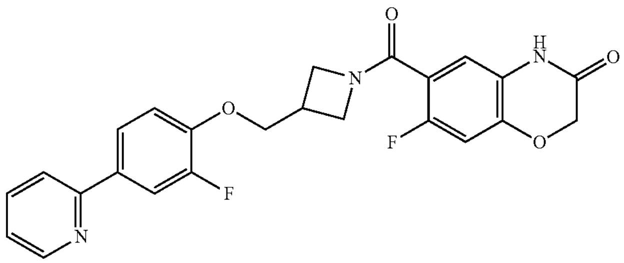 [SMILES: O=C1COc2cc(F)c(C(=O)N3CC(COc4ccc(-c5ccccn5)cc4F)C3)cc2N1] | 452.1 |
| 228 | 7-fluoro-6-((3-((2-fluoro-4-(5-fluoropyridin-2-yl)phenoxy)methyl)azetidin-1-yl)carbonyl)-2H-1,4-benzoxazin-3(4H)-one | 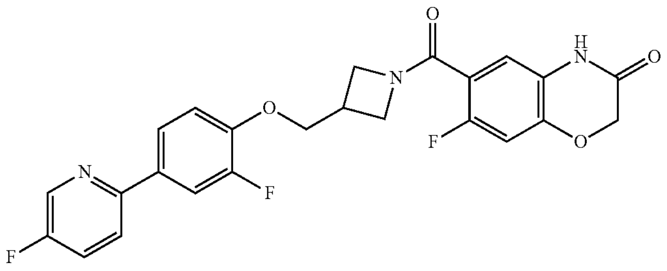 [SMILES: O=C1COc2cc(F)c(C(=O)N3CC(COc4ccc(-c5ccc(F)cn5)cc4F)C3)cc2N1] | 470.1 |

TABLE 2-16-continued

| | | | |
|---|---|---|---|
| 229 | 6-((3-((4-(5-chloropyridin-2-yl)-2-fluorophenoxy)methyl)azetidin-1-yl)carbonyl)-7-fluoro-2H-1,4-benzoxazin-3(4H)-one | 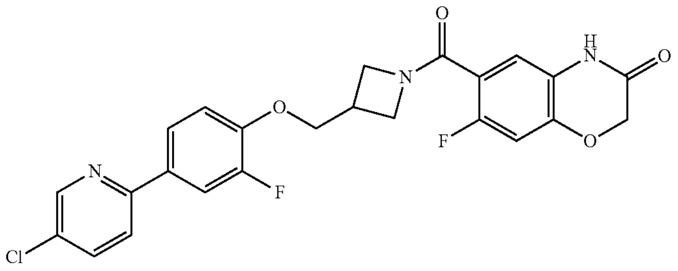 [SMILES: O=C1COc2cc(F)c(C(=O)N3CC(COc4ccc(-c5ccc(Cl)cn5)cc4F)C3)cc2N1] | 486.1 |
| 230 | 7-fluoro-6-((3-((2-fluoro-4-(6-methylpyridin-2-yl)phenoxy)methyl)azetidin-1-yl)carbonyl)-2H-1,4-benzoxazin-3(4H)-one | 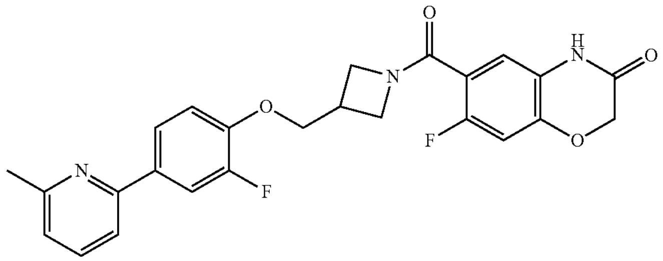 | 466.1 |
| 231 | 7-fluoro-6-((3-((2-fluoro-4-(3-methylpyridin-2-yl)phenoxy)methyl)azetidin-1-yl)carbonyl)-2H-1,4-benzoxazin-3(4H)-one | 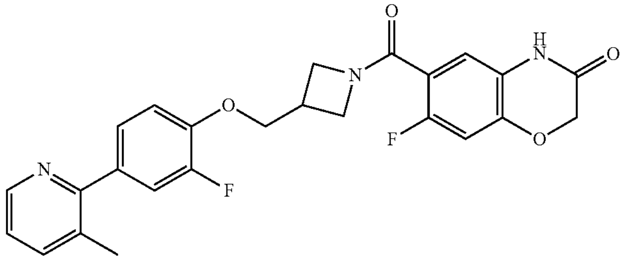 [SMILES: Cc1cccnc1-c1ccc(OCC2CN(C(=O)c3cc4c(cc3F)OCC(=O)N4)C2)c(F)c1] | 466.1 |
| 232 | 6-((3-((4-(2-chloropyridin-3-yl)-2-fluorophenoxy)methyl)azetidin-1-yl)carbonyl)-7-fluoro-2H-1,4-benzoxazin-3(4H)-one | 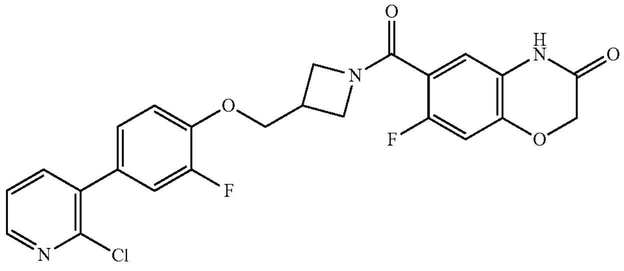 [SMILES: O=C1COc2cc(F)c(C(=O)N3CC(COc4ccc(-c5cccnc5Cl)cc4F)C3)cc2N1] | 486.1 |
| 233 | 6-((3-((4-(2-ethylpyridin-3-yl)-2-fluorophenoxy)methyl)azetidin-1-yl)carbonyl)-7-fluoro-2H-1,4-benzoxazin-3(4H)-one | 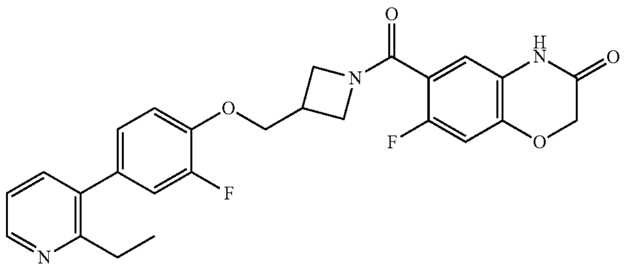 [SMILES: CCc1ncccc1-c1ccc(OCC2CN(C(=O)c3cc4c(cc3F)OCC(=O)N4)C2)c(F)c1] | 480.1 |

TABLE 2-17

| | | | |
|---|---|---|---|
| 234 | 7-fluoro-6-((3-((2-fluoro-4-(5-fluoropyridin-3-yl)phenoxy)methyl)azetidin-1-yl)carbonyl)-2H-1,4-benzoxazin-3(4H)-one | 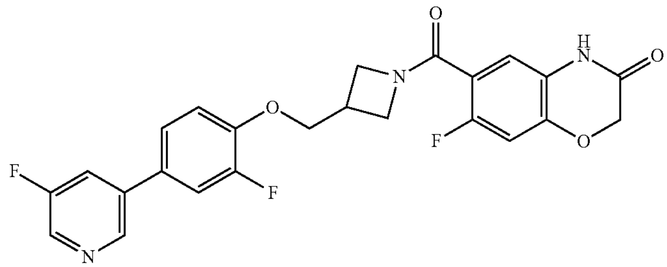 [SMILES: O=C1COc2cc(F)c(C(=O)N3CC(COc4ccc(-c5cncc(F)c5)cc4F)C3)cc2N1] | 470.1 |
| 235 | 6-((3-((4-(5-chloropyridin-3-yl)-2-fluorophenoxy)methyl)azetidin-1-yl)carbonyl)-7-fluoro-2H-1,4-benzoxazin-3(4H)-one | 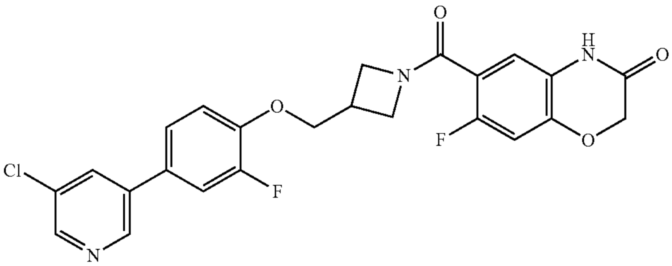 [SMILES: O=C1COc2cc(F)c(C(=O)N3CC(COc4ccc(-c5cncc(Cl)c5)cc4F)C3)cc2N1] | 486.1 |
| 236 | 7-fluoro-6-((3-((2-fluoro-4-(5-methylpyridin-3-yl)phenoxy)methyl)azetidin-1-yl)carbonyl)-2H-1,4-benzoxazin-3(4H)-one | 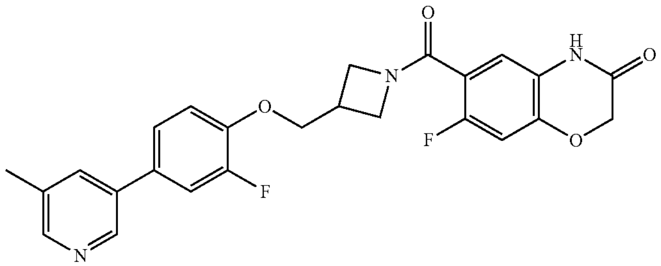 [SMILES: Cc1cncc(-c2ccc(OCC3CN(C(=O)c4cc5c(cc4F)OCC(=O)N5)C3)c(F)c2)c1] | 466.2 |
| 237 | 7-fluoro-6-((3-((2-fluoro-4-(4-methylpyridin-3-yl)phenoxy)methyl)azetidin-1-yl)carbonyl)-2H-1,4-benzoxazin-3(4H)-one | 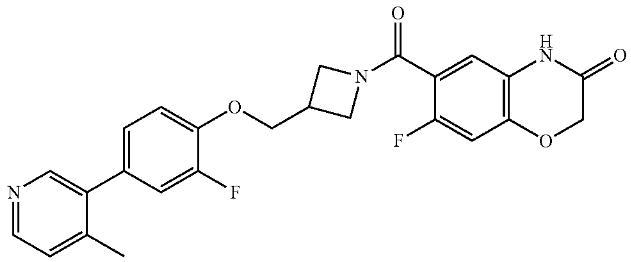 [SMILES: Cc1ccncc1-c1ccc(OCC2CN(C(=O)c3cc4c(cc3F)OCC(=O)N4)C2)c(F)c1] | 466.1 |
| 238 | 7-fluoro-6-((3-((2-fluoro-4-(6-fluoropyridin-3-yl)phenoxy)methyl)azetidin-1-yl)carbonyl)-2H-1,4-benzoxazin-3(4H)-one | 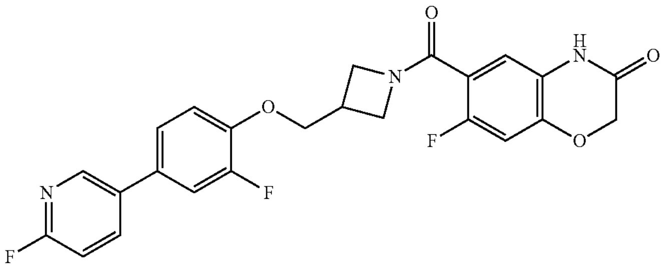 [SMILES: O=C1COc2cc(F)c(C(=O)N3CC(COc4ccc(-c5ccc(F)nc5)cc4F)C3)cc2N1] | 470.1 |
| 239 | 7-fluoro-6-((3-((2-fluoro-4-(pyridin-4-yl)phenoxy)methyl)azetidin-1-yl)carbonyl)-2H-1,4-benzoxazin-3(4H)-one | 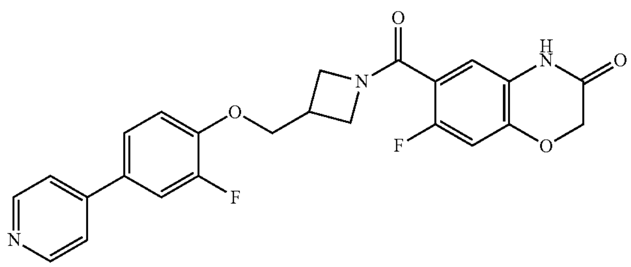 [SMILES: O=C1COc2cc(F)c(C(=O)N3CC(COc4ccc(-c5ccncc5)cc4F)C3)cc2N1] | 452.1 |

TABLE 2-17-continued

| | | | |
|---|---|---|---|
| 240 | 7-fluoro-6-((3-((2-fluoro-4-(2-fluoropyridin-4-yl)phenoxy)methyl)azetidin-1-yl)carbonyl)-2H-1,4-benzoxazin-3(4H)-one | 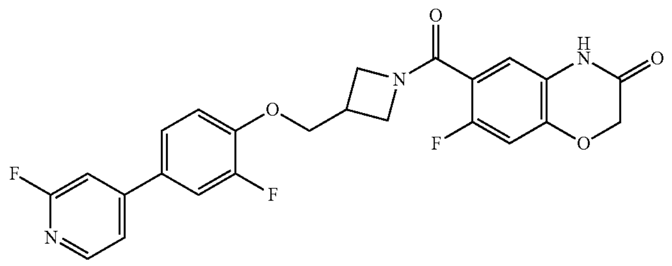 [SMILES: O=C1COc2cc(F)c(C(=O)N3CC(COc4ccc(-c5ccnc(F)c5)cc4F)C3)cc2N1] | 470.1 |
| 241 | 6-((3-((4-(2-chloropyridin-4-yl)-2-fluorophenoxy)methyl)azetidin-1-yl)carbonyl)-7-fluoro-2H-1,4-benzoxazin-3(4H)-one | 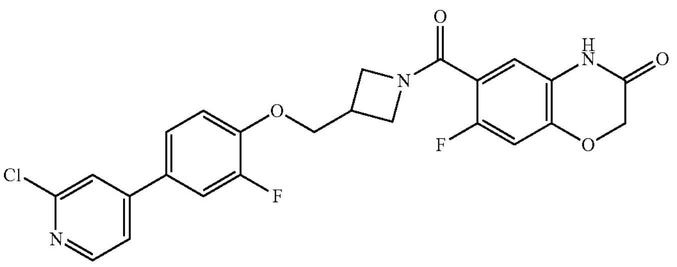 [SMILES: O=C1COc2cc(F)c(C(=O)N3CC(COc4ccc(-c5ccnc(Cl)c5)cc4F)C3)cc2N1] | 486.1 |
| 242 | 7-fluoro-6-((3-((2-fluoro-4-(3-fluoropyridin-4-yl)phenoxy)methyl)azetidin-1-yl)carbonyl)-2H-1,4-benzoxazin-3(4H)-one | 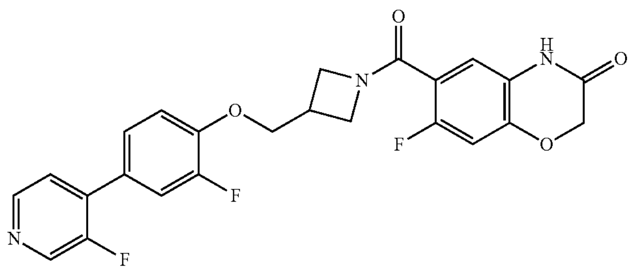 | 470.1 |

TABLE 2-18

| | | | |
|---|---|---|---|
| 243 | 6-((3-((4-(3-chloropyridin-4-yl)-2-fluorophenoxy)methyl)azetidin-1-yl)carbonyl)-7-fluoro-2H-1,4-benzoxazin-3(4H)-one | 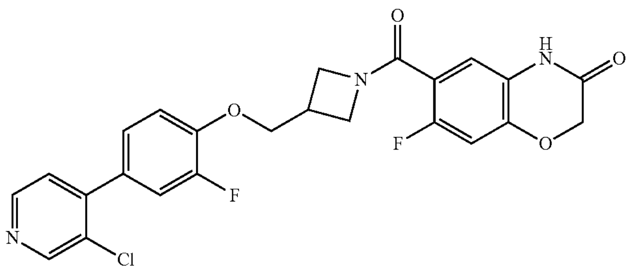 [SMILES: O=C1COc2cc(F)c(C(=O)N3CC(COc4ccc(-c5ccncc5F)cc4F)C3)cc2N1] | 486.1 |
| 244 | 6-((3-((4-(3,6-dihydro-2H-pyran-4-yl)-2-fluorophenoxy)methyl)azetidin-1-yl)carbonyl)-7-fluoro-2H-1,4-benzoxazin-3(4H)-one | 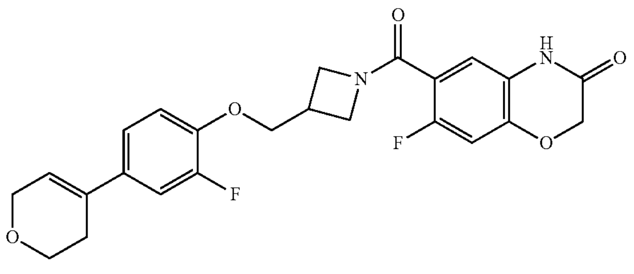 [SMILES: O=C1COc2cc(F)c(C(=O)N3CC(COc4ccc(C5=CCOCC5)cc4F)C3)cc2N1] | 457.2 |

TABLE 2-18-continued

| | | | |
|---|---|---|---|
| 245 | 7-fluoro-6-((3-((2-fluoro-4-(1-methyl-1,2,3,6-tetrahydropyridin-4-yl)phenoxy)methyl)azetidin-1-yl)carbonyl)-2H-1,4-benzoxazin-3(4H)-one | 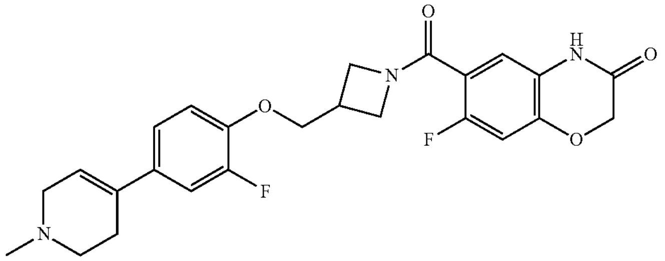 [SMILES: CN1CC=C(c2ccc(OCC3CN(C(=O)c4cc5c(cc4F)OCC(=O)N5)C3)c(F)c2)CC1] | 470.2 |
| 246 | 7-fluoro-6-((3-((2-fluoro-4-(1-methyl-1H-pyrazol-4-yl)phenoxy)methyl)azetidin-1-yl)carbonyl)-2H-1,4-benzoxazin-3(4H)-one | 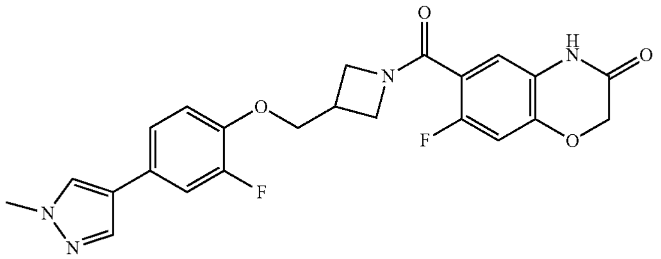 [SMILES: Cn1cc(-c2ccc(OCC3CN(C(=O)c4cc5c(cc4F)OCC(=O)N5)C3)c(F)c2)cn1] | 455.1 |
| 247 | 6-((3-((4-(1-(difluoromethyl)-1H-pyrazol-4-yl)-2-fluorophenoxy)methyl)azetidin-1-yl)carbonyl)-7-fluoro-2H-1,4-benzoxazin-3(4H)-one | 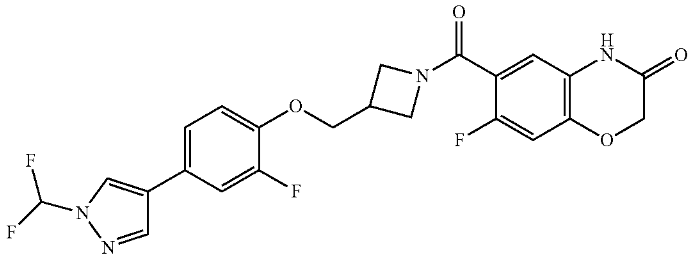 [SMILES: O=C1COc2cc(F)c(C(=O)N3CC(COc4ccc(-c5cnn(C(F)F)c5)cc4F)C3)cc2N1] | 491.1 |
| 248 | 6-((3-((4-(1-cyclopropyl-1H-pyrazol-4-yl)-2-fluorophenoxy)methyl)azetidin-1-yl)carbonyl)-7-fluoro-2H-1,4-benzoxazin-3(4H)-one | 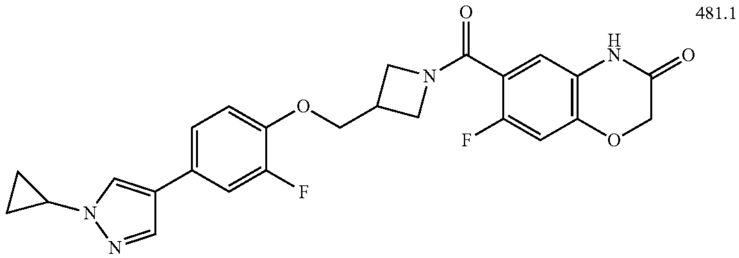 | 481.1 |
| 249 | 6-((3-((4-(1,3-dimethyl-1H-pyrazol-4-yl)-2-fluorophenoxy)methyl)azetidin-1-yl)carbonyl)-7-fluoro-2H-1,4-benzoxazin-3(4H)-one | 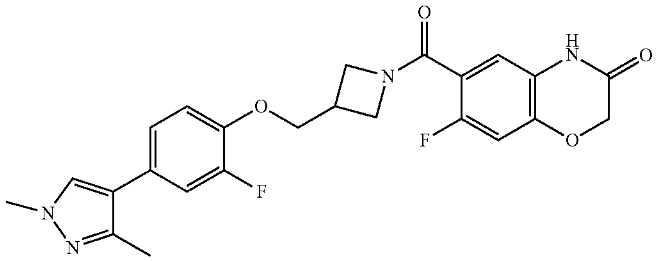 [SMILES: Cc1nn(C)cc1-c1ccc(OCC2CN(C(=O)c3cc4c(cc3F)OCC(=O)N4)C2)c(F)c1] | 469.2 |
| 250 | 6-((3-((4-(1,5-dimethyl-1H-pyrazol-4-yl)-2-fluorophenoxy)methyl)azetidin-1-yl)carbonyl)-7-fluoro-2H-1,4-benzoxazin-3(4H)-one | 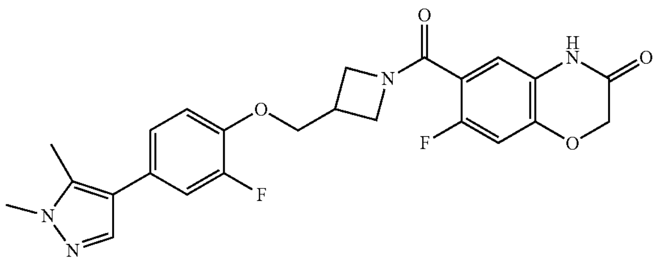 [SMILES: Cc1c(-c2ccc(OCC3CN(C(=O)c4cc5c(cc4F)OCC(=O)N5)C3)c(F)c2)cnn1C] | 469.2 |

TABLE 2-18-continued

| | | | |
|---|---|---|---|
| 251 | 7-fluoro-6-((3-((2-fluoro-4-(1,3,5-trimethyl-1H-pyrazol-4-yl)phenoxy)methyl)azetidin-1-yl)carbonyl)-2H-1,4-benzoxazin-3(4H)-one | 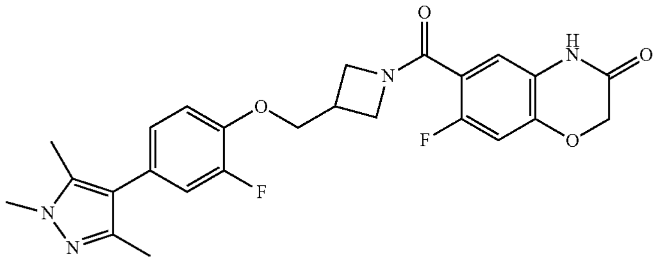 [SMILES: Cc1nn(C)c(C)c1-c1ccc(OCC2CN(C(=O)c3cc4c(cc3F)OCC(=O)N4)C2)c(F)c1] | 483.1 |

TABLE 2-19

| | | | |
|---|---|---|---|
| 252 | 7-fluoro-6-((3-((2-fluoro-4-(1-methyl-1H-pyrazol-3-yl)phenoxy)methyl)azetidin-1-yl)carbonyl)-2H-1,4-benzoxazin-3(4H)-one | 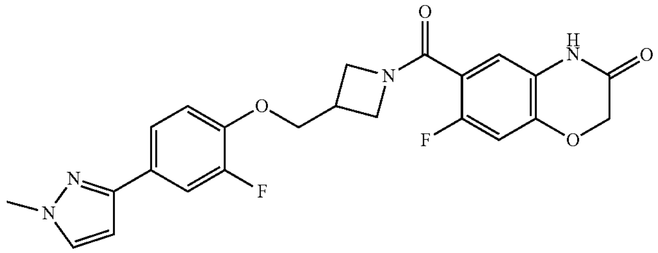 [SMILES: Cn1ccc(-c2ccc(OCC3CN(C(=O)c4cc5c(cc4F)OCC(=O)N5)C3)c(F)c2)n1] | 455.1 |
| 253 | 6-((3-((4-(1,5-dimethyl-1H-pyrazol-3-yl)-2-fluorophenoxy)methyl)azetidin-1-yl)carbonyl)-7-fluoro-2H-1,4-benzoxazin-3(4H)-one | 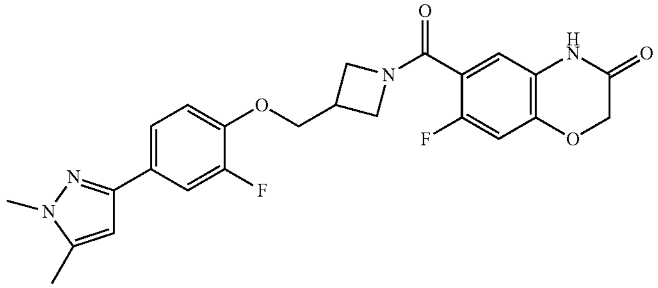 [SMILES: Cc1cc(-c2ccc(OCC3CN(C(=O)c4cc5c(cc4F)OCC(=O)N5)C3)c(F)c2)nn1C] | 469.2 |
| 254 | 7-fluoro-6-((3-((2-fluoro-4-(1-methyl-1H-pyrazol-5-yl)phenoxy)methyl)azetidin-1-yl)carbonyl)-2H-1,4-benzoxazin-3(4H)-one | 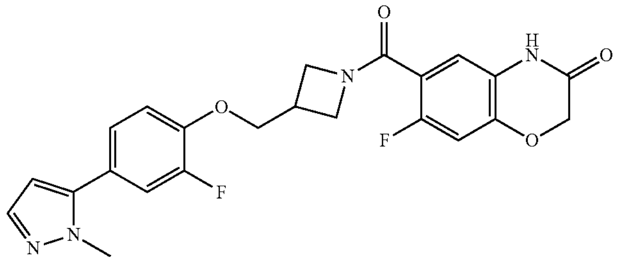 [SMILES: Cn1nccc1-c1ccc(OCC2CN(C(=O)c3cc4c(cc3F)OCC(=O)N4)C2)c(F)c1] | 455.1 |
| 255 | 7-fluoro-6-((3-((2-fluoro-4-(1-methyl-1H-pyrrol-2-yl)phenoxy)methyl)azetidin-1-yl)carbonyl)-2H-1,4-benzoxazin-3(4H)-one | 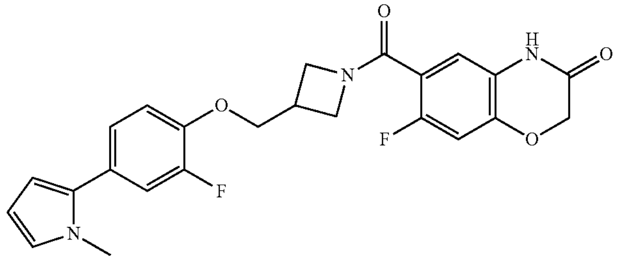 [SMILES: Cn1cccc1-c1ccc(OCC2CN(C(=O)c3cc4c(cc3F)OCC(=O)N4)C2)c(F)c1] | 454.2 |

TABLE 2-19-continued

| | | | |
|---|---|---|---|
| 256 | 7-fluoro-6-((3-((2-fluoro-4-(6-(trifluoromethyl)pyridin-3-yl)phenoxy)methyl)azetidin-1-yl)carbonyl)-2H-1,4-benzoxazin-3(4H)-one | 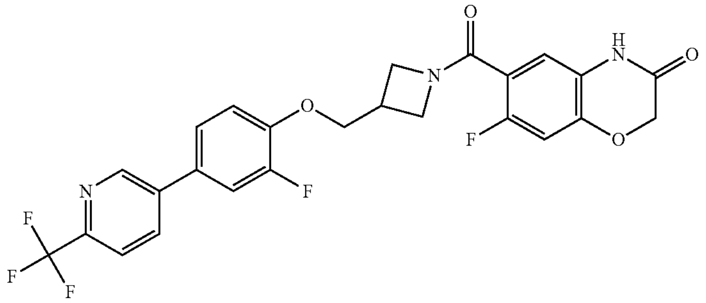 [SMILES: O=C1COc2cc(F)c(C(=O)N3CC(COc4ccc(-c5ccc(C(F)(F)F)nc5)cc4F)C3)cc2N1] | 520.1 |
| 257 | 6-((3-((4-(2,3-dihydro-1-benzofuran-5-yl)-2-fluorophenoxy)methyl)azetidin-1-yl)carbonyl)-7-fluoro-2H-1,4-benzoxazin-3(4H)-one | 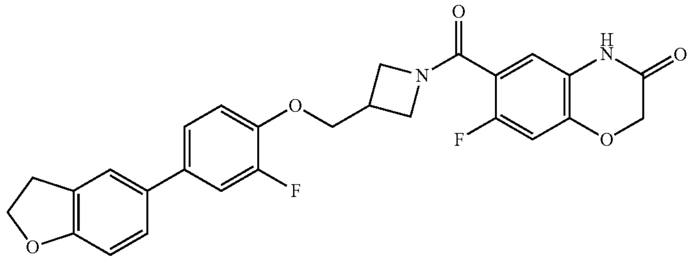 [SMILES: O=C1COc2cc(F)c(C(=O)N3CC(COc4ccc(-c5ccc6c(c5)CCO6)cc4F)C3)cc2N1] | 493.2 |
| 258 | 7-fluoro-6-((3-((2-fluoro-4-(2-(trifluoromethyl)pyridin-5-yl)phenoxy)methyl)azetidin-1-yl)carbonyl)-2H-1,4-benzoxazin-3(4H)-one | 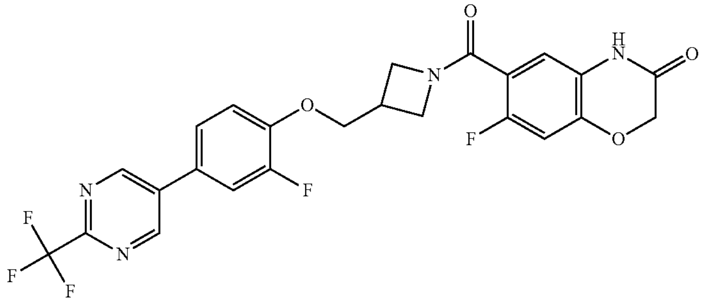 [SMILES: O=C1COc2cc(F)c(C(=O)N3CC(COc4ccc(-c5cnc(C(F)(F)F)nc5)cc4F)C3)cc2N1] | 521.1 |
| 259 | 6-((3-((4-(1,3-dimethyl-1H-pyrazol-5-yl)-2-fluorophenoxy)methyl)azetidin-1-yl)carbonyl)-7-fluoro-2H-1,4-benzoxazin-3(4H)-one | 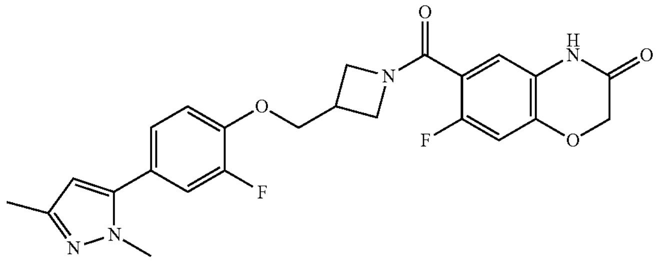 [SMILES: Cc1cc(-c2ccc(OCC3CN(C(=O)c4cc5c(cc4F)OCC(=O)N5)C3)c(F)c2)n(C)n1] | 469.2 |
| 260 | 6-((3-((4-(2,4-dimethyl-1,3-thiazol-5-yl)-2-fluorophenoxy)methyl)azetidin-1-yl)carbonyl)-7-fluoro-2H-1,4-benzoxazin-3(4H)-one | 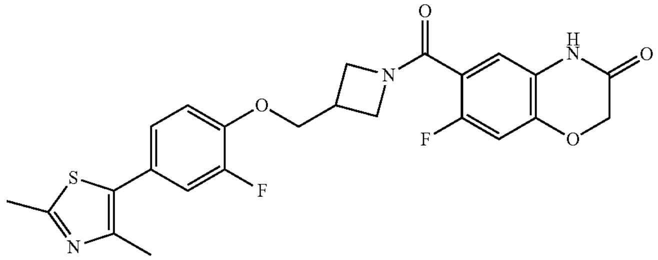 [SMILES: Cc1nc(C)c(-c2ccc(OCC3CN(C(=O)c4cc5c(cc4F)OCC(=O)N5)C3)c(F)c2)s1] | 486.1 |

TABLE 2-20

| | | | |
|---|---|---|---|
| 261 | 7-fluoro-6-((3-((2-fluoro-4-(pyridin-3-yl)phenoxy)methyl)azetidin-1-yl)carbonyl)-2H-1,4-benzoxazin-3(4H)-one | 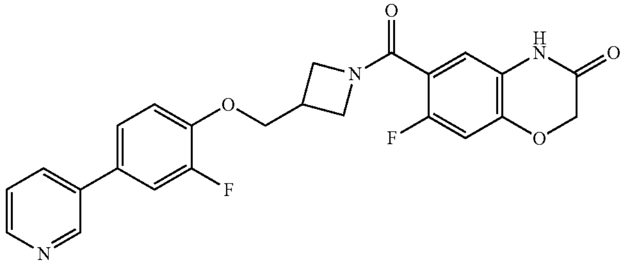 [SMILES: O=C1COc2cc(F)c(C(=O)N3CC(COc4ccc(-c5cccnc5)cc4F)C3)cc2N1] | 452.1 |
| 262 | 7-fluoro-6-((3-((2-fluoro-4-(2-methylpyridin-3-yl)phenoxy)methyl)azetidin-1-yl)carbonyl)-2H-1,4-benzoxazin-3(4H)-one | 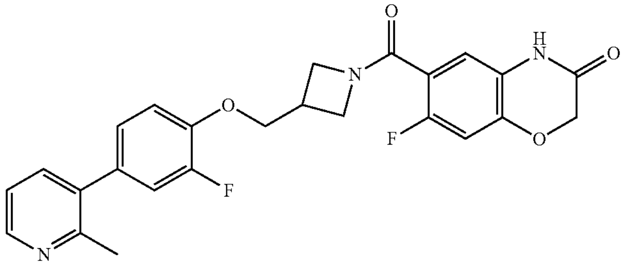 [SMILES: Cc1ncccc1-c1ccc(OCC2CN(C(=O)c3cc4c(cc3F)OCC(=O)N4)C2)c(F)c1] | 466.1 |
| 263 | 7-fluoro-6-((3-((2-fluoro-4-(6-methylpyridin-3-yl)phenoxy)methyl)azetidin-1-yl)carbonyl)-2H-1,4-benzoxazin-3(4H)-one | 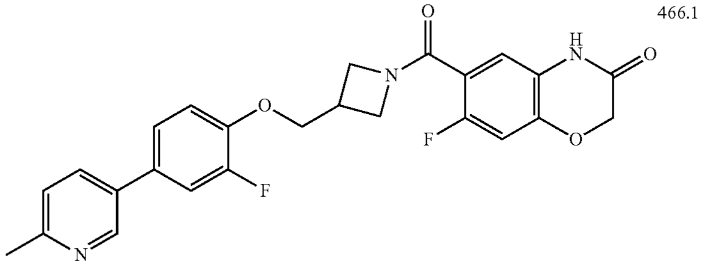 | 466.1 |
| 264 | 7-fluoro-6-((3-((2-fluoro-4-(2-methylpyridin-4-yl)phenoxy)methyl)azetidin-1-yl)carbonyl)-2H-1,4-benzoxazin-3(4H)-one | 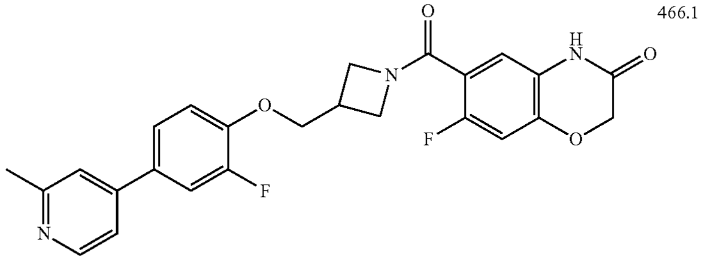 | 466.1 |
| 265 | 6-((3-((4-chloro-2-(1,3-dimethyl-1H-pyrazol-4-yl)phenoxy)methyl)azetidin-1-yl)carbonyl)-7-fluoro-2H-1,4-benzoxazin-3(4H)-one | 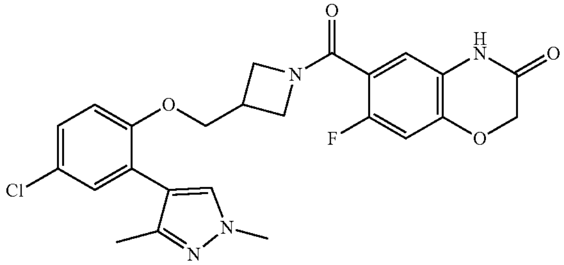 [SMILES: Cc1nn(C)cc1-c1cc(Cl)ccc1OCC1CN(C(=O)c2cc3c(cc2F)OCC(=O)N3)C1] | 485.1 |
| 266 | 6-((3-((4-chloro-2-(1,5-dimethyl-1H-pyrazol-4-yl)phenoxy)methyl)azetidin-1-yl)carbonyl)-7-fluoro-2H-1,4-benzoxazin-3(4H)-one | 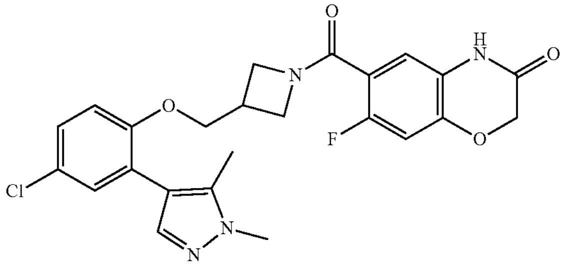 [SMILES: Cc1c(-c2cc(Cl)ccc2OCC2CN(C(=O)c3cc4c(cc3F)OCC(=O)N4)C2)cnn1C] | 485.1 |

TABLE 2-20-continued

| | | | |
|---|---|---|---|
| 267 | 6-((3-((4-chloro-2-(1,3,5-trimethyl-1H-pyrazol-4-yl)phenoxy)methyl)azetidin-1-yl)carbonyl)-7-fluoro-2H-1,4-benzoxazin-3(4H)-one | 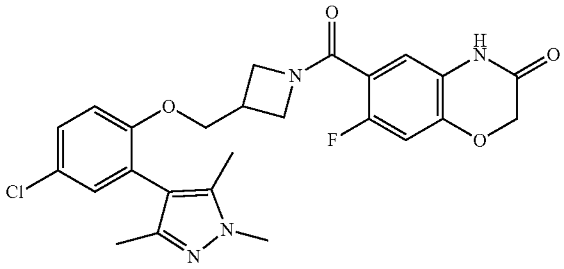 [SMILES: Cc1nn(C)c(C)c1-c1cc(Cl)ccc1OCC1CN(C(=O)c2cc3c(cc2F)OCC(=O)N3)C1] | 499.1 |
| 268 | 6-((3-((4-chloro-2-(2,4-dimethyl-1,3-thiazol-5-yl)phenoxy)methyl)azetidin-1-yl)carbonyl)-7-fluoro-2H-1,4-benzoxazin-3(4H)-one | 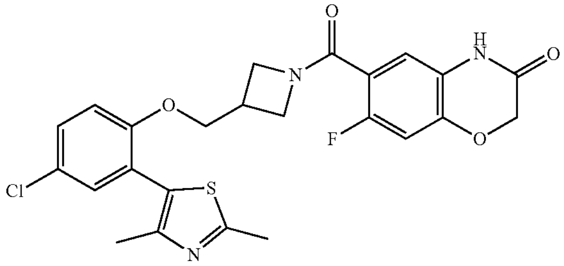 [SMILES: Cc1nc(C)c(-c2cc(Cl)ccc2OCC2CN(C(=O)c3cc4c(cc3F)OCC(=O)N4)C2)s1] | 502.1 |
| 269 | 7-fluoro-6-((3-((3-fluoro-4-methylphenoxy)methyl)azetidin-1-yl)carbonyl)-2H-1,4-benzoxazin-3(4H)-one | 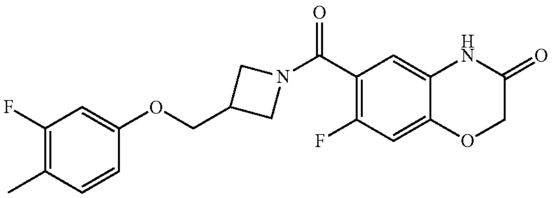 [SMILES: Cc1ccc(OCC2CN(C(=O)c3cc4c(cc3F)OCC(=O)N4)C2)cc1F] | 389.1 |

TABLE 2-21

| | | | |
|---|---|---|---|
| 270 | 6-((3-((4-(difluoromethoxy)phenoxy) methyl)azetidin-1-yl) carbonyl)-7-fluoro-2H-1,4-benzoxazin-3(4H)-one | 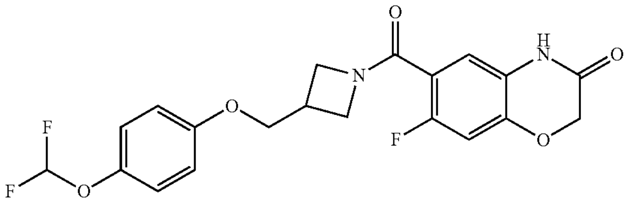 [SMILES: O=C1COc2cc(F)c(C(=O)N3CC(COc4ccc(OC(F)F)cc4)C3)cc2N1] | 423.1 |
| 271 | 6-((3-((benzyloxy)methyl)azetidin-1-yl)carbonyl)-7-fluoro-2H-1,4-benzoxazin-3(4H)-one | 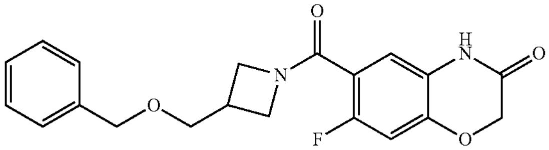 [SMILES: O=C1COc2cc(F)c(C(=O)N3CC(COCc4ccccc4)C3)cc2N1] | 371.1 |
| 272 | 6-((3-((1,3-benzothiazol-5-ylmethoxy)methyl)azetidin-1-yl)carbonyl)-7-fluoro-2H-1,4-benzoxazin-3(4H)-one | 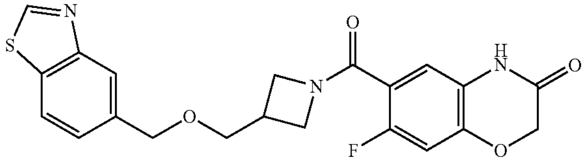 [SMILES: O=C1COc2cc(F)c(C(=O)N3CC(COCc4ccc5scnc5c4)C3)cc2N1] | 428.2 |
| 273 | 6-((3-((2,3-dihydro-1-benzofuran-6-yloxy)methyl)azetidin-1-yl)carbonyl)-7-fluoro-2H-1,4-benzoxazin-3(4H)-one | 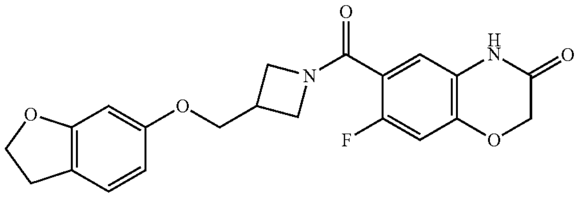 [SMILES: O=C1COc2cc(F)c(C(=O)N3CC(COc4ccc5c(c4)OCC5)C3)cc2N1] | 399.1 |

TABLE 2-21-continued

| | | | |
|---|---|---|---|
| 274 | 7-fluoro-6-((4-((pyrazolo[1,5-a]pyridin-4-yloxy)methyl)piperidin-1-yl)carbonyl)-2H-1,4-benzoxazin-3(4H)-one | 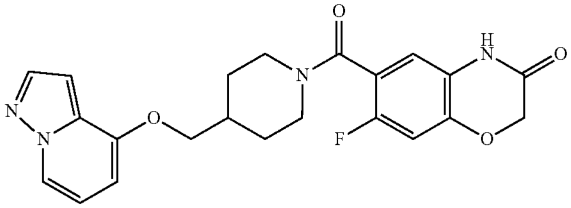 [SMILES: O=C1COc2cc(F)c(C(=O)N3CCC(COc4cccn5nccc45)CC3)cc2N1] | 425.1 |
| 275 | 7-fluoro-6-((4-((pyrazolo[1,5-a]pyridin-7-yloxy)methyl)piperidin-1-yl)carbonyl)-2H-1,4-benzoxazin-3(4H)-one | 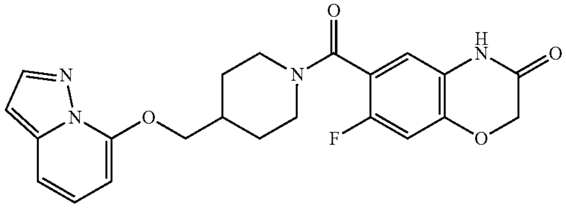 [SMILES: O=C1COc2cc(F)c(C(=O)N3CCC(COc4cccc5ccnn45)CC3)cc2N1] | 425.2 |
| 276 | 7-fluoro-6-((3-((2-fluoro-4-(4-methylpyridin-2-yl)phenoxy)methyl)azetidin-1-a]pyridin-4-yloxy)methyl)piperidin-1-yl)carbonyl)-2H-1,4-benzoxazin-3(4H)-one | 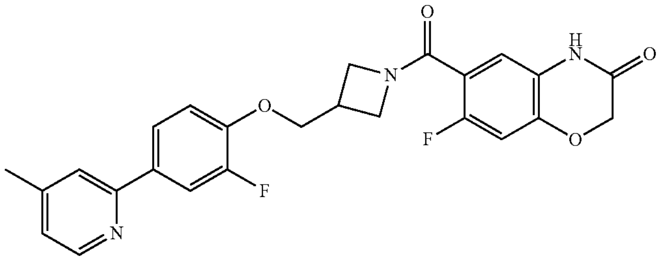 [SMILES: Cc1ccnc(-c2ccc(OCC3CN(C(=O)c4cc5c(cc4F)OCC(=O)N5)C3)c(F)c2)c1] | 466.3 |
| 277 | 7-fluoro-6-((3-((3-fluoro-4-(trifluoromethyl)phenoxy)methyl)azetidin-1-yl)carbonyl)-2H-1,4-benzoxazin-3(4H)-one | 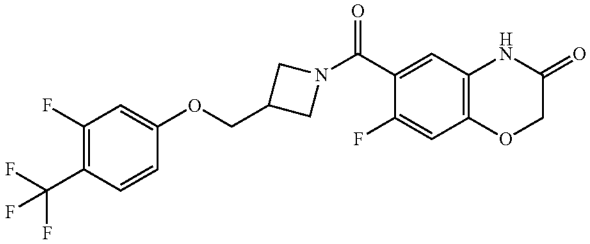 [SMILES: O=C1COc2cc(F)c(C(=O)N3CC(COc4ccc(C(F)(F)F)c(F)c4)C3)cc2N1] | 443.2 |
| 278 | 7-fluoro-6-((3-((4-fluoro-3-(trifluoromethyl)phenoxy)methyl)azetidin-1-yl)carbonyl)-2H-1,4-benzoxazin-3(4H)-one | 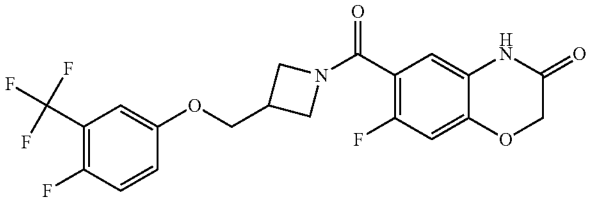 [SMILES: O=C1COc2cc(F)c(C(=O)N3CC(COc4ccc(F)c(C(F)(F)F)c4)C3)cc2N1] | 443.1 |

TABLE 2-22

| | | | |
|---|---|---|---|
| 279 | 6-((3-((3,4-dihydro-2H-pyrano[2,3-b]pyridin-6-yloxy)methyl)azetidin-1-yl)carbonyl)-7-fluoro-2H-1,4-benzoxazin-3(4H)-one | 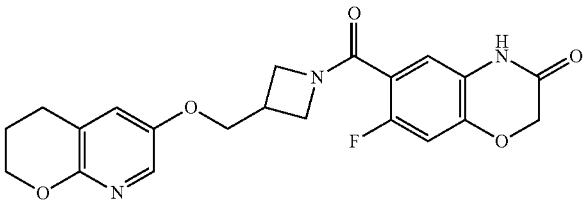 [SMILES: O=C1COc2cc(F)c(C(=O)N3CC(COc4cnc5c(c4)CCCO5)C3)cc2N1] | 414.1 |

TABLE 2-22-continued

| | | | |
|---|---|---|---|
| 280 | 6-((3-((cyclohexyloxy)methyl)azetidin-1-yl)carbonyl)-7-fluoro-2H-1,4-benzoxazin-3(4H)-one | 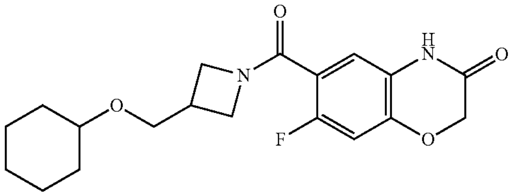 [SMILES: O=C1COc2cc(F)c(C(=O)N3CC(COC4CCCCC4)C3)cc2N1] | 363.2 |
| 281 | 6-((3-((2-chloro-4-fluorophenoxy)methyl)azetidin-1-yl)carbonyl)-5,7-difluoro-2H-1,4-benzoxazin-3(4H)-one | 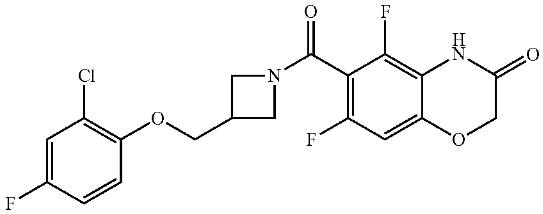 [SMILES: O=C1COc2cc(F)c(C(=O)N3CC(COc4ccc(F)cc4Cl)C3)c(F)c2N1] | 427.1 |
| 282 | 6-((3-(((4,4-difluorocyclohexyl)oxy)methyl)azetidin-1-yl)carbonyl)-7-fluoro-2H-1,4-benzoxazin-3(4H)-one | 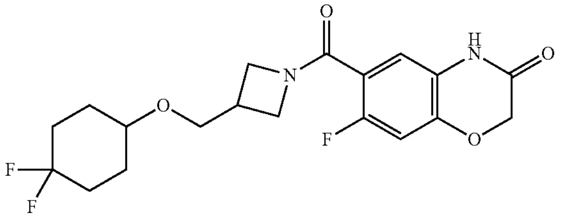 [SMILES: O=C1COc2cc(F)c(C(=O)N3CC(COC4CCC(F)(F)CC4)C3)cc2N1] | 399.1 |
| 283 | 6-((3-((2-chloro-4-fluorophenoxy)methyl)-3-methylazetidin-1-yl)carbonyl)-7-fluoro-2H-1,4-benzoxazin-3(4H)-one | 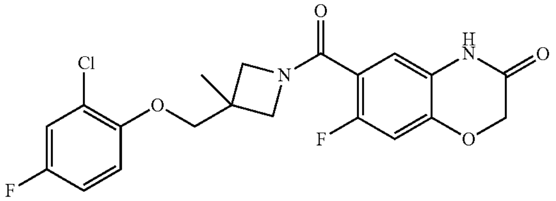 [SMILES: CC1(COc2ccc(F)cc2Cl)CN(C(=O)c2cc3c(cc2F)OCC(=O)N3)C1] | 423.1 |

Example 291

6-((3-((2-chloro-4-(3-fluoroazetidin-1-yl)phenoxy)methyl)azetidin-1-yl)carbonyl)-7-fluoro-2H-1,4-benzoxazin-3 (4H)-one A) tert-butyl 3-((4-bromo-2-chlorophenoxy)methyl)azetidine-1-carboxylate To a solution of tert-butyl 3-(hydroxymethyl)azetidine-1-carboxylate (0.500 g), 4-bromo-2-chlorophenol (0.554 g) and triphenylphosphine (0.840 g) in THF (10 mL) was added DIAD (0.631 mL) at room temperature, and the reaction mixture was stirred overnight. The reaction mixture was concentrated under reduced pressure, and the residue was purified by silica gel column chromatography (ethyl acetate/hexane) to give the title compound (1.00 g).

$^1$H NMR (300 MHz, DMSO-$d_6$) δ1.37 (9H, s), 2.89-3.03 (1H, m), 3.66-3.78 (2H, m), 3.87-3.98 (2H, m), 4.18 (2H, d, J=5.9 Hz), 7.14 (1H, d, J=8.9 Hz), 7.50 (1H, dd, J=8.9, 2.5 Hz), 7.67 (1H, d, J=2.5 Hz).

B) 3-((4-bromo-2-chlorophenoxy)methyl)azetidine tosylate

A mixture of tert-butyl 3-((4-bromo-2-chlorophenoxy)methyl)azetidine-1-carboxylate (0.300 g), p-TsOH—$H_2O$ (0.182 g) and ethyl acetate (5 mL) was heated under reflux for 3 hr. The resulting precipitate was collected, washed with ethyl acetate, and dried under reduced pressure to give the title compound (0.290 g).

$^1$H NMR (300 MHz, DMSO-$d_6$) δ2.29 (3H, s), 3.19-3.27 (1H, m), 3.83-3.96 (2H, m), 3.99-4.09 (2H, m), 4.20 (2H, d, J=5.9 Hz), 7.06-7.20 (3H, m), 7.43-7.57 (3H, m), 7.71 (1H, d, J=2.5 Hz), 8.54 (2H, brs).

C) 6-(3-((4-bromo-2-chlorophenoxy)methyl)azetidine-1-carbonyl)-7-fluoro-2H-benzo[b][1,4]oxazin-3 (4H)-one To a mixture of 3-((4-bromo-2-chlorophenoxy)methyl)azetidine tosylate (0.280 g), 7-fluoro-3-oxo-3,4-dihydro-2H-benzo[b][1,4]oxazine-6-carboxylic acid (0.110 g) and DMF (2 mL) were added HATU (0.297 g) and TEA (0.580 mL), and the mixture was stirred overnight at room temperature. The reaction mixture was diluted with ethyl acetate/water, and extracted with ethyl acetate. The organic layer was washed with water and saturated brine, dried over anhydrous sodium sulfate, and concentrated under reduced pressure. The residue was purified by silica gel column chromatography (ethyl acetate/hexane) to give the title compound (0.130 g).

$^1$H NMR (300 MHz, DMSO-$d_6$) δ2.99-3.18 (1H, m), 3.84-3.96 (2H, m), 4.09-4.27 (4H, m), 4.65 (2H, s), 6.92-7.05 (2H, m), 7.14 (1H, d, J=8.9 Hz), 7.49 (1H, dd, J=8.7, 2.5 Hz), 7.67 (1H, d, J=2.5 Hz), 10.83 (1H, s).

D) 6-((3-((2-chloro-4-(3-fluoroazetidin-1-yl)phenoxy)methyl)azetidin-1-yl)carbonyl)-7-fluoro-2H-1,4-benzoxazin-3(4H)-one To a solution of 3-fluoroazetidine hydrochloride (38.0 mg) in toluene (4 mL) were added 6-(3-((4-bromo-2-chlorophenoxy)methyl)azetidine-1-carbonyl)-7-fluoro-2H-benzo[b][1,4]oxazin-3(4H)-one (80.0 mg), sodium tert-butoxide (98.0 mg), tris(dibenzylideneacetone)dipalladium (0) (15.6 mg) and 2-dicyclohexylphosphino-2',4',6'-tri-iso-propyl-1,1'-biphenyl (16.2 mg), and the mixture was heated under microwave irradiation at 110° C. for 45 min. To the reaction mixture was added water, and the mixture was passed through Celite pad, and the filtrate was extracted with ethyl acetate. The organic layer was washed with water and saturated brine, dried over anhydrous sodium sulfate, and concentrated under reduced pressure. The residue was purified by silica gel column chromatography (NH, ethyl acetate/hexane) to give the title compound (16.0 mg).

$^1$H NMR (300 MHz, DMSO-$d_6$) δ2.96-3.12 (1H, m), 3.72-3.96 (4H, m), 4.00-4.24 (6H, m), 4.65 (2H, s), 5.28-5.61 (1H, m), 6.41 (1H, dd, J=8.9, 2.8 Hz), 6.56 (1H, d, J=2.6 Hz), 6.90-7.12 (3H, m), 10.83 (1H, s).

Example 322

6-((3-((2-chloro-4-fluorobenzyl)oxy)azetidin-1-yl)carbonyl)-7-fluoro-2H-1,4-benzoxazin-3(4H)-one

A) tert-butyl 3-((2-chloro-4-fluorobenzyl)oxy)azetidine-1-carboxylate

To a solution of tert-butyl 3-hydroxyazetidine-1-carboxylate (1.00 g) in DMF (10 mL) was added 60% sodium hydride (0.277 g) at 0° C. The mixture was stirred at room temperature for 10 min, 2-chloro-4-fluorobenzyl chloride (1.03 g) was added thereto, and the mixture was stirred overnight at 60° C. The mixture was poured into saturated aqueous sodium hydrogencarbonate solution, and extracted with ethyl acetate. The organic layer was washed with saturated brine, dried over anhydrous magnesium sulfate, and concentrated under reduced pressure. The residue was purified by silica gel column chromatography (ethyl acetate/hexane) to give the title compound (1.82 g).

$^1$H NMR (300 MHz, DMSO-$d_6$) δ1.37 (9H, s), 3.65-3.75 (2H, m), 3.96-4.08 (2H, m), 4.31-4.42 (1H, m), 4.48 (2H, s), 7.19-7.29 (1H, m), 7.47 (1H, dd, J=8.9, 2.6 Hz), 7.57 (1H, dd, J=8.6, 6.4 Hz).

B) 3-((2-chloro-4-fluorobenzyl)oxy)azetidine tosylate

A mixture of tert-butyl 3-((2-chloro-4-fluorobenzyl)oxy)azetidine-1-carboxylate (1.82 g), p-TsOH—$H_2O$ (1.21 g) and ethyl acetate (10 mL) was heated under reflux for 1.5 hr. The mixture was concentrated under reduced pressure, and triturated with ethyl acetate to give the title compound (1.73 g).

$^1$H NMR (300 MHz, DMSO-$d_6$) δ2.29 (3H, s), 3.80-3.92 (2H, m), 4.11-4.21 (2H, m), 4.43-4.52 (1H, m), 4.53 (2H, s), 7.07-7.14 (2H, m), 7.22-7.33 (1H, m), 7.42-7.53 (3H, m), 7.59 (1H, dd, J=8.6, 6.3 Hz), 8.62 (2H, brs).

C) 6-((3-((2-chloro-4-fluorobenzyl)oxy)azetidin-1-yl)carbonyl)-7-fluoro-2H-1, 4-benzoxazin-3(4H)-one A mixture of 3-((2-chloro-4-fluorobenzyl)oxy)azetidine tosylate (0.388 g), 7-fluoro-3-oxo-3,4-dihydro-2H-benzo[b][1,4]oxazine-6-carboxylic acid (0.211 g), HOBt-$H_2O$ (0.184 g), EDCI (0.230 g), TEA (0.418 mL) and DMF (5 mL) was stirred at room temperature for 5 hr. The reaction mixture was diluted with water, and the resulting precipitate was collected by filtration, and dried under reduced pressure. The crude crystals were recrystallized from methanol/ethyl acetate to give the title compound (0.222 g).

$^1$H NMR (300 MHz, DMSO-$d_6$) δ3.80-3.97 (2H, m), 4.15-4.29 (2H, m), 4.42-4.49 (1H, m), 4.51 (2H, s), 4.66 (2H, s), 6.93-7.03 (2H, m), 7.19-7.29 (1H, m), 7.47 (1H, dd, J=8.9, 2.5 Hz), 7.58 (1H, dd, J=8.6, 6.4 Hz), 10.83 (1H, s).

The compounds of Examples 284 to 290, 292 to 321 and 323 to 356 in the following tables were produced according to the methods described in the above-mentioned Examples, or methods analogous thereto. The compounds of Examples are shown in the following Tables 3-1 to 3-9. MS in the tables means actual measured value.

TABLE 3-1

| Ex. No. | IUPAC NAME | STRUCTURE | MS |
|---|---|---|---|
| 284 | 7-fluoro-6-((4-((5,6,7,8-tetrahydronaphthalen-2-yloxy)methyl)piperidin-1-yl)carbonyl)-2H-1,4-benzoxazin-3(4H)-one | 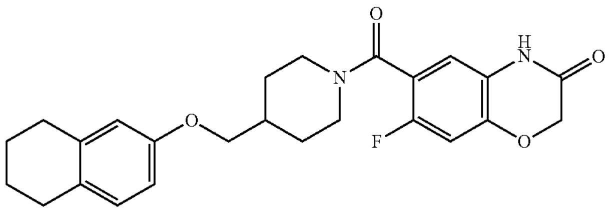 [SMILES: O=C1COc2cc(F)c(C(=O)N3CCC(COc4ccc5c(c4)CCCC5)CC3)cc2N1] | 439.2 |
| 285 | 7-fluoro-6-((4-(phenoxymethyl)piperidin-1-yl)carbonyl)-2H-1,4-benzoxazin-3(4H)-one | 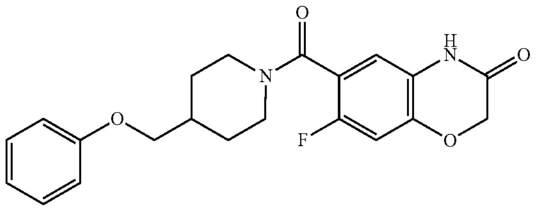 [SMILES: O=C1COc2cc(F)c(C(=O)N3CCC(COc4ccccc4)CC3)cc2N1] | 385.1 |

TABLE 3-1-continued

| Ex. No. | IUPAC NAME | STRUCTURE | MS |
|---|---|---|---|
| 286 | 6-((3-(((1-bromo,-5,6,7,8-tetrahydronaphthalen-2-yl)oxy)methyl)azetidin-1-yl)carbonyl)-7-fluoro-2H-1,4-benzoxazin-3(4H)-one | 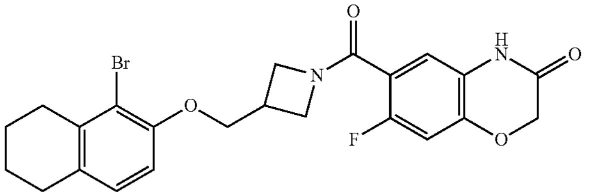 [SMILES: O=C1COc2cc(F)c(C(=O)N3CC(COc4ccc5c(c4Br)CCCC5)C3)cc2N1] | 489.1 |
| 287 | 7-fluoro-6-((3-((4-fluoro-3-methylphenoxy)methyl) azetidin-1-yl)carbonyl)-2H-1,4-benzoxazin-3(4H)-one | 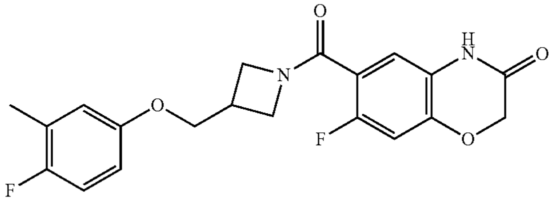 [SMILES: Cc1cc(OCC2CN(C(=O)c3cc4c(cc3F)OCC(=O)N4)C2)ccc1F] | 389.4 |
| 288 | 6-((3-((4-(difluoromethyl)-2-fluorophenoxy)methyl)azetidin-1-yl)carbonyl)-7-fluoro-2H-1,4-benzoxazin-3(4H)-one | 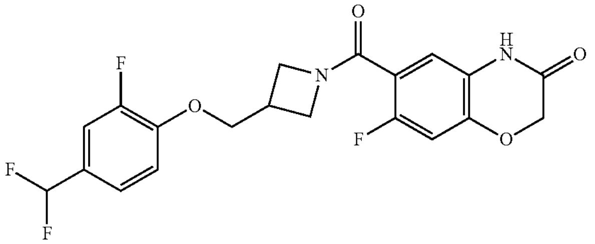 [SMILES: O=C1COc2cc(F)c(C(=O)N3CC(COc4ccc(C(F)F)cc4F)C3)cc2N1] | 425.1 |
| 289 | 7-fluoro-6-((3-((2-fluoro-4-(6-fluoropyridin-2-yl)phenoxy)methyl)azetidin-1-yl)carbonyl)-2H-1,4-benzoxazin-3(4H)-one | 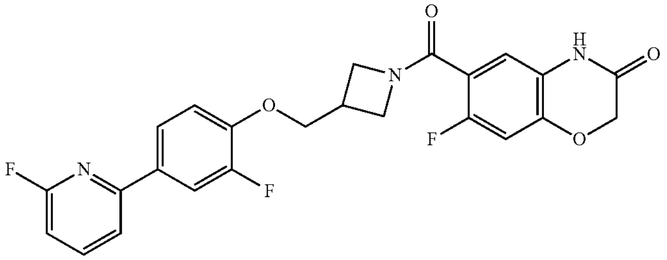 [SMILES: O=C1COc2cc(F)c(C(=O)N3CC(COc4ccc(-c5cccc(F)n5)cc4F)C3)cc2N1] | 470.2 |
| 290 | 7-fluoro-6-((3-((2-fluoro-4-(6-fluoro-2-methylpyridin-3-yl)phenoxy)methyl)azetidin-1-yl)carbonyl)-2H-1,4-benzoxazin-3(4H)-one | 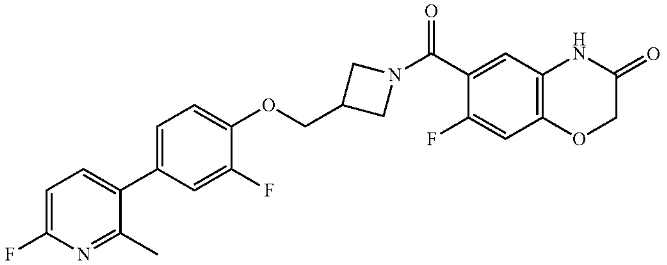 [SMILES: Cc1nc(F)ccc1-c1ccc(OCC2CN(C(=O)c3cc4c(cc3F)OCC(=O)N4)C2)c(F)c1] | 484.2 |
| 291 | 6-((3-((2-chloro-4-(3-fluoroazetidin-1-yl)phenoxy)methyl)azetidin-1-yl)carbonyl)-7-fluoro-2H-1,4-benzoxazin-3(4H)-one | 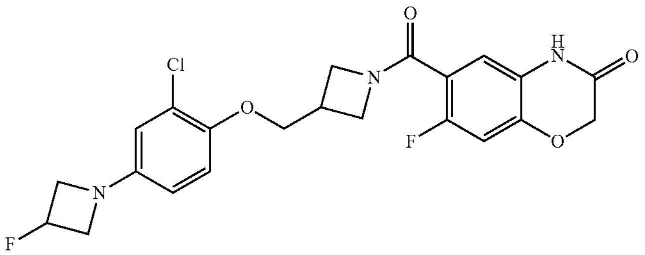 [SMILES: O=C1COc2cc(F)c(C(=O)N3CC(COc4ccc(N5CC(F)C5)cc4Cl)C3)cc2N1] | 464.1 |

TABLE 3-1-continued

| Ex. No. | IUPAC NAME | STRUCTURE | MS |
|---|---|---|---|
| 292 | 7-fluoro-6-((3-((2-fluoro-4-(3-fluoroazetidin-1-yl)phenoxy)methyl)azetidin-1-yl)carbonyl)-2H-1,4-benzoxazin-3(4H)-one | 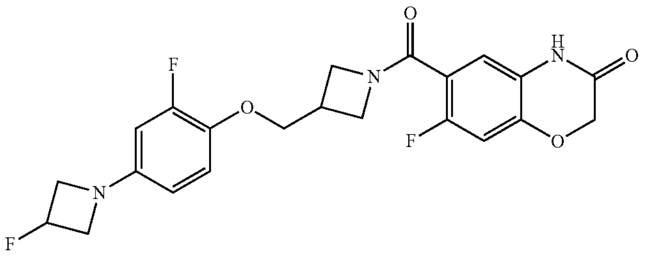 [SMILES: O=C1COc2cc(F)c(C(=O)N3CC(COc4ccc(N5CC(F)C5)cc4F)C3)cc2N1] | 448.1 |

TABLE 3-2

| | | | |
|---|---|---|---|
| 293 | 6-((4-(1-(2-chloro-4-fluorophenoxy)ethyl)piperidin-1-yl)carbonyl)-7-fluoro-2H-1,4-benzoxazin-3(4H)-one | 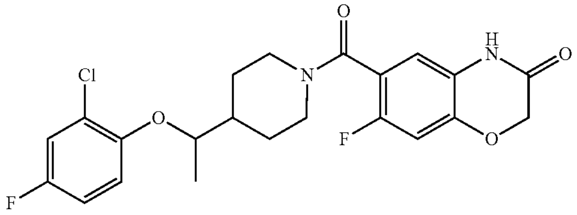 [SMILES: CC(Oc1ccc(F)cc1Cl)C1CCN(C(=O)c2cc3c(cc2F)OCC(=O)N3)CC1] | 451.0 |
| 294 | 6-((4-(1-(2,4-difluorophenoxy)ethyl)piperidin-1-yl)carbonyl)-7-fluoro-2H-1,4-benzoxazin-3(4H)-one | 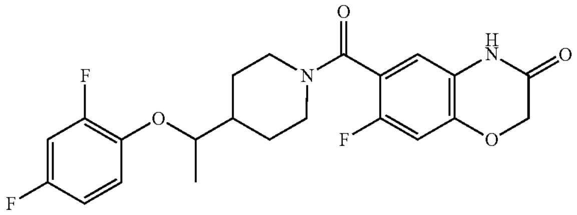 [SMILES: CC(Oc1ccc(F)cc1F)C1CCN(C(=O)c2cc3c(cc2F)OCC(=O)N3)CC1] | 435.1 |
| 295 | 6-((4-(1-(2-chloro-4-fluorophenoxy)ethyl)piperidin-1-yl)carbonyl)-7-fluoro-2H-1,4-benzoxazin-3(4H)-one (optical isomer) | 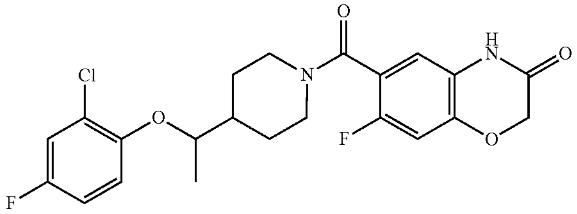 [SMILES: CC(Oc1ccc(F)cc1Cl)C1CCN(C(=O)c2cc3c(cc2F)OCC(=O)N3)CC1] | 451.1 |
| 296 | 6-((4-(1-(2-chloro-4-fluorophenoxy)ethyl)piperidin-1-yl)carbonyl)-7-fluoro-2H-1,4-benzoxazin-3(4H)-one (optical isomer) | 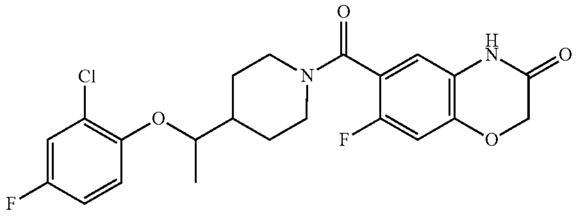 [SMILES: CC(Oc1ccc(F)cc1Cl)C1CCN(C(=O)c2cc3c(cc2F)OCC(=O)N3)CC1] | 451.1 |
| 297 | 6-((3-(1-(2-chloro-4-fluorophenoxy)ethyl)azetidin-1-yl)carbonyl)-7-fluoro-2H-1,4-benzoxazin-3(4H)-one | 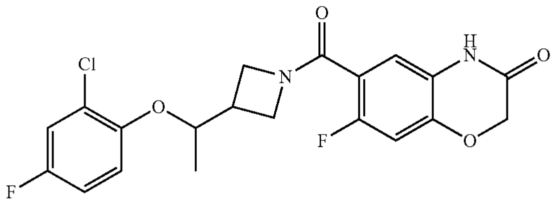 [SMILES: CC(Oc1ccc(F)cc1Cl)C1CN(C(=O)c2cc3c(cc2F)OCC(=O)N3)C1] | 423.1 |

TABLE 3-2-continued

| | | | |
|---|---|---|---|
| 298 | 6-((3-(1-(2,4-difluorophenoxy)ethyl)azetidin-1-yl)carbonyl)-7-fluoro-2H-1,4-benzoxazin-3(4H)-one | 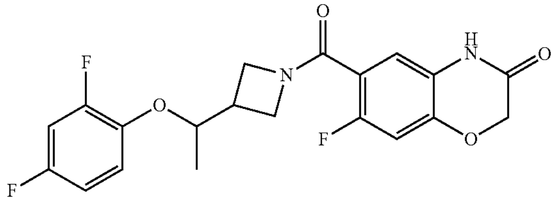 [SMILES: CC(Oc1ccc(F)cc1F)C1CN(C(=O)c2cc3c(cc2F)OCC(=O)N3)C1] | 407.0 |
| 299 | 7-fluoro-6-((3-(1-(1H-indazol-6-yloxy)ethyl)azetidin-1-yl) carbonyl)-2H-1,4-benzoxazin-3(4H)-one | 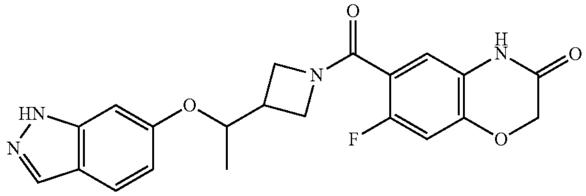 [SMILES: CC(Oc1ccc2cn[nH]c2c1)C1CN(C(=O)c2cc3c(cc2F)OCC(=O)N3)C1] | 411.2 |
| 300 | 6-((3-(1-(2,4-difluorophenoxy)ethyl)azetidin-1-yl)carbonyl)-7-fluoro-2H-1,4-benzoxazin-3(4H)-one (optical isomer) | 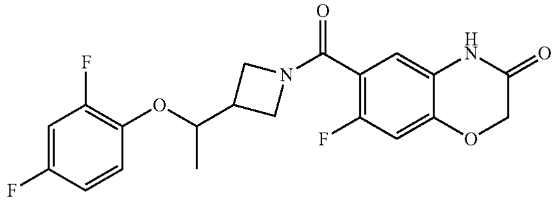 [SMILES: CC(Oc1ccc(F)cc1F)C1CN(C(=O)c2cc3c(cc2F)OCC(=O)N3)C1] | 407.1 |
| 301 | 6-((3-(1-(2,4-difluorophenoxy)ethyl)azetidin-1-yl)carbonyl)-7-fluoro-2H-1,4-benzoxazin-3(4H)-one (optical isomer) | 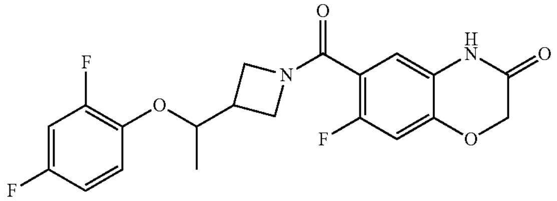 [SMILES: CC(Oc1ccc(F)cc1F)C1CN(C(=O)c2cc3c(cc2F)OCC(=O)N3)C1] | 407.1 |

TABLE 3-3

| | | | |
|---|---|---|---|
| 302 | 6-((3-(1-(2,3-difluorophenoxy)ethyl)azetidin-1-yl)carbonyl)-7-fluoro-2H-1,4-benzoxazin-3(4H)-one | 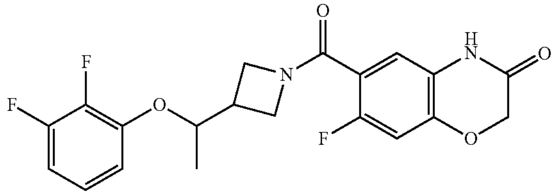 [SMILES: CC(Oc1cccc(F)c1F)C1CN(C(=O)c2cc3c(cc2F)OCC(=O)N3)C1] | 407.1 |
| 303 | 6-((3-(1-(2,5-difluorophenoxy)ethyl)azetidin-1-yl)carbonyl)-7-fluoro-2H-1,4-benzoxazin-3(4H)-one | 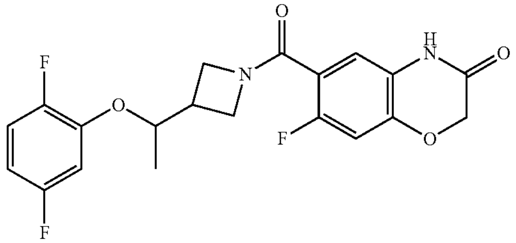 [SMILES: CC(Oc1cc(F)ccc1F)C1CN(C(=O)c2cc3c(cc2F)OCC(=O)N3)C1] | 407.1 |
| 304 | 6-((3-(1-(3,4-difluorophenoxy)ethyl)azetidin-1-yl)carbonyl)-7-fluoro-2H-1,4-benzoxazin-3(4H)-one | 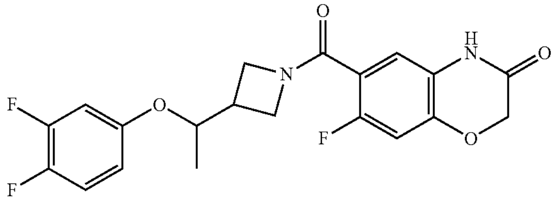 [SMILES: CC(Oc1ccc(F)c(F)c1)C1CN(C(=O)c2cc3c(cc2F)OCC(=O)N3)C1] | 407.1 |

TABLE 3-3-continued

| | | | |
|---|---|---|---|
| 305 | 6-((3-(1-(3,5-difluorophenoxy)ethyl)azetidin-1-yl)carbonyl)-7-fluoro-2H-1,4-benzoxazin-3(4H)-one | 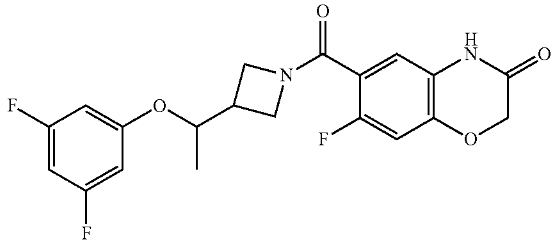 [SMILES: CC(Oc1cc(F)cc(F)c1)C1CN(C(=O)c2cc3c(cc2F)OCC(=O)N3)C1] | 407.1 |
| 306 | 6-((3-(1-(2,6-difluorophenoxy)ethyl)azetidin-1-yl)carbonyl)-7-fluoro-2H-1,4-benzoxazin-3(4H)-one | 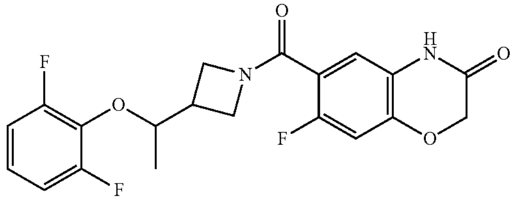 [SMILES: CC(Oc1c(F)cccc1F)C1CN(C(=O)c2cc3c(cc2F)OCC(=O)N3)C1] | 407.1 |
| 307 | 6-((3-(1-(4-chloro-2-fluorophenoxy)-2-hydroxyethyl)azetidin-1-yl)carbonyl)-7-fluoro-2H-1,4-benzoxazin-3(4H)-one | 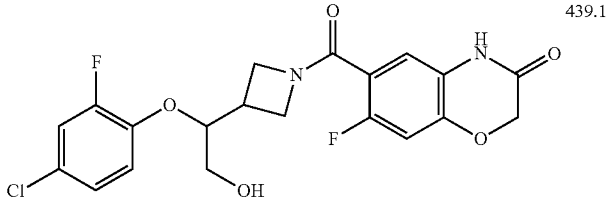 | 439.1 |
| 308 | 6-((3-(2-(2,4-difluorophenoxy)propan-2-yl)azetidin-1-yl)carbonyl)-7-fluoro-2H-1,4-benzoxazin-3(4H)-one | 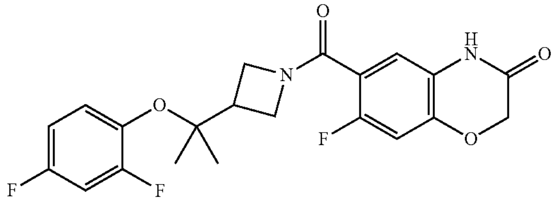 [SMILES: CC(C)(Oc1ccc(F)cc1F)C1CN(C(=O)c2cc3c(cc2F)OCC(=O)N3)C1] | 421.1 |
| 309 | 6-((3-(1-(4-chloro-2-fluorophenoxy)-2-methoxyethyl)azetidin-1-yl)carbonyl)-7-fluoro-2H-1,4-benzoxazin-3(4H)-one | 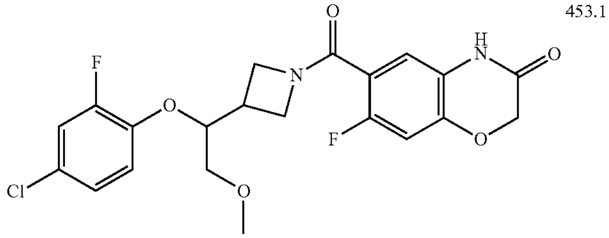 | 453.1 |
| 310 | 6-((3-(1-(2,3-difluorophenoxy)ethyl)azetidin-1-yl)carbonyl)-7-fluoro-2H-1,4-benzoxazin-3(4H)-one (optical isomer) | 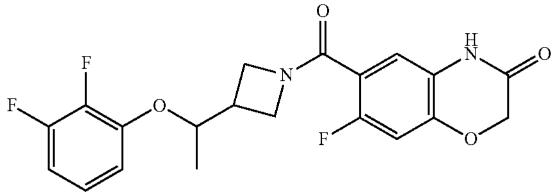 [SMILES: CC(Oc1cccc(F)c1F)C1CN(C(=O)c2cc3c(cc2F)OCC(=O)N3)C1] | 407.1 |

TABLE 3-4

| | | | |
|---|---|---|---|
| 311 | 6-((3-(1-(2,3-difluorophenoxy)ethyl)azetidin-1-yl)carbonyl)-7-fluoro-2H-1,4-benzoxazin-3(4H)-one (optical isomer) | 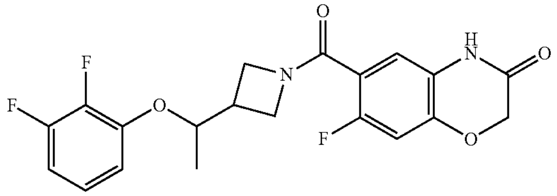 [SMILES: CC(Oc1cccc(F)c1F)C1CN(C(=O)c2cc3c(cc2F)OCC(=O)N3)C1] | 407.1 |

TABLE 3-4-continued

| | | | |
|---|---|---|---|
| 312 | 6-((3-(1-(3,4-difluorophenoxy)ethyl)azetidin-1-yl)carbonyl)-7-fluoro-2H-1,4-benzoxazin-3(4H)-one (optical isomer) | 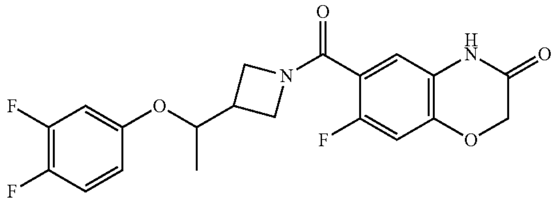 [SMILES: CC(Oc1ccc(F)c(F)c1)C1CN(C(=O)c2cc3c(cc2F)OCC(=O)N3)C1] | 407.1 |
| 313 | 6-((3-(1-(3,4-difluorophenoxy)ethyl)azetidin-1-yl)carbonyl)-7-fluoro-2H-1,4-benzoxazin-3(4H)-one (optical isomer) | 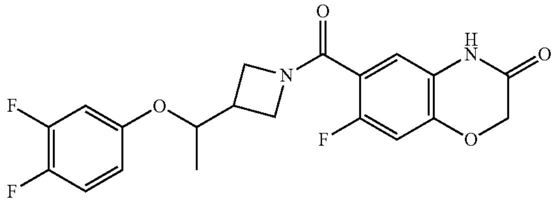 [SMILES: CC(Oc1ccc(F)c(F)c1)C1CN(C(=O)c2cc3c(cc2F)OCC(=O)N3)C1] | 407.2 |
| 314 | 6-((3-(1-(3,5-difluorophenoxy)ethyl)azetidin-1-yl)carbonyl)-7-fluoro-2H-1,4-benzoxazin-3(4H)-one (optical isomer) | 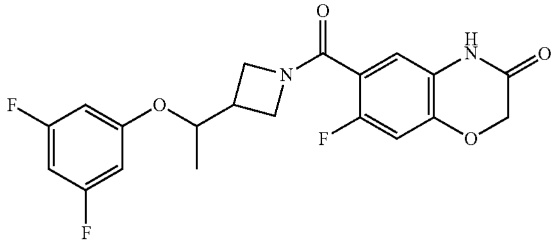 [SMILES: CC(Oc1cc(F)cc(F)c1)C1CN(C(=O)c2cc3c(cc2F)OCC(=O)N3)C1] | 407.1 |
| 315 | 6-((3-(1-(3,5-difluorophenoxy)ethyl)azetidin-1-yl)carbonyl)-7-fluoro-2H-1,4-benzoxazin-3(4H)-one (optical isomer) | 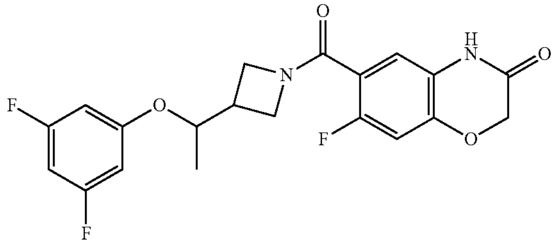 [SMILES: CC(Oc1cc(F)cc(F)c1)C1CN(C(=O)c2cc3c(cc2F)OCC(=O)N3)C1] | 407.1 |
| 316 | 7-fluoro-6-((3-(1-(2,3,4-trifluorophenoxy)ethyl) azetidin-1-yl)carbonyl)-2H-1,4-benzoxazin-3(4H)-one | 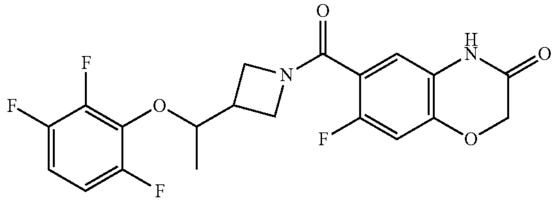 [SMILES: CC(Oc1c(F)ccc(F)c1F)C1CN(C(=O)c2cc3c(cc2F)OCC(=O)N3)C1] | 425.1 |
| 317 | 7-fluoro-6-((3-(1-(2,3,4-trifluorophenoxy)ethyl) azetidin-1-yl)carbonyl)-2H-1,4-benzoxazin-3(4H)-one (optical isomer) | 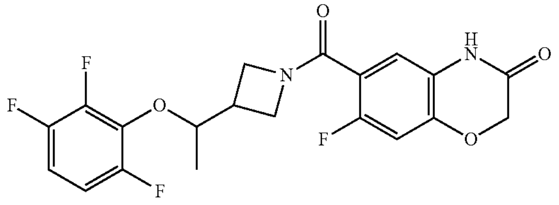 [SMILES: CC(Oc1c(F)ccc(F)c1F)C1CN(C(=O)c2cc3c(cc2F)OCC(=O)N3)C1] | 425.1 |
| 318 | 7-fluoro-6-((3-(1-(2,3,4-trifluorophenoxy)ethyl) azetidin-1-yl)carbonyl)-2H-1,4-benzoxazin-3(4H)-one (optical isomer) | 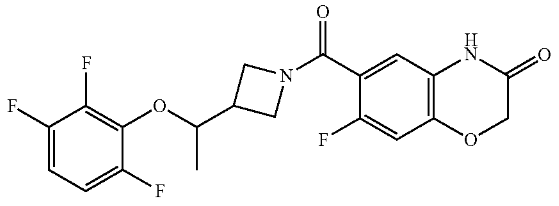 [SMILES: CC(Oc1c(F)ccc(F)c1F)C1CN(C(=O)c2cc3c(cc2F)OCC(=O)N3)C1] | 425.1 |

TABLE 3-4-continued

| | | | |
|---|---|---|---|
| 319 | 6-((3-(1-(2,5-difluorophenoxy)ethyl)azetidin-1-yl)carbonyl)-7-fluoro-2H-1,4-benzoxazin-3(4H)-one (optical isomer) | 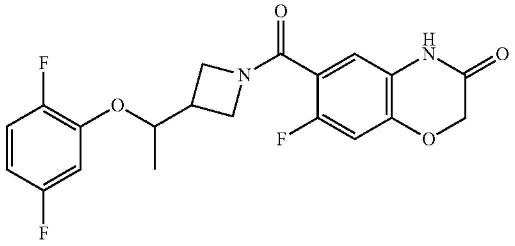 [SMILES: CC(Oc1cc(F)ccc1F)C1CN(C(=O)c2cc3c(cc2F)OCC(=O)N3)C1] | 407.0 |

TABLE 3-5

| | | | |
|---|---|---|---|
| 320 | 6-((3-(1-(2,5-difluorophenoxy)ethyl)azetidin-1-yl)carbonyl)-7-fluoro-2H-1,4-benzoxazin-3(4H)-one (optical isomer) | 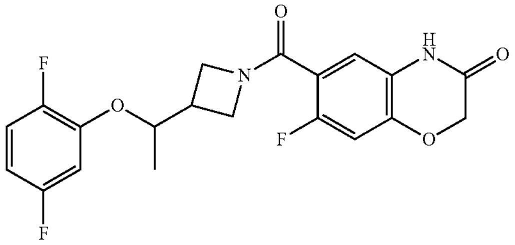 [SMILES: CC(Oc1cc(F)ccc1F)C1CN(C(=O)c2cc3c(cc2F)OCC(=O)N3)C1] | 407.0 |
| 321 | 7-((4-(benzyloxy)piperidin-1-yl)carbonyl)-1H-pyrido[2,3-b][1,4]oxazin-2(3H)-one | 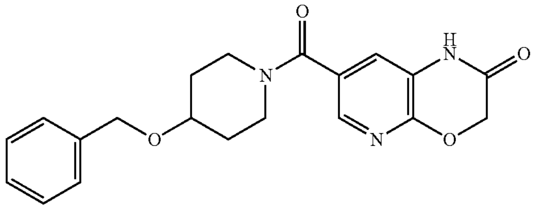 [SMILES: O=C1COc2ncc(C(=O)N3CCC(OCc4ccccc4)CC3)cc2N1] | 368.0 |
| 322 | 6-((3-((2-chloro-4-fluorobenzyl)oxy)azetidin-1-yl)carbonyl)-7-fluoro-2H-1,4-benzoxazin-3(4H)-one | 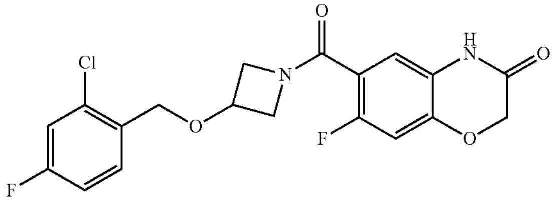 [SMILES: O=C1COc2cc(F)c(C(=O)N3CC(OCc4ccc(F)cc4Cl)C3)cc2N1] | 409.0 |
| 323 | 6-((3-((2-chloro-4-fluorobenzyl)oxy)azetidin-1-yl)carbonyl)-2H-1,4-benzoxazin-3(4H)-one | 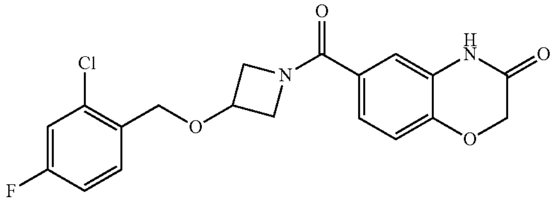 [SMILES: O=C1COc2ccc(C(=O)N3CC(OCc4ccc(F)cc4Cl)C3)cc2N1] | 391.0 |
| 324 | 6-((3-((2,4-dichlorobenyzl)oxy)azetidin-1-yl)carbonyl)-7-fluoro-2H-1,4-benzoxazin-3(4H)-one | 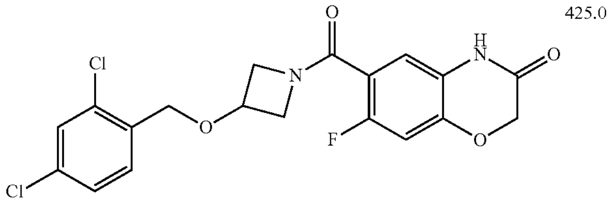 | 425.0 |
| 325 | 6-((3-((2,4-dichlorobenzyl)oxy)azetidin-1-yl)carbonyl)-2H-1,4-benzoxazin-3(4H)-one | 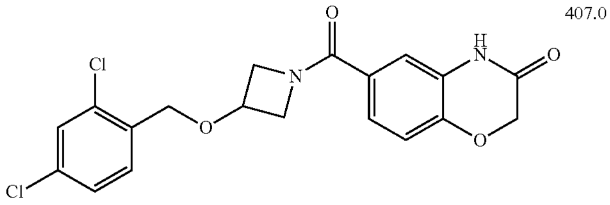 | 407.0 |

TABLE 3-5-continued

| | | | |
|---|---|---|---|
| 326 | 6-((3-(benzyloxy)azetidin-1-yl)carbonyl)-2H-1,4-benzoxazin-3(4H)-one | 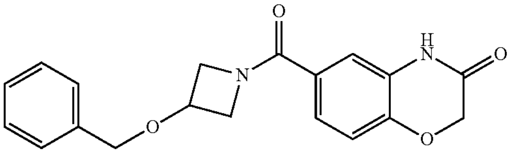 [SMILES: O=C1COc2ccc(C(=O)N3CC(OCc4ccccc4)C3)cc2N1] | 339.2 |
| 327 | 6-((3-(benzyloxy)azetidin-1-yl)carbonyl)-7-fluoro-2H-1,4-benzoxazin-3(4H)-one | 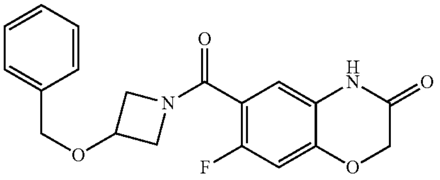 [SMILES: O=C1COc2cc(F)c(C(=O)N3CC(OCc4ccccc4)C3)cc2N1] | 357.1 |
| 328 | 7-fluoro-6-((3-((3-methoxybenzyl)oxy)azetidin-1-yl)carbonyl)-2H-1,4-benzoxazin-3(4H)-one | 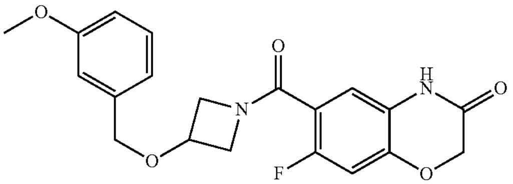 [SMILES: COc1cccc(COC2CN(C(=O)c3cc4c(cc3F)OCC(=O)N4)C2)c1] | 387.2 |

TABLE 3-6

| | | | |
|---|---|---|---|
| 329 | 7-fluoro-6-((3-((3-methylbenzyl)oxy)azetidin-1-yl)carbonyl)-2H-1,4-benzoxazin-3(4H)-one | 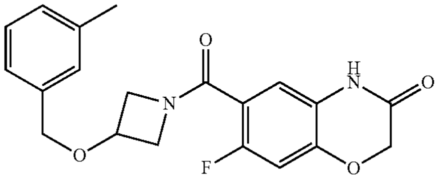 [SMILES: Cc1cccc(COC2CN(C(=O)c3cc4c(cc3F)OCC(=O)N4)C2)c1] | 371.1 |
| 330 | 7-fluoro-6-((3-((2-fluorobenzyl)oxy)azetidin-1-yl)carbonyl)-2H-1,4-benzoxazin-3(4H)-one | 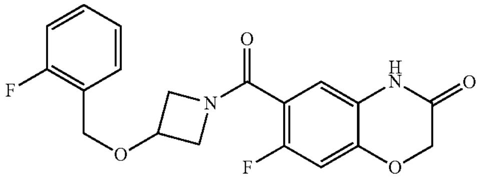 [SMILES: O=C1COc2cc(F)c(C(=O)N3CC(OCc4ccccc4F)C3)cc2N1] | 375.1 |
| 331 | 7-fluoro-6-((3-((3-fluorobenzyl)oxy)azetidin-1-yl)carbonyl)-2H-1,4-benzoxazin-3(4H)-one | 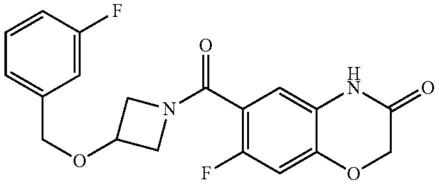 | 375.2 |
| 332 | 7-fluoro-6-((3-((4-fluorobenzyl)oxy)azetidin-1-yl)carbonyl)-2H-1,4-benzoxazin-3(4H)-one | 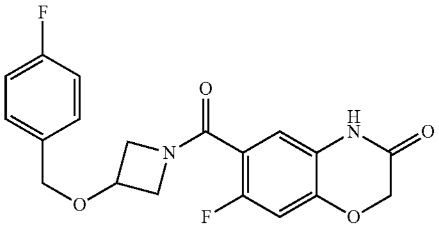 [SMILES: O=C1COc2cc(F)c(C(=O)N3CC(OCc4ccc(F)cc4)C3)cc2N1] | 375.1 |

TABLE 3-6-continued

| | | | |
|---|---|---|---|
| 333 | 2-(((1-((7-fluoro-3-oxo-3,4-dihydro-2H-1,4-benzoxazin-6-yl)carbonyl)azetidin-3-yl)oxy)methyl)benzonitrile | 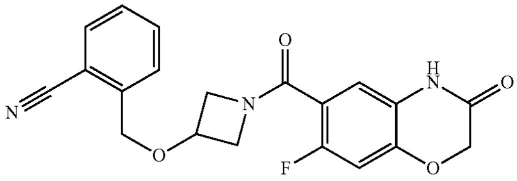 [SMILES: N#Cc1ccccc1COC1CN(C(=O)c2cc3c(cc2F)OCC(=O)N3)C1] | 382.1 |
| 334 | 3-(((1-((7-fluoro-3-oxo-3,4-dihydro-2H-1,4-benzoxazin-6-yl)carbonyl)azetidin-3-yl)oxy)methyl)benzonitrile | 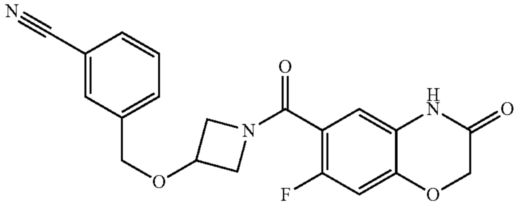 [SMILES: N#Cc1cccc(COC2CN(C(=O)c3cc4c(cc3F)OCC(=O)N4)C2)c1] | 382.0 |
| 335 | 4-(((1-((7-fluoro-3-oxo-3,4-dihydro-2H-1,4-benzoxazin-6-yl)carbonyl)azetidin-3-yl)oxy)methyl)benzonitrile | 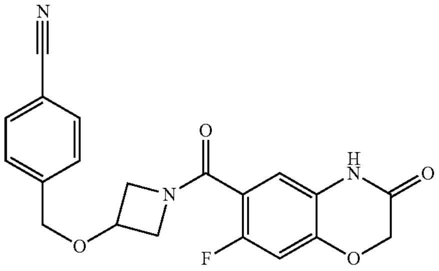 [SMILES: N#Cc1ccc(COC2CN(C(=O)c3cc4c(cc3F)OCC(=O)N4)C2)cc1] | 382.1 |
| 336 | 6-((3-((3-chlorobenzyl)oxy)azetidin-1-yl)carbonyl)-7-fluoro-2H-1,4-benzoxazin-3(4H)-one | 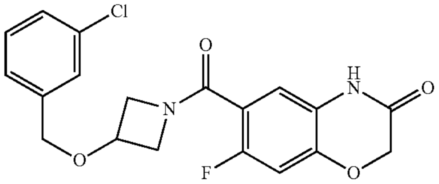 [SMILES: O=C1COc2cc(F)c(C(=O)N3CC(OCc4cccc(Cl)c4)C3)cc2N1] | 391.0 |
| 337 | 7-fluoro-6-((3-((4-(methylsulfonyl)benzyl)oxy)azetidin-1-yl)carbonyl)-2H-1,4-benzoxazin-3(4H)-one | 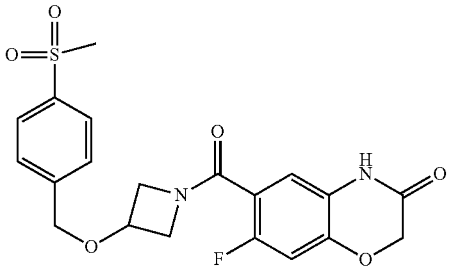 [SMILES: CS(=O)(=O)c1ccc(COC2CN(C(=O)c3cc4c(cc3F)OCC(=O)N4)C2)cc1] | 435.1 |

TABLE 3-7

| | | | |
|---|---|---|---|
| 338 | 7-fluoro-6-((3-((4-(1H-pyrazol-1-yl)benzyl)oxy)azetidin-1-yl)carbonyl)-2H-1,4-benzoxazin-3(4H)-one | 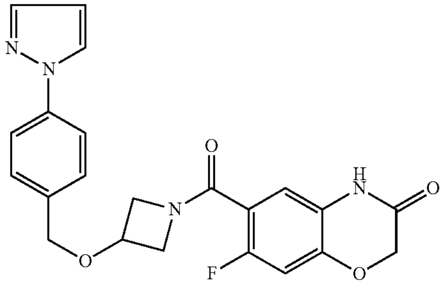 [SMILES: O=C1COc2cc(F)c(C(=O)N3CC(OCc4ccc(-n5cccn5)cc4)C3)cc2N1] | 423.1 |

TABLE 3-7-continued

| | | | |
|---|---|---|---|
| 339 | 6-((3-((3-difluoromethyl) benzyl)oxy)azetidin-1-yl)carbonyl)-7-fluoro-2H-1,4-benzoxazin-3(4H)-one | 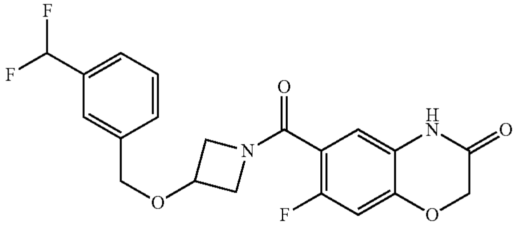 [SMILES: O=C1COc2cc(F)c(C(=O)N3CC(OCc4cccc(C(F)F)c4)C3)cc2N1] | 407.1 |
| 340 | 6-((3-((3-difluoromethoxy) benzyl)oxy)azetidin-1-yl)carbonyl)-7-fluoro-2H-1,4-benzoxazin-3(4H)-one | 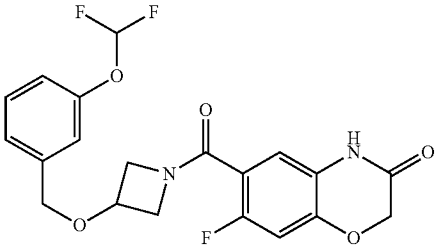 [SMILES: O=C1COc2cc(F)c(C(=O)N3CC(OCc4cccc(OC(F)F)c4)C3)cc2N1] | 423.1 |
| 341 | 6-((3-((2-difluoromethoxy) benzyl)oxy)azetidin-1-yl)carbonyl)-7-fluoro-2H-1,4-benzoxazin-3(4H)-one | 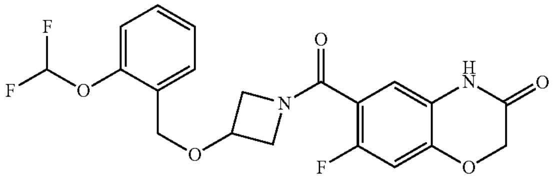 [SMILES: O=C1COc2cc(F)c(C(=O)N3CC(OCc4ccccc4OC(F)F)C3)cc2N1] | 423.1 |
| 342 | 6-((3-((2-chlorobenzyl)oxy) azetidin-1-yl)carbonyl)-7-fluoro-2H-1,4-benzoxazin-3(4H)-one | 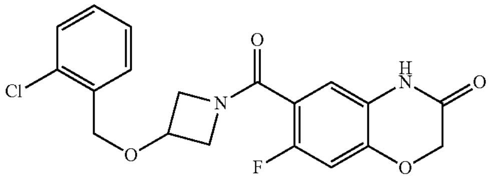 [SMILES: O=C1COc2cc(F)c(C(=O)N3CC(OCc4ccccc4Cl)C3)cc2N1] | 391.1 |
| 343 | 6-((3-((4-chlorobenzyl)oxy) azetidin-1-yl)carbonyl)-7-fluoro-2H-1,4-benzoxazin-3(4H)-one | 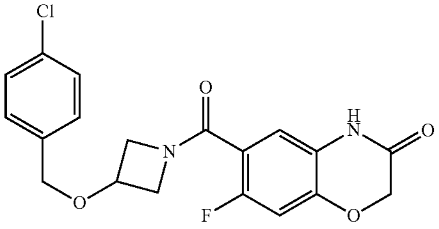 [SMILES: O=C1COc2cc(F)c(C(=O)N3CC(OCc4ccc(Cl)cc4)C3)cc2N1] | 391.1 |
| 344 | 6-((3-(1,3-benzothiazol-5-ylmethoxy) azetidin-1-yl)carbonyl)-7-fluoro-2H-1,4-benzoxazin-3(4H)-one | 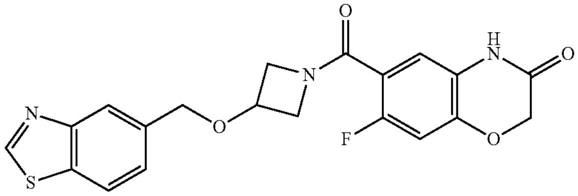 [SMILES: O=C1COc2cc(F)c(C(=O)N3CC(OCc4ccc5scnc5c4)C3)cc2N1] | 414.1 |
| 345 | 7-fluoro-6-((3-((2-fluoro-4-(trifluoromethyl)benzyl)oxy) azetidin-1-yl)carbonyl)-2H-1,4-benzoxazin-3(4H)-one | 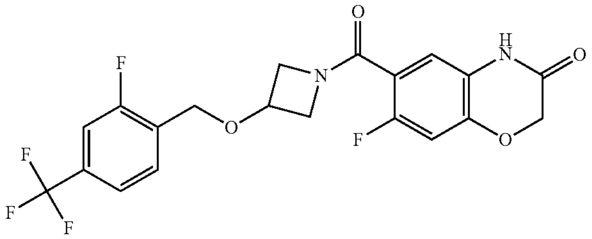 [SMILES: O=C1COc2cc(F)c(C(=O)N3CC(OCc4ccc(C(F)(F)F)cc4F)C3)cc2N1] | 443.2 |

TABLE 3-7-continued

| | | | |
|---|---|---|---|
| 346 | 7-fluoro-6-((3-(5,6,7,8-tetrahydronaphthalen-2-ylmethoxy)azetidin-1-yl)carbonyl)-2H-1,4-benzoxazin-3(4H)-one | 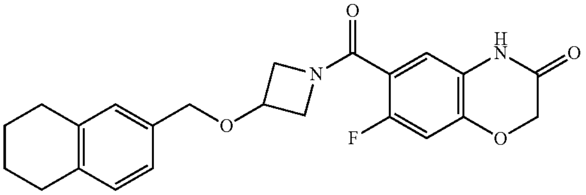 [SMILES: O=C1COc2cc(F)c(C(=O)N3CC(OCc4ccc5c(c4)CCCC5)C3)cc2N1] | 411.2 |

TABLE 3-8

| | | | |
|---|---|---|---|
| 347 | 6-((3-((2-chloro-4-methoxybenzyl)oxy)azetidin-1-yl)carbonyl)-7-fluoro-2H-1,4-benzoxazin-3(4H)-one | 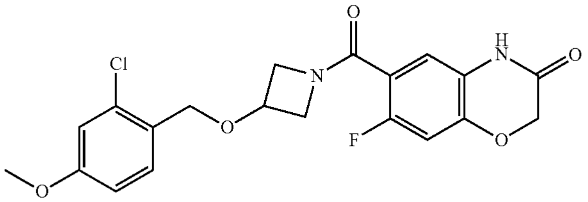 [SMILES: COc1ccc(COC2CN(C(=O)c3cc4c(cc3F)OCC(=O)N4)C2)c(Cl)c1] | 421.0 |
| 348 | 7-fluoro-6-((3-((3-fluoro-4-methoxybenzyl)oxy)azetidin-1-yl)carbonyl)-2H-1,4-benzoxazin-3(4H)-one | 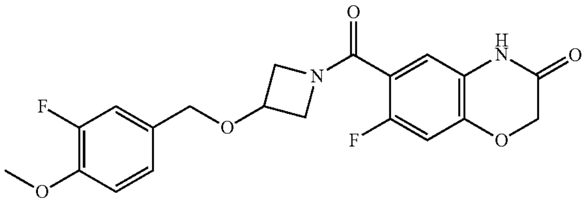 [SMILES: COc1ccc(COC2CN(C(=O)c3cc4c(cc3F)OCC(=O)N4)C2)cc1F] | 405.1 |
| 349 | 6-((3-((4-chloro-2-fluorobenzyl)oxy)azetidin-1-yl)carbonyl)-7-fluoro-2H-1,4-benzoxazin-3(4H)-one | 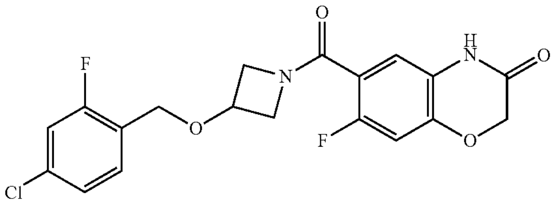 [SMILES: O=C1COc2cc(F)c(C(=O)N3CC(OCc4ccc(Cl)cc4F)C3)cc2N1] | 409.1 |
| 350 | 7-fluoro-6-((3-((2-fluoro-4-methylbenzyl)oxy)azetidin-1-yl)carbonyl)-2H-1,4-benzoxazin-3(4H)-one | 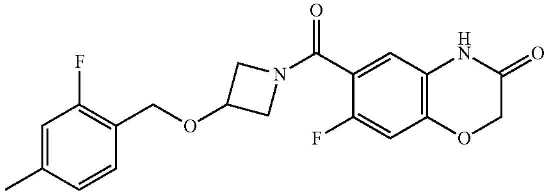 [SMILES: Cc1ccc(COC2CN(C(=O)c3cc4c(cc3F)OCC(=O)N4)C2)c(F)c1] | 389.2 |
| 351 | 7-fluoro-6-((3-((3-fluoro-4-(trifluoromethyl)benzyl)oxy)azetidin-1-yl)carbonyl)-2H-1,4-benzoxazin-3(4H)-one | 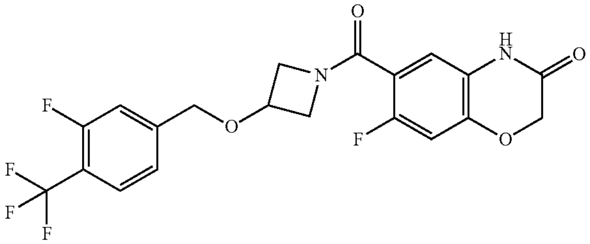 [SMILES: O=C1COc2cc(F)c(C(=O)N3CC(OCc4ccc(C(F)(F)F)c(F)c4)C3)cc2N1] | 443.1 |
| 352 | 6-((3-((4-(difluoromethyl)-2-fluorobenzyl)oxy)azetidin-1-yl)carbonyl)-7-fluoro-2H-1,4-benzoxazin-3(4H)-one | 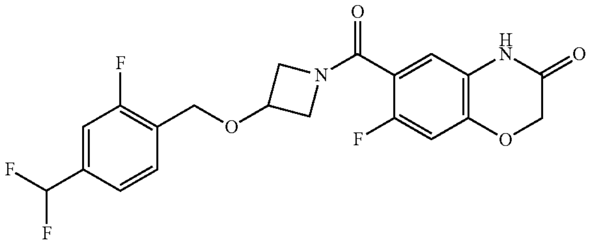 [SMILES: O=C1COc2cc(F)c(C(=O)N3CC(OCc4ccc(C(F)F)cc4F)C3)cc2N1] | 425.1 |

TABLE 3-8-continued

| | | | |
|---|---|---|---|
| 353 | 6-((3-((2-chloro-4-(3-fluoroazetidin-1-yl)benzyl)oxy)azetidin-1-yl)carbonyl)-7-fluoro-2H-1,4-benzoxazin-3(4H)-one | 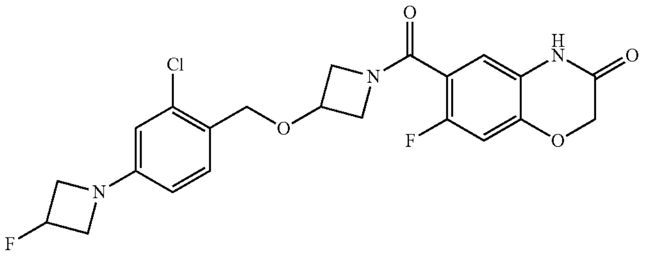 [SMILES: O=C1COc2cc(F)c(C(=O)N3CC(OCc4ccc(N5CC(F)C5)cc4Cl)C3)cc2N1] | 464.2 |
| 354 | 7-fluoro-6-((3-(1-(4-fluorophenyl)ethoxy)azetidin-1-yl)carbonyl)-2H-1,4-benzoxazin-3(4H)-one | 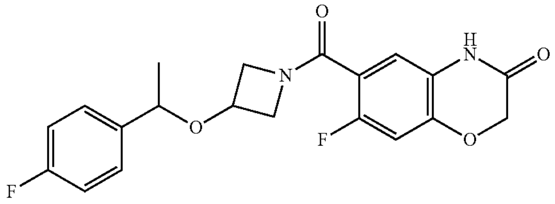 [SMILES: CC(OC1CN(C(=O)c2cc3c(cc2F)OCC(=O)N3)C1)c1ccc(F)cc1] | 389.1 |
| 355 | 6-((4-(difluoro(4-fluorophenyl)methyl)piperidin-1-yl)carbonyl)-2H-1,4-benzoxazin-3(4H)-one | 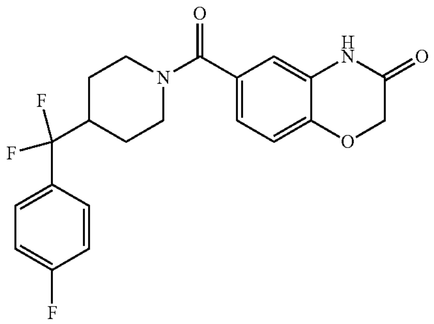 [SMILES: O=C1COc2ccc(C(=O)N3CCC(C(F)(F)c4ccc(F)cc4)CC3)cc2N1] | 405.1 |

TABLE 3-9

| | | | |
|---|---|---|---|
| 356 | 6-((3-(2-(2-chloro-4-fluorophenyl)-2,2-difluoroethyl)azetidin-1-yl)carbonyl)-7-fluoro-2H-1,4-benzoxazin-3(4H)-one | 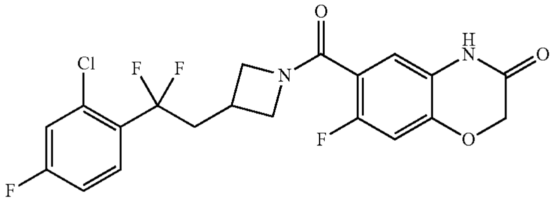 [SMILES: O=C1COc2cc(F)c(C(=O)N3CC(CC(F)(F)c4ccc(F)cc4Cl)C3)cc2N1] | 443.2 |

The compounds of Reference Examples 1 to 6 in the following table can also be produced according to the methods described in the above-mentioned Examples, or methods analogous thereto.

TABLE 4

| Ex. No. | IUPAC NAME | STRUCTURE |
|---|---|---|
| 1 | 4-methyl-6-((4-(phenoxymethyl)piperidin-1-yl)carbonyl)-2H-1,4-benzoxazin-3(4H)-one | 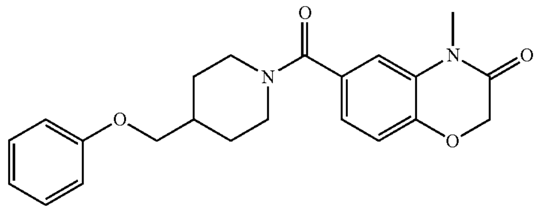 [SMILES: CN1C(=O)COc2ccc(C(=O)N3CCC(COc4ccccc4)CC3)cc21] |

TABLE 4-continued

| Ex. No. | IUPAC NAME | STRUCTURE |
|---|---|---|
| 2 | 3,4-dihydro-2H-1,4-benzoxazin-6-yl(4-(phenoxymethyl) piperidin-1-yl) methanone | 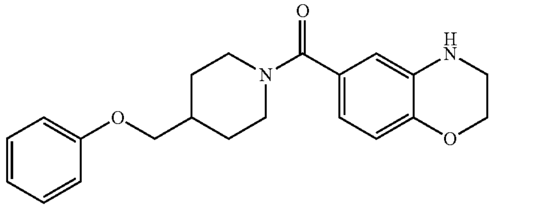 [SMILES: O=C(c1ccc2c(c1)NCCO2)N1CCC(COc2ccccc2)CC1] |
| 3 | 5-(3-oxo-3-(4-(phenoxymethyl) piperidin-1-yl) propyl)morpholin-3-one | 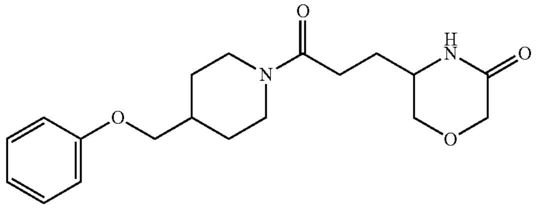 [SMILES: O=C1COCC(CCC(=O)N2CCC(COc3ccccc3)CC2)N1] |
| 4 | 7-((4-((2-chloro-4-fluorophenoxy)methyl) piperidin-1-yl)carbonyl)-1,4-dihydro-2H-3,1-benzoxazin-2-one | 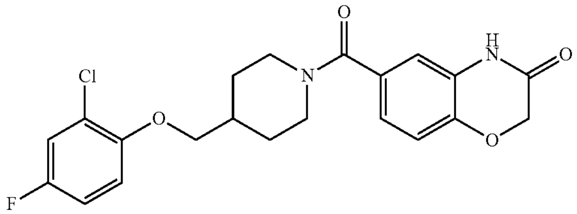 [SMILES: O=C1COc2ccc(C(=O)N3CCC(COc4ccc(F)cc4Cl)CC3)cc2N1] |
| 5 | 6-((4-((2-chloro-4-fluorophenoxy)methyl) piperidin-1-yl)carbonyl)-1H-thieno[2,3-b][1,4] oxazin-2(3H)-one | 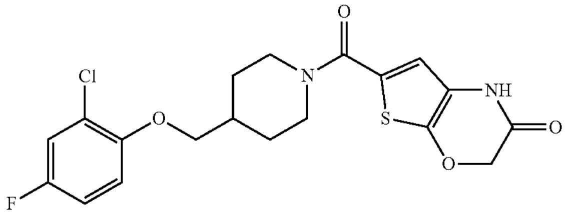 [SMILES: O=C1COc2sc(C(=O)N3CCC(COc4ccc(F)cc4Cl)CC3)cc2N1] |
| 6 | 6-((4-((2-chloro-4-fluorophenoxy)methyl) piperidin-1-yl)carbonyl)-2H-thieno[3,2-b][1,4] oxazin-3(4H)-one | 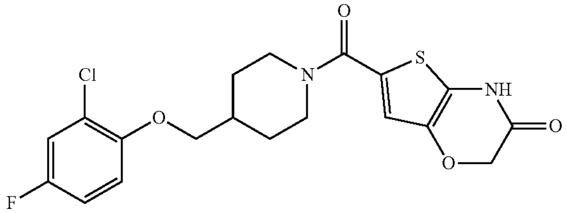 [SMILES: O=C1COc2cc(C(=O)N3CCC(COc4ccc(F)cc4Cl)CC3)sc2N1] |

Experimental Example 1: Cloning of Human MGLL Encoding MAGL Protein and Construction of Expression Plasmid Human MGLL cDNA was obtained by PCR using human ORF Clone (DNAForm; Clone ID: 100004585) as a template. For PCR, two kinds of primers:

```
                                    [SEQ ID NO: 1]
5'-CCACCATCATCACGGATCCATGCCAGAGGAAAGTTCCCCCA-3'
and

                                    [SEQ ID NO: 2]
5'-TGGTGCTCGAGTGCGGCCGCTCAGGGTGGGGACGCAGTTC-3'
```

and PrimeSTAR MAX DNA Polymerase (Takara Bio Inc.) were used, and (1) reaction at 98° C. for 1 min, (2) 25 cycles of reaction at 98° C. for 10 sec and 68° C. for 10 sec as one cycle, and (3) reaction at 72° C. for 1 min were performed. The obtained PCR product was digested with Bam HI and Not I (Takara Bio Inc.), inserted into the Bam HI/Not I site of pET21HH(V) (pET21a (Novagen) inserted with His ×6 and TEV Protease recognition sequence) by using Ligation High (Toyobo Co., Ltd.), and introduced into ECOS™ JM109 (Nippon Gene Co., Ltd.), whereby expression plasmid pET21HH(V)/His-hMGLLv2 for *Escherichia coli* was constructed.

Experimental Example 2: Preparation of Recombinant Polyhistidine Tagged Human MAGL Protein Recombinant His-hMAGL protein was prepared by transforming ECOS™ Competent *E. coli* BL21(DE3) (Nippon Gene Co., Ltd.) with the pET21HH(V)/His-hMGLLv2 plasmid prepared above. *Escherichia coli* obtained by transformation was inoculated to 10 mL of LB medium (1% peptone, 0.5% yeast extract, 0.5% sodium chloride, 0.01% ampicillin), and cultured at 30° C. for 16 hr. The obtained culture medium (5 mL) was transplanted into a 2 L Sakaguchi flask containing 1 L of main fermentation medium (1.05% M9 MEDIUM BROTH (AMRESCO LLC), 0.5% yeast extract, 1.5% sorbitol, 1.5% casamino acid, 0.024% magnesium sulfate, 0.01% antifoaming agent PE-L (Wako Pure Chemical Industries, Ltd.), 0.01% ampicillin), and shaking culture at 37° C. and 150 rpm was started. When the turbidity of the culture medium reached about 500 Klett unit, the culture temperature was lowered to 16° C., isopropyl-β-D-thiogalactopyranoside (IPTG) was added to a final concentration of 1 mM, and the mixture was further cultured for 19 hr. After the completion of culture, the culture medium was centrifuged (4° C., 6,000 rpm, 10 min) to give His-hMAGL-expressed *Escherichia coli*. Then, the His-hMAGL-expressed *Escherichia coli* was suspended in 50 mM Tris-HCl (pH 8.0, 100 ml) containing 1% Triton X-100, 20 mM imidazole, 3 mM DTT, 5 U/mL Benzonase (Merck) and 150 mM NaCl, and the suspension was sufficiently cooled, and subjected to sonication at AMPLITUDE=60%, 15 sec/ON, 30 sec/OFF for 3 min using ¾" solid type crushed horn of BRANSON Digital Sonifier 450 (Central Scientific Commerce, Inc.). Furthermore, the homogenate was centrifuged (4° C., 6,000 rpm, 20 min) and the supernatant was obtained. As the purification apparatus, AKTA explorer 10 s (GE Healthcare Japan Corporation) was used at 4° C. To the obtained supernatant was added 5M NaCl to the final salt concentration of 0.3 M, and the mixture was flown through and adsorbed to 5 mL of Ni-NTA Superflow Cartridges (QIAGEN) equilibrated in advance with buffer A (50 mM Tris-HCl (pH 8.0) containing 0.05% TritonX-100, 1 mM DTT, 300 mM NaCl). The column was sufficiently washed with buffer A containing 20 mM imidazole and His-hMAGL was eluted with buffer A containing imidazole at a final concentration of 250 mM. The eluate was further subjected to gel filtration using HiLoad 16/600 Superdex 200 pg (GE Healthcare Japan Corporation) equilibrated with 50 mM Tris-HCl pH 8.0 containing 10% glycerol, 0.05% TritonX-100, 1 mM DTT and 150 mM NaCl. The eluted fraction was concentrated by Amicon Ultra-15 10K (Merck Millipore) to give purified His-hMAGL protein. The protein concentration was measured by BCA Protein Assay Kit (Thermo Fisher Scientific) using BSA as the standard.

Experimental Example 3: Measurement of MAGL Inhibitory Activity

The His-hMAGL obtained above was diluted with enzyme reaction buffer (10 mM Tris-HCl, pH 7.5, 1 mM EDTA, 0.025 (w/v) % Triton X-100, 0.01% Bovine serum albumin) to a concentration of 7.5 ng/mL. To each well of a 384 well assay plate (Greiner 781280) was added a solution (5 μL) of a test compound dissolved in dimethyl sulfoxide (DMSO), which was diluted with the above-mentioned enzyme reaction buffer, then His-hMAGL solution (5 μL) diluted to a concentration of 7.5 ng/mL was added and the mixture was incubated at room temperature for 60 min. Thereafter, to each well was added 5 μL of 150 μM 2-arachidonylglycerol (Tocris Bioscience), and the mixture was incubated at room temperature for 10 min. Then, 10 μL of 2% formic acid (Wako Pure Chemical Industries, Ltd.) was added to stop the reaction. Furthermore, acetonitrile (50 μL) containing 3 μM arachidonic acid-d8 (Cayman Chemical Company) was added and the mixture was stirred.

The amount of arachidonic acid in the obtained enzyme reaction mixture was calculated by measuring by RapidFire-mass spectrometry and correcting by the amount of arachidonic acid-d8. High Throughput online solid phase extraction was performed using RapidFire 300™ system (Agilent Technologies, Inc.). Samples were loaded on SPE C4 cartridge (Agilent Technologies, Inc.) and desalted with 0.2 (v/v) % acetic acid (Wako Pure Chemical Industries, Ltd.) in ultrapure water/acetonitrile (70/30, v/v) at a flow rate of 1.5 mL/min, eluted at a flow rate of 0.5 mL/min with 0.2 (v/v) % acetic acid dissolved in acetonitrile/ultrapure water (90/10, v/v), and injected into the mass spectrometry part. The injection needle was washed with ultrapure water (500 millisecond) and acetonitrile (500 millisecond) to minimize carry-over. The suction time (injection loop 5 μL), load/cleansing time, elution time and re-equilibration time were adjusted to 300, 3000, 4250 and 1000 milliseconds, respectively, and the total cycle time was adjusted to about 10.0 seconds. The RapidFire300 system was controlled by RapidFire UI software version 3.6 (Agilent Technologies, Inc.).

The mass spectrometry of the resultant product was performed using API4000™ triple quadrupole mass spectrometer (AB SCIEX) equipped with an electrospray ion sauce (TurboIon Spray™) in a negative selected reaction monitoring (SRM) mode. The conditions of SRM are shown below. The parameters of the instrument were optimized as follows: capillary temperature 600° C., ion spray voltage −4.5 kV, collision gas 8, curtain gas 15 psi, ion source gas 1 60 psi, ion source gas 2 60 psi. The mass spectrometer was controlled by Analyst™ software version 1.5.1 (AB SCIEX). The peak area integration was analyzed using RapidFire integrator software version 3.6 (Agilent Technologies, Inc.).

MAGL inhibitory rate (%) was calculated according to the following calculation formula.

(1−(arachidonic acid production amount of test compound addition group−arachidonic acid production amount of enzyme−free group)÷(arachidonic acid production amount of test compound-free group−arachidonic acid production amount of enzyme-free group))×100

The results are shown in the following Table 5.

TABLE 5

| Example | % inhibition (10 μM) |
|---|---|
| 6 | 98 |
| 7 | 100 |
| 12 | 99 |
| 13 | 99 |
| 14 | 80 |
| 17 | 101 |
| 18 | 100 |
| 19 | 100 |
| 20 | 99 |
| 21 | 99 |
| 22 | 95 |
| 23 | 100 |
| 24 | 101 |
| 25 | 100 |
| 26 | 101 |
| 27 | 101 |
| 28 | 100 |
| 29 | 96 |
| 30 | 98 |
| 31 | 97 |
| 32 | 99 |
| 33 | 99 |
| 34 | 98 |
| 35 | 98 |
| 36 | 104 |
| 37 | 101 |
| 38 | 84 |

TABLE 5-continued

| Example | % inhibition (10 μM) |
|---|---|
| 39 | 100 |
| 40 | 95 |
| 41 | 103 |
| 42 | 99 |
| 43 | 100 |
| 44 | 90 |
| 45 | 98 |
| 46 | 98 |
| 47 | 98 |
| 48 | 89 |
| 49 | 92 |
| 52 | 102 |
| 53 | 96 |
| 54 | 98 |
| 55 | 96 |
| 56 | 101 |
| 57 | 99 |
| 58 | 100 |
| 59 | 102 |
| 60 | 92 |
| 61 | 94 |
| 62 | 86 |
| 63 | 93 |
| 64 | 101 |
| 65 | 96 |
| 66 | 104 |
| 67 | 101 |
| 68 | 96 |
| 69 | 99 |
| 70 | 100 |
| 71 | 100 |
| 72 | 100 |
| 73 | 102 |
| 74 | 102 |
| 75 | 102 |
| 76 | 105 |
| 77 | 105 |
| 78 | 100 |
| 79 | 103 |
| 80 | 100 |
| 81 | 99 |
| 82 | 101 |
| 83 | 86 |
| 84 | 97 |
| 85 | 102 |
| 86 | 98 |
| 87 | 102 |
| 88 | 96 |
| 89 | 90 |
| 90 | 98 |
| 91 | 99 |
| 92 | 99 |
| 93 | 100 |
| 94 | 97 |
| 95 | 97 |
| 96 | 100 |
| 97 | 100 |
| 98 | 99 |
| 99 | 99 |
| 100 | 98 |
| 101 | 99 |
| 102 | 102 |
| 103 | 102 |
| 104 | 100 |
| 105 | 97 |
| 106 | 101 |
| 107 | 101 |
| 108 | 99 |
| 109 | 103 |
| 110 | 97 |
| 111 | 98 |
| 112 | 101 |
| 113 | 101 |
| 114 | 99 |
| 115 | 103 |
| 116 | 103 |
| 117 | 102 |
| 118 | 99 |

TABLE 5-continued

| Example | % inhibition (10 μM) |
|---|---|
| 119 | 102 |
| 120 | 101 |
| 121 | 99 |
| 122 | 102 |
| 123 | 102 |
| 124 | 100 |
| 125 | 98 |
| 126 | 102 |
| 127 | 99 |
| 128 | 93 |
| 129 | 99 |
| 130 | 103 |
| 131 | 101 |
| 132 | 99 |
| 133 | 98 |
| 134 | 102 |
| 135 | 101 |
| 136 | 98 |
| 137 | 99 |
| 138 | 100 |
| 139 | 92 |
| 140 | 100 |
| 141 | 102 |
| 142 | 102 |
| 143 | 100 |
| 144 | 98 |
| 145 | 88 |
| 146 | 97 |
| 147 | 102 |
| 148 | 102 |
| 149 | 85 |
| 150 | 100 |
| 151 | 92 |
| 152 | 101 |
| 153 | 100 |
| 154 | 95 |
| 155 | 101 |
| 156 | 100 |
| 157 | 100 |
| 158 | 103 |
| 159 | 103 |
| 160 | 100 |
| 161 | 102 |
| 162 | 102 |
| 163 | 100 |
| 164 | 102 |
| 165 | 103 |
| 166 | 98 |
| 167 | 100 |
| 168 | 101 |
| 169 | 97 |
| 170 | 104 |
| 171 | 98 |
| 172 | 100 |
| 173 | 98 |
| 174 | 102 |
| 175 | 97 |
| 176 | 95 |
| 177 | 91 |
| 178 | 94 |
| 179 | 100 |
| 180 | 96 |
| 181 | 99 |
| 182 | 98 |
| 183 | 99 |
| 184 | 100 |
| 185 | 100 |
| 186 | 97 |
| 187 | 98 |
| 188 | 97 |
| 189 | 102 |
| 190 | 102 |
| 191 | 102 |
| 192 | 99 |
| 193 | 102 |
| 194 | 103 |
| 195 | 101 |
| 196 | 94 |

TABLE 5-continued

| Example | % inhibition (10 μM) |
|---|---|
| 197 | 104 |
| 198 | 100 |
| 199 | 103 |
| 200 | 102 |
| 201 | 101 |
| 202 | 100 |
| 203 | 103 |
| 204 | 100 |
| 205 | 103 |
| 206 | 104 |
| 207 | 100 |
| 208 | 98 |
| 209 | 101 |
| 210 | 101 |
| 211 | 101 |
| 212 | 94 |
| 213 | 100 |
| 214 | 104 |
| 215 | 99 |
| 216 | 97 |
| 217 | 104 |
| 218 | 99 |
| 219 | 101 |
| 220 | 102 |
| 221 | 102 |
| 222 | 101 |
| 223 | 102 |
| 224 | 103 |
| 225 | 85 |
| 226 | 101 |
| 227 | 97 |
| 228 | 94 |
| 229 | 88 |
| 230 | 95 |
| 231 | 100 |
| 232 | 99 |
| 233 | 100 |
| 234 | 97 |
| 235 | 100 |
| 236 | 99 |
| 237 | 99 |
| 238 | 99 |
| 239 | 100 |
| 240 | 102 |
| 241 | 101 |
| 242 | 100 |
| 243 | 101 |
| 244 | 100 |
| 245 | 96 |
| 246 | 96 |
| 247 | 96 |
| 248 | 98 |
| 249 | 101 |
| 250 | 101 |
| 251 | 100 |
| 252 | 99 |
| 253 | 102 |
| 254 | 102 |
| 255 | 102 |
| 256 | 98 |
| 257 | 99 |
| 258 | 98 |
| 259 | 100 |
| 260 | 100 |
| 261 | 98 |
| 262 | 98 |
| 263 | 97 |
| 264 | 101 |
| 265 | 99 |
| 266 | 99 |
| 267 | 101 |
| 268 | 101 |
| 269 | 101 |
| 270 | 101 |
| 271 | 95 |
| 272 | 100 |
| 273 | 101 |
| 274 | 102 |

TABLE 5-continued

| Example | % inhibition (10 μM) |
|---|---|
| 275 | 99 |
| 276 | 97 |
| 277 | 104 |
| 278 | 103 |
| 279 | 101 |
| 280 | 102 |
| 281 | 100 |
| 282 | 99 |
| 283 | 101 |
| 284 | 96 |
| 285 | 98 |
| 286 | 98 |
| 287 | 100 |
| 288 | 101 |
| 289 | 88 |
| 290 | 100 |
| 291 | 100 |
| 292 | 100 |
| 293 | 102 |
| 294 | 99 |
| 295 | 101 |
| 296 | 101 |
| 297 | 99 |
| 298 | 99 |
| 299 | 100 |
| 300 | 102 |
| 301 | 99 |
| 302 | 102 |
| 303 | 103 |
| 304 | 99 |
| 305 | 100 |
| 306 | 100 |
| 308 | 104 |
| 309 | 98 |
| 310 | 99 |
| 311 | 103 |
| 312 | 101 |
| 313 | 103 |
| 314 | 98 |
| 315 | 102 |
| 316 | 102 |
| 317 | 100 |
| 318 | 100 |
| 319 | 101 |
| 320 | 100 |
| 322 | 101 |
| 323 | 99 |
| 324 | 102 |
| 325 | 101 |
| 326 | 98 |
| 327 | 99 |
| 328 | 101 |
| 329 | 100 |
| 330 | 102 |
| 331 | 100 |
| 332 | 98 |
| 333 | 101 |
| 334 | 98 |
| 335 | 102 |
| 336 | 101 |
| 337 | 92 |
| 338 | 101 |
| 339 | 103 |
| 340 | 100 |
| 341 | 101 |
| 342 | 102 |
| 343 | 102 |
| 344 | 99 |
| 345 | 101 |
| 346 | 101 |
| 347 | 102 |
| 348 | 100 |
| 349 | 100 |
| 350 | 101 |
| 351 | 99 |
| 352 | 101 |
| 353 | 100 |
| 354 | 102 |

TABLE 5-continued

| Example | % inhibition (10 μM) |
|---|---|
| 355 | 101 |
| 356 | 102 |

Experimental Example 4: Measurement of Intracerebral 2-AG and Arachidonic Acid Concentrations As the mouse, 8-week-old male C57BL/6J mice (CLEA Japan, Inc.) were used (6 mice/group). Administration solutions were prepared by suspending the test compounds (compound 1 (compound of Example 102), compound 2 (compound of Example 188) and compound 3 (compound of Example 322)) in 0.5% methylcellulose solution (Wako Pure Chemical Industries, Ltd.). The dose of the test compound was adjusted to be 10 mg/kg/10 mL. The test compounds were administered by gavage at 10 mg/kg. The cerebrum was isolated after the administration of the test compound (isolation time after the administration of the test compound is shown in Table 6), and the cerebrum hemisphere was extracted. The obtained cerebrum hemisphere was frozen on dry ice, and the frozen tissue weight was measured.

The cerebral tissue weight was measured, and the cerebral tissue was homogenized with 9-fold (v/w) of isopropanol (IPA) relative to the cerebral tissue weight. The prepared cerebral homogenate was centrifuged at 15000 rpm for 5 min, and the supernatant (5 μL) was mixed with internal standard solution (95 μL) ([5,6,8,9,11,12,14,15-D8]-(5Z,8Z,11Z,14Z)5,8,11,14-eicosatetraenoic acid (AA-$d_8$, 0.5 nmol/mL IPA) and [5,6,8,9,11,12,14,15-D8]-(5Z,8Z,11Z,14Z)-5,8,11,14-eicosatetraenoyl-2-glycerol ester (2-AG-$d_8$, 0.5 nmol/mL IPA)) to give a sample solution. The sample solution (5 μL) was injected to liquid chromatography mass spectrometer to perform quantitative analysis.

For liquid chromatography, Shimadzu LC20A system (Shimadzu Corporation) was used. The separation was performed by gradient elution method with mobile phase A (0.01% acetic acid-1 mM ammonia-2 μM disodium ethylenediaminetetraacetate/water) and mobile phase B (0.01% acetic acid-0.2 mM ammonia/ethanol-isopropanol (3:2, v/v)) using XBridge C18 (2.5 μm, 2.1×50 mm, Waters) at column temperature of 60° C., at flow rate of 0.3 mL/min. The gradient conditions are as follows: 0-1 min, 1% B; 1-1.2 min, 1-55% B; 1.2-2.7 min, 55-75% B; 2.7-3.5 min, 75-99% B; 3.5-6 min, 99% B; 6-8 min, 1% B.

For mass spectrometer, QTRAP5500 (AB SCIEX) was used. The eluate from the liquid chromatography was directly ionized by turbospray ionization method, where (5Z,8Z,11Z,14Z)5,8,11,14-eicosatetraenoic acid (AA) and AA-$d_8$ were measured by negative ionization mode, and (5Z,8Z,11Z,14Z)5,8,11,14-eicosatetraenoyl-2-glycerol ester (2-AG) and 2-AG-$d_8$ were measured by positive ionization mode. Detection conditions of the mass spectrometer are shown in Table 7.

A solution for calibration curve was prepared to the final concentration of 0.025, 0.05, 0.1, 0.25, 0.5, 1.25, 2.5, 5 nmol/mL of IPA. These solutions were mixed with 95 μL of internal standard solution, and the mixture (5 μL) was injected to liquid chromatography mass spectrometer to perform analysis. The calibration curve was drawn by regression line with a weighting of 1/x, and the quantitativity was confirmed by accuracy of 100±15% and $R^2$>0.995.

Figure 2:
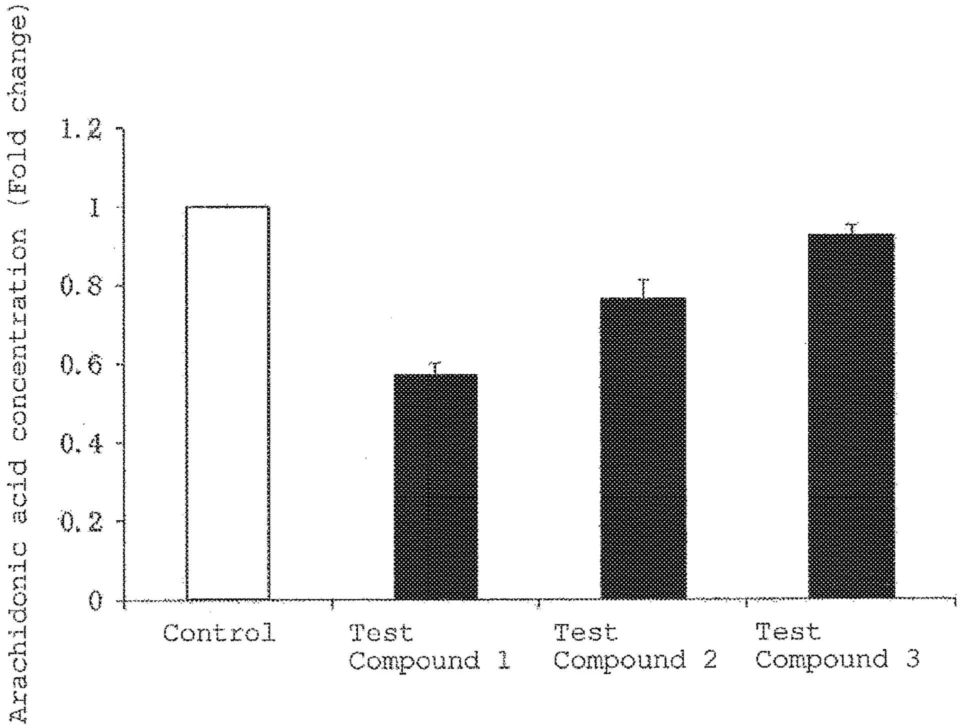
FIG. 2 shows changes in AA concentrations of compounds 1 to 3 in Experimental Example 4.

The changes in 2-AG and arachidonic acid concentrations were calculated by the following formula. the concentration of test compound administration group/the concentration of control group The results are shown in FIG. 1 and FIG. 2.

TABLE 6

| test compound | isolation time after the administration of test compound (hour) |
|---|---|
| compound 1 | 2 |
| compound 2 | 4 |
| compound 3 | 1 |

TABLE 7

| mass spectrometer parameter | | | | | | | | |
|---|---|---|---|---|---|---|---|---|
| target molecule | polarity | Q1 | Q3 | retention time (msec) | DP (V) | EP (V) | CE (V) | CXP (V) |
| arachidonic acid | − | 303.2 | 205.2 | 20 | −90 | −11 | −17 | −15 |
| arachidonic acid-d8 | − | 311.3 | 267.3 | 20 | −90 | −4 | −19 | −10 |
| 2-arachidonyl glycerol | + | 379.3 | 91 | 20 | 170 | 4.3 | 68 | 41 |
| 2-arachidonyl glycerol-d8 | + | 387.3 | 294.3 | 20 | 150 | 10 | 19 | 15 |

DP: declustering potential
EP: entrance potential
CE: cleavage energy
CXP: collision cell exit potential

Formulation Examples

Medicaments containing the compound of the present invention as an active ingredient can be produced, for example, by the following formulations.

1. Capsule

| | |
|---|---|
| (1) compound obtained in Example 1 | 10 mg |
| (2) lactose | 90 mg |
| (3) microcrystalline cellulose | 70 mg |
| (4) magnesium stearate | 10 mg |
| 1 capsule | 180 mg |

The total amount of the above-mentioned (1), (2) and (3) and 5 mg of (4) are blended and granulated, and 5 mg of the remaining (4) is added. The whole mixture is sealed in a gelatin capsule.

2. Tablet

| | |
|---|---|
| (1) compound obtained in Example 1 | 10 mg |
| (2) lactose | 35 mg |
| (3) cornstarch | 150 mg |
| (4) microcrystalline cellulose | 30 mg |
| (5) magnesium stearate | 5 mg |
| 1 tablet | 230 mg |

The total amount of the above-mentioned (1), (2) and (3), 20 mg of (4) and 2.5 mg of (5) are blended and granulated, and 10 mg of the remaining (4) and 2.5 mg of the remaining (5) are added and the mixture is compression formed to give a tablet.

INDUSTRIAL APPLICABILITY

According to the present invention, a compound having an MAGL inhibitory action, which is expected to be useful as an agent for the prophylaxis or treatment of neurodegenerative diseases (e.g., Alzheimer's disease, Parkinson's disease, Huntington's disease, amyotrophic lateral sclerosis, traumatic brain injury, glaucoma, multiple sclerosis etc.), anxiety disorder, pains (e.g., inflammatory pain, cancerous pain, neurogenic pain etc.), epilepsy, depression and the like can be provided.

This application is based on patent application No. 2015-067930 filed on Mar. 30, 2015 in Japan and No. 2015-169733 filed on Aug. 28, 2015 in Japan, the contents of which are encompassed in full herein.

SEQUENCE LISTING

<110> TAKEDA PHARMACEUTICAL COMPANY LIMITED
<120> HETEROCYCLIC COMPOUND
<130> 092445
<150> JP 2015-067930
<151>2015-3-30
<150> JP 2015-169733
<151>2015-8-28
<160>2
<170> PatentIn version 3.5
<210>1
<211>41
<212> DNA
<213> Artificial Sequence
<220>
<223> primer
<400>1
ccaccatcat cacggatcca tgccagagga aagttccccc a 41
<210>2
<211>40
<212> DNA
<213> Artificial Sequence
<220>
<223> primer
<400>2
tggtgctcga gtgcggccgc tcagggtggg gacgcagttc 40

```
SEQUENCE LISTING

<160> NUMBER OF SEQ ID NOS: 2

<210> SEQ ID NO 1
<211> LENGTH: 41
<212> TYPE: DNA
<213> ORGANISM: Artificial Sequence
<220> FEATURE:
<223> OTHER INFORMATION: primer

<400> SEQUENCE: 1

ccaccatcat cacggatcca tgccagagga aagttccccc a                41


<210> SEQ ID NO 2
<211> LENGTH: 40
<212> TYPE: DNA
<213> ORGANISM: Artificial Sequence
<220> FEATURE:
<223> OTHER INFORMATION: primer

<400> SEQUENCE: 2

tggtgctcga gtgcggccgc tcagggtggg gacgcagttc                 40
```

The invention claimed is:

1. A compound represented by the formula (I):

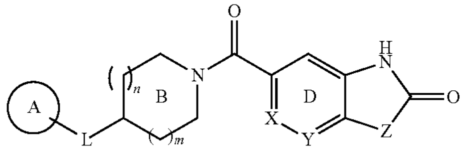

(I)

wherein m and n are each independently 0 or 1,

Ring A is an optionally further substituted cyclic group,

Ring B is an azetidine ring, a pyrrolidine ring or a piperidine ring, each of which is an optionally further substituted, Ring D is an optionally further substituted 6-membered aromatic ring, L is —$CH_2$—O—$CH_2$—, —O—$CR^1R^2$—, —$CH(R^1)$—O—, —$CF_2$—$CH_2$—, —$CH_2$—$CF_2$— or —$CF_2$—, $R^1$ and $R^2$ is each independently a hydrogen atom, or an optionally substituted $C_{1-6}$ alkyl group, X and Y are each independently a carbon atom or a nitrogen atom, Z is —O—$CH_2$—, —NR—$CH_2$—, —$CH_2$—$CH_2$—, —CH═CH—, —$CH_2$—, —O—, —S— or —NR—, and R is a substituent, provided that 7-((4-(phenoxymethyl)piperidin-1-yl)carbonyl)-1H-pyrido[2,3-b][1,4]oxazin-2(3H)-one, 7-((4-((3-methoxyphenoxy)methyl)piperidin-1-yl)carbonyl)-1H-pyrido[2,3-b][1,4]oxazin-2(3H)-one, and 7-((4-((2-methoxyphenoxy)methyl)piperidin-1-yl)carbonyl)-1H-pyrido[2,3-b][1,4]oxazin-2(3H)-one are excluded, or a salt thereof.

2. A compound represented by the formula (I):

(I)

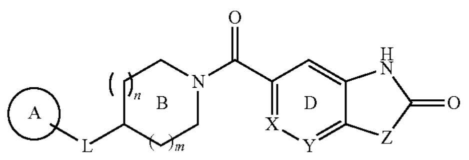

wherein m and n are each independently 0 or 1,

Ring A is an optionally further substituted cyclic group,

Ring B is an azetidine ring, a pyrrolidine ring or a piperidine ring, each of which is an optionally further substituted, Ring D is an optionally further substituted 6-membered aromatic ring, L is —$CH_2$—O—$CH_2$— or —O—$CH_2$—, X and Y are each independently a carbon atom or a nitrogen atom, Z is —O—$CH_2$—, —NR—$CH_2$—, —$CH_2$—$CH_2$—, —CH═CH—, —$CH_2$—, —O—, —S— or —NR—, and R is a substituent, provided that 7((4-(phenoxymethyl)piperidin-1-yl)carbonyl)-1H-pyrido[2,3-b][1,4]oxazin-2(3H)-one, 7-((4-((3-methoxyphenoxy)methyl)piperidin-1-yl)carbonyl)-1H-pyrido [2,3-b][1,4]oxazin-2(3H)-one, and 7((44(2-methoxyphenoxy)methyl)piperidin-1-yl)carbonyl)-1H-pyrido [2,3-b][1,4]oxazin-2(3H)-one are excluded, or a salt thereof.

3. The compound or salt according to claim 1, wherein Ring B is an optionally further substituted azetidine ring, or an optionally further substituted piperidine ring.

4. The compound or salt according to claim 1, wherein Ring B is an optionally further substituted azetidine ring.

5. The compound or salt according to claim 1, wherein X and Y are both carbon atoms.

6. The compound or salt according to claim 1, wherein Z is —O—$CH_2$— or —O—.

7. The compound or salt according to claim 1, wherein L is —O—$CH_2$— or —$CH_2$—O—.

8. The compound or salt according to claim 1, wherein Ring A is (1) a $C_{6-14}$ aryl group which is optionally further substituted and optionally fused with a $C_{3-10}$ cycloalkane, (2) an optionally further substituted pyridyl group, (3) an optionally further substituted pyrimidinyl group, (4) an optionally further substituted imidazopyridyl group, (5) an optionally further substituted benzothiazolyl group, (6) an optionally further substituted indazolyl group, (7) an optionally further substituted pyrazolyl group, (8) an optionally further substituted benzoxazolyl group, (9) an optionally further substituted benzisoxazolyl group,

(10) an optionally further substituted quinoxalinyl group,

(11) an optionally further substituted quinolyl group,

(12) an optionally further substituted isoquinolyl group,

(13) an optionally further substituted pyrazolopyridyl group,

(14) an optionally further substituted $C_{3-10}$ cycloalkyl group,

(15) an optionally further substituted tetrahydropyranyl group,

(16) an optionally further substituted dihydrobenzofuryl group, or

(17) an optionally further substituted dihydropyranopyridyl group.

9. The compound or salt according to claim 1, wherein m and n are each independently 0 or 1;

Ring A is (1) a $C_{6-14}$ aryl group which is optionally fused with a $C_{3-10}$ cycloalkane wherein the $C_{6-14}$ aryl group is optionally further substituted by 1 to 3 substituents selected from (i) a halogen atom, (ii) an optionally halogenated $C_{1-6}$ alkoxy group, (iii) a cyano group, (iv) a $C_{1-6}$ alkyl group optionally substituted by 1 to 3 substituents selected from (a) a halogen atom, and (b) a hydroxy group, (v) a $C_{3-10}$ cycloalkyl group, (vi) a $C_{2-6}$ alkenyl group, (vii) a $C_{1-6}$ alkoxy-carbonyl group, (viii) a $C_{1-6}$ alkylsulfonyl group, (ix) a $C_{6-14}$ aryl group optionally substituted by 1 to 3 $C_{1-6}$ alkoxy groups, (x) a $C_{6-14}$ aryloxy group, (xi) a 5- to 14-membered aromatic heterocyclic group optionally substituted by 1 to 3 substituents selected from (a) a halogen atom, (b) a $C_{1-6}$ alkyl group optionally substituted by 1 to 3 halogen atoms, and (c) a $C_{3-10}$ cycloalkyl group, and (xii) a 3- to 14-membered non-aromatic heterocyclic group optionally substituted by 1 to 3 substituents selected from (a) a $C_{1-6}$ alkyl group, and (b) a halogen atom, (2) a 5- to 14-membered aromatic heterocyclic group optionally further substituted by 1 to 3 substituents selected from (i) a halogen atom, (ii) a $C_{1-6}$ alkyl group, (iii) an amino group, (iv) a $C_{1-6}$ alkyl-carbonyl group, (v) a $C_{6-14}$ aryl group optionally substituted by 1 to 3 halogen atoms, and
(vi) a 5- to 14-membered aromatic heterocyclic group optionally substituted by 1 to 3 $C_{1-6}$ alkyl groups,
(3) a $C_{3-10}$ cycloalkyl group optionally further substituted by 1 to 3 halogen atoms, or
(4) a 3- to 14-membered non-aromatic heterocyclic group optionally further substituted by 1 to 3 $C_{1-6}$ alkyl groups;
Ring B is
(1) an azetidine ring optionally further substituted by 1 to 3 substituents selected from
(i) a halogen atom, and
(ii) a $C_{1-6}$ alkyl group,
(2) a pyrrolidine ring, or
(3) a piperidine ring optionally further substituted by 1 to 3 substituents selected from
(i) a halogen atom,
(ii) a hydroxy group, and
(iii) a cyano group;
Ring D is
(1) a benzene ring optionally further substituted by 1 to 3 substituents selected from
(i) a halogen atom,
(ii) a $C_{1-6}$ alkyl group, and
(iii) a $C_{1-6}$ alkoxy group, or
(2) a pyridine ring optionally further substituted by 1 to 3 $C_{1-6}$ alkyl groups;
L is
(1) $—CH_2—O—CH_2—$,
(2) $—O—CR^1R^2—$ wherein $R^1$ and $R^2$ is each independently
(1) a hydrogen atom, or
(2) a $C_{1-6}$ alkyl group optionally substituted by one substituent selected from a hydroxy group and a $C_{1-6}$ alkoxy group,
(3) $—CH(R^1)—O—$ wherein $R^1$ is a hydrogen atom or a $C_{1-6}$ alkyl group,
(4) $—CF_2—CH_2—$, or
(5) $—CF_2—$;
X is a carbon atom or a nitrogen atom;
Y is a carbon atom or a nitrogen atom; and
Z is $—O—CH_2—$, $—CH_2—CH_2—$, $—CH{=}CH—$, $—CH_2—$ or $—O—$.

10. The compound or salt according to claim 1, wherein m and n are both 0 or both 1;
Ring A is
(1) a phenyl group further substituted by 1 to 3 substituents selected from
(i) a halogen atom,
(ii) a cyano group,
(iii) an optionally halogenated $C_{1-6}$ alkyl group,
(iv) a $C_{2-6}$ alkenyl group,
(v) a pyridyl group optionally substituted by 1 to 3 substituents selected from
(a) a halogen atom, and
(b) a $C_{1-6}$ alkyl group, and
(vi) an azetidinyl group optionally substituted by 1 to 3 halogen atoms,
(2) an indanyl group,
(3) a tetrahydronaphthyl group, or
(4) a pyridyl group optionally further substituted by 1 to 3 halogen atoms;
Ring B is
(1) an azetidine ring, or
(2) a piperidine ring optionally further substituted by 1 to 3 hydroxy groups;
Ring D is
(1) a benzene ring optionally further substituted by 1 to 3 substituents selected from
(i) a halogen atom,
(ii) a $C_{1-6}$ alkyl group, and
(iii) a $C_{1-6}$ alkoxy group, or
(2) a pyridine ring;
L is $—O—CH_2—$ or $—CH_2—O—$;
X is a carbon atom;
Y is a carbon atom or a nitrogen atom; and
Z is $—O—CH_2—$ or $—O—$.

11. The compound or salt according to claim 1, wherein m and n are both 0 or both 1;
Ring A is
(1) a phenyl group further substituted by 1 to 3 substituents selected from
(i) a halogen atom,
(ii) a cyano group,
(iii) an optionally halogenated $C_{1-6}$ alkyl group,
(iv) a pyridyl group optionally substituted by 1 to 3 substituents selected from
(a) a halogen atom, and
(b) a $C_{1-6}$ alkyl group, and
(v) an azetidinyl group optionally substituted by 1 to 3 halogen atoms,
(2) a tetrahydronaphthyl group, or
(3) a pyridyl group optionally further substituted by 1 to 3 halogen atoms;
Ring B is an azetidine ring or a piperidine ring;
Ring D is
(1) a benzene ring optionally further substituted by 1 to 3 halogen atoms, or
(2) a pyridine ring;
L is $—O—CH_2—$ or $—CH_2—O—$;
X is a carbon atom;
Y is a carbon atom or a nitrogen atom; and
Z is $—O—CH_2—$.

12. The compound or salt according to claim 1, wherein m and n are both 0;
Ring A is
(1) a phenyl group further substituted by 1 to 3 substituents selected from
(i) a pyridyl group optionally substituted by 1 to 3 substituents selected from
(a) a halogen atom, and
(b) a $C_{1-6}$ alkyl group, and
(ii) an azetidinyl group optionally substituted by 1 to 3 halogen atoms;
Ring B is an azetidine ring;
Ring D is a benzene ring further substituted by 1 to 3 halogen atoms;
L is $—O—CH_2—$ or $—CH_2—O—$;
X is a carbon atom;
Y is a carbon atom; and
Z is $—O—CH_2—$.

13. The compound or salt according to claim 1, wherein m and n are both 0;
Ring A is
(1) a phenyl group further substituted by 1 to 3 substituents selected from
(i) a halogen atom,
(ii) an optionally halogenated $C_{1-6}$ alkyl group, and
(iii) an azetidinyl group optionally substituted by 1 to 3 halogen atoms, or (2) a tetrahydronaphthyl group;

Ring B is an azetidine ring;

Ring D is a benzene ring further substituted by 1 to 3 halogen atoms;

L is —O—$CH_2$— or —$CH_2$—O—;

X is a carbon atom;

Y is a carbon atom; and

Z is —O—$CH_2$—.

14. 7-Fluoro-6-((3-((5,6,7,8-tetrahydronaphthalen-2-yloxy)methyl)azetidin-1-yl)carbonyl)-2H-1,4-benzoxazin-3(4H)-one, or a salt thereof.

15. 7-Fluoro-6-((3-((2-fluoro-4-(trifluoromethyl)phenoxy)methyl)azetidin-1-yl)carbonyl)-2H-1,4-benzoxazin-3(4H)-one, or a salt thereof.

16. 6-((3-((2-Chloro-4-(3-fluoroazetidin-1-yl)phenoxy)methyl)azetidin-1-yl)carbonyl)-7-fluoro-2H-1,4-benzoxazin-3(4H)-one, or a salt thereof.

17. 6-((3-((2-Chloro-4-fluorobenzyl)oxy)azetidin-1-yl)carbonyl)-7-fluoro-2H-1,4-benzoxazin-3(4H)-one, or a salt thereof.

18. A medicament comprising a compound represented by the formula (I):

(I)

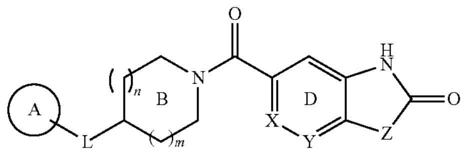

wherein m and n are each independently 0 or 1,

Ring A is an optionally further substituted cyclic group,

Ring B is an azetidine ring, a pyrrolidine ring or a piperidine ring, each of which is an optionally further substituted, Ring D is an optionally further substituted 6-membered aromatic ring, L is —$CH_2$—O—$CH_2$—, —O—$CR'R^2$—, —$CH(R^1)$—O—, —$CF_2$—$CH_2$—, —$CH_2$—$CF_2$— or —$CF_2$—, $R^1$ and $R^2$ is each independently a hydrogen atom, or an optionally substituted $C_{1-6}$ alkyl group, X and Y are each independently a carbon atom or a nitrogen atom, Z is —O—$CH_2$—, —NR—$CH_2$—, —$CH_2$—$CH_2$—, —CH=CH—, —$CH_2$—, —O—, —S— or —NR—, and R is a substituent, or a salt thereof.

19. A method of inhibiting monoacylglycerol lipase in a mammal, which comprises administering an effective amount of a compound represented by the formula (I):

(I)

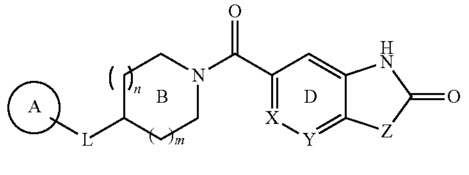

wherein m and n are each independently 0 or 1,

Ring A is an optionally further substituted cyclic group,

Ring B is an azetidine ring, a pyrrolidine ring or a piperidine ring, each of which is an optionally further substituted, Ring D is an optionally further substituted 6-membered aromatic ring, L is —$CH_2$—O—$CH_2$—, —O—$CR'R^2$—, —$CH(R^1)$—O—, —$CF_2$—$CH_2$—, —$CH_2$—$CF_2$— or —$CF_2$—, $R^1$ and $R^2$ is each independently a hydrogen atom, or an optionally substituted $C_{1-6}$ alkyl group, X and Y are each independently a carbon atom or a nitrogen atom, Z is —O—$CH_2$—, —NR—$CH_2$—, —$CH_2$—$CH_2$—, —CH=CH—, —$CH_2$—, —O—, —S— or —NR—, and R is a substituent, or a salt thereof, to the mammal.

20. A method for the prophylaxis or treatment of Alzheimer's disease, Parkinson's disease, Huntington's disease, amyotrophic lateral sclerosis, multiple sclerosis, anxiety disorder, pain, epilepsy or depression in a mammal, which comprises administering an effective amount of a compound represented by the formula (I):

(I)

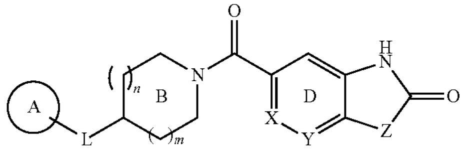

wherein m and n are each independently 0 or 1,

Ring A is an optionally further substituted cyclic group,

Ring B is an azetidine ring, a pyrrolidine ring or a piperidine ring, each of which is an optionally further substituted, Ring D is an optionally further substituted 6-membered aromatic ring, L is —$CH_2$—O—$CH_2$—, —O—$CR^1R^2$—, —$CH(R^1)$—O—, —$CF_2$—$CH_2$—, —$CH_2$—$CF_2$— or —$CF_2$—, $R^1$ and $R^2$ is each independently a hydrogen atom, or an optionally substituted $C_{1-6}$ alkyl group, X and Y are each independently a carbon atom or a nitrogen atom, Z is —O—$CH_2$—, —NR—$CH_2$—, —$CH_2$—$CH_2$—, —CH=CH—, —$CH_2$—, —O—, —S— or —NR—, and R is a substituent, or a salt thereof, to the mammal.

* * * * *